US012404243B2

(12) United States Patent
Jung et al.

(10) Patent No.: US 12,404,243 B2
(45) Date of Patent: *Sep. 2, 2025

(54) INHIBITORS OF THE Wnt/BETA-CATENIN PATHWAY

(71) Applicant: The Regents of the University of California, Oakland, CA (US)

(72) Inventors: Michael E. Jung, Los Angeles, CA (US); Xiaohong Chen, Los Angeles, CA (US); Cun-Yu Wang, Los Angeles, CA (US); Jiong Li, Van Nuys, CA (US); Jie Zheng, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/125,961

(22) Filed: Mar. 24, 2023

(65) Prior Publication Data

US 2024/0059654 A1 Feb. 22, 2024

Related U.S. Application Data

(63) Continuation of application No. 16/962,751, filed as application No. PCT/US2019/015875 on Jan. 30, 2019, now Pat. No. 11,708,329.

(60) Provisional application No. 62/623,976, filed on Jan. 30, 2018.

(51) Int. Cl.
| | | |
|---|---|---|
| *C07D 295/16* | (2006.01) | |
| *A61P 35/00* | (2006.01) | |
| *C07C 235/62* | (2006.01) | |
| *C07C 237/04* | (2006.01) | |
| *C07C 237/38* | (2006.01) | |
| *C07C 311/07* | (2006.01) | |
| *C07D 211/86* | (2006.01) | |
| *C07D 213/06* | (2006.01) | |
| *C07D 213/38* | (2006.01) | |
| *C07D 213/40* | (2006.01) | |
| *C07D 213/50* | (2006.01) | |
| *C07D 213/55* | (2006.01) | |
| *C07D 213/68* | (2006.01) | |
| *C07D 213/89* | (2006.01) | |
| *C07D 295/088* | (2006.01) | |
| *C07D 295/135* | (2006.01) | |
| *C07D 295/15* | (2006.01) | |
| *C07D 401/06* | (2006.01) | |
| *C07D 401/12* | (2006.01) | |
| *C07D 401/14* | (2006.01) | |
| *C07D 405/14* | (2006.01) | |
| *C07D 409/14* | (2006.01) | |

(52) U.S. Cl.
CPC .......... *C07D 213/68* (2013.01); *A61P 35/00* (2018.01); *C07C 235/62* (2013.01); *C07C 237/04* (2013.01); *C07C 237/38* (2013.01); *C07C 311/07* (2013.01); *C07D 211/86* (2013.01); *C07D 213/06* (2013.01); *C07D 213/38* (2013.01); *C07D 213/40* (2013.01); *C07D 213/50* (2013.01); *C07D 213/55* (2013.01); *C07D 213/89* (2013.01); *C07D 295/088* (2013.01); *C07D 295/135* (2013.01); *C07D 295/15* (2013.01); *C07D 295/16* (2013.01); *C07D 401/06* (2013.01); *C07D 401/12* (2013.01); *C07D 401/14* (2013.01); *C07D 405/14* (2013.01); *C07D 409/14* (2013.01)

(58) Field of Classification Search
CPC .......................... C07D 295/16; C07D 295/135
See application file for complete search history.

(56) References Cited

U.S. PATENT DOCUMENTS

| | | | |
|---|---|---|---|
| 6,147,374 A | 11/2000 | Tanaka et al. | |
| 6,664,272 B2 | 12/2003 | Snyder et al. | |
| 7,582,655 B2 | 9/2009 | Dimmock et al. | |
| 9,359,196 B2 | 6/2016 | Awasthi et al. | |
| 11,708,329 B2 * | 7/2023 | Jung ..................... | C07C 235/82 |
| | | | 514/217.04 |
| 2002/0027268 A1 | 3/2002 | Tanaka et al. | |
| 2021/0371384 A1 | 12/2021 | Jung et al. | |

FOREIGN PATENT DOCUMENTS

| | | |
|---|---|---|
| CN | 103936667 A | 7/2014 |
| CN | 105541700 A | 5/2016 |
| EP | 3045445 A1 | 7/2016 |
| WO | WO-2012/024282 A2 | 2/2012 |
| WO | WO-2014/182744 A1 | 11/2014 |
| WO | WO-2019/152536 A1 | 8/2019 |
| WO | WO-2024/145585 A1 | 7/2024 |

OTHER PUBLICATIONS

A machine generated English translation of CN 103936667 A from WIPO (Song et al.), 2014. (Year: 2014).*
Al-Hujaily et al., "PAC, a novel curcumin analogue, has anti-breast cancer properties with higher efficiency on ER-negative cells," Breast Cancer Res. Tr. 128(1):97-107 (2011).
Anthwal et al., "C5-curcuminoid-dithiocarbamate based molecular hybrids: synthesis and anti-inflammatory and anti-cancer activity evaluation," RSC Adv. 4(54):28756-28764 (2014).
Anthwal et al., "Synthesis of 4-piperidone based curcuminoids with anti-inflammatory and anti-proliferation potential in human cancer cell lines," Anti-Cancer Agent ME 16(7):841-851 (2016).

(Continued)

*Primary Examiner* — Laura L Stockton
(74) *Attorney, Agent, or Firm* — Foley Hoag LLP; David P. Halstead; Alexander J. Chatterley

(57) ABSTRACT

The present disclosure relates to compounds that are capable of modulating the WNT/Beta-Catenin pathway. The disclosure further relates to methods of treating colorectal cancer and other WNT/Beta-Catenin mediated cancers.

16 Claims, 20 Drawing Sheets

(56) References Cited

OTHER PUBLICATIONS

Anthwal et al., "Synthesis, characterization and in vitro anticancer activity of C-5 curcumin analogues with potential to inhibit TNF-a-induced NF-?B activation," BioMed Research International, 2014:1-10 (2014).
Bazzaro et al., "alpha, beta-Unsaturated carbonyl system of chalcone-based derivatives is responsible for broad inhibition of proteasomal activity and preferential killing of human papilloma virus (HPV) positive cervical cancer cells," J. Med. Chem. 54(2):449-456 (2011).
CAS Registry No. 162843-62-1 (1995).
Das et al., "Design, synthesis and cytotoxic properties of novel 1-[4-(2-alkylaminoethoxy) phenylcarbonyl]-3, 5-bis (arylidene)-4-piperidones and related compounds," Eur. J. Med. Chem. 42(1):71-80 (2007).
Davis et al., "Syntheses and Cytotoxic Properties of the Curcumin Analogs 2,6-Bis (benzylidene)-4-phenylcyclohexanones," Arch. Pharm. 341(7):440-445 (2008).
Extended European Search Report for EP Application No. 1974914.0 dated Oct. 11, 2021.
Huber et al., "Synthesis and antiproliferative activity of cyclic arylidene ketones: a direct comparison of monobenzylidene and dibenzylidene derivatives," Monatshefte Chem. 146(6):973-981 (2015).
International Search Report and Written Opinion for International Application No. PCT/US2019/015875 dated May 15, 2019.
Jadhav et al., "Synthesis and Anticancer Evaluation of Furfurylidene 4-Piperidone Analogs," Arch. Pharm. 347(6):407-414 (2014).
Ji et al., "4-Carbonyl-2, 6-dibenzylidenecyclohexanone derivatives as small molecule inhibitors of STAT3 signaling pathway," Bioorgan. Med. Chem. 24(23):6174-6182 (2016).
Kia et al., "(3E,5E)-3,5-Dibenzylidene-1-[3-(piperidin-1-yl) propanoyl]piperidin-4-one," Acta Cryst. E. E67(6):o1299-o1300 (2011).
Lellek et al., "An Efficient Synthesis of Substituted Pyrazoles from One-Pot Reaction of Ketones, Aldehydes, and Hydrazine Monohydrochloride," Synlett, 29(08):1071-1075 (2018).
Leow et al., "Functionalized curcumin analogs as potent modulators of the Wnt/beta-catenin signaling pathway," Eur. J. Med. Chem. 71:61-80 (2014).
Machine generated English translation of CN 103936667 A (Song et al.) (2014).
Makarov et al., "Synthesis, characterization and structure-activity relationship of novel N-phosphorylated E, E-3, 5-bis (thienylidene) piperid-4-ones," Eur. J. Med. Chem. 45(3):992-1000 (2009).
PubChem CID 3574340, National Center for Biotechnology Information. PubChem Compound Summary for CID 3574340, 2,6-Dibenzylidene-4-phenylcyclohexan-1-one. https://pubchem.ncbi.nlm.nih.gov/compound/26-Dibenzylidene-4-phenylcyclohexan-1-one. Accessed Oct. 22, 2021, create date Sep. 9, 2005. (Year: 2005).
Rao et al., "Photoactive liquid crystalline polymers: A comprehensive study of linear and hyperbranched polymers synthesized by A2B2, A2B3, A3B2, and A3B3 approaches," J. Polym Sci. Pol. Chem. 49(6):1319-1330 (2011).
Rowe et al., "Handbook of Pharmaceutical Excipients," Pharmaceutical Press, (pp. 238-240 and 766-770) (2009).
Schmitt et al., "Fluoro and pentafluorothio analogs of the antitumoral curcuminoid EF24 with superior antiangiogenic and vascular-disruptive effects," Bioorgan. Med. Chem. 25(17):4894-4903 (2017).
Selvakumar et al., "Synthesis and biological evaluation of some curcumin analogs and their derivatives," Rasayan J. Chem. 3(2):260-265 (2010).
Written Opinion of International Preliminary Examining Authority for International Application No. PCT/US2019/015879 dated Jan. 9, 2020.
Wu et al., "Anti-lung cancer activity pf the curcumin analog JZ534 in vitro," Biomed. Res. Int. 1-10 (2015).
Wu et al., "Threonine 41 in beta-Catenin Serves as a Key Phosphorylation Relay Residue in beta-Catenin Degradation," Biochem. 45(16):5319-5323 (2006).
Zhou et al., "Recent advancements in PARP inhibitors-based targeted cancer therapy", Precision Clinical Medicine, 3(3): 187-201 (2020).
Huber et al., "Novel cyclic C5-curcuminoids penetrating the blood-brain barrier: Design, synthesis and antiproliferative activity against astrocytoma and neuroblastoma cells", European Journal of Pharmaceutical Sciences 173 (2022): 106184.
International Search Report and Written Opinion for Application No. PCT/US23/86435 dated May 2, 2024.
Invitation to Pay Additional Fees for International Application No. PCT/US23/86435 dated Apr. 2, 2024.
U.S. Appl. No. 16/962,751, Granted.
Petrucci et al., "General Chemistry" (8th ed.). 2002 Prentice Hall. pp. 665-709.
Shriver et al., "Inorganic Chemistry" (3rd ed.). (1999) Oxford University Press. ISBN 0-19-850331-8. Sec. 5.2 Solvent Leveling, pp. 148-150.

* cited by examiner

INHIBITORS OF THE Wnt/BETA-CATENIN PATHWAY

RELATED APPLICATIONS

This application is a continuation of U.S. application Ser. No. 16/962,751, filed Jul. 16, 2020, which is the § 371 National Stage of PCT/US2019/015875, filed Jan. 30, 2019; which claims the benefit of U.S. Provisional Application No. 62/623,976, filed Jan. 30, 2018, the contents of each of which are fully incorporated by reference herein.

BACKGROUND

The Wnt-β-catenin signaling pathway plays a critical role in development, stem cell self-renewal, and oncogenesis. The Wnt/β-catenin signaling pathway has been found to be associated with various types of human cancers, most notably colorectal cancers (CRCs) due to adenomatous polyposis coli (APC) and CTNNB1 (β-catenin) mutations (Bienz, M. & Clevers, H. Cell 103, 311-320 (2000); Nature 487, 330-337, 2012); Fearon, E. R. & Vogelstein, B. Cell, 61, 759-767 (1990). However, no approved drugs are available in the clinic for treatment of these cancers via the targeting of the Wnt signaling pathway, despite substantial effort invested into therapeutic development of Wnt inhibitors in the past two decades (Novellasdemunt, L., Antas, P. & Li, V. S. Am J Physiol Cell Physiol 309, C511-521, 2015; Nusse, R. & Clevers, H. Cell 169, 985-999, 2017). Thus, an unmet need exists for inhibitors of β-catenin.

SUMMARY OF THE INVENTION

In certain aspects, the present disclosure provides compound of Formula I, Formula II, or Formula III:

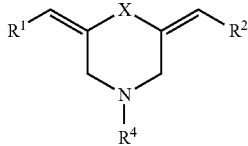
Formula I

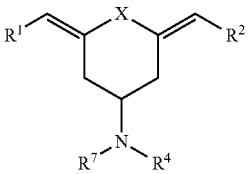
Formula II

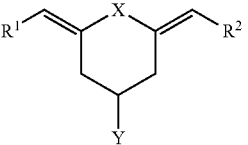
Formula III or a pharmaceutically acceptable salt thereof, wherein,
X is C=O, $NR^3$, C=$NR^3$, S, S=O, S(=O)$_2$, or C=S;
Y is heteroaryl, aryl, or C(O)N($R^7$)($R^4$);
$R^1$ and $R^2$ are independently selected from aryl, heteroaryl, and heterocyclyl;
$R^4$ is hydrogen, alkyl, alkenyl, acyl, aryl, heteroaryl, C(O)aryl, C(O)alkyl, C(O)Oalkyl, C(O)Oaryl, C(O)Oheteroaryl, C(O)N($R^{5a}R^{5b}$), aralkyl, alkylsulfonyl, or

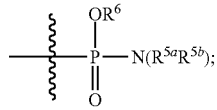

$R^{5a}$ and $R^{5b}$ are independently selected from H, alkyl, aralkyl, and aryl;
$R^6$ is H, alkyl, or aryl; and
$R^3$ and $R^7$ are each independently H or alkyl.

In certain embodiments, the present disclosure provides compounds of Formula I, Formula II, and pharmaceutically acceptable salts thereof.

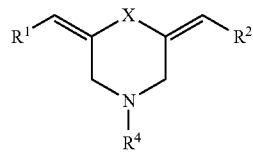
Formula I

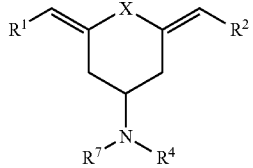
Formula II wherein,
X is C=O, $NR^3$, C=$NR^3$, S, S=O, S(=O)$_2$, or C=S;
$R^1$ and $R^2$ are independently selected from aryl, heteroaryl, and heterocyclyl;
$R^4$ is alkyl, alkenyl, acyl, C(O)aryl, C(O)alkyl, C(O)Oalkyl, C(O)Oaryl, C(O)Oheteroaryl, C(O)N($R^{5a}R^{5b}$), aralkyl, alkylsulfonyl, or

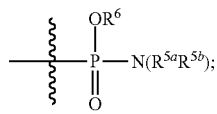

$R^{5a}$ and $R^{5b}$ are independently selected from H, alkyl, aralkyl, and aryl;
$R^6$ is H, alkyl, or aryl; and
$R^3$ and $R^7$ are each independently H or alkyl.

In certain aspects, the present disclosure provides methods of inhibiting β-catenin, comprising of administering to a subject an effective amount of a compound of Formula I, Formula II, or Formula III.

In certain aspects, the present disclosure provides methods of treating cancer comprising of administering to a subject in need of a treatment for cancer an effective amount of a compound of Formula I, Formula II, or Formula III. In some embodiments, the cancer is colorectal cancer.

DETAILED DESCRIPTION OF THE INVENTION

Figure 1:
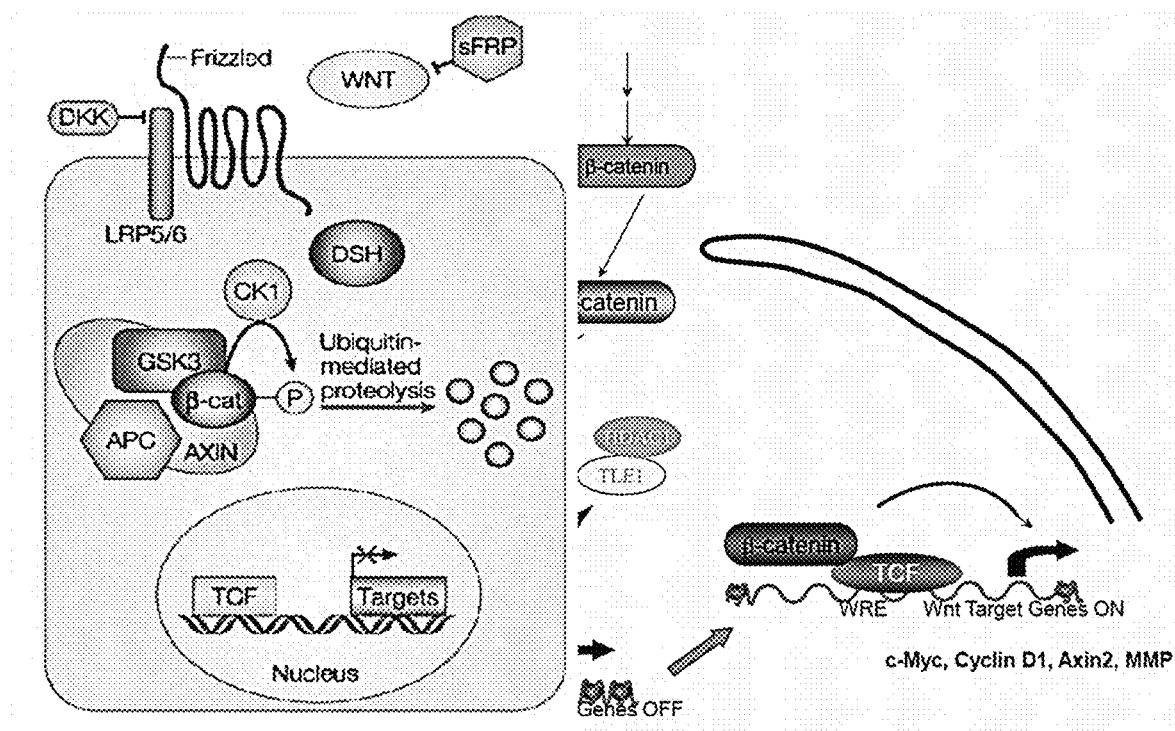
FIG. 1. The Wnt-β-catenin signaling pathway plays a critical role in development, stem cell self-renewal, and oncogenesis. The level of Wnt/β-catenin signaling is dependent on the stability and cellular location of β-catenin.
Figure 2:
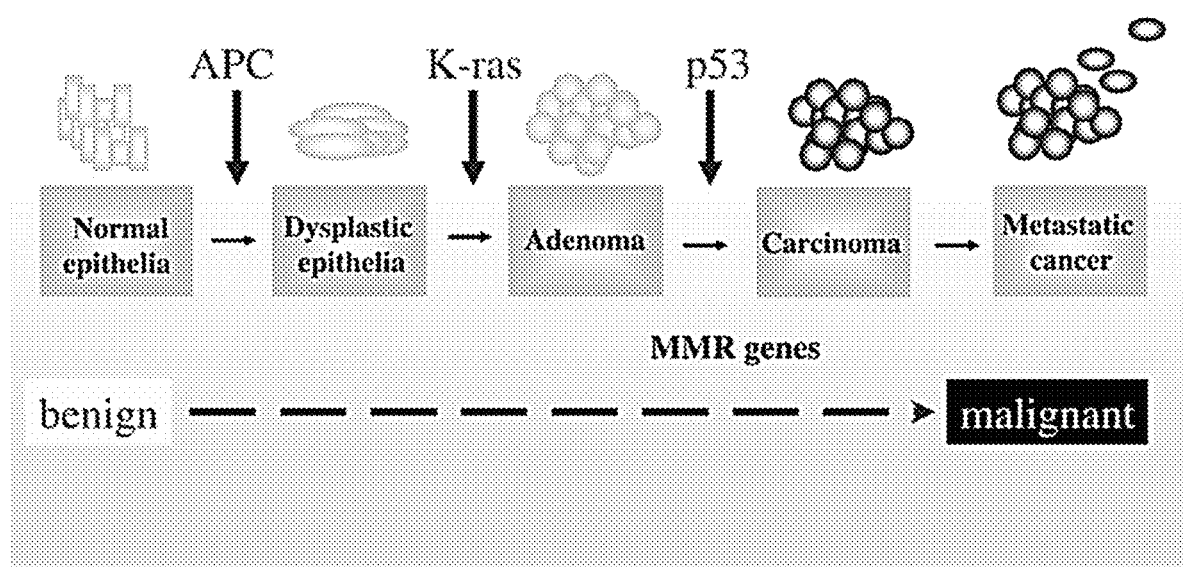
FIG. 2. The hyper activated Wnt/β-catenin signaling pathway has been found to be associated with various types of human cancers, most notably colorectal cancers (CRCs) due to APC and CTNNB1 (β-catenin) mutations.
Figure 3:
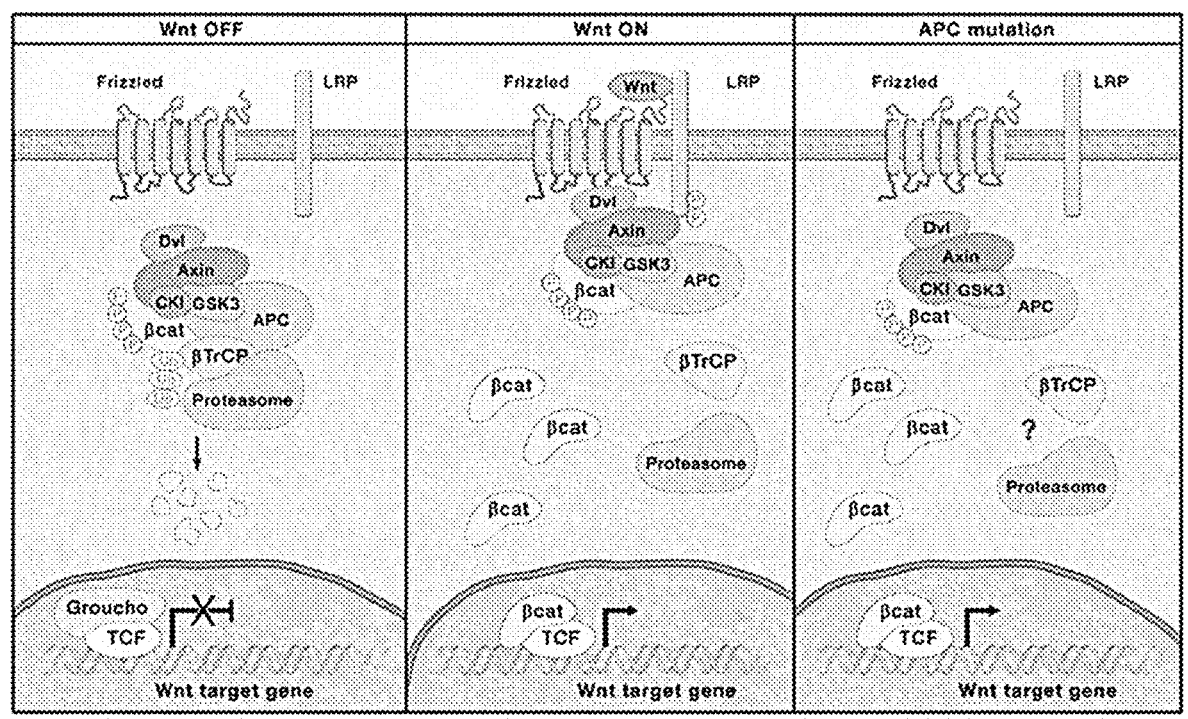
FIG. 3. Left: In the absence of a Wnt signal, β-catenin is degraded by a complex of proteins including Axin, APC, the Ser/Thr kinases GSK-3 and CK1, protein phosphatase 2A (PP2A), and the E3-ubiquitin ligase β-TrCP. The complex interacts with a β-TrCP recognition site on β-catenin by phosphorylation of a conserved Ser/Thr rich sequence near the amino terminus. Phosphorylation requires scaffolding of GSK-3 and CK1 and β-catenin by Axin. After phosphorylation and ubiquitination, β-catenin is degraded by the proteasome. Dvl is also required for activating the pathway. In the nucleus, TCF is in an inactive state as a result of binding to the repressor Groucho. Center: Binding of Wnt to its receptors induces the association of Axin with phosphorylated lipoprotein receptor-related protein (LRP). The destruction complex decomposes, and β-catenin is stabilized. β-catenin subsequently binds to TCF in the nucleus and upregulates target genes. Right: Mutations in APC disrupt the degradation complex, thereby leading to the activation of the Wnt-β-catenin signaling pathway.
Figure 4:
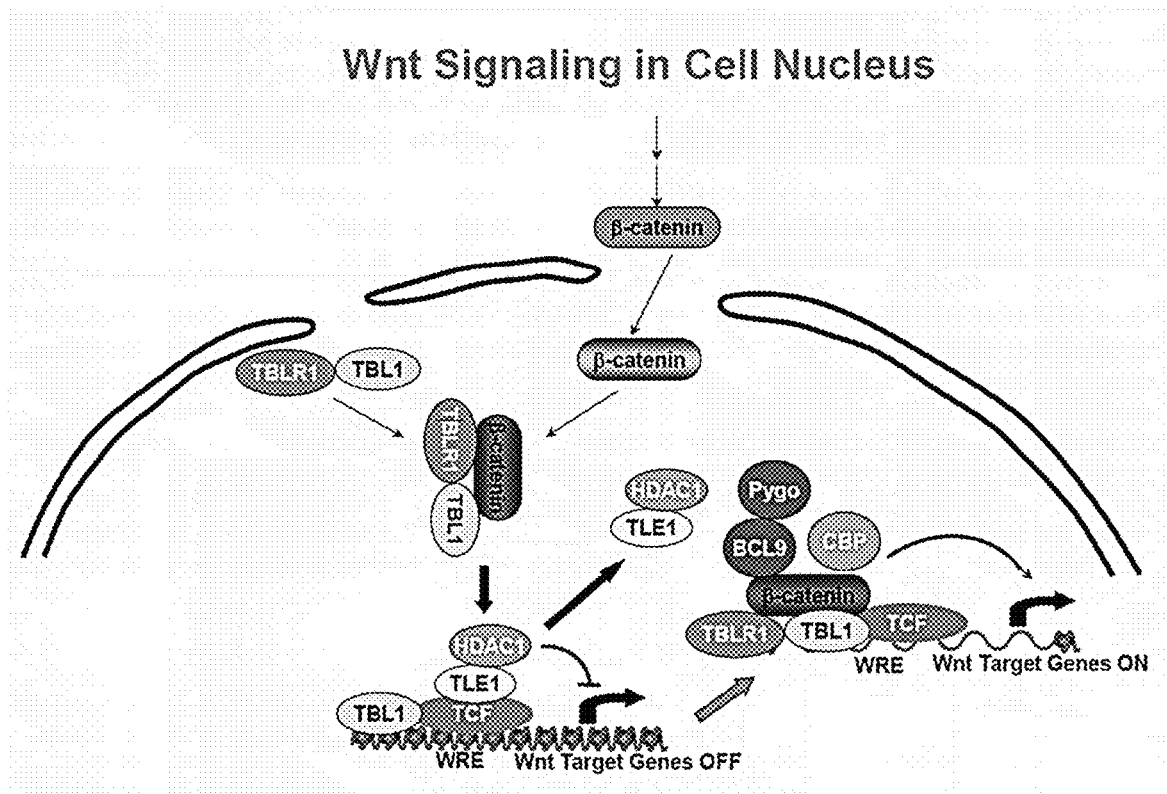
FIG. 4. In the absence of Wnt signaling, TCF interacts with corepressors TLE1 and HDAC1, found on the chromatin, which repress Wnt target genes. On Wnt stimulation, stabilized β-catenin is translocated to the nucleus and interacts with TBL1/TBLR1. TBL1/TBLR1 and β-catenin mutually facilitate their binding to the Wnt target-gene promoter, and as a result displace the corepressors TLE and HDAC1. In addition to relieving TCF repression, β-catenin activates Wnt target gene expression by recruiting transcriptional coactivators, such as BCL9/PYGO and CBP.

The Wnt-β-catenin signaling pathway plays a critical role in development, stem cell self-renewal, and oncogenesis. The level of Wnt/β-catenin signaling is determined by the stability and cellular location of β-catenin. In the absence of Wnt stimulation, there is a small pool of cytosolic β-catenin due to constitutive phosphorylation by a complex containing AXIN, APC and GSK3. Phospho-β-catenin is then by the ubiquitin/proteasome degradation pathway. Upon Wnt stimulation, the AXIN/APC/GSK3 complex is antagonized, causing the accumulation of phosphorylated β-catenin, which translocates into the nucleus. There it complexes with transcription factors, most notably members of the TCF family of DNA-binding proteins. Without β-catenin, TCFs are thought to function as repressors of Wnt target gene expression, in part by interacting with transcriptional co-repressors of the Groucho/TLE family proteins, which recruit HDACs to maintain the gene silencing. β-catenin directly displaces TLE from TCF through competitive binding. In addition to relieving TCF repression, β-catenin may activate Wnt target gene expression by recruiting additional proteins to TCF-bound chromatin. The N-terminal portion of β-catenin binds to BCL9 and BCL9 acts as an adaptor between β-catenin and PYGO2 which promotes transcriptional activation. Several transcription complexes or coactivators, including TBL1/TBLR1, the histone acetyl transferase CBP/p300, polymerase-associated factor 1 (PAF1) and the chromatin remodeler BRG1 have been identified to be recruited by the central of C-terminus part of β-catenin. These interactions contribute to the ability of TCF/β-catenin to activate Wnt target genes, supporting the model that β-catenin converts TCFs from repressors into transcriptional activators.

Abnormal activation of Wnt/β-catenin signaling has been demonstrated to play an important role in the development of colorectal cancer (Dow, L. E. et al. Cell 161, 1539-1552, 2015; Clevers, H. & Nusse, R. Cell 149, 1192-1205, 2012; Nusse, R. & Clevers, H. Cell 169, 985-999, 2017). The transition of an intestinal epithelial cell into a fully transformed metastatic colorectal cancer cell follows a series of inactivating and activating mutations of various tumor suppressors and oncogenes (Fearon, E. R. Annu Rev Pathol 6, 479-507, 2011). The initiating event of intestinal carcinogenesis is commonly caused by mutations in the key components of the Wnt signaling pathway (e.g., APC or CTNNB1), which lead to stabilization of β-catenin and subsequent constitutive transcription by the β-catenin/TCF complex. This triggers expansion and transformation of the stem cell compartment and leads subsequently to the development of adenomatous polyps (van de Wetering, M. et al. Cell 111, 241-250, 2002). During the course of tumorigenesis, additional mutations in other oncogenes and tumor suppressors, such as KRAS and TP53, are usually acquired. Tumors continue to progress once carcinomas have formed and accumulated loss of tumor suppressor genes correlates with the ability of the carcinomas to metastasize and cause death. However, no approved drugs are available in the clinic for treatment via targeting of the Wnt signaling pathway, despite substantial effort invested into therapeutic development of Wnt inhibitors in the past two decades (Novellasdemunt, L., Antas, P. & Li, V. S. Am J Physiol Cell Physiol 309, C511-521, 2015; Nusse, R. & Clevers, H. Cell 169, 985-999, 2017).

In certain aspects, the present disclosure provides compound of Formula I, Formula II, or a pharmaceutically acceptable salt thereof:

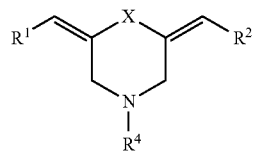

Formula I

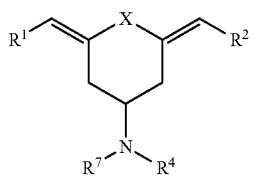

Formula II

-continued

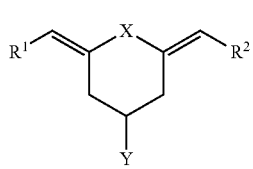
Formula III wherein,
X is C=O, NR³, C=NR³, S, S=O, S(=O)₂, or C=S;
Y is heteroaryl, aryl, or C(O)N(R⁷)(R⁴);
R¹ and R² are independently selected from aryl, heteroaryl, and heterocyclyl;
R⁴ is hydrogen, alkyl, alkenyl, acyl, aryl, heteroaryl, C(O)aryl, C(O)alkyl, C(O)Oalkyl, C(O)Oaryl, C(O)Oheteroaryl, C(O)N(R⁵ᵃR⁵ᵇ), aralkyl, alkylsulfonyl, or

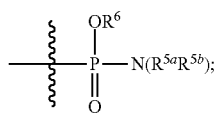

R⁵ᵃ and R⁵ᵇ are independently selected from H, alkyl, aralkyl, and aryl;
R⁶ is H, alkyl, or aryl; and
R³ and R⁷ are each independently H or alkyl.

In other embodiments, R⁴ is hydrogen. In yet other embodiments, R⁴ is not hydrogen. In other embodiments, R⁴ is alkyl, alkenyl, acyl, aryl, heteroaryl, C(O)aryl, C(O)alkyl, C(O)Oalkyl, C(O)Oaryl, C(O)Oheteroaryl, C(O)N(R⁵ᵃR⁵ᵇ), aralkyl, alkylsulfonyl, or

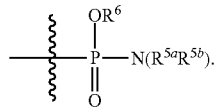

In certain embodiments of Formula I, Formula II, or Formula III, R¹ is aryl or heteroaryl. In certain embodiments, R¹ is aryl, such as phenyl or naphthyl, preferably fluorophenyl or difluorophenyl, most preferably 3-fluorophenyl or 3,4-difluorophenyl. In other embodiments, R¹ is heteroaryl, such as pyridyl, furanyl, thiophenyl, indolyl, or benzofuranyl. In certain embodiments, R¹ is further substituted with at least one substituent selected from alkyl, alkoxy, halo (e.g., fluoro, chloro, or bromo, preferably fluoro), aralkyl, and C(O)Oalkyl. In certain preferred embodiments, R¹ is further substituted with halo (e.g., fluoro, chloro, or bromo, preferably fluoro) or alkyl (e.g., trifluoromethyl).

In certain embodiments of Formula I, Formula II, or Formula III, R² is aryl or heteroaryl. In certain embodiments, R² is aryl, such as phenyl or naphthyl, preferably fluorophenyl or difluorophenyl, most preferably 3-fluorophenyl or 3,4-difluorophenyl. In other embodiments, R² is heteroaryl, such as pyridyl, furanyl, thiophenyl, indolyl, or benzofuranyl. In certain embodiments, R² is further substituted with at least one substituent selected from alkyl, alkoxy, halo (e.g., fluoro, chloro, or bromo, preferably fluoro), aralkyl, and C(O)Oalkyl. In certain preferred embodiments, R² is further substituted with halo (e.g., fluoro, chloro, or bromo, preferably fluoro) or alkyl (e.g., trifluoromethyl).

In certain embodiments of Formula I, Formula II, or Formula III, R¹ and R² are different. In other preferred embodiments, R¹ and R² are the same.

In certain embodiments, the compound is represented by Formula I:

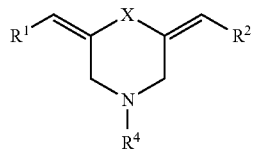
Formula I or a pharmaceutically acceptable salt thereof, wherein,
X is C=O, NRs, C=NR³, S, S=O, S(=O)₂, or C=S;
R¹ and R² are independently selected from aryl, heteroaryl, and heterocyclyl;
R⁴ is alkyl, alkenyl, acyl, C(O)aryl, C(O)alkyl, C(O)Oalkyl, C(O)Oaryl, C(O)Oheteroaryl, C(O)N(R⁵ᵃR⁵ᵇ), aralkyl, alkylsulfonyl, or

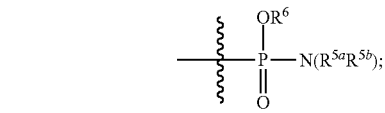

R⁵ᵃ and R⁵ᵇ are independently selected from H, alkyl, aralkyl, and aryl;
R⁶ is H, alkyl, or aryl; and
R³ and R⁷ are each independently H or alkyl.

In certain embodiments, the compound is represented by Formula II:

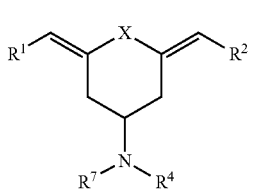
Formula II or a pharmaceutically acceptable salt thereof, wherein,
X is C=O, NR³, C=NR³, S, S=O, S(=O)₂, or C=S;
R¹ and R² are independently selected from aryl, heteroaryl, and heterocyclyl;

In certain embodiments, X is S(=O)₂.

In certain embodiments of Formula I or Formula II, the compound is represented by Formula Ia or Formula IIa:

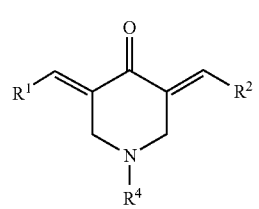
Formula Ia

-continued

Formula IIa

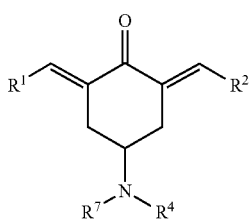

or a pharmaceutically acceptable salt thereof.

In certain embodiments of Formula I, the compound is represented by Formula Ib

Formula Ib

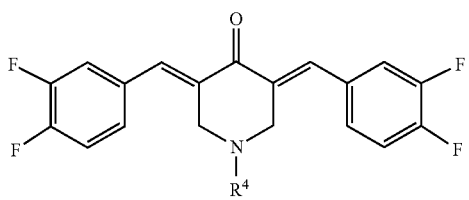

or a pharmaceutically acceptable salt thereof.

In certain embodiments of Formula I, the compound is represented by Formula Ic or Id:

Formula Ic

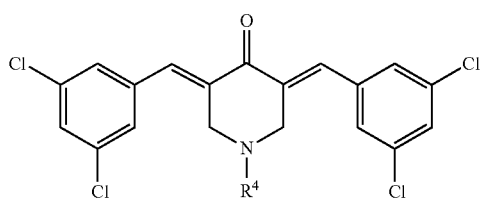

Formula Id

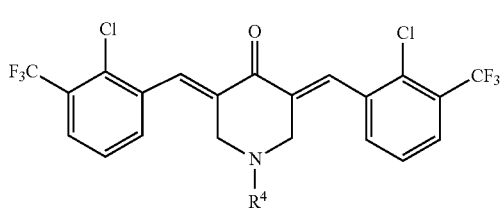

or a pharmaceutically acceptable salt thereof.

In certain embodiments of Formula II, the compound is represented by Formula IIb:

Formula IIb

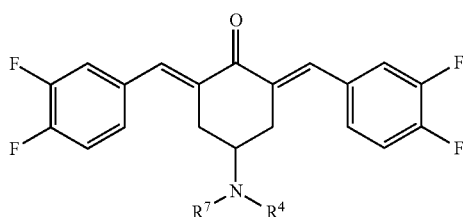

or a pharmaceutically acceptable salt thereof.

In certain embodiments of Formula II, the compound is represented by Formula IIc or IId:

Formula IIc

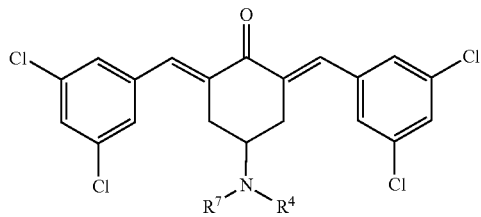

Formula IId

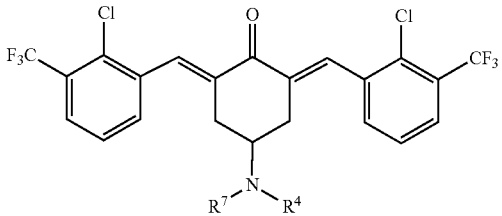

or a pharmaceutically acceptable salt thereof.

In certain embodiments of Formula I or Formula II, $R^4$ is $C(O)N(R^{5a}R^{5b})$ or

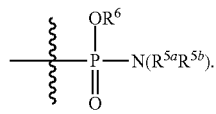

In certain embodiments, $R^4$ is

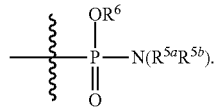

In certain embodiments, $R^{5a}$ and $R^{5b}$ are both alkyl, such as methyl. In certain embodiments, $R^6$ is aryl, such as phenyl. In other preferred embodiments, $R^4$ is $C(O)N(R^{5a}R^{5b})$.

In certain embodiments of Formula I or Formula II, $R^{5a}$ is alkyl, such as methyl or ethyl. In certain embodiments, $R^{5a}$ is further substituted with hydroxyl or amino, such as dimethylamino. In certain embodiments, $R^5$, is aryl, such as phenyl.

In certain embodiments of Formula I or Formula II, in certain preferred embodiments, $R^{5b}$ is H. In other embodiments, $R^{5b}$ is aralkyl, such as benzyl. In yet other embodiments, $R^{5b}$ is alkyl, such a methyl.

In certain embodiments of Formula I or Formula II, $R^4$ is alkyl, alkenyl, acyl, C(O)alkyl, C(O)Oalkyl, aralkyl, or alkylsulfonyl. In certain preferred embodiments, $R^4$ is further substituted with at least one basic amino substituent. In certain embodiments, the basic amino substituent is $NH_2$. In other embodiments, the basic amino substituent is alkylamino, preferably dialkylamino, such as dimethylamino, diethylamino, or di(methoxyethyl)amino. In certain preferred embodiments the basic aminosubstituent is di(methoxyethyl)amino. In other embodiments, the basic amino substituent is a basic nitrogen containing heterocycle, such as azepanyl, pyrrolidinyl (e.g., pyrrolidine or N-methyl pyrrolidine), piperidyl, morpholinyl, piperazinyl (e.g., N-methylpiperazine or 1-(4-fluorophenyl)piperazine), piperidonyl, or thiomorpholinyl.

In certain embodiments of Formula I or Formula II, $R^4$ is further substituted with at least one substituent selected from C(O)Oalkyl (such as C(O)Omethyl, or C(O)Oethyl), C(O)alkyl (such as acetyl), alkenyl (such as dimethyl fumaratyl or aminoallyl (e.g., dimethylaminoallyl)), thio (such as phenylthio), alkenyl (such as vinyl), carboxyl, amido (such as C(O)pyrrolidinyl), and alkyloxy (such as methoxy).

In yet other embodiments of Formula I or Formula II, $R^4$ is C(O)alkyl. In certain embodiments, the alkyl is further substituted with carbamodithioate (e.g., morpholine carbodithioate).

In yet other preferred embodiments of Formula I or Formula II, $R^4$ is C(O)aryl or C(O)Oaryl. In certain embodiments, the aryl of $R^4$ is further substituted, preferably at a para position, with at least one basic amino substituent. In certain embodiments, the basic amino substituent is amino, preferably dialkylamino, such as dimethylamino. In other embodiments, the basic amino substituent is aminoalkyloxy (such as dimethylaminoethyloxy, diethylaminoethyloxy, or 2-(piperidin-1-yl)ethanoxy), aminoalkylthio (such as dimethylaminoethylthio), or aminoalkylamino (such as dimethylaminoethylamino). In certain preferred embodiments, the basic amino subsitutent is dimethylaminoethyloxy or diethylaminoethyloxy. In other embodiments, the basic amino substituent is aminoalkyloxy (e.g., morpholinylalkyloxy).

In certain embodiments of Formula I or Formula II, the aryl of $R^4$ is further substituted, preferably at a para-position, with at least one substituent selected from alkyl, such as trifluoromethyl, and halo, such as fluoro or chloro. In other embodiments, the aryl of $R^4$ is further substituted, preferably at a para-position, with at least one substituent selected from alkynloxy (e.g., ethynyloxy).

In certain preferred embodiments of Formula I or Formula II, the aryl of $R^4$ is further substituted, preferably at a meta- or ortho-position, with at least one substituent selected from alkyl, such as trifluoromethyl, and halo, such as fluoro or chloro.

In other embodiments of Formula I or Formula II, $R^4$ is alkylsulfonyl, and is preferably further substituted with amino, preferably dialkylamino, such as dimethylamino or diethylamino, or alkyoxy, such as methoxy.

In certain embodiments of Formula I or Formula II, the compound is represented by Formula IIe:

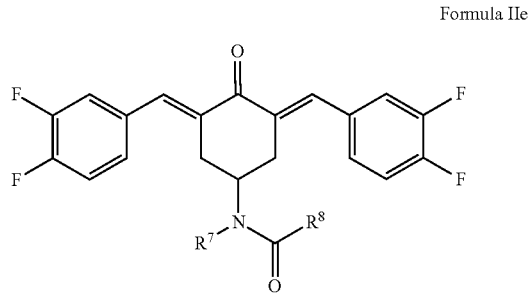

Formula IIe wherein
$R^7$ is H or alkyl; and
$R^8$ is aminoalkyl or aryl.

In certain embodiments, the compound of Formula IIe is a pharmaceutically acceptable salt of the compound of Formula IIe.

In other embodiments, $R^8$ is aryl, such as phenyl, further substituted (preferably at a para-position) with aminoalkyl, such as dimethylaminoethyl, or aminoalkoxy, such as 2-(piperidin-1-yl)ethyloxy.

In certain embodiments, the compound is represented by Formula III:

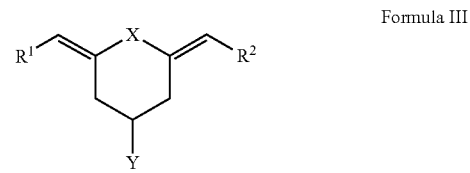

Formula III or a pharmaceutically acceptable salt thereof.

In certain embodiments of Formula III, the compound is represented by Formula IIIa:

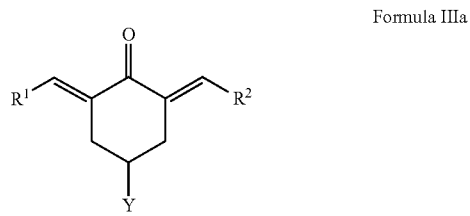

Formula IIIa or a pharmaceutically acceptable salt thereof.

In certain embodiments of Formula III, Y is aryl. In certain the aryl is substituted with at least one basic amino substituent. In certain embodiments, the basic amino substituent is $NH_2$. In certain embodiments, the basic amino substituent is alkylamino, preferably dialkylamino, such as dimethylamino, diethylamino, or di(methoxyethyl)amino. In certain embodiments, the basic amino substituent is aminoalkyloxy (such as dimethylaminoethyloxy, diethylaminoethyloxy, or 2-(piperidin-1-yl)ethanoxy), aminoalkylthio (such as dimethylaminoethylthio), or aminoalkylamino (such as dimethylaminoethylamino). In certain preferred embodiments, the basic amino substituent is aminoalkyloxy (such as dimethylaminoethyloxy, diethylaminoethyloxy or 2-(piperidin-1-yl)ethanoxy). In even more preferred embodiments, the basic amino substituent is dimethylaminoethyloxy. In other embodiments, the basic amino substituent is a basic nitrogen containing heterocycle, such as azepanyl, pyrrolidinyl (e.g., pyrrolidine or N-methyl pyrrolidine), piperidyl, morpholinyl, piperazinyl (e.g., N-methylpiperazine or 1-(4-fluorophenyl)piperazine), piperidonyl, or thiomorpholinyl. In yet other embodiments, the basic amino substituent is aminoalkyloxy (e.g., morpholinylalkyloxy). In certain embodiments, the aryl is further substituted with at least one substituent selected from C(O)Oalkyl (such as C(O)Omethyl, or C(O)Oethyl), C(O)alkyl (such as acetyl), alkenyl (such as dimethyl fumaratyl or aminoallyl (e.g., dimethylaminoallyl)), thio (such as phenylthio), alkenyl (such as vinyl), carboxyl, amido (such as C(O)pyrrolidinyl), and alkyloxy (such as methoxy).

In other embodiments of Formula III, Y is C(O)N($R^7$)($R^4$).

In certain embodiments of Formula III, $R^7$ is alkyl, such as methyl. In other preferred embodiments, $R^7$ is H.

In certain preferred embodiments of Formula III, $R^4$ is aryl. In certain embodiments, the aryl is further substituted, preferably at a para position, with at least one basic amino substituent. In certain embodiments, the basic amino substituent is amino, preferably dialkylamino, such as dimethylamino. In certain embodiments, the basic amino substituent is aminoalkyl, preferably dialkylaminoalkyl, such as dimethylaminomethyl or dimethylaminoethyl. In certain embodiments, the basic amino substituent is aminoalkyloxy (such as dimethylaminoethyloxy, diethylaminoethyloxy, or 2-(piperidin-1-yl)ethanoxy), aminoalkylthio (such as dimethylaminoethylthio), or aminoalkylamino (such as dimethylaminoethylamino). In certain preferred embodiments, the basic amino substituent is aminoalkyloxy (such as dimethylaminoethyloxy, diethylaminoethyloxy or 2-(piperidin-1-yl)ethanoxy). In even more preferred embodiments, the basic amino substituent is dimethylaminoethyloxy. In other embodiments, the basic amino substituent is aminoalkyloxy (e.g., morpholinylalkyloxy). In certain embodiments, the aryl is further substituted, preferably at a para-position, with at least one substituent selected from alkyl, such as trifluoromethyl, and halo, such as fluoro or chloro. In other embodiments, the aryl is further substituted, preferably at a para-position, with at least one substituent selected from alkynloxy (e.g., ethynyloxy). In yet other embodiments, the aryl is further substituted, preferably at a meta- or ortho-position, with at least one substituent selected from alkyl, such as trifluoromethyl, and halo, such as fluoro or chloro.

In certain embodiments of Formula I or Formula II, $R^7$ is alkyl, such as methyl. In other preferred embodiments, $R^7$ is H. In certain preferred embodiments of Formula IIe, $R^8$ is aminoalkyl, preferably dialkylaminoalkyl, such as dimethylaminoethyl.

In certain aspects, the compound is selected from a compound of Table 1.

TABLE 1

Exemplary Compounds of the Present Invention

JC001

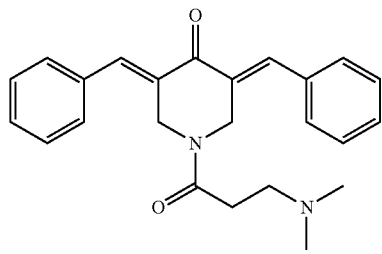

MW = 374.48

JC002

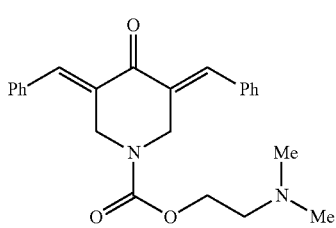

MW = 390.48

TABLE 1-continued

Exemplary Compounds of the Present Invention

JC003

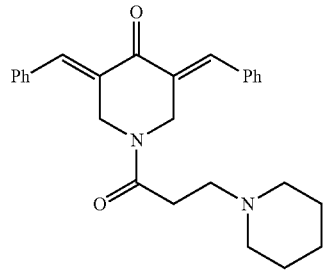

MW = 414.55

JC004

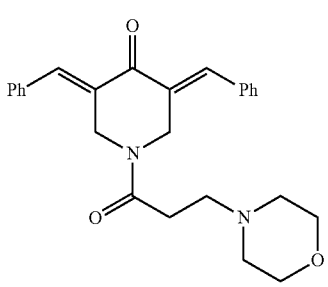

MW = 416.52

JC005

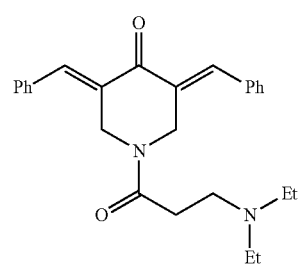

MW = 439

JC006

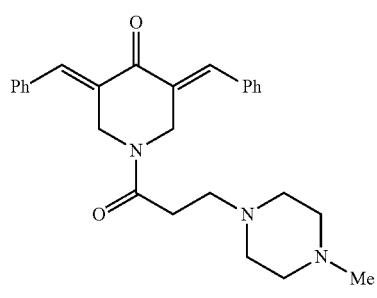

MW = 466.02

JC007

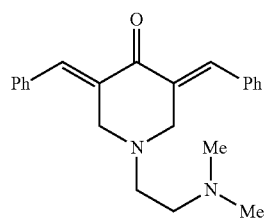

MW = 346.47

TABLE 1-continued
Exemplary Compounds of the Present Invention
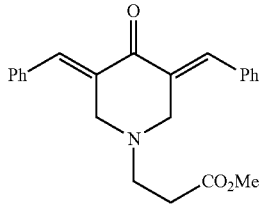
JC008
MW = 361.44
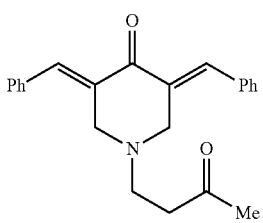
JC009
MW = 345.44
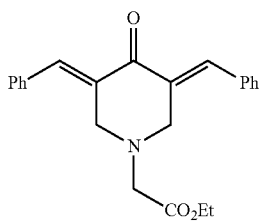
JC010
MW = 361.44
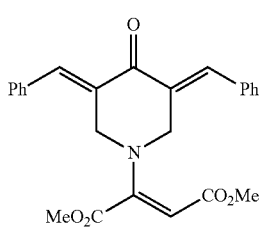
JC011
MW = 417.46
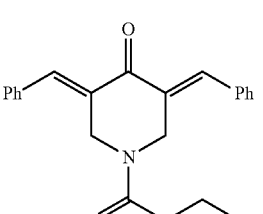
JC012
MW = 439.57
TABLE 1-continued
Exemplary Compounds of the Present Invention
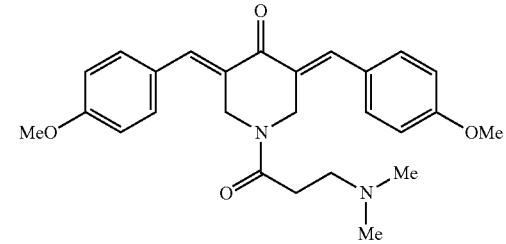
JC013
MW = 434.53
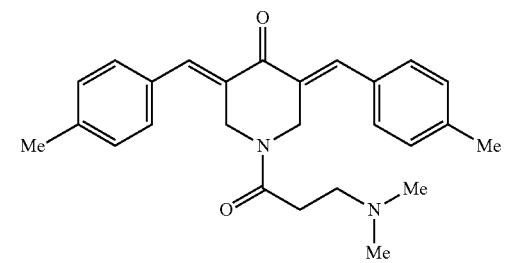
JC014
MW = 402.53
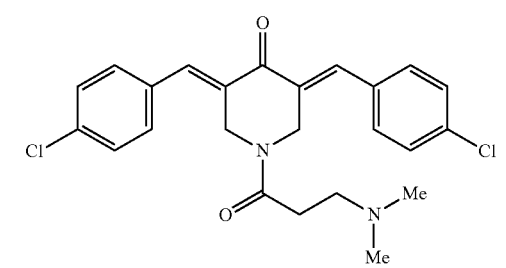
JC015
MW = 443.37
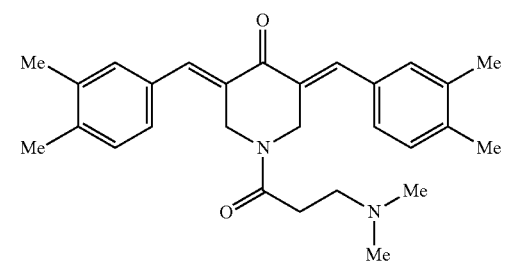
JC016
MW = 430.58
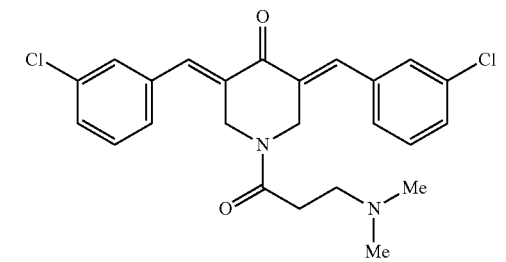
JC017
MW = 443.37

TABLE 1-continued

Exemplary Compounds of the Present Invention

JC018, MW = 510.47

JC019, MW = 354.40

JC020, MW = 386.53

JC021, MW = 376.45

JC022, MW = 510.47

TABLE 1-continued

Exemplary Compounds of the Present Invention

JC023, MW = 510.48

JC024, MW = 410.46

JC025, MW = 410.46

JC026, MW = 446.45

JC027, MW = 479.35

TABLE 1-continued
Exemplary Compounds of the Present Invention
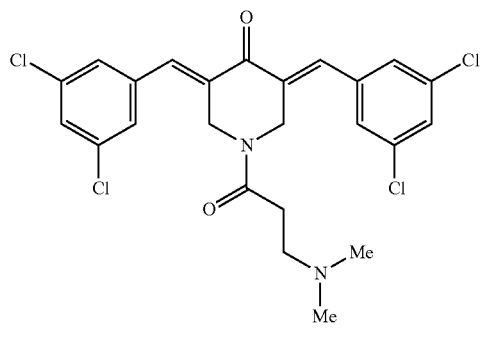
JC028
MW = 512.25
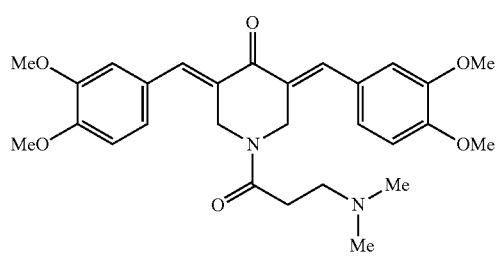
JC029
MW = 494.59
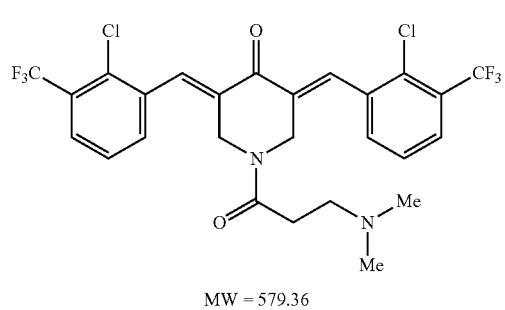 [SMILES: CN(C)CCC(=O)N1C/C(=C\c2cccc(C(F)(F)F)c2)C(=O)/C(=C/c2cccc(C(F)(F)F)c2)C1]
JC030
MW = 579.36
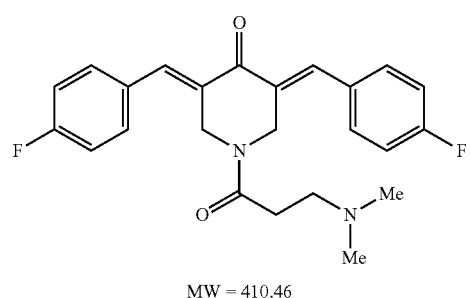 [SMILES: CN(C)CCC(=O)N1C/C(=C\c2ccc(F)cc2)C(=O)/C(=C/c2ccc(F)cc2)C1]
JC031
MW = 410.46
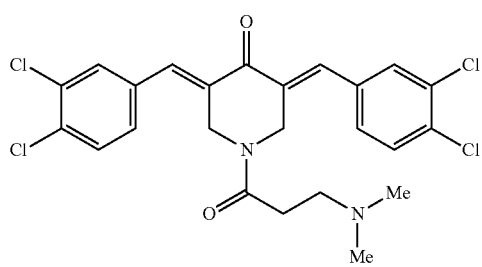
JC032
MW = 512.25
TABLE 1-continued
Exemplary Compounds of the Present Invention
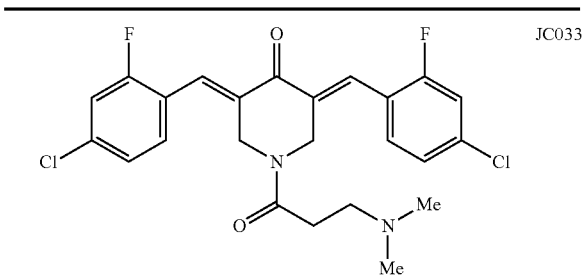
JC033
MW = 479.35
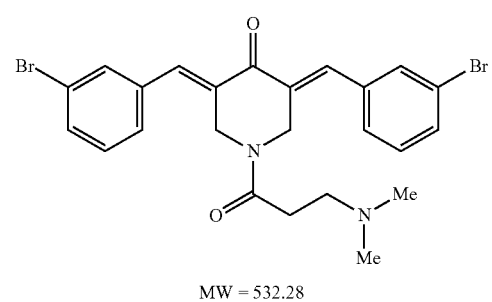 [SMILES: CN(C)CCC(=O)N1C/C(=C\c2cccc(Br)c2)C(=O)/C(=C/c2cccc(Br)c2)C1]
JC034
MW = 532.28
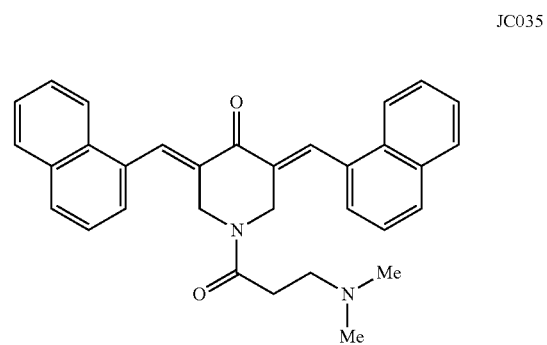
JC035
MW = 474.60
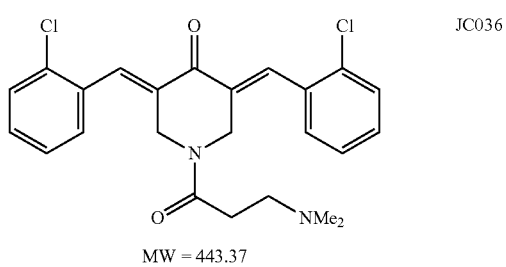
JC036
MW = 443.37
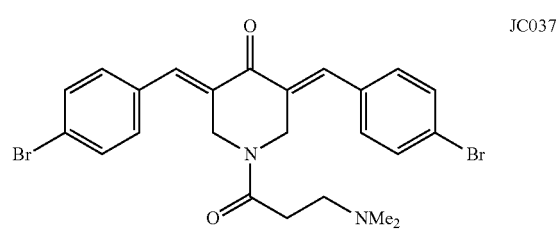
JC037
MW = 532.28

TABLE 1-continued
Exemplary Compounds of the Present Invention
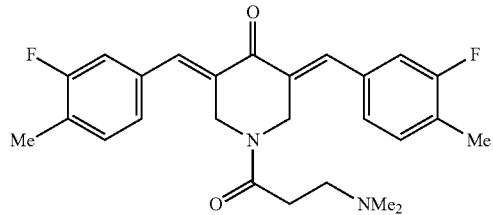
JC038
MW = 438.52
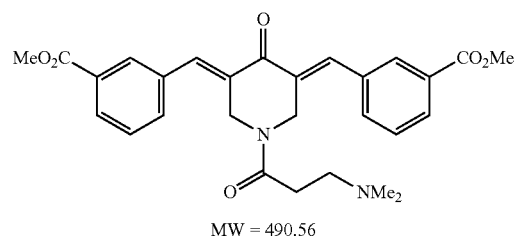 [SMILES: COC(=O)c1cccc(/C=C2\CN(C(=O)CCN(C)C)C/C(=C\c3cccc(C(=O)OC)c3)C2=O)c1]
JC039
MW = 490.56
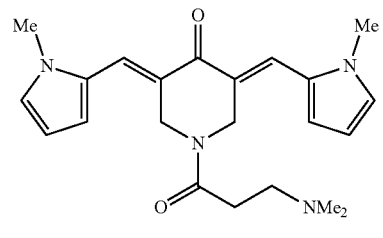
JC040
MW = 380.49
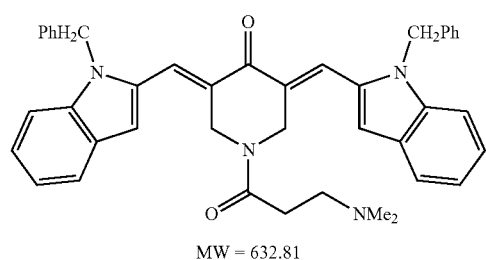
JC041
MW = 632.81
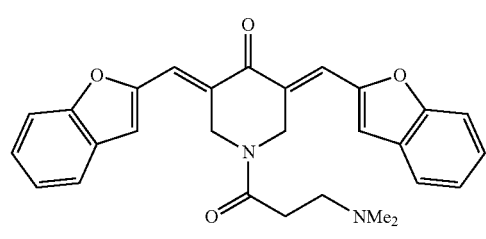
JC043
MW = 454.53
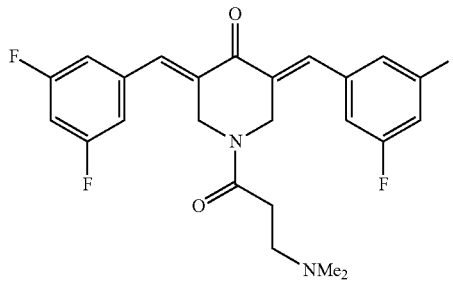
JC044
MW = 446.45
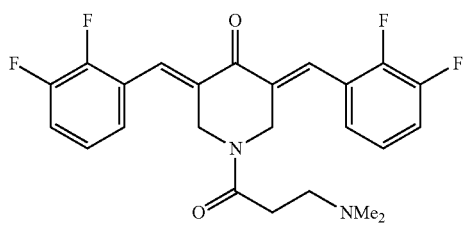
JC045
MW = 446.45
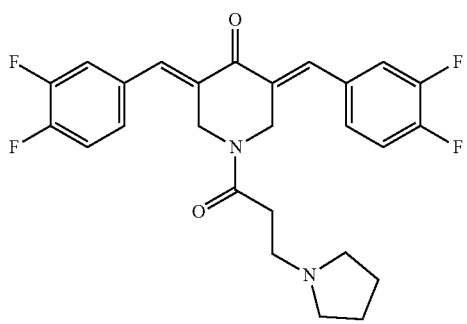
JC046
MW = 472.48
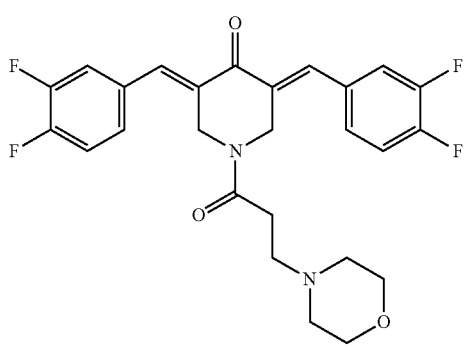
JC047
MW = 488.48

TABLE 1-continued
Exemplary Compounds of the Present Invention
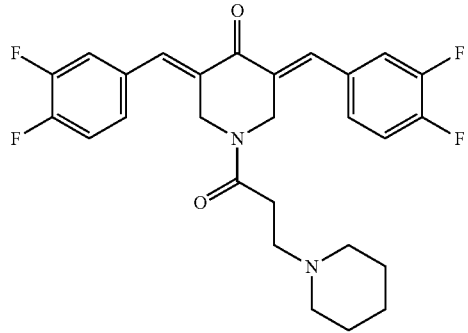
JC048
MW = 486.51
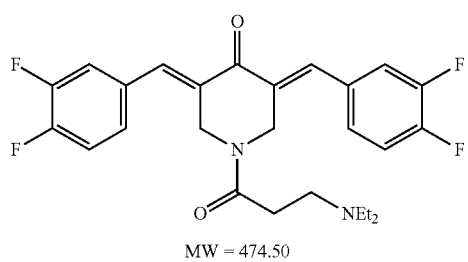
JC049
MW = 474.50
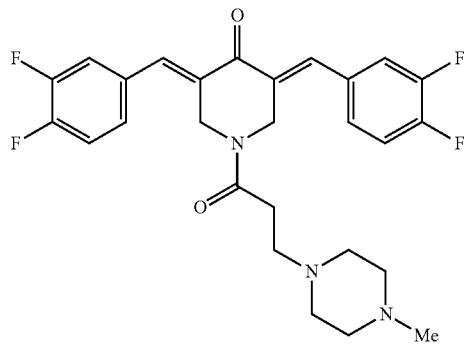
JC050
MW = 501.53
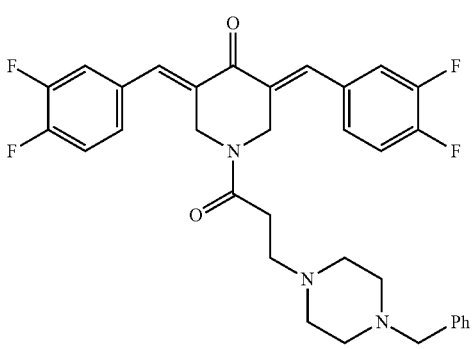
JC051
MW = 577.62
TABLE 1-continued
Exemplary Compounds of the Present Invention
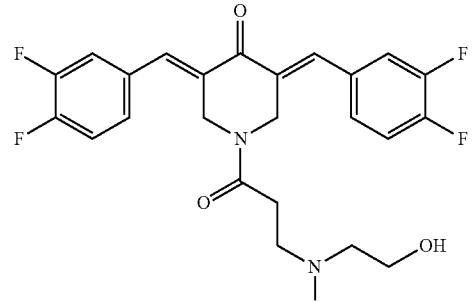
JC052
MW = 476.47
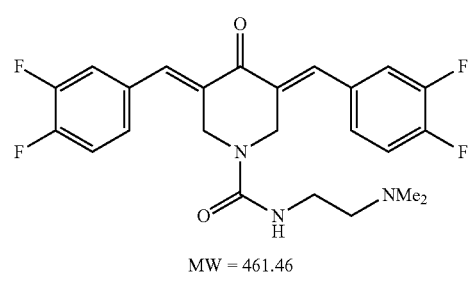 [SMILES: CN(C)CCNC(=O)N1C/C(=C\c2ccc(F)c(F)c2)C(=O)/C(=C/c2ccc(F)c(F)c2)C1]
JC053
MW = 461.46
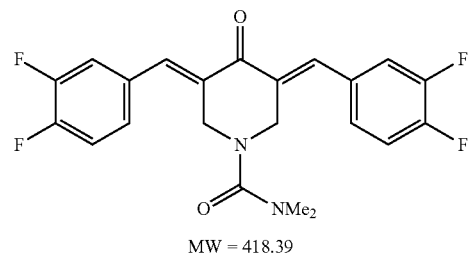 [SMILES: CN(C)C(=O)N1C/C(=C\c2ccc(F)c(F)c2)C(=O)/C(=C/c2ccc(F)c(F)c2)C1]
JC054
MW = 418.39
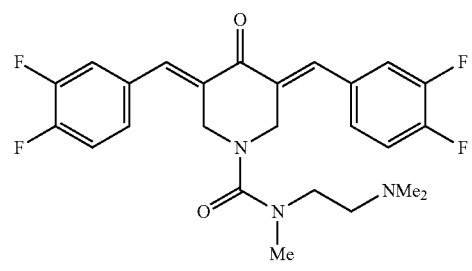
JC055
MW = 475.49
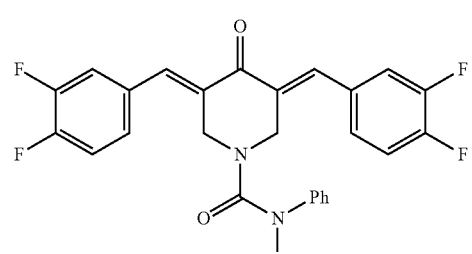
JC056
MW = 466.44

TABLE 1-continued
Exemplary Compounds of the Present Invention
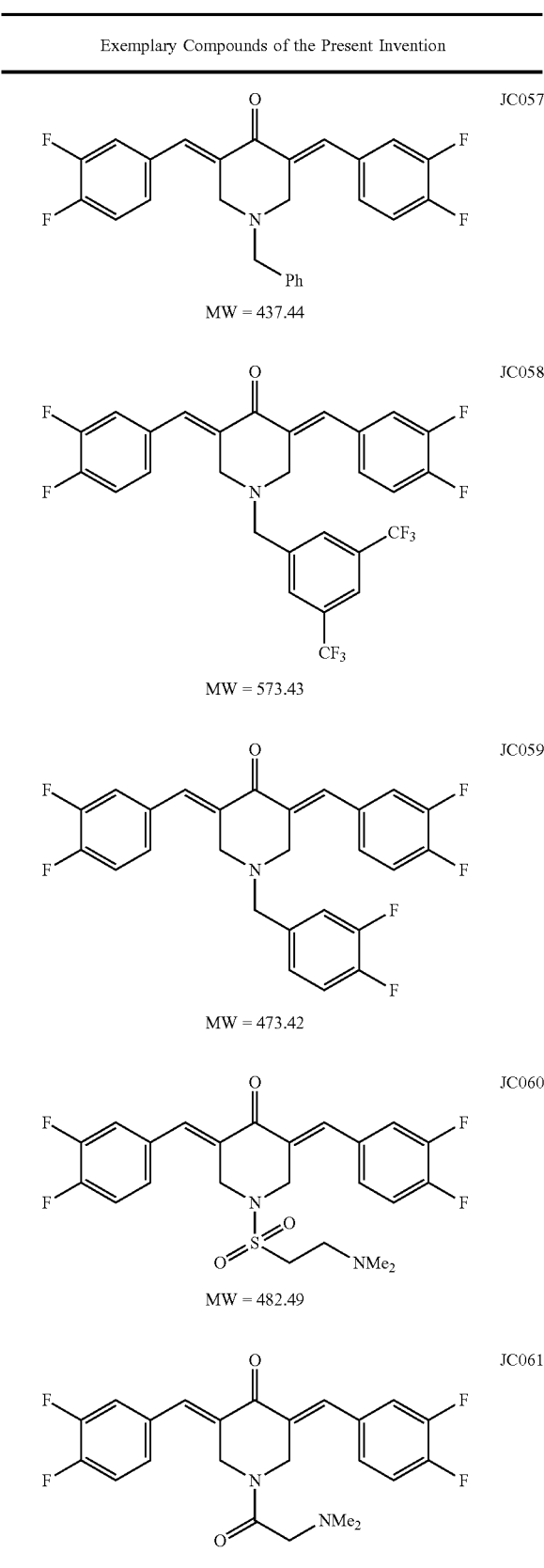
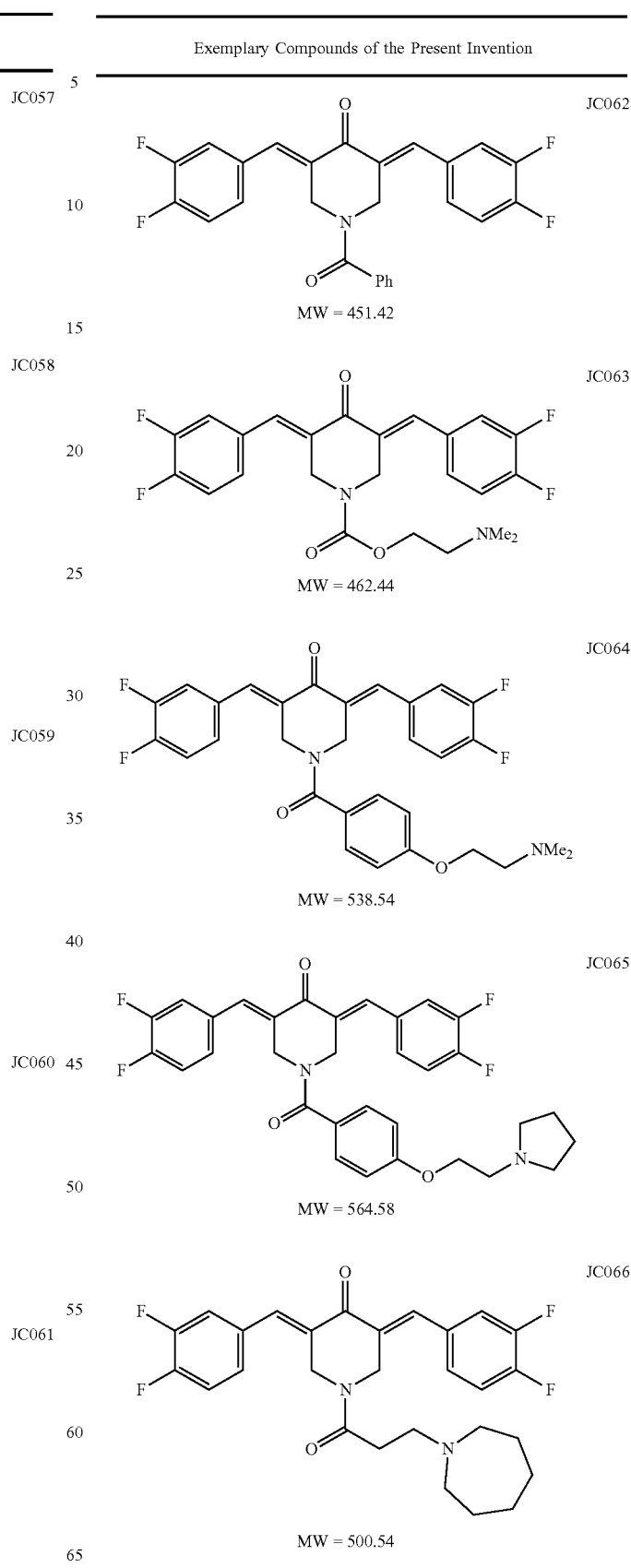

TABLE 1-continued
Exemplary Compounds of the Present Invention
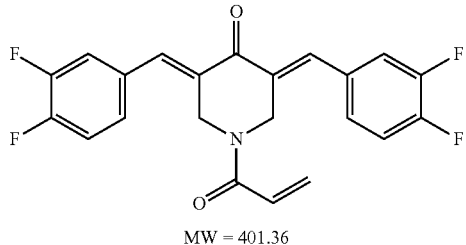 [SMILES: C=CC(=O)N1C/C(=C\c2ccc(F)c(F)c2)C(=O)/C(=C/c2ccc(F)c(F)c2)C1]
JC067
MW = 401.36
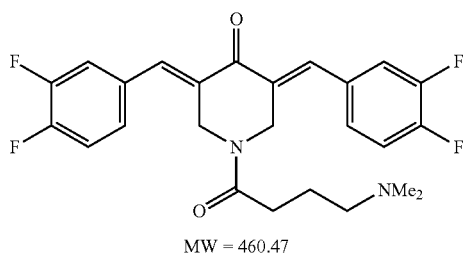 [SMILES: CN(C)CCCC(=O)N1C/C(=C\c2ccc(F)c(F)c2)C(=O)/C(=C/c2ccc(F)c(F)c2)C1]
JC068
MW = 460.47
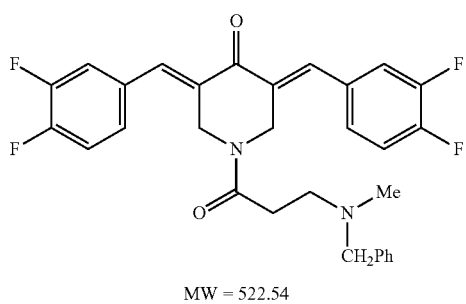
JC069
MW = 522.54
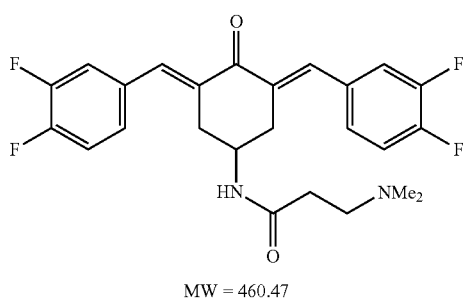 [SMILES: CN(C)CCC(=O)NC1C/C(=C\c2ccc(F)c(F)c2)C(=O)/C(=C/c2ccc(F)c(F)c2)C1]
JC070
MW = 460.47
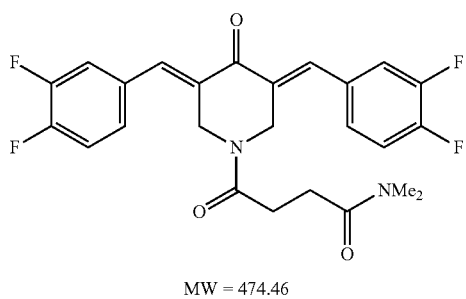 [SMILES: CN(C)C(=O)CCC(=O)N1C/C(=C\c2ccc(F)c(F)c2)C(=O)/C(=C/c2ccc(F)c(F)c2)C1]
JC071
MW = 474.46
TABLE 1-continued
Exemplary Compounds of the Present Invention
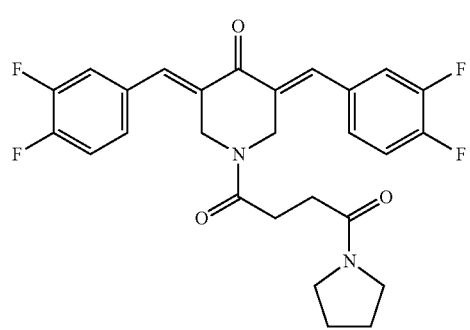
JC072
MW = 500.49
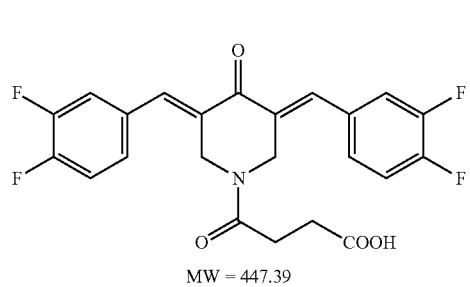 [SMILES: O=C(O)CCC(=O)N1C/C(=C\c2ccc(F)c(F)c2)C(=O)/C(=C/c2ccc(F)c(F)c2)C1]
JC073
MW = 447.39
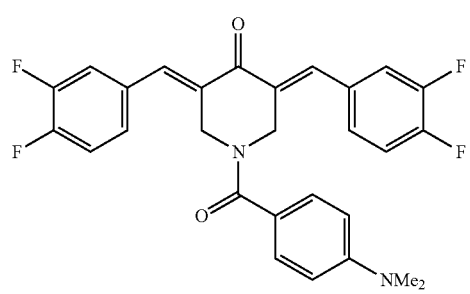
JC074
MW = 494.49
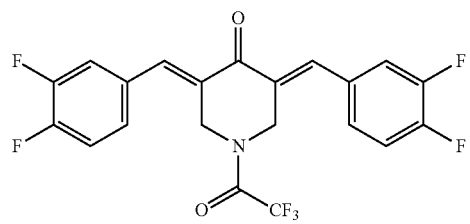
JC075
MW = 494.49
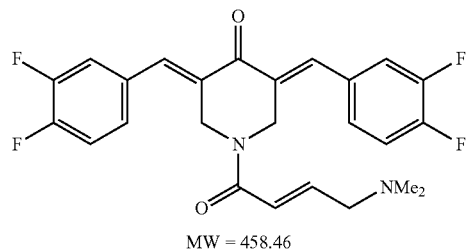 [SMILES: CN(C)C/C=C/C(=O)N1C/C(=C\c2ccc(F)c(F)c2)C(=O)/C(=C/c2ccc(F)c(F)c2)C1]
JC076
MW = 458.46

TABLE 1-continued
Exemplary Compounds of the Present Invention
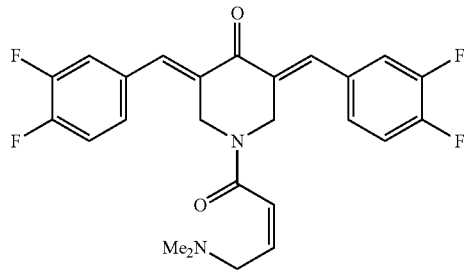
JC077
MW = 458.46
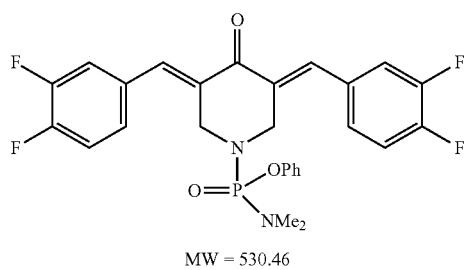 [SMILES: CN(C)P(=O)(Oc1ccccc1)N1C/C(=C\c2ccc(F)c(F)c2)C(=O)/C(=C/c2ccc(F)c(F)c2)C1]
JC078
MW = 530.46
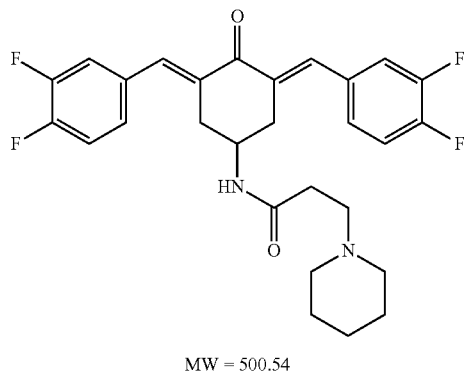 [SMILES: O=C(CCN1CCCCC1)NC1C/C(=C\c2ccc(F)c(F)c2)C(=O)/C(=C/c2ccc(F)c(F)c2)C1]
JC080
MW = 500.54
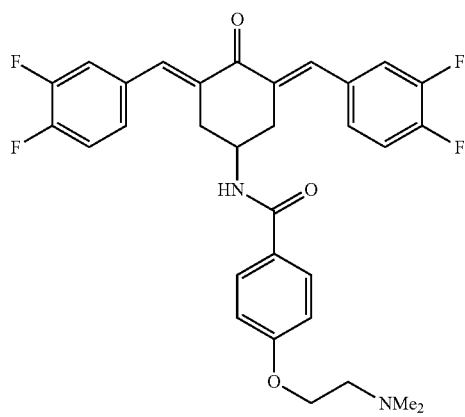
JC081
MW = 552.57
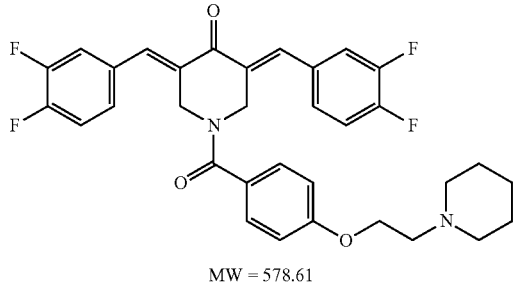 [SMILES: O=C1/C(=C/c2ccc(F)c(F)c2)CN(C(=O)c2ccc(OCCN3CCCCC3)cc2)C/C1=C\c1ccc(F)c(F)c1]
JC082
MW = 578.61
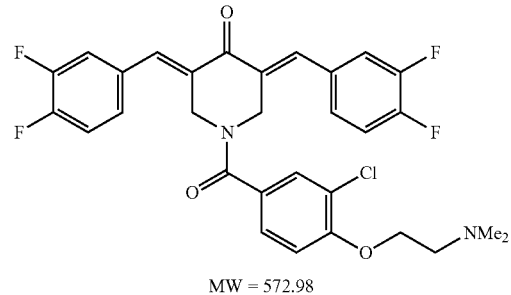 [SMILES: CN(C)CCOc1ccc(C(=O)N2C/C(=C\c3ccc(F)c(F)c3)C(=O)/C(=C/c3ccc(F)c(F)c3)C2)cc1Cl]
JC083
MW = 572.98
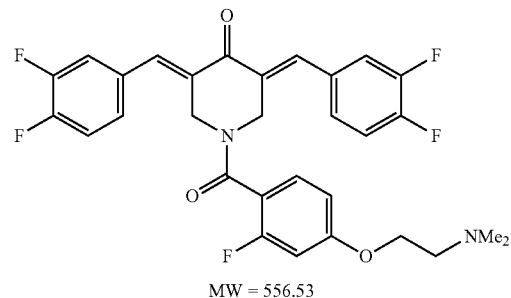 [SMILES: CN(C)CCOc1ccc(C(=O)N2C/C(=C\c3ccc(F)c(F)c3)C(=O)/C(=C/c3ccc(F)c(F)c3)C2)c(F)c1]
JC084
MW = 556.53
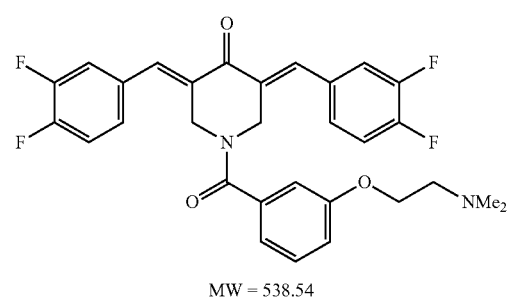 [SMILES: CN(C)CCOc1cccc(C(=O)N2C/C(=C\c3ccc(F)c(F)c3)C(=O)/C(=C/c3ccc(F)c(F)c3)C2)c1]
JC085
MW = 538.54
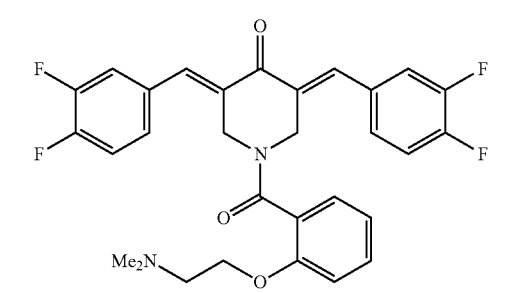
JC086
MW = 538.54

TABLE 1-continued
Exemplary Compounds of the Present Invention
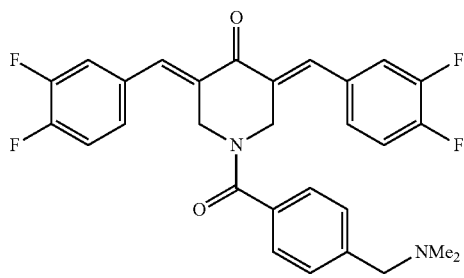
JC087
MW = 508.52
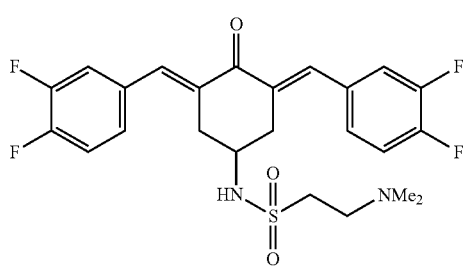
JC088
MW = 496.52
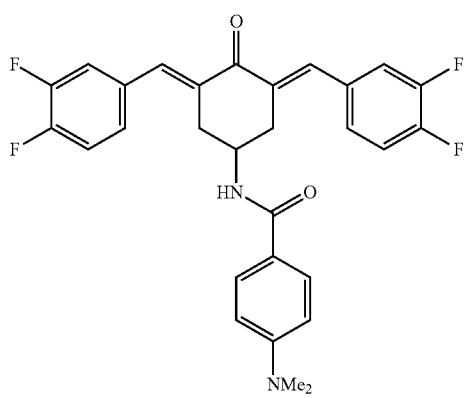
JC089
MW = 508.52
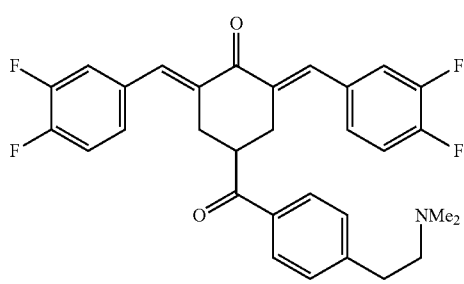
JC090
MW = 522.54
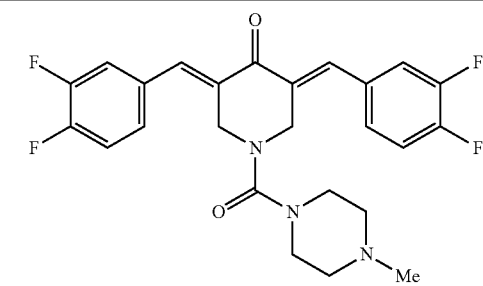
JC091
MW = 473.47
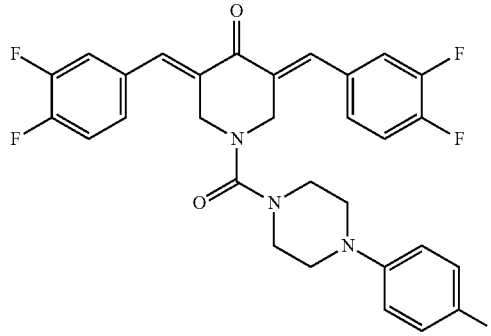
JC092
MW = 553.53
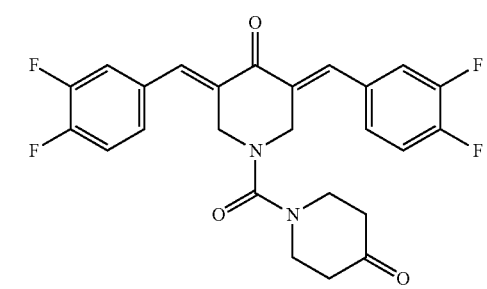
JC093
MW = 472.44
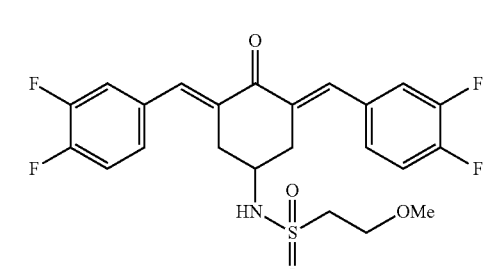
JC094
MW = 469.45

TABLE 1-continued
Exemplary Compounds of the Present Invention
JC095
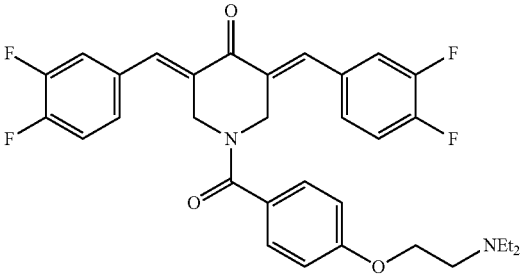
MW = 572.59
JC096
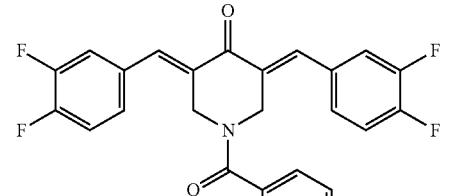
MW = 581.59
JC097
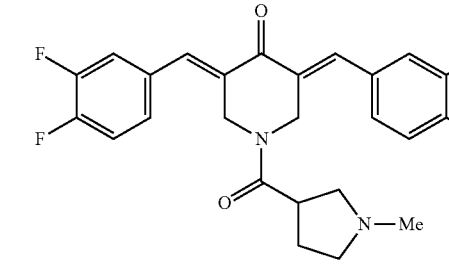
MW = 474.50
JC098
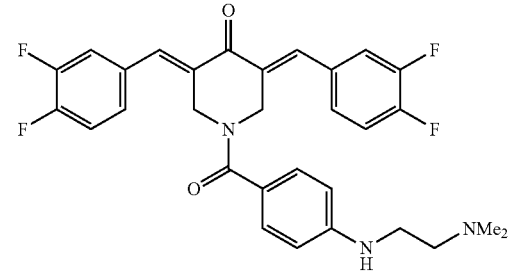
MW = 510.16
JC099
MW = 566.22
JC100
MW = 554.60
JC101
MW = 458.46
JC102
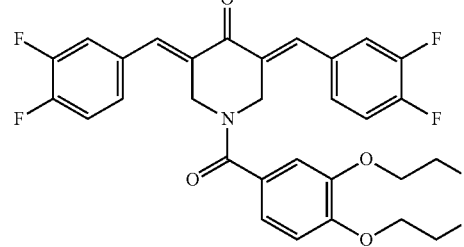
MW = 537.56
JC103
MW = 625.66

TABLE 1-continued
Exemplary Compounds of the Present Invention
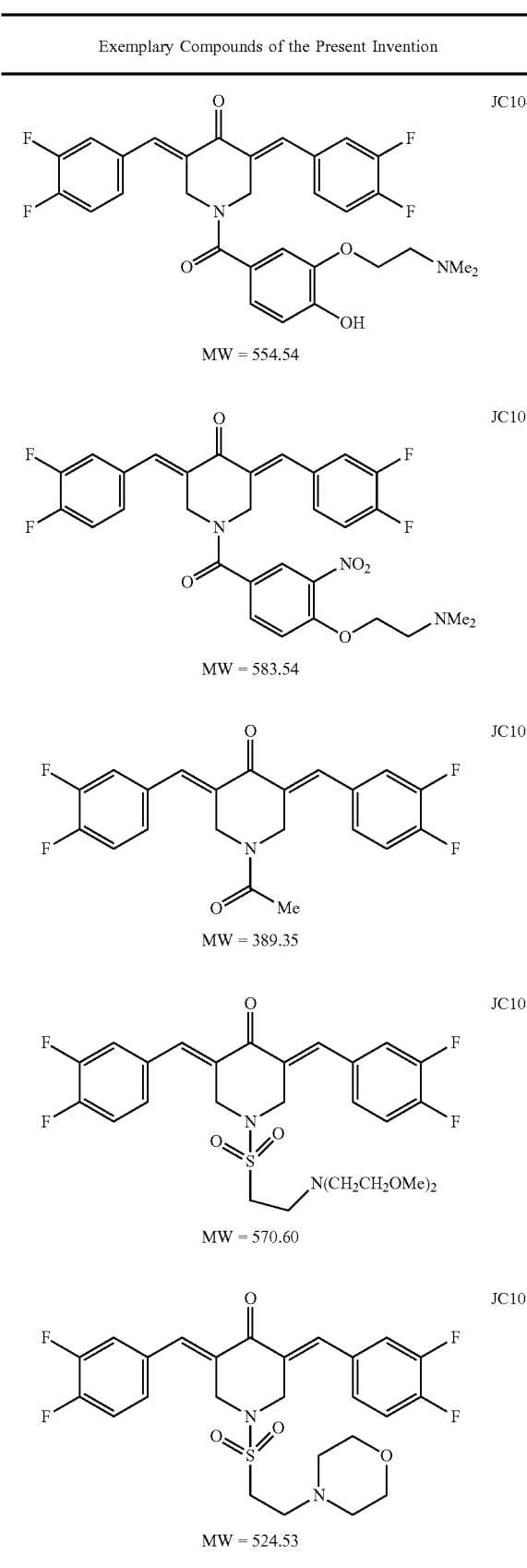
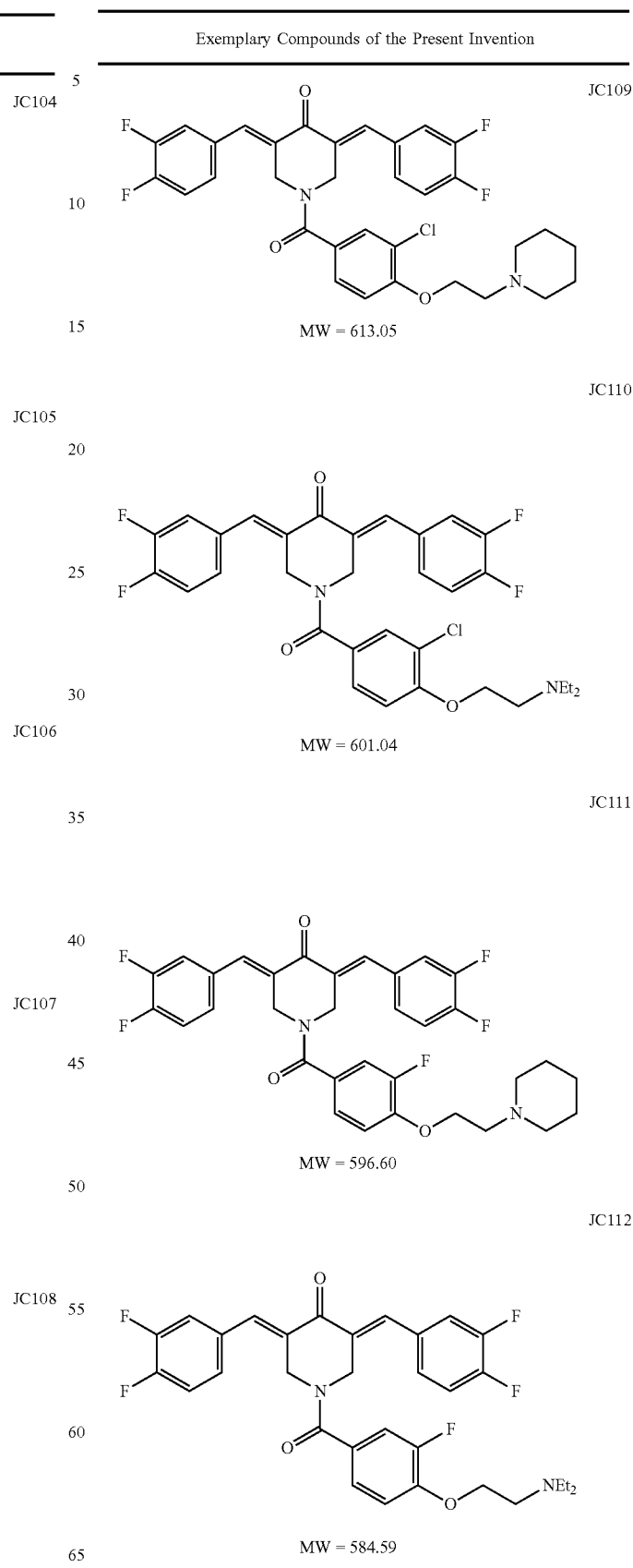

TABLE 1-continued
Exemplary Compounds of the Present Invention
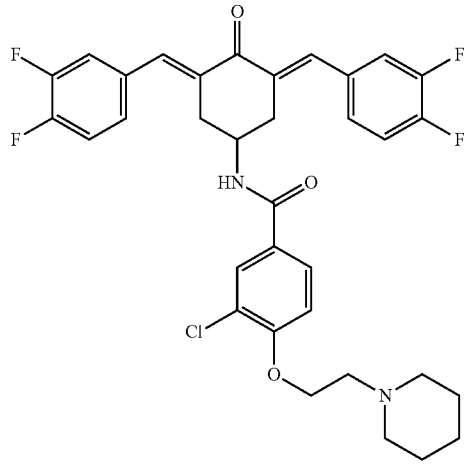
JC113
MW = 627.08
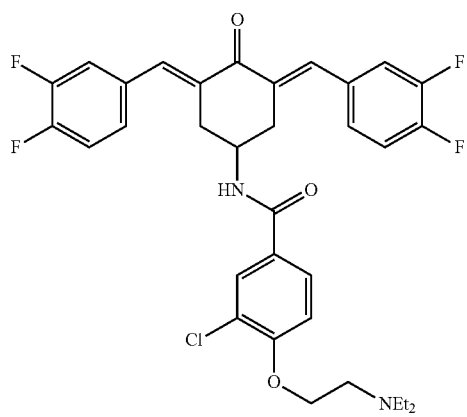
JC114
MW = 615.07
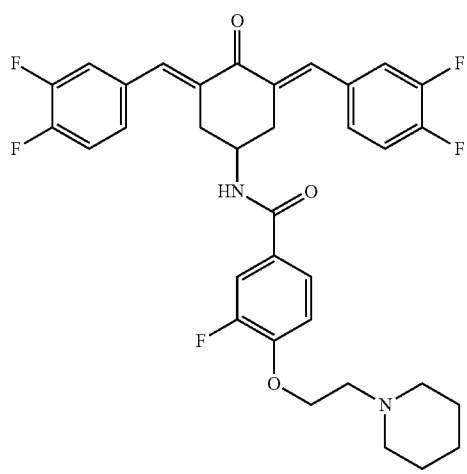
JC115
MW = 610.63
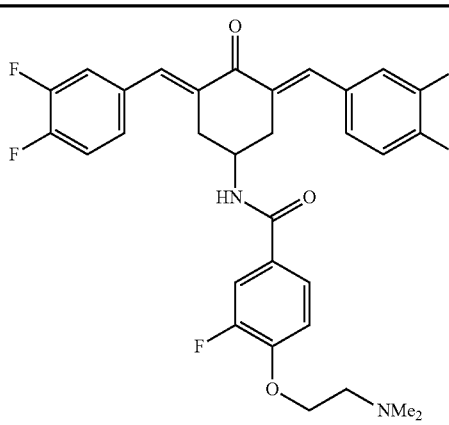
JC116
MW = 598.61
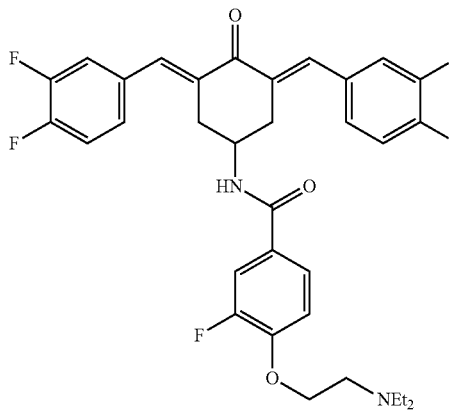
JC117
MW = 570.56
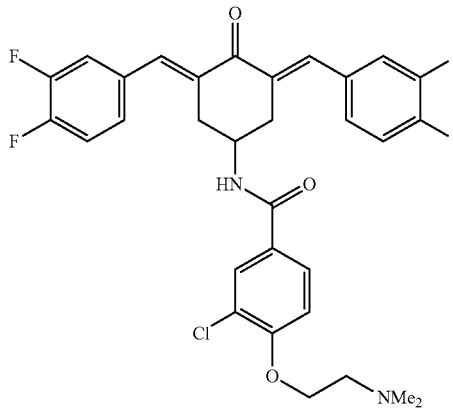
JC118
MW = 587.01
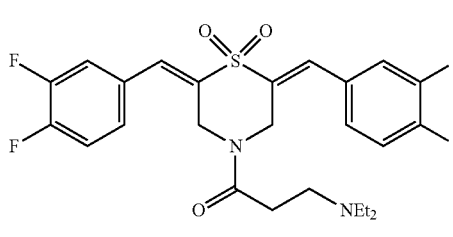
JC119
MW = 510.55

TABLE 1-continued
Exemplary Compounds of the Present Invention
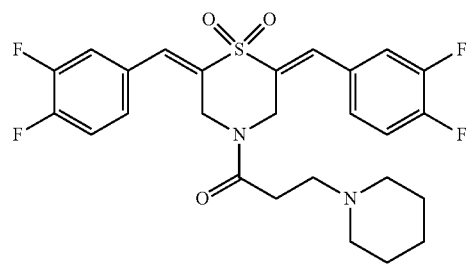
JC120
MW = 522.56
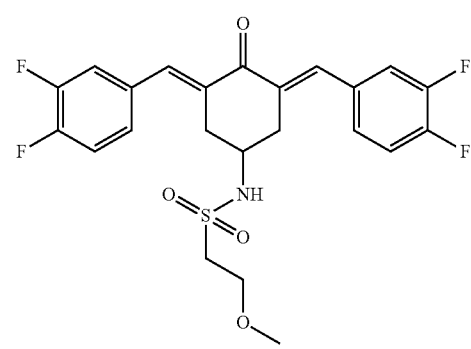 [SMILES: COCCS(=O)(=O)NC1C/C(=C\c2ccc(F)c(F)c2)C(=O)/C(=C/c2ccc(F)c(F)c2)C1]
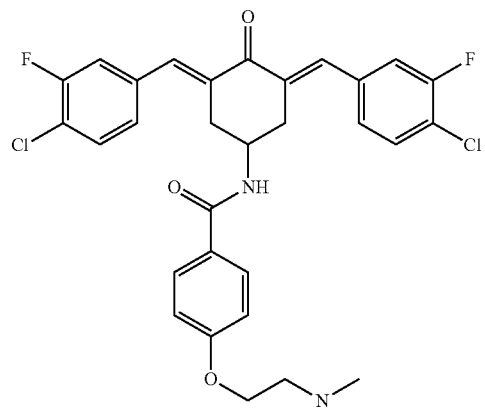
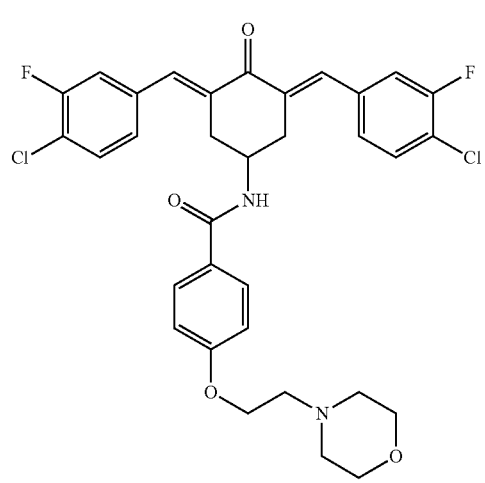 [SMILES: O=C1/C(=C/c2ccc(Cl)c(F)c2)CC(NC(=O)c2ccc(OCCN3CCOCC3)cc2)C/C1=C\c1ccc(Cl)c(F)c1]
TABLE 1-continued
Exemplary Compounds of the Present Invention
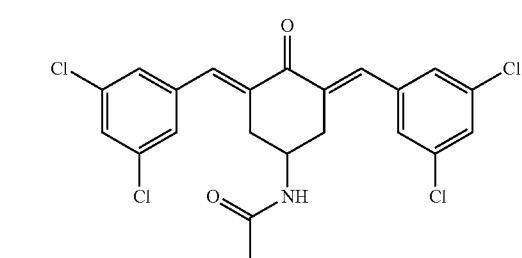
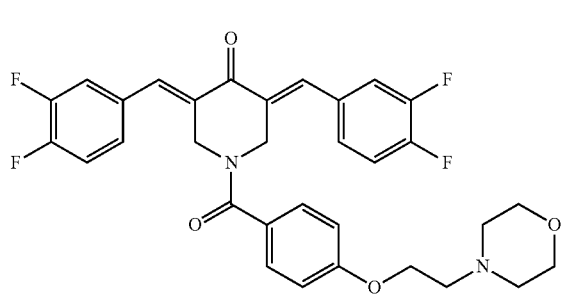 [SMILES: O=C1/C(=C/c2ccc(F)c(F)c2)CN(C(=O)c2ccc(OCCN3CCOCC3)cc2)C/C1=C\c1ccc(F)c(F)c1]

TABLE 1-continued
Exemplary Compounds of the Present Invention
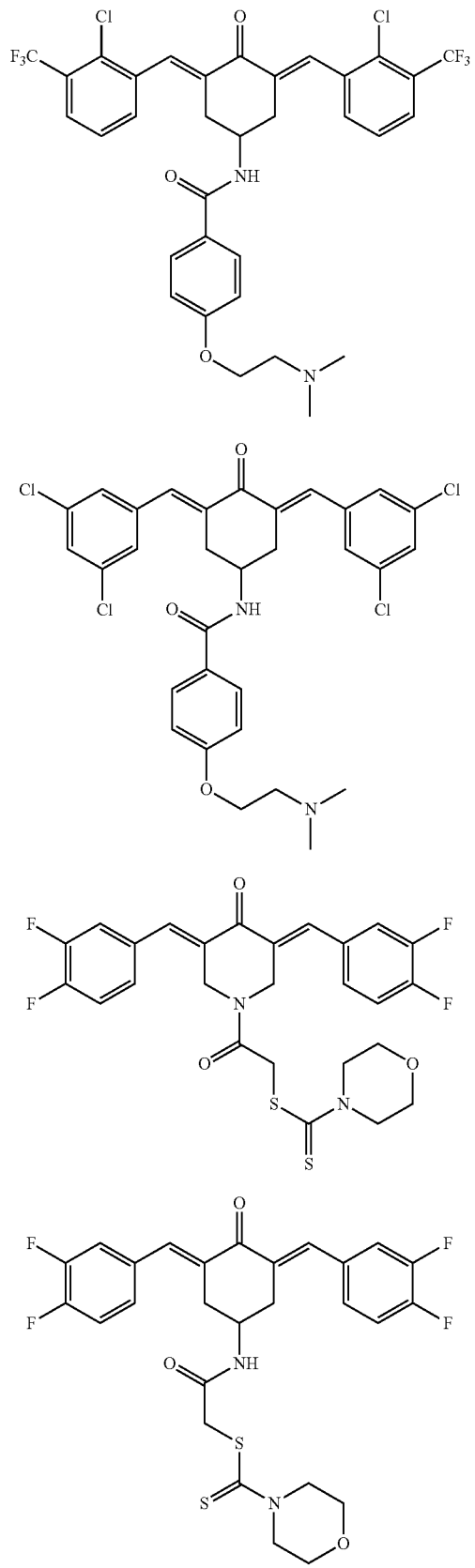
TABLE 1-continued
Exemplary Compounds of the Present Invention
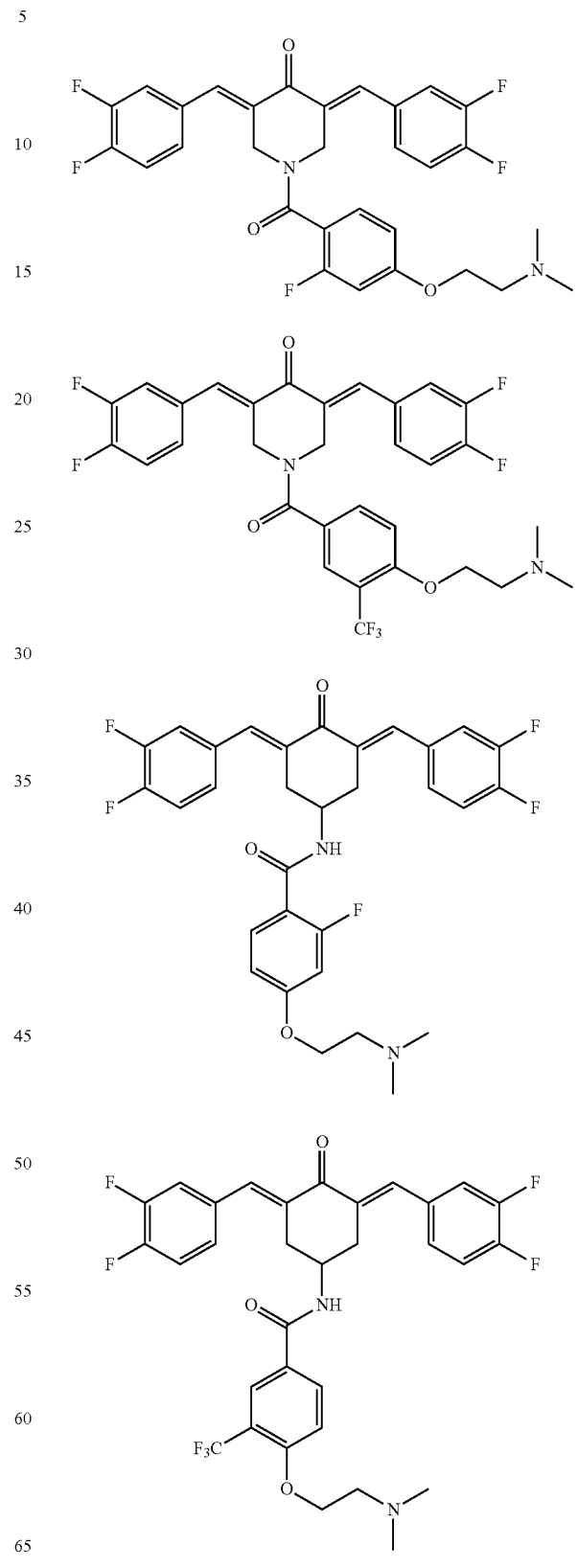

TABLE 1-continued
Exemplary Compounds of the Present Invention
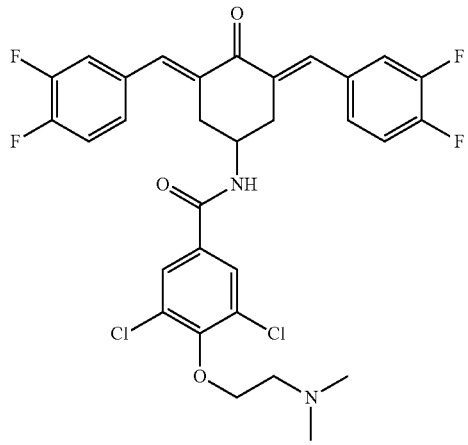 [SMILES: CN(C)CCOc1c(Cl)cc(C(=O)NC2C/C(=C\c3ccc(F)c(F)c3)C(=O)/C(=C/c3ccc(F)c(F)c3)C2)cc1Cl]
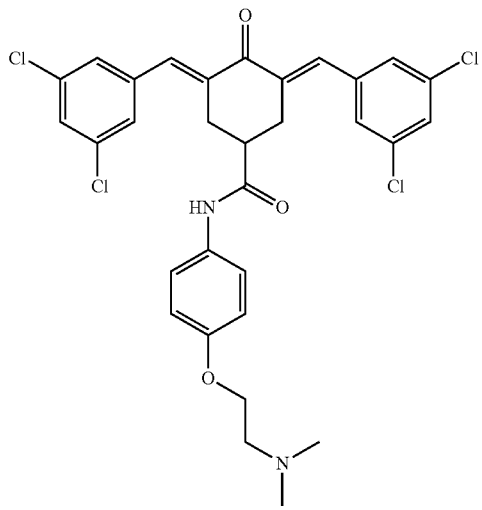
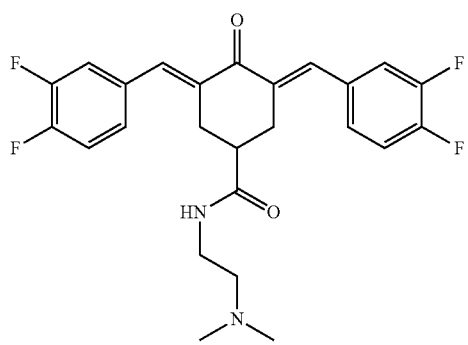 [SMILES: CN(C)CCNC(=O)C1C/C(=C\c2ccc(F)c(F)c2)C(=O)/C(=C/c2ccc(F)c(F)c2)C1]
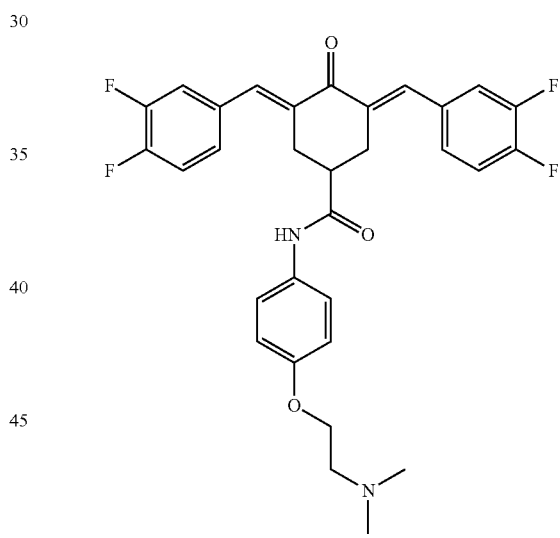
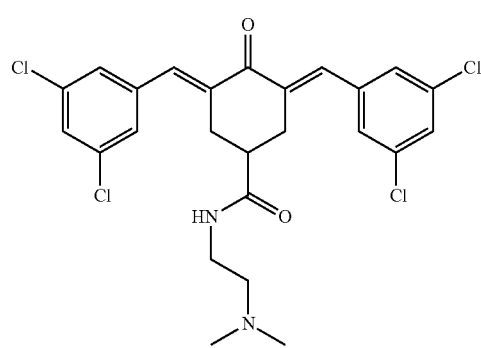 [SMILES: CN(C)CCNC(=O)C1C/C(=C\c2cc(Cl)cc(Cl)c2)C(=O)/C(=C/c2cc(Cl)cc(Cl)c2)C1]
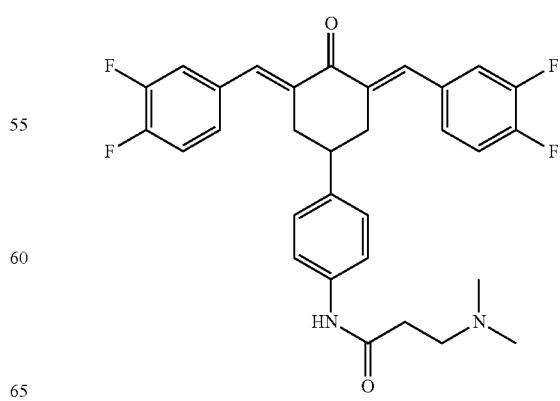

TABLE 1-continued

Exemplary Compounds of the Present Invention

In certain aspects, the present disclosure provides pharmaceutical compositions comprising a compound of Formula I, II, or III, and a pharmaceutically acceptable excipient.

In certain embodiments, the present disclosure provides a method of inhibiting β-catenin or a variant thereof, comprising administering to a subject a compound or composition of Formula I, II, or III. In certain embodiments, the β-catenin is wild type. In certain embodiments, the β-catenin is mutated. In certain embodiments, the β-catenin is β-catenin*. In certain embodiments, the β-catenin is mutated at Ser33, Ser37, Thr41 and Ser45. In certain embodiments, the β-catenin is mutated at Ser33, Ser37, Thr41 or Ser45.

In certain aspects, the present disclosure provides methods of treating cancer comprising of administering to a subject in need of a treatment for cancer an effective amount of a compound of Formula I, Formula II, Formula III, or of a compound described herein. In certain embodiments, the cancer is bladder cancer, bone cancer, brain cancer, breast cancer, cardiac cancer, cervical cancer, colon cancer, colorectal cancer, esophageal cancer, fibrosarcoma, gastric cancer, gastrointestinal cancer, head, spine and neck cancer, Kaposi's sarcoma, kidney cancer, leukemia, liver cancer, lymphoma, melanoma, multiple myeloma, pancreatic cancer, penile cancer, testicular germ cell cancer, thymoma and thymic carcinoma, lung cancer, ovarian cancer, and prostate cancer. In certain embodiments, the cancer is colorectal cancer.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, MA (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, C.A. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known. The ability of such agents to inhibit AR or promote AR degradation may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—CH$_2$—O-alkyl, —OP(O)(O-alkyl)$_2$ or —CH$_2$—OP(O)(O-alkyl)$_2$. Preferably, "substituted" refers to the replacement of one to four hydrogen radicals in a given structure with the substituents mentioned above. More preferably, one to three hydrogen radicals are replaced by the substituents as mentioned above. It is understood that the substituent can be further substituted.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto.

Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" or "$C_x-C_y$", when used in conjunction with a chemical moiety, such as, acyl, acyloxy, alkyl, alkenyl, alkynyl, or alkoxy is meant to include groups that contain from x to y carbons in the chain. Coalkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS—.

The term "amide", as used herein, refers to a group

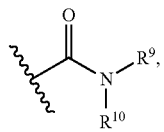

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

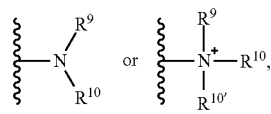

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

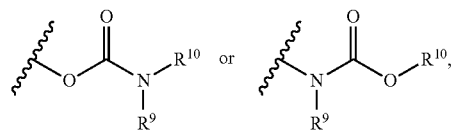

wherein $R^9$ and $R^{10}$ independently represent hydrogen or a hydrocarbyl group.

The term "carbocyclylalkyl", as used herein, refers to an alkyl group substituted with a carbocycle group.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms.

The term "carbocyclylalkyl", as used herein, refers to an alkyl group substituted with a carbocycle group.

The term "carbonate" is art-recognized and refers to a group —OCO$_2$—.

The term "carboxy", as used herein, refers to a group represented by the formula —CO$_2$H.

The term "ester", as used herein, refers to a group —C(O)OR$^9$ wherein R$^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —OSO$_3$H, or a pharmaceutically acceptable salt thereof.

The term "sulfonamide" is art-recognized and refers to the group represented by the general formulae

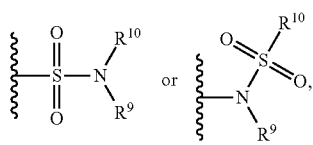

wherein R$^9$ and R$^{10}$ independently represents hydrogen or hydrocarbyl.

The term "sulfoxide" is art-recognized and refers to the group-S(O)—.

The term "sulfonate" is art-recognized and refers to the group SO$_3$H, or a pharmaceutically acceptable salt thereof.

The term "sulfone" is art-recognized and refers to the group —S(O)$_2$—.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —C(O)SR$^9$ or —SC(O)R$^9$ wherein R$^9$ represents a hydrocarbyl.

The term "thioether", as used herein, is equivalent to an ether, wherein the oxygen is replaced with a sulfur.

The term "urea" is art-recognized and may be represented by the general formula

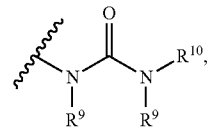

wherein R$^9$ and R$^{10}$ independently represent hydrogen or a hydrocarbyl.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by Formula I, II, or III. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I, II, or III are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of Formula I, II, or III for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I, II, or III or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of Formula I, II, or III). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula I, II, or III. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

The term "Log of solubility", "Log S" or "log S" as used herein is used in the art to quantify the aqueous solubility of a compound. The aqueous solubility of a compound significantly affects its absorption and distribution characteristics. A low solubility often goes along with a poor absorption. Log S value is a unit stripped logarithm (base 10) of the solubility measured in mol/liter.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals.

A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the invention may be used alone or conjointly administered with another type of therapeutic agent.

The present disclosure includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, 1-ascorbic acid, 1-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

EXAMPLES

The invention now being generally described, it will be more readily understood by reference to the following examples which are included merely for purposes of illustration of certain aspects and embodiments of the present invention, and are not intended to limit the invention.

Example 1: Preparation of Exemplary Compounds

General Procedure A:

Certain compounds disclosed herein (e.g., JC001-JC006 and their analogues) were generally prepared by reaction of the corresponding aldehydes, e.g., benzaldehyde, with piperidin-4-one hydrogen chloride in the present of 40% aq. sodium hydroxide to give the (3,5-diarylmethylidene)piperidone, e.g., (3,5-dibenzylidene)piperidin-4-one. Acylation of (3,5-dibenzylidene)piperidin-4-one with acryloyl chloride under basic conditions afforded the 1-acryloyl (3,5-dibenzylidene)piperidin-4-one. Michael addition of an amine, e.g., dimethylamine, afforded the (3,5-diarylmethylidene-1-(3-dialkylamino)propanoyl)piperidin-4-one, e.g., (3,5-dibenzyl-idene-1-(3-dimethylamino)propanoyl)piperidin-4-one.

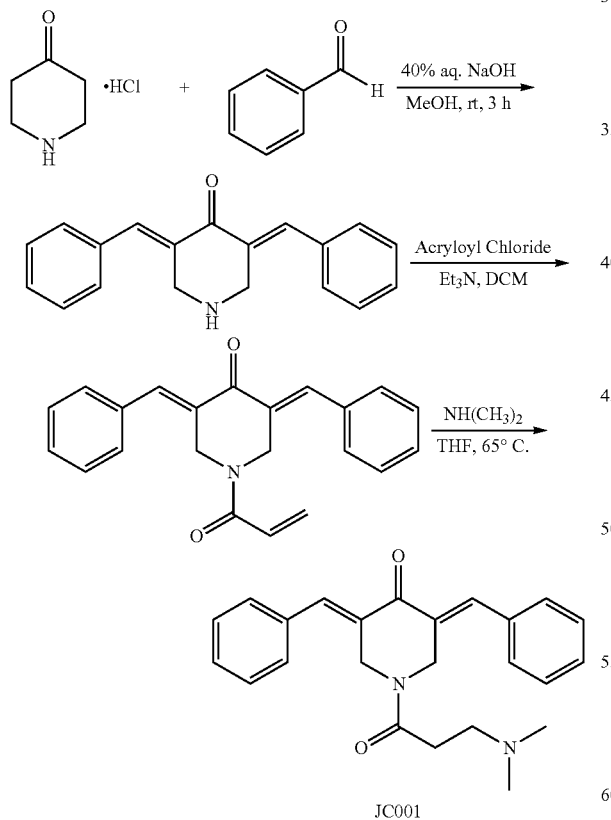

Preparation of JC001

To a mixture of piperidin-4-one hydrogen chloride (135.59 mg, 1 mmol, 1.0 equiv.) and methanol (2.0 mL) in a round bottom flask was added dropwise 40% aqueous sodium hydroxide (1.0 mL) and the reaction mixture was stirred for 5 min. To this mixture was added benzaldehyde (265.3 mg, 2.5 mmol, 2.5 equiv.). The reaction mixture was then allowed to stir at 21° C. for 3 h at which time a yellow solid had precipitated. The yellow precipitate thus obtained was filtered, washed with water and cold methanol and dried to get pure piperidone product (242 mg, 88% yield).

A mixture of 3,5-di((E)-benzylidene)piperidin-4-one (137.7 mg, 0.5 mmol, 1.0 equiv.) and anhydrous triethylamine (105 µL, 0.75 mmol, 1.5 equiv.) in dichloromethane was maintained at 0° C. (ice bath). To this cooled mixture was added dropwise acryloyl chloride (61 µL, 0.75 mmol, 1.5 equiv.). After the complete addition of the acryloyl chloride, the reaction mixture was slowly warmed up to 21° C. and stirred for a further 4 h. After completion of the reaction, the solvent was evaporated and the residue thus obtained was washed with water, filtered and dried. The crude amide product was pure enough to be used for the next step.

A mixture of crude 1-acryloyl-3,5-di((E)-benzylidene) piperidin-4-one (164.7 mg, 0.5 mmol, 1.0 equiv.), 2,6-bis (1,1-dimethylethyl)-4-methylphenol (1.1 mg, 0.005 mmol, 1%) and dimethylamine (2N in THF) (0.375 mL, 0.75 mmol, 1.5 equiv.) in 1.0 mL anhydrous THF was heated to 65° C. under argon for 12 h. The solvent was evaporated and flash chromatography of the residue (gradient elution 5% methanol/EtOAc-10% methanol/EtOAc) to give a yellow solid, dried the solvent by vacuum and added dry DCM (10 mL), filtered by cotton to get JC001 (131 mg, 70% yield) as a yellow solid.

The following compounds were synthesized by procedure A: JC001, JC002, JC003, JC004, JC005, JC006, JC012, JC013, JC014, JC015, JC016, JC017, JC018, JC019, JC020, JC021, JC022, JC023, JC024, JC025, JC027, JC028, JC029, JC030, JC031, JC032, JC033, JC034, JC035, JC036, JC037, JC038, JC039, JC040, JC041, JC042, JC043, JC044, JC045, JC046, JC142.

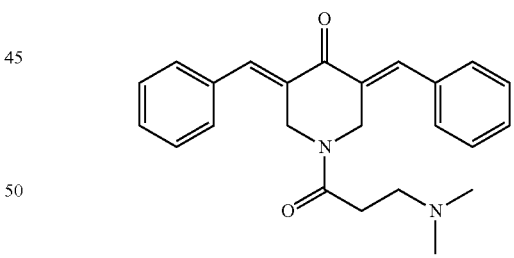

3,5-Di((E)-benzylidene)-1-(3-(dimethylamino)propanoyl)piperidin-4-one (JC001)

1H NMR (400 MHz, CD3OD) δ 7.80 (br s, 2H), 7.38-7.50 (m, 10H), 4.91 (s, 2H), 4.81 (s, 2H), 2.46 (t, J=7.5 Hz, 2H), 2.36 (t, J=7.5 Hz, 2H), 2.02 (s, 6H).

13C NMR (100 MHz, CD3OD) δ 186.4, 170.7, 137.7, 136.9, 134.6, 134.4, 132.1, 131.9, 130.2, 130.1, 129.5, 129.4, 128.7, 128.5, 54.1, 46.3, 43.5, 43.2, 29.9.

HR-APCI m/z calcd for $C_{24}H_{26}N_2O_2$[M+H]=375.20725, found 375.20679.

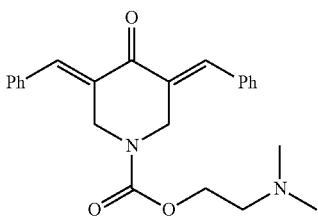 [SMILES: CN(C)CCOC(=O)N1C/C(=C\c2ccccc2)C(=O)/C(=C/c2ccccc2)C1]

2-(Dimethylamino)ethyl 3,5-di((E)-benzylidene)-4-oxopiperidine-1-carboxylate (JC002)

$^1$H NMR (400 MHz, DMSO-d$_6$) δ 7.68 (br s, 2H), 7.40-7.52 (m, 10H), 4.73 (br s, 4H), 3.91 (t, J=5.4 Hz, 2H), 2.22 (t, J=5.5 Hz, 2H), 1.90 (s, 6H).
$^{13}$C NMR (100 MHz, DMSO-d$_6$) δ 186.2, 154.9, 136.8 (2C), 134.8 (2C), 132.9 (2C), 130.9 (2C), 130.0 (2C), 129.3 (2C), 64.1, 57.6, 45.6 (2C), 45.3 (2C).

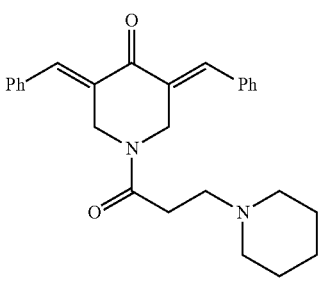 [SMILES: O=C1/C(=C/c2ccccc2)CN(C(=O)CCN2CCCCC2)C/C1=C\c1ccccc1]

3,5-Di((E)-benzylidene)-1-(3-(piperidin-1-yl)propanoyl)piperidin-4-one (JC003)

$^1$H NMR (400 MHz, CDCl$_3$) δ 7.84 (s, 1H), 7.80 (s, 1H), 7.43-7.37 (m, 10H), 4.88 (s, 2H), 4.70 (s, 2H), 2.58 (t, J=7.2 Hz, 2H), 2.39 (t, J=7.1 Hz, 2H), 2.23 (m, 4H), 1.49 (m, 4H), 1.36 (m, 2H).
$^{13}$C NMR (100 MHz, CDCl$_3$) δ 186.8, 170.4, 138.5, 137.3, 134.6, 134.4, 131.7, 131.8, 130.6, 130.2, 129.6 (2C), 128.9, 128.8, 54.3, 54.1, 46.3, 43.6, 30.2, 25.4, 23.8.

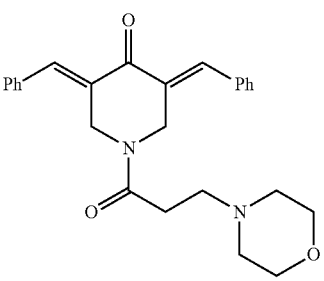

3,5-Di((E)-benzylidene)-1-(3-morpholinopropanoyl)piperidin-4-one (JC004)

$^1$H NMR (400 MHz, CDCl$_3$) δ 7.85 (s, 1H), 7.81 (s, 1H), 7.36 (m, 10H), 4.89 (s, 2H), 4.69 (s, 2H), 3.55 (m, 4H), 2.52 (t, J=7.0 Hz, 2H), 2.31 (t, J=7.1 Hz, 2H), 2.19 (m, 4H).
$^{13}$C NMR (100 MHz, CDCl$_3$) δ 186.7, 170.8, 138.6, 137.2, 134.6, 134.5, 131.9, 131.7, 130.7, 130.2, 129.7 (2C), 128.9, 128.8, 66.7, 54.1, 53.3, 46.3, 43.7, 30.4.

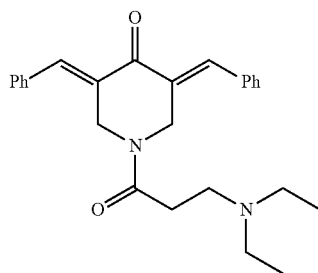 [SMILES: CCN(CC)CCC(=O)N1C/C(=C\c2ccccc2)C(=O)/C(=C/c2ccccc2)C1]

3,5-Di((E)-benzylidene)-1-(3-(diethylamino)propanoyl)piperidin-4-one (JC005)

$^1$H NMR (400 MHz, CDCl$_3$) δ 7.83 (s, 1H), 7.79 (s, 1H), 7.38 (m, 10H), 4.88 (s, 2H), 4.70 (s, 2H), 2.63 (t, J=8.0 Hz, 2H), 2.27 (t, J=8.0 Hz, 2H), 2.29 (q, J=7.2 Hz, 4H), 0.85 (t, J=7.1 Hz, 6H).
$^{13}$C NMR (100 MHz, CDCl$_3$) δ 186.7, 170.8, 138.4, 137.2, 134.6, 134.4, 131.9, 131.7, 130.6, 130.2, 129.6, 129.5, 128.9, 128.8, 48.5, 46.8, 46.4, 30.8, 11.6.

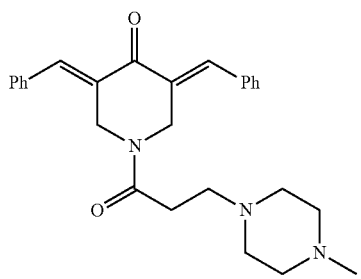 [SMILES: CN1CCN(CCC(=O)N2C/C(=C\c3ccccc3)C(=O)/C(=C/c3ccccc3)C2)CC1]

3,5-Di((E)-benzylidene)-1-(3-(4-methylpiperazin-1-yl)propanoyl)piperidin-4-one (JC006)

$^1$H NMR (400 MHz, CDCl$_3$) δ 7.80 (s, 1H), 7.76 (s, 1H), 7.37 (m, 10H), 4.85 (s, 2H), 4.65 (s, 2H), 2.50 (t, J=8.0 Hz, 2H), 2.26 (t, J=8.0 Hz, 2H), 2.20 (m, 8H), 2.17 (s, 3H).
$^{13}$C NMR (100 MHz, CDCl$_3$) δ 186.6, 170.5, 138.5, 137.1, 134.5, 134.4, 131.9, 131.7, 130.6, 130.1, 129.6 (2C), 128.8 (2C), 64.9, 53.7, 62.8, 46.3, 43.6, 30.6.

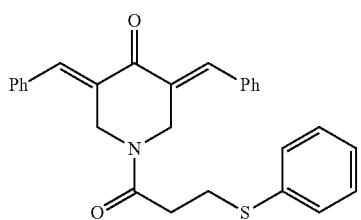 [SMILES: O=C1/C(=C/c2ccccc2)CN(C(=O)CCSc2ccccc2)C/C1=C\c1ccccc1]

3,5-Di((E)-benzylidene)-1-(3-(phenylthio)propanoyl)piperidin-4-one (JC012)

$^1$H NMR (400 MHz, CDCl$_3$) δ 7.84 (br s, 2H), 7.27 (m, 15H), 4.92 (s, 2H), 4.64 (s, 2H), 3.09 (t, J=7.3 Hz, 2H), 2.45 (t, J=7.3 Hz, 2H).

$^{13}$C NMR (100 MHz, CDCl$_3$) δ 186.6, 169.8, 138.6, 137.5, 135.5, 134.6, 134.3, 131.5, 130.6, 130.1, 129.6, 129.5, 129.0, 128.9 (2C), 128.8 (2C), 126.3, 46.2, 43.6, 32.8, 28.9.

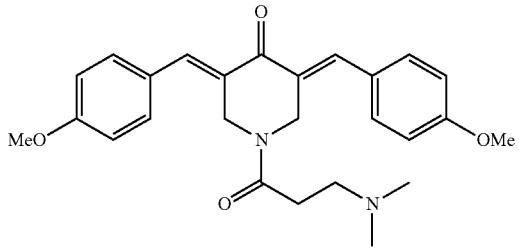 [SMILES: COc1ccc(/C=C2\CN(C(=O)CCN(C)C)C/C(=C\c3ccc(OC)cc3)C2=O)cc1]

1-(3-(Dimethylamino)propanoyl)-3,5-bis((E)-4-methoxybenzylidene)piperidin-4-one (JC013)

$^1$H NMR (400 MHz, CDCl$_3$) δ 7.82 (s, 1H), 7.74 (s, 1H), 7.46 (d, J=8.0 Hz, 2H), 7.35 (d, J=8.0 Hz, 2H), 6.96 (m, 4H), 4.91 (s, 2H), 4.73 (s, 2H), 3.85 (s, 6H), 2.50 (t, J=7.4 Hz, 2H), 2.36 (t, J=7.4 Hz, 2H), 2.08 (s, 6H).

$^{13}$C NMR (100 MHz, CDCl$_3$) δ 186.4, 170.4, 160.7 (2C), 137.9, 136.7, 132.7, 132.1, 130.0, 129.7, 127.4, 127.1, 114.4, 114.3, 55.4, 54.9, 46.3, 45.2, 43.5, 31.3.

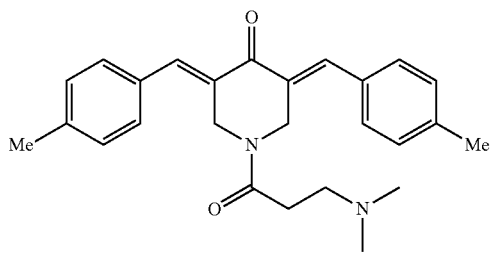 [SMILES: Cc1ccc(/C=C2\CN(C(=O)CCN(C)C)C/C(=C\c3ccc(C)cc3)C2=O)cc1]

1-(3-(Dimethylamino)propanoyl)-3,5-bis((E)-4-methylbenzylidene)piperidin-4-one (JC014)

$^1$H NMR (400 MHz, CDCl$_3$) δ 7.78 (s, 1H), 7.73 (s, 1H), 7.25 (m, 8H), 4.84 (s, 2H), 4.65 (s, 2H), 2.49 (t, J=7.4 Hz, 2H), 2.32 (m, 8H), 2.05 (s, 6H).

$^{13}$C NMR (100 MHz, CDCl$_3$) δ 186.6, 170.1, 140.1, 140.0, 139.9, 138.3, 137.2, 131.9, 131.6, 131.1, 130.9, 130.8, 130.3, 129.7 (2C), 129.6, 129.5 (2C), 54.7, 46.3, 44.9, 43.6, 31.0, 21.4.

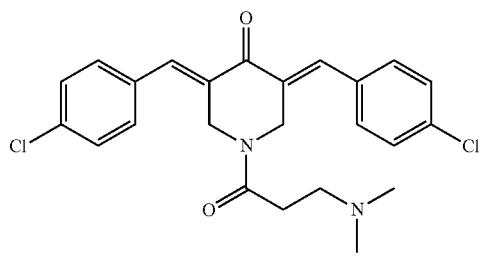 [SMILES: CN(C)CCC(=O)N1C/C(=C\c2ccc(Cl)cc2)C(=O)/C(=C/c2ccc(Cl)cc2)C1]

3,5-Bis((E)-4-chlorobenzylidene)-1-(3-(dimethylamino)propanoyl)piperidin-4-one (JC015)

$^1$H NMR (400 MHz, CDCl$_3$) δ 7.81 (s, 1H), 7.76 (s, 1H), 7.38 (m, 8H), 4.87 (s, 2H), 4.71 (s, 2H), 2.51 (t, J=7.4 Hz, 2H), 2.34 (t, J=7.3 Hz, 2H), 2.09 (s, 6H).

$^{13}$C NMR (100 MHz, CDCl$_3$) δ 186.1, 170.3, 137.0, 135.9, 135.8, 135.7, 132.9, 132.8, 132.0 (2C), 131.8, 131.4, 129.2, 129.1, 54.8, 46.3, 45.1, 43.3, 31.2.

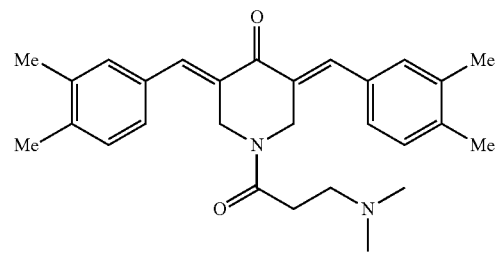 [SMILES: Cc1ccc(/C=C2\CN(C(=O)CCN(C)C)C/C(=C\c3ccc(C)c(C)c3)C2=O)cc1C]

1-(3-(Dimethylamino)propanoyl)-3,5-bis((E)-3,4-dimethylbenzylidene)piperidin-4-one (JC016)

$^1$H NMR (400 MHz, CDCl$_3$) δ 7.79 (s, 1H), 7.74 (s, 1H), 7.14 (m, 6H), 4.88 (s, 2H), 4.68 (s, 2H), 2.51 (t, J=7.1 Hz, 2H), 2.33 (t, J=7.2 Hz, 2H), 2.26 (s, 12H), 2.06 (s, 6H).

$^{13}$C NMR (100 MHz, CDCl$_3$) δ 186.7, 170.2, 138.8 (2C), 138.6, 137.4, 137.2, 136.9, 132.4 (2C), 132.1, 131.6, 131.0, 130.8, 130.2, 130.1, 128.4, 127.6, 54.7, 46.4, 44.9, 43.7, 31.0, 19.9.

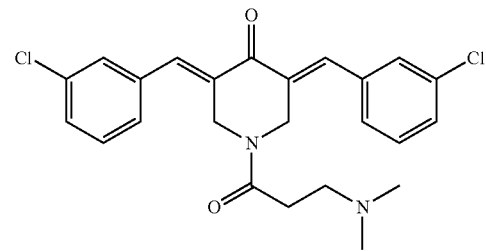 [SMILES: CN(C)CCC(=O)N1C/C(=C\c2cccc(Cl)c2)C(=O)/C(=C/c2cccc(Cl)c2)C1]

3,5-Bis((E)-3-chlorobenzylidene)-1-(3-(dimethylamino)propanoyl)piperidin-4-one (JC017)

$^1$H-NMR (400 MHz, CDCl$_3$) δ 7.76 (s, 1H), 7.71 (s, 1H), 7.29 (m, 8H), 4.85 (s, 2H), 4.69 (s, 2H), 2.49 (t, J=7.3 Hz, 2H), 2.31 (t, J=7.3 Hz, 2H), 2.07 (s, 6H).

$^{13}$C NMR (100 MHz, CDCl$_3$) δ 186.1, 170.5, 137.1, 136.2, 136.1, 135.9, 134.9, 134.8, 132.7 (2C), 130.2 (2C), 129.8 (2C), 129.7 (2C), 128.5, 128.1, 54.8, 46.3, 45.2, 43.4, 31.2.

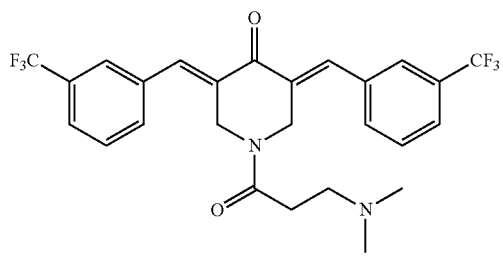 [SMILES: CN(C)CCC(=O)N1C/C(=C\c2cccc(C(F)(F)F)c2)C(=O)/C(=C/c2cccc(C(F)(F)F)c2)C1]

1-(3-(Dimethylamino)propanoyl)-3,5-bis((E)-3-(trifluoromethyl)benzylidene)piperidin-4-one (JC018)

$^1$H NMR (400 MHz, CDCl$_3$) δ 7.88 (s, 1H), 7.84 (s, 1H), 7.62 (m, 8H), 4.89 (s, 2H), 4.75 (s, 2H), 2.59 (t, J=7.3 Hz, 2H), 2.38 (t, J=7.3 Hz, 2H), 2.13 (s, 6H).
$^{13}$C NMR (100 MHz, CDCl$_3$) δ 185.9, 170.4, 136.9 (2C), 135.8, 135.2, 135.0, 133.2, 132.9 (2C), 131.6 (q, J$_{C-CF}$=36 Hz), 131.4 (q, J$_{C-CF}$=36 Hz), 129.5, 129.4, 127.1, 126.6, 126.2, 126.1, 123.7 (q, J$_{CF}$=270 Hz, 2C), 54.7, 46.2, 45.0, 43.2, 31.1.

(3E,5E)-1-(3-(Dimethylamino)propanoyl)-3,5-bis(furan-2-ylmethylene)piperidin-4-one (JC019)

$^1$H NMR (400 MHz, CDCl$_3$) δ 7.55 (s, 2H), 7.44 (m, 2H), 6.68 (m, 2H), 6.48 (m, 2H), 4.97 (s, 2H), 4.91 (s, 2H), 2.56 (s, 4H), 2.13 (s, 6H).
$^{13}$C NMR (100 MHz, CDCl$_3$) δ 185.6, 170.6, 151.7, 151.6, 145.8, 145.7, 128.3, 127.9, 123.4, 121.9, 118.5, 118.0, 112.8, 112.6, 55.1, 46.1, 45.3, 43.4, 31.6.

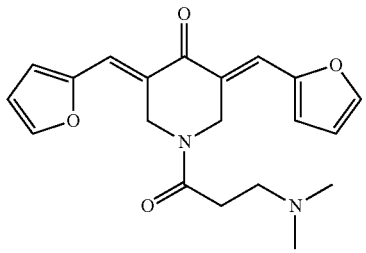 [SMILES: CN(C)CCC(=O)N1C/C(=C\c2ccco2)C(=O)/C(=C/c2ccco2)C1]

(3E,5E)-1-(3-(Dimethylamino)propanoyl)-3,5-bis(thiophen-2-ylmethylene)piperidin-4-one (JC020)

$^1$H NMR (400 MHz, CDCl$_3$) δ 7.98 (br s, 2H), 7.60 (m, 2H), 7.39 (m, 2H), 7.17 (m, 2H), 4.95 (s, 2H), 4.82 (s, 2H), 2.62 (m, 4H), 2.19 (s, 6H).
$^{13}$C NMR (100 MHz, CDCl$_3$) δ 185.2, 170.5, 138.3, 137.7, 134.1, 133.8, 131.4, 131.0, 130.1, 129.1, 128.5, 128.4 (2C), 128.1, 54.9, 46.2, 45.4, 43.1, 31.6.

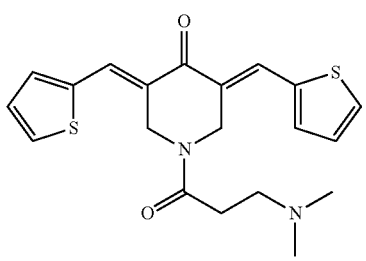 [SMILES: CN(C)CCC(=O)N1C/C(=C\c2cccs2)C(=O)/C(=C/c2cccs2)C1]

(3E,5E)-1-(3-(Dimethylamino)propanoyl)-3,5-bis(pyridin-2-ylmethylene)piperidin-4-one (JC021)

$^1$H NMR (400 MHz, CDCl$_3$) δ 8.72 (t, J=4.8 Hz, 2H), 7.75 (m, 2H), 7.68 (s, 1H), 7.64 (s, 1H), 7.49 (t, J=7.8 Hz, 2H), 7.23 (m, 2H), 5.38 (s, 2H), 5.31 (s, 2H), 2.59 (m, 4H), 2.16 (s, 6H).
$^{13}$C NMR (100 MHz, CDCl$_3$) δ 188.1, 170.8, 154.4 (2C), 149.9, 149.7, 136.8, 136.3, 136.0, 135.6, 134.9, 132.8, 128.3, 127.6, 123.4, 123.0, 55.1, 46.6, 45.3, 44.7, 31.5.

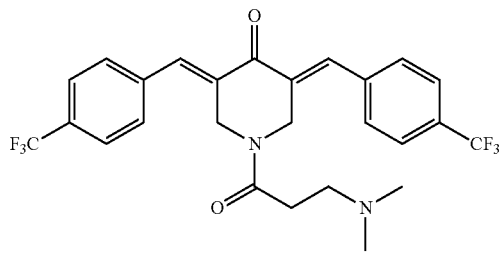

1-(3-(Dimethylamino)propanoyl)-3,5-bis((E)-4-(trifluoromethyl)benzylidene)piperidin-4-one (JC022)

$^1$H NMR (400 MHz, CDCl$_3$) δ 7.85 (br s, 2H), 7.68 (m, 4H), 7.54 (m, 4H), 4.89 (s, 2H), 4.74 (s, 2H), 2.55 (t, J=7.3 Hz, 2H), 2.35 (t, J=7.4 Hz, 2H), 2.10 (s, 6H).
$^{13}$C NMR (100 MHz, CDCl$_3$) δ 186.0, 170.3, 137.8, 137.7, 136.8, 135.9, 133.3 (2C), 131.4 (q, J$_{C-CF}$=33 Hz), 131.2 (q, J$_{C-CF}$=33 Hz), 130.5, 130.2, 125.8, 125.7, 123.7 (q, J$_{CF}$=273 Hz, 2C), 54.7, 46.3, 44.9, 43.2, 31.0.

HR-APCI m/z calcd for C$_{26}$H$_{24}$F$_6$N$_2$O$_2$[M+H]= 511.18202, found 511.18173.

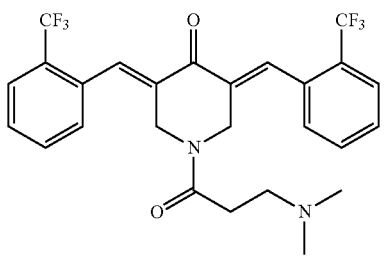

1-(3-(Dimethylamino)propanoyl)-3,5-bis((E)-2-(trifluoromethyl)benzylidene)piperidin-4-one (JC023)

$^1$H NMR (400 MHz, CDCl$_3$) δ 7.97 (br s, 2H), 7.66 (m, 2H), 7.41 (m, 6H), 4.55 (s, 2H), 4.41 (s, 2H), 2.40 (t, J=7.5 Hz, 2H), 2.14 (t, J=7.3 Hz, 2H), 1.96 (s, 6H).
$^{13}$C NMR (126 MHz, CDCl$_3$) δ 185.9, 170.4, 136.9, 135.9, 135.1, 135.0, 133.2, 132.9 (2C), 131.9 (q, J$_{C-CF}$=32 Hz), 131.4 (q, J$_{C-CF}$=32 Hz), 129.6, 129.4, 127.1 (2C), 126.6, 126.2, 126.1, 123.6 (q, J$_{CF}$=274 Hz, 2C), 54.3, 45.9, 44.5, 42.9, 30.1.

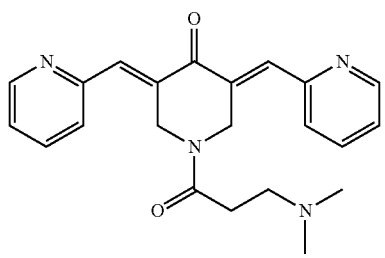 [SMILES: CN(C)CCC(=O)N1C/C(=C\c2ccccn2)C(=O)/C(=C/c2ccccn2)C1]

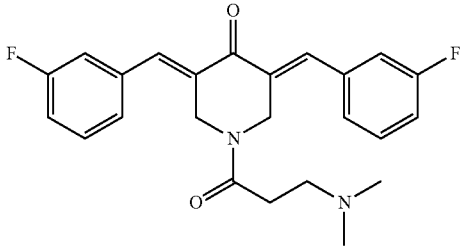 [SMILES: CN(C)CCC(=O)N1C/C(=C\c2cccc(F)c2)C(=O)/C(=C/c2cccc(F)c2)C1]

1-(3-(Dimethylamino)propanoyl)-3,5-bis((E)-3-fluorobenzylidene)piperidin-4-one (JC024)

¹H NMR (400 MHz, CDCl₃) δ 7.74 (br s, 2H), 7.34 (m, 8H), 4.85 (s, 2H), 4.70 (s, 2H), 2.50 (t, J=7.2 Hz, 2H), 2.32 (t, J=7.3 Hz, 2H), 2.07 (s, 6H).

¹³C NMR (100 MHz, CDCl₃) δ 186.2, 170.3, 162.7 (d, $J_{CF}$=240 Hz) (2C), 137.2, 136.5 (2C), 136.1, 132.6 (2C), 130.6, 130.4, 126.3, 125.9, 117.0 (d, $J_{C-CF}$=22 Hz), 116.7 (d, $J_{C-CF}$=22 Hz) (2C), 116.5 (d, $J_{C-CF}$=19 Hz), 54.7, 46.3, 45.1, 43.4, 31.1.

¹⁹F NMR (376 MHz, CDCl₃) δ −111.4 (s, 1F), −112.0 (s, 1F).

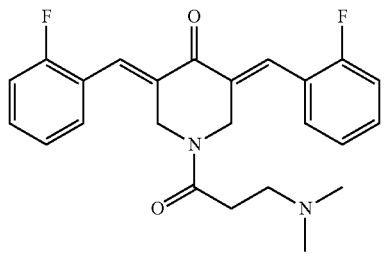 [SMILES: CN(C)CCC(=O)N1C/C(=C\c2ccccc2F)C(=O)/C(=C/c2ccccc2F)C1]

1-(3-(Dimethylamino)propanoyl)-3,5-bis((E)-2-fluorobenzylidene)piperidin-4-one (JC025)

¹H NMR (400 MHz, CDCl₃) δ 7.85 (s, 1H), 7.81 (s, 1H), 7.17 (m, 8H), 4.73 (s, 2H), 4.54 (s, 2H), 2.44 (t, J=7.3 Hz, 2H), 2.25 (t, J=7.4 Hz, 2H), 2.01 (s, 6H).

¹³C NMR (100 MHz, CDCl₃) δ 185.8, 170.3, 161.0 (d, $J_{CF}$=250 Hz), 160.5 (d, $J_{CF}$ 249 Hz), 133.6, 133.3, 131.6, 131.4, 131.0, 130.7 (2C), 130.3, 124.4, 124.2, 122.5 (d, $J_{C-CF}$=13 Hz), 122.3 (d, $J_{C-CF}$=14 Hz), 116.2 (d, $J_{C-CF}$=22 Hz), 115.9 (d, $J_{C-CF}$=22 Hz), 54.7, 46.5, 45.0, 43.4, 31.0.

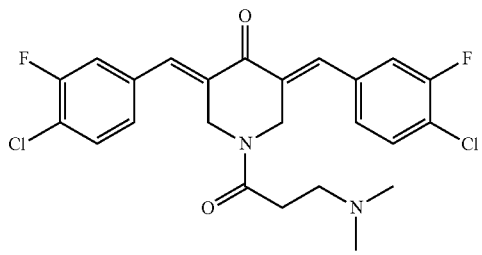 [SMILES: CN(C)CCC(=O)N1C/C(=C\c2ccc(Cl)c(F)c2)C(=O)/C(=C/c2ccc(Cl)c(F)c2)C1]

3,5-Bis((E)-4-chloro-3-fluorobenzylidene)-1-(3-(dimethylamino)propanoyl)piperidin-4-one (JC027)

¹H NMR (500 MHz, CD₃OD) δ 7.52 (m, 4H), 7.26 (m, 4H), 4.84 (s, 2H), 4.80 (s, 2H), 2.63 (t, J=7.2 Hz, 2H), 2.50 (t, J=7.3 Hz, 2H), 2.19 (s, 6H).

¹³C NMR (126 MHz, CD₃OD) δ 185.3, 170.5, 157.7 (d, $J_{CF}$=249 Hz), 157.6 (d, $J_{CF}$=248 Hz), 135.2, 135.1, 134.9, 134.5, 133.0 (2C), 130.8, 130.6, 126.9 (2C), 121.8 (d, $J_{C-CF}$=18 Hz), 121.6 (d, $J_{C-CF}$=18 Hz), 117.8, 117.7, 54.1, 46.1, 43.4, 42.6, 29.4.

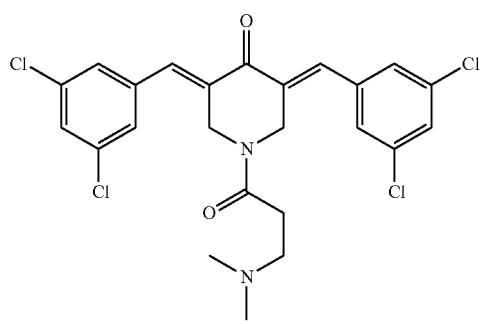 [SMILES: CN(C)CCC(=O)N1C/C(=C\c2cc(Cl)cc(Cl)c2)C(=O)/C(=C/c2cc(Cl)cc(Cl)c2)C1]

3,5-Bis((E)-3,5-dichlorobenzylidene)-1-(3-(dimethylamino)propanoyl)piperidin-4-one (JC028)

¹H NMR (400 MHz, CDCl₃) δ 7.61 (s, 1H), 7.56 (s, 1H), 7.40-7.10 (m, 6H), 4.79 (s, 2H), 4.66 (s, 2H), 2.50 (t, J=7.4 Hz, 2H), 2.31 (t, J=7.2 Hz, 2H), 2.08 (s, 6H).

¹³C NMR (100 MHz, CDCl₃) δ 185.4, 170.4, 137.1 (2C), 135.7 (2C), 135.4, 134.7, 133.5 (2C), 129.6, 129.4, 128.4, 128.0, 54.8, 46.3, 45.2, 43.2, 31.2.

HR-APCI m/z calcd for $C_{24}H_{22}Cl_4N_2O_2$[M+H]= 513.04841, found 513.04884.

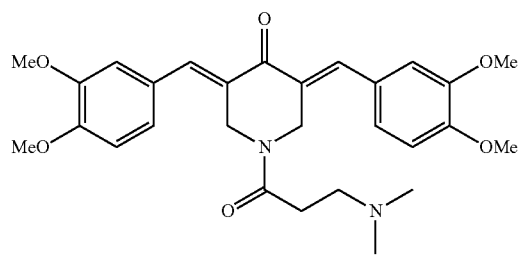 [SMILES: COc1ccc(/C=C2\CN(C(=O)CCN(C)C)C/C(=C\c3ccc(OC)c(OC)c3)C2=O)cc1OC]

3,5-Bis((E)-3,4-dimethoxybenzylidene)-1-(3-(dimethylamino)propanoyl)piperidin-4-one (JC029)

¹H NMR (400 MHz, CDCl₃) δ 7.74 (s, 1H), 7.69 (s, 1H), 6.87 (m, 6H), 4.86 (s, 2H), 4.69 (s, 2H), 3.85 (s, 12H), 2.44 (t, J=7.2 Hz, 2H), 2.30 ((t, J=7.1 Hz, 2H), 2.02 (s, 6H).

¹³C NMR (100 MHz, CDCl₃) δ 186.3, 170.4, 150.4 (2C), 149.1, 148.9, 138.2, 137.1, 130.2, 129.9, 127.7, 127.4, 124.5, 123.5, 1130.8, 113.6, 111.2 (2C), 55.9 (2C), 54.9, 46.4, 45.2, 43.5, 31.4.

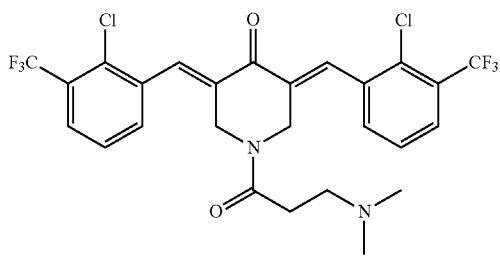 [SMILES: CN(C)CCC(=O)N1C/C(=C\c2cccc(C(F)(F)F)c2Cl)C(=O)/C(=C/c2cccc(C(F)(F)F)c2Cl)C1]

3,5-Bis((E)-2-chloro-3-(trifluoromethyl)benzylidene)-1-(3 (dimethylamino)propanoyl)piperidin-4-one (JC030)

$^1$H NMR (400 MHz, CDCl$_3$) δ 7.97 (br s, 2H), 7.69 (m, 3H), 7.41 (m, 3H), 4.68 (s, 2H), 4.51 (s, 2H), 2.47 (t, J=7.1 Hz, 2H), 2.25 (t, J=7.0 Hz, 2H), 2.06 (s, 6H).
$^{13}$C NMR (100 MHz, CDCl$_3$) δ 185.6, 170.3, 135.4 (2C), 134.9, 134.2, 133.9 (2C), 133.3 (2C), 132.8, 132.7, 130.0 (q, J$_{C—CF}$=38 Hz), 129.4 (q, J$_{C—CF}$=38 Hz), 128.4, 128.1, 126.8 (2C), 122.6 (q, J$_{CF}$=272 Hz, 2C), 54.7, 46.1, 45.1, 42.8, 31.2.

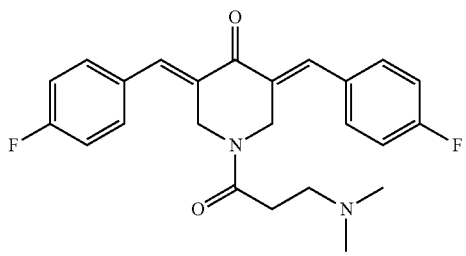 [SMILES: CN(C)CCC(=O)N1C/C(=C\c2ccc(F)cc2)C(=O)/C(=C/c2ccc(F)cc2)C1]

1-(3-(Dimethylamino)propanoyl)-3,5-bis((E)-4-fluorobenzylidene)piperidin-4-one (JC031)

$^1$H NMR (400 MHz, CDCl$_3$) δ 7.73 (s, 1H), 7.71 (s, 1H), 7.35 (m, 4H), 7.05 (m, 4H), 4.80 (s, 2H), 4.65 (s, 2H), 2.47 (t, J=7.4 Hz, 2H), 2.30 (t, J=7.3 Hz, 2H), 2.03 (s, 6H).
$^{13}$C NMR (100 MHz, CDCl$_3$) δ 186.2, 170.3, 163.2 (d, J$_{CF}$=250 Hz, 2C), 137.2, 136.1, 132.6 (d, J$_{C—C—CF}$=7.9 Hz, 2C), 132.2 (d, J$_{C—C—CF}$=7.4 Hz, 2C), 131.4, 131.3, 130.7, 130.5, 116.1 (d, J$_{C—CF}$=21 Hz, 2C), 115.9 (d, J$_{C—CF}$=21 Hz, 2C), 54.8, 46.3, 45.1, 43.3, 31.0.

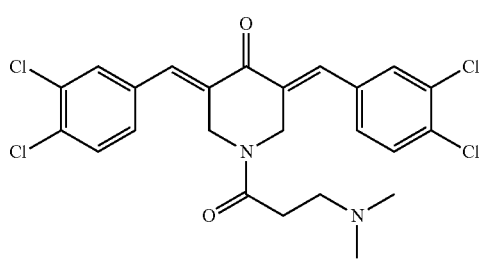 [SMILES: CN(C)CCC(=O)N1C/C(=C\c2ccc(Cl)c(Cl)c2)C(=O)/C(=C/c2ccc(Cl)c(Cl)c2)C1]

3,5-Bis((E)-3,4-dichlorobenzylidene)-1-(3-(dimethylamino)propanoyl)piperidin-4-one (JC032)

$^1$H NMR (400 MHz, CDCl$_3$) δ 7.73 (s, 1H), 7.70 (s, 1H), 7.46 (m, 4H), 7.25 (m, 2H), 4.85 (s, 2H), 4.72 (s, 2H), 2.57 (t, J=7.2 Hz, 2H), 2.38 (t, J=7.2 Hz, 2H), 2.15 (s, 6H).
$^{13}$C NMR (100 MHz, CDCl$_3$) δ 185.6, 170.3, 135.9, 135.0, 134.3, 134.1 (2C), 133.8, 133.3, 133.1, 132.7 (2C), 132.0, 131.6, 131.0, 130.8, 129.4, 129.1, 54.7, 46.3, 45.2, 43.2, 31.1.

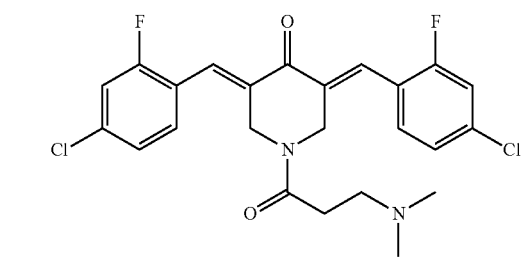 [SMILES: CN(C)CCC(=O)N1C/C(=C\c2ccc(Cl)cc2F)C(=O)/C(=C/c2ccc(Cl)cc2F)C1]

3,5-Bis((E)-4-chloro-2-fluorobenzylidene)-1-(3-(dimethylamino)propanoyl)piperidin-4-one (JC033)

$^1$H NMR (400 MHz, CD$_3$OD) δ 7.77 (s, 2H), 7.46 (m, 2H), 7.27 (m, 4H), 4.78 (s, 2H), 4.72 (s, 2H), 2.63 (t, J=7.1 Hz, 2H), 2.45 (t, J=7.2 Hz, 2H), 2.21 (s, 6H)
$^{13}$C NMR (126 MHz, CDCl$_3$) δ 185.5, 170.0, 160.8 (d, J$_{CF}$=256 Hz), 160.3 (d, J$_{CF}$=256 Hz), 136.8, 136.7, 133.6, 133.5, 131.4, 131.3, 130.1, 129.5, 125.1, 124.9, 121.2 (d, J$_{C—CF}$=13 Hz), 120.7 (d, J$_{C—CF}$=13 Hz), 117.2 (d, J$_{C—CF}$=25 Hz), 116.9 (d, J$_{C—CF}$=25 Hz), 54.6, 46.5, 45.0, 43.4, 30.8.

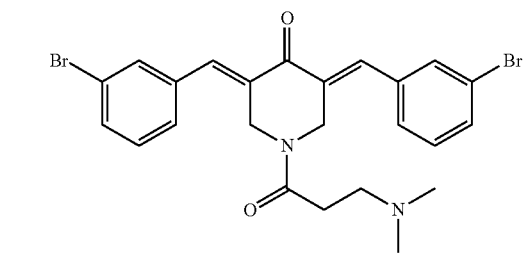 [SMILES: CN(C)CCC(=O)N1C/C(=C\c2cccc(Br)c2)C(=O)/C(=C/c2cccc(Br)c2)C1]

3,5-Bis((E)-3-bromobenzylidene)-1-(3-(dimethylamino)propanoyl)piperidin-4-one (JC034)

$^1$H NMR (400 MHz, CDCl$_3$) δ 7.77 (s, 1H), 7.73 (s, 1H), 7.49 (m, 4H), 7.40 (m, 4H), 4.87 (s, 2H), 4.70 (s, 2H), 2.53 (t, J=7.3 Hz, 2H), 2.33 (t, J=7.2 Hz, 2H), 2.10 (s, 6H).
$^{13}$C NMR (126 MHz, CDCl$_3$) δ 186.1, 170.4, 137.1, 136.5, 136.3, 135.9 (2C), 133.2, 132.6 (2C), 132.5, 130.5, 130.3, 128.9, 128.5, 123.1, 122.8, 54.7, 46.3, 45.1, 43.4, 31.1.

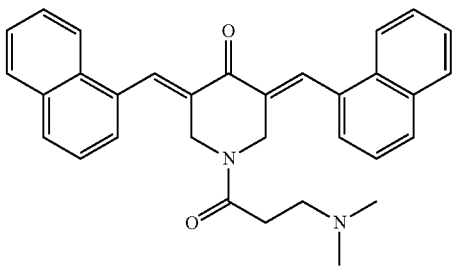 [SMILES: CN(C)CCC(=O)N1C/C(=C\c2cccc3ccccc23)C(=O)/C(=C/c2cccc3ccccc23)C1]

1-(3-(Dimethylamino)propanoyl)-3,5-bis((E)-naph-thalen-1-ylmethylene)piperidin-4-one (JC035)

¹H NMR (400 MHz, CDCl₃) δ 8.52 (br s, 2H), 7.94 (m, 6H), 7.51 (m, 8H), 4.81 (s, 2H), 4.58 (s, 2H), 2.37 (t, J=7.2 Hz, 2H), 2.09 (t, J=7.1 Hz, 2H), 1.81 (s, 6H).

¹³C NMR (126 MHz, CDCl₃) δ 186.7, 170.1, 137.0, 135.9, 133.7, 133.6 (2C), 133.4, 132.0, 131.8, 131.5, 130.2, 130.0, 128.8, 128.7, 127.3 (2C), 127.1 (2C), 127.0, 126.8, 126.7, 126.4, 125.2, 125.1, 124.5, 54.5, 46.4, 44.6, 43.6, 30.8.

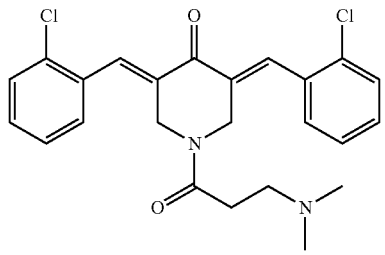 [SMILES: CN(C)CCC(=O)N1C/C(=C\c2ccccc2Cl)C(=O)/C(=C/c2ccccc2Cl)C1]

3,5-Bis((E)-2-chlorobenzylidene)-1-(3-(dimethyl-amino)propanoyl)piperidin-4-one (JC036)

¹H NMR (400 MHz, CDCl₃) δ 7.97 (br s, 2H), 7.27 (m, 8H), 4.73 (s, 2H), 4.53 (s, 2H), 2.49 (t, J=7.4 Hz, 2H), 2.26 (t, J=7.4 Hz, 2H), 2.07 (s, 6H).

¹³C NMR (126 MHz, CDCl₃) δ 186.2, 170.2, 135.6, 135.2, 134.8, 134.7, 133.1, 133.0, 132.8 (2C), 130.8, 130.5, 130.3 (2C), 130.2, 130.0, 126.8 (2C), 54.6, 46.1, 44.9, 43.2, 30.9.

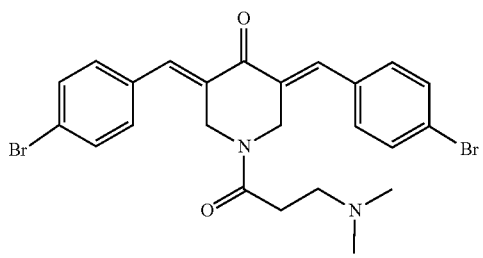 [SMILES: CN(C)CCC(=O)N1C/C(=C\c2ccc(Br)cc2)C(=O)/C(=C/c2ccc(Br)cc2)C1]

3,5-Bis((E)-4-bromobenzylidene)-1-(3-(dimethyl-amino)propanoyl)piperidin-4-one (JC037)

¹H NMR (400 MHz, CDCl₃) δ 7.77 (s, 1H), 7.73 (s, 1H), 7.61 (m, 4H), 7.29 (m, 4H), 4.85 (s, 2H), 4.70 (s, 2H), 2.59 (t, J=7.3 Hz, 2H), 2.40 (t, J=7.3 Hz, 2H), 2.16 (s, 6H).

¹³C NMR (126 MHz, CDCl₃) δ 186.1, 170.0, 137.1, 136.2, 133.3, 133.1, 132.2, 132.0, 131.9 (2C), 131.6 (2C), 124.3, 124.2, 54.6, 46.3, 45.0, 43.3, 30.8.

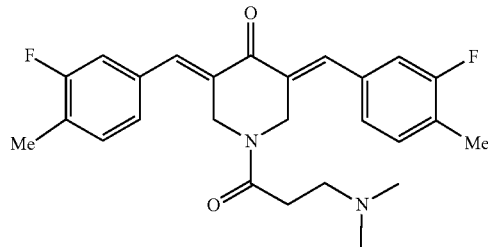 [SMILES: Cc1ccc(/C=C2\CN(C(=O)CCN(C)C)C/C(=C\c3ccc(C)c(F)c3)C2=O)cc1F]

1-(3-(Dimethylamino)propanoyl)-3,5-bis((E)-3-fluoro-4-methylbenzylidene)piperidin-4-one (JC038)

¹H NMR (400 MHz, CDCl₃) δ 7.78 (s, 1H), 7.73 (s, 1H), 7.24 (m, 2H), 7.08 (m, 4H), 4.89 (s, 2H), 4.72 (s, 2H), 2.59 (t, J=7.3 Hz, 2H), 2.40 (t, J=7.3 Hz, 2H), 2.32 (s, 6H), 2.15 (s, 6H).

¹³C NMR (126 MHz, CDCl₃) δ 186.2, 170.1, 161.1 (d, $J_{CF}$=245 Hz, 2C), 137.3 (2C), 136.2 (2C), 133.9 (dd, $J_{C-C-CF}$=6.6 Hz, $J_{C-C-CF}$=4.2 Hz), 132.0 (2C), 131.7 (2C), 127.0 (dd, $J_{C-C-CF}$=6.4 Hz, $J_{C-C-CF}$=3.5 Hz), 126.4, 125.9, 116.7 (d, $J_{C-CF}$=20 Hz), 116.4 (d, $J_{C-CF}$=20 Hz), 54.7, 46.3, 44.9, 43.4, 30.9, 14.6 (2C).

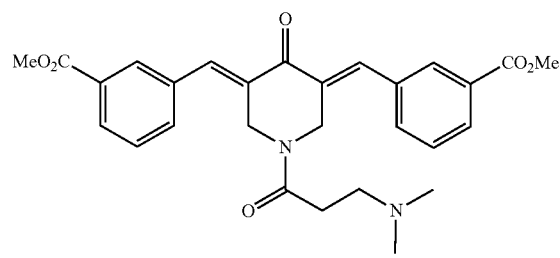 [SMILES: COC(=O)c1cccc(/C=C2\CN(C(=O)CCN(C)C)C/C(=C\c3cccc(C(=O)OC)c3)C2=O)c1]

Dimethyl 3,3'-((1E,1'E)-(1-(3-(dimethylamino)pro-panoyl)-4-oxopiperidine-3,5-diylidene) bis(meth-aneylidene))dibenzoate (JC039)

¹H NMR (400 MHz, CDCl₃) δ 8.04 (m, 4H), 7.84 (s, 1H), 7.83 (s, 1H), 7.52 (m, 4H), 4.89 (s, 2H), 4.73 (s, 2H), 3.91 (s, 6H), 2.44 (t, J=6.9 Hz, 2H), 2.26 (t, J=7.0 Hz, 2H), 2.00 (s, 6H).

¹³C NMR (100 MHz, CDCl₃) δ 186.1, 170.4, 166.4, 166.2, 137.5, 136.2, 134.8, 134.6, 134.5, 134.3, 132.6 (2C), 131.4, 130.9, 130.8, 130.5, 129.1, 128.9, 54.8, 52.4 (2C), 46.4, 45.2, 43.4, 31.2.

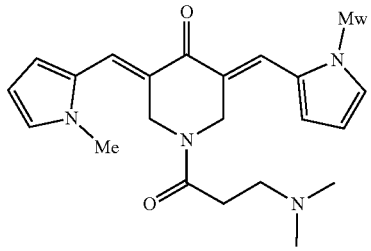

(3E,5E)-1-(3-(Dimethylamino)propanoyl)-3,5-bis((1-methyl-1H-pyrrol-2-yl)methylene)piperidin-4-one (JC040)

¹H NMR (400 MHz, CDCl₃) δ 7.71 (s, 2H), 6.80 (m, 2H), 6.54 (m, 1H), 6.38 (m, 1H), 6.21 (m, 2H), 4.75 (s, 2H), 4.62 (s, 2H), 3.68 (s, 6H), 2.49 (m, 4H), 2.10 (s, 6H).

¹³C NMR (100 MHz, CDCl₃) δ 184.9, 170.5, 128.9, 128.6, 127.7 (2C), 126.5, 126.3, 124.2, 123.2, 116.2, 115.2, 110.1, 110.0, 55.1, 46.6, 45.4, 43.5, 34.5, 34.4, 31.6.

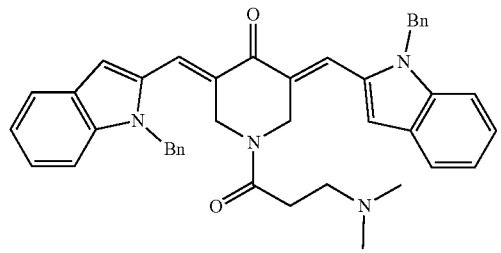 [SMILES: CN(C)CCC(=O)N1C/C(=C\c2cc3ccccc3n2Cc2ccccc2)C(=O)/C(=C/c2cc3ccccc3n2Cc2ccccc2)C1]

(3E,5E)-3,5-Bis((1-benzyl-1H-indol-2-yl)methylene)-1-(3-(dimethylamino)propanoyl) piperidin-4-one (JC041)

¹H NMR (400 MHz, CDCl₃) δ 8.26 (s, 2H), 7.94 (m, 2H), 7.31 (m, 14H), 7.14 (m, 4H), 5.41 (s, 4H), 4.87 (s, 2H), 4.71 (s, 2H), 2.53 (t, J=7.1 Hz, 2H), 2.47 (t, J=7.1 Hz, 2H), 2.06 (s, 6H).

¹³C NMR (100 MHz, CDCl₃) δ 185.2, 170.2, 136.3, 130.8, 130.1, 129.8, 129.0, 128.9, 128.0, 127.6, 126.9, 126.7, 123.6, 123.4, 121.4, 121.3, 119.6, 119.4, 115.0, 112.2, 110.3, 54.9, 50.8, 47.0, 45.3, 44.2, 31.2.

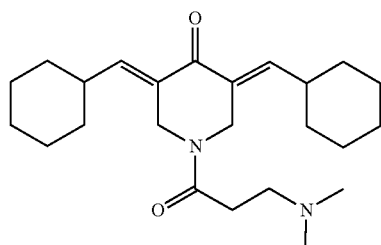

(3E,5E)-3,5-Bis(cyclohexylmethylene)-1-(3-(dimethylamino)propanoyl)piperidin-4-one (JC042)

¹H NMR (400 MHz, CDCl₃) δ 6.72 (s, 1H), 6.69 (s, 1H), 4.50 (s, 2H), 4.38 (s, 2H), 2.63 (t, J=7.1 Hz, 2H), 2.53 (t, J=7.1 Hz, 2H), 2.24 (s, 6H), 1.68 (m, 10H), 1.24 (m, 12H).

¹³C NMR (100 MHz, CDCl₃) δ 186.6, 170.0, 147.0, 145.7, 129.9, 129.6, 55.0, 45.4, 44.9, 41.6, 37.4, 37.2, 31.9, 31.7, 31.5, 25.7, 25.6, 25.3.

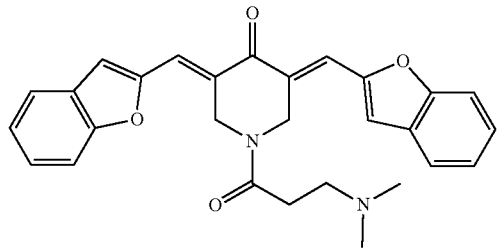 [SMILES: CN(C)CCC(=O)N1C/C(=C\c2cc3ccccc3o2)C(=O)/C(=C/c2cc3ccccc3o2)C1]

(3E,5E)-3,5-Bis(benzofuran-2-ylmethylene)-1-(3-(dimethylamino)propanoyl)piperidin-4-one (JC043)

¹H NMR (400 MHz, CDCl₃) δ 7.59 (m, 4H), 7.52 (m, 2H), 7.37 (m, 2H), 7.25 (m, 2H), 7.06 (m, 2H), 5.22 (s, 2H), 5.16 (s, 2H), 2.72 (app. s, 4H), 2.21 (s, 6H).

¹³C NMR (100 MHz, CDCl₃) δ 185.5, 170.6, 156.2, 156.1, 153.0, 152.8, 131.1, 130.4, 128.1, 127.9, 127.0, 126.8, 124.0, 123.8, 123.5, 122.6, 122.1, 121.9, 115.1, 114.5, 111.8, 111.5, 55.0, 46.3, 45.2, 43.9, 31.2.

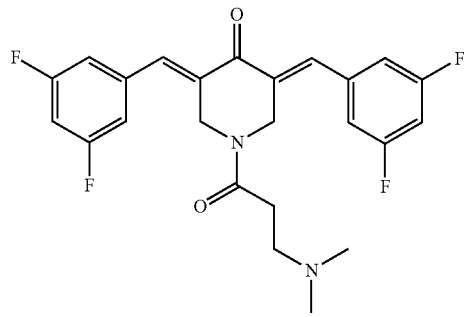 [SMILES: CN(C)CCC(=O)N1C/C(=C\c2cc(F)cc(F)c2)C(=O)/C(=C/c2cc(F)cc(F)c2)C1]

3,5-Bis((E)-3,5-difluorobenzylidene)-1-(3-(dimethylamino)propanoyl)piperidin-4-one (JC044)

¹H NMR (400 MHz, CDCl₃) δ 7.83 (br s, 2H), 7.43 (s, 1H), 7.30 (s, 1H), 6.96 (s, 2H), 4.75 (s, 2H), 4.58 (s, 2H), 2.57 (t, J=7.4 Hz, 2H), 2.37 (t, J=7.4 Hz, 2H), 2.14 (s, 6H).

¹³C NMR (126 MHz, CDCl₃) δ 185.7, 170.2, 151.1 (dd, J_{CF}=252.5 Hz, J_{C—CF}=13 Hz, 2C), 150.3 (dd, J_{CF}=252.5 Hz, J_{C—CF}=12 Hz, 2C), 136.7, 134.3, 133.2 (dd, J_{C—C—CF}=5.8 Hz, J_{C—C—CF}=3.5 Hz, 2C), 131.8, 130.3, 129.6 (dd, J_{C—C—CF}=5.8 Hz, J_{C—C—CF}=3.5 Hz, 2C), 118.8 (d, J_{C—CF}=18 Hz, 2C), 117.6 (d, J_{C—CF}=20 Hz, 2C), 54.6, 46.5, 44.9, 43.3, 30.8.

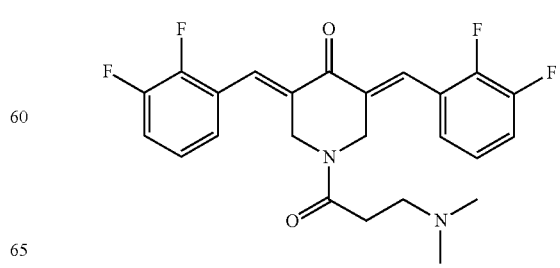

3,5-Bis((E)-2,3-difluorobenzylidene)-1-(3-(dimethylamino)propanoyl)piperidin-4-one (JC045)

$^1$H NMR (400 MHz, CDCl$_3$) δ 7.83 (br s, 2H), 7.12 (m, 6H), 4.75 (s, 2H), 4.58 (s, 2H), 2.48 (t, J=7.4 Hz, 2H), 2.29 (t, J=7.4 Hz, 2H), 2.07 (s, 6H).
$^{13}$C NMR (126 MHz, CDCl$_3$) δ 185.5, 170.4, 151.1 (dd, J$_{CF}$=254 Hz, J$_{C-CF}$=14 Hz, 2C), 150.4 (dd, J$_{CF}$=251 Hz, J$_{C-CF}$=14 Hz, 2C), 134.2, 130.1, 129.4, 125.5, 124.6 (2C), 124.3 (2C), 118.6 (d, J$_{C-CF}$=17 Hz, 2C), 118.5 (d, J$_{C-CF}$=17 Hz, 2C), 54.7, 46.6, 45.1, 43.4, 31.0.

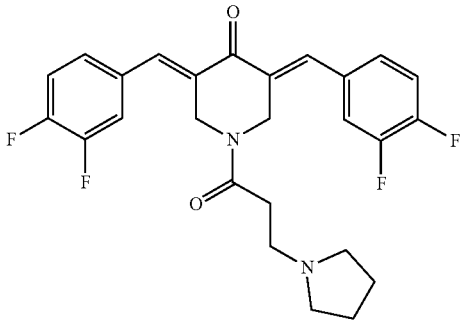 [SMILES: O=C1/C(=C/c2ccc(F)c(F)c2)CN(C(=O)CCN2CCCC2)C/C1=C\c1ccc(F)c(F)c1]

3,5-Bis((E)-3,4-difluorobenzylidene)-1-(3-(pyrrolidin-1-yl)propanoyl)piperidin-4-one (JC046)

$^1$H NMR (400 MHz, CDCl$_3$) δ 7.71 (br s, 2H), 7.21 (m, 6H), 4.83 (s, 2H), 4.74 (s, 2H), 2.92 (t, J=7.3 Hz, 2H), 2.65 (t, J=7.3 Hz, 2H), 2.62 (m, 4H), 1.83 (m, 4H).
$^{13}$C NMR (100 MHz, CDCl$_3$) δ 185.9, 169.6, 151.1 (dd, J$_{CF}$=254 Hz, J$_{C-CF}$=13 Hz, 2C), 150.4 (dd, J$_{CF}$=251 Hz, J$_{C-CF}$=14 Hz, 2C), 136.2, 135.7, 131.9 (dd, J$_{C-C-CF}$=5.8 Hz, J$_{C-C-CF}$=3.5 Hz, 2C), 131.5, 131.3, 127.2 (dd, J$_{C-C-CF}$=5.8 Hz, J$_{C-C-CF}$=4.2 Hz, 2C), 119.2 (d, J$_{C-CF}$=17 Hz, 2C), 118.4 (d, J$_{C-CF}$=17 Hz, 2C), 64.0, 51.2, 46.4, 43.1, 31.2, 29.7, 23.4, 22.8.

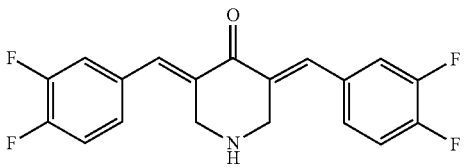 [SMILES: O=C1/C(=C/c2ccc(F)c(F)c2)CNC/C1=C\c1ccc(F)c(F)c1]

3,5-Bis((E)-3,4-difluorobenzylidene)piperidin-4-one (142)

$^1$H NMR (400 MHz, CDCl$_3$) δ 7.67 (br s, 2H), 7.17 (m, 6H), 4.11 (br s 4H).
$^{13}$C NMR (100 MHz, CDCl$_3$) δ 187.3, 150.7 (dd, J$_{CF}$=251 Hz, J$_{C-CF}$=13 Hz, 2C), 150.3 (dd, J$_{CF}$=248 Hz, J$_{C-CF}$=13 Hz, 2C), 135.3 (2C), 133.9 (2C), 132.1 (dd, J$_{C-C-CF}$=6.1 Hz, J$_{C-C-CF}$=4.1 Hz, 2C), 127.1 (dd, J$_{C-C-CF}$=6.3 Hz, J$_{C-C-CF}$=3.5 Hz, 2C), 119.0 (d, J$_{C-CF}$=18 Hz, 2C), 117.6 (d, J$_{C-CF}$=18 Hz, 2C), 47.9.

General Procedure B:

Compound JC049-JC053 and their analogues were generally prepared by reaction of 3,4-difluoro-benzaldehyde, with piperidin-4-one hydrogen chloride in the present of 40% aq. sodium hydroxide to give 3,5-bis((E)-3,4-difluorobenzylidene)piperidin-4-one. Acylation of this 3,5-bis((E)-3,4-difluorobenzyl-idene)piperidin-4-one with acryloyl chloride under basic conditions afforded the 1-acryloyl 3,5-bis((E)-3,4-difluorobenzylidene)piperidin-4-one. Michael addition of an amine, e.g., diethylamine, afforded the 1-(3-(dialkylamino)propanoyl)-3,5-bis((E)-3,4-difluorobenzylidene)piperidin-4-one, e.g., 1-(3-(diethyl-amino)propanoyl)-3,5-bis((E)-3,4-difluorobenzylidene)piperidin-4-one.

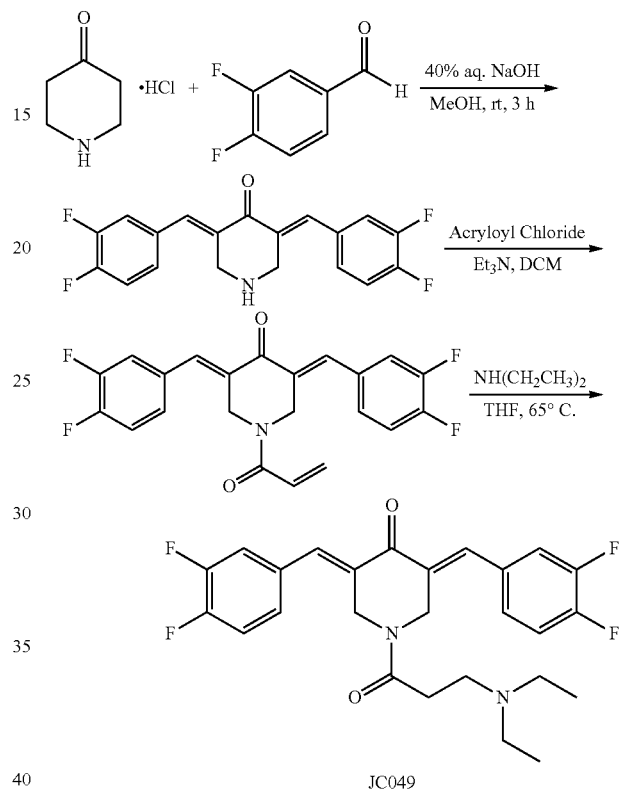

JC049

Preparation of JC049

To the mixture of piperidin-4-one hydrogen chloride (135.59 mg, 1 mmol, 1.0 equiv.) and methanol (2.0 mL) in a round bottom flask was added dropwise 40% aqueous sodium hydroxide (1.0 mL) and the reaction mixture was stirred for 5 min. To this mixture was added 3,4-difluorobenzaldehyde (355.3 mg, 2.5 mmol, 2.5 equiv.). The reaction mixture was then allowed to stir at 21° C. for 3 h, at which time a yellow solid had precipitated. The precipitate thus obtained was filtered, washed with water and cold methanol and dried to get the pure piperidone product (285 mg, 80% yield).

A mixture of 3,5-bis((E)-3,4-difluorobenzylidene)piperidin-4-one (173.7 mg, 0.5 mmol, 1.0 equiv.) and anhydrous triethylamine (105 μL, 0.75 mmol, 1.5 equiv.) in dichloromethane was maintained at 0° C. (ice bath). To this cooled mixture was added dropwise acryloyl chloride (61 μL, 0.75 mmol, 1.5 equiv.). After the complete addition of the acryloyl chloride, the reaction mixture was slowly warmed up to 21° C. and stirred for a further 4 h.

After completion of the reaction, the solvent was evaporated and the residue thus obtained was washed with water, filtered and dried. The crude amide product was pure enough to be used for the next step.

A mixture of the crude 1-acryloyl-3,5-bis((E)-3,4-difluorobenzylidene)piperidin-4-one (200.7 mg, 0.5 mmol, 1.0 equiv.), 2,6-bis(1,1-dimethylethyl)-4-methylphenol (1.1 mg, 0.005 mmol, 1%) and diethylamine (54.9 mg, 0.75 mmol, 1.5 equiv.) in 1.0 mL anhydrous THF was heated to 65° C. under argon for 12 h. The solvent was evaporated and flash chromatography of the residue (gradient elution 10% methanol/EtOAc-20% methanol/EtOAc) gave the desired compound JC049 (151.8 mg, 64% yield) as a yellow solid.

The following compounds were synthesized by procedure B: JC026, JC047, JC048, JC049, JC050, JC051, JC052, JC069, JC079, JC096.

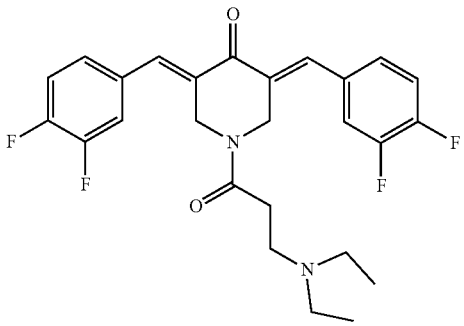 [SMILES: CCN(CC)CCC(=O)N1C/C(=C\c2ccc(F)c(F)c2)C(=O)/C(=C/c2ccc(F)c(F)c2)C1]

1-(3-(Diethylamino)propanoyl)-3,5-bis((E)-3,4-difluorobenzylidene)piperidin-4-one (JC049)

$^1$H NMR (400 MHz, $d_6$-Acetone) δ 7.65 (br s, 2H), 7.55 (m, 2H), 7.43 (m, 4H), 4.90 (br s, 4H), 2.62 (t, J=7.2 Hz, 2H), 2.36 (m, 6H), 0.85 (t, J=7.1 Hz, 6H).

$^{13}$C NMR (126 MHz, CDCl$_3$) δ 186.0, 170.7, 151.1 (dd, $J_{CF}$=254 Hz, $J_{C\text{—}CF}$=14 Hz, 2C), 150.4 (dd, $J_{CF}$=251 Hz, $J_{C\text{—}CF}$=14 Hz, 2C), 136.3, 135.4, 132.2, 132.1, 131.5, 131.3, 127.2, 126.8, 119.2 (d, $J_{C\text{—}CF}$=18 Hz), 118.9 (d, $J_{C\text{—}CF}$=18 Hz), 118.1 (d, $J_{C\text{—}CF}$=18 Hz), 117.9 (d, $J_{C\text{—}CF}$=17 Hz), 48.6, 47.0, 46.4, 43.1, 31.0, 11.4.

$^{19}$F NMR (376 MHz, CDCl$_3$) δ −133.9 (m, 1F), −134.3 (m, 1F), −135.5 (m, 1F), −136.1 (m, 1F).

HR-APCI m/z calcd for C$_{26}$H$_{26}$F$_4$N$_2$O$_2$[M+H]= 475.20087, found 475.20080.

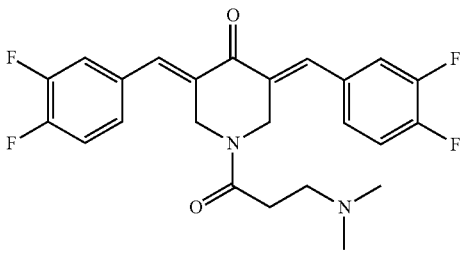 [SMILES: CN(C)CCC(=O)N1C/C(=C\c2ccc(F)c(F)c2)C(=O)/C(=C/c2ccc(F)c(F)c2)C1]

3,5-Bis((E)-3,4-difluorobenzylidene)-1-(3-(dimethylamino)propanoyl)piperidin-4-one (JC026)

$^1$H NMR (400 MHz, $d_6$-Acetone) δ 7.66 (br s, 2H), 7.58 (m, 2H), 7.44 (m, 4H), 4.91 (br s, 4H), 2.41 (s, 4H), 2.00 (s, 6H).

$^{13}$C NMR (126 MHz, CDCl$_3$) δ 185.9, 170.3, 151.1 (dd, $J_{CF}$=254 Hz, $J_{C\text{—}CF}$=13 Hz) (2C), 150.4 (dd, $J_{CF}$=250 Hz, $J_{C\text{—}CF}$=13 Hz) (2C), 136.3, 135.4, 132.1 (2C), 131.5, 131.3, 127.2, 126.8, 119.2 (d, $J_{C\text{—}CF}$=18 Hz), 118.9 (d, $J_{C\text{—}CF}$=17 Hz), 118.1 (d, $J_{C\text{—}CF}$=17 Hz), 117.9 (d, $J_{C\text{—}CF}$=17 Hz), 54.7, 46.3, 45.2, 43.1, 31.2.

$^{19}$F NMR (376 MHz, CDCl$_3$) δ −133.8 (m, 1F), −134.3 (m, 1F), −135.5 (m, 1F), −136.1 (m, 1F).

HR-APCI m/z calcd for C$_{24}$H$_{22}$F$_4$N$_2$O$_2$[M+H]= 447.16957, found 447.16993.

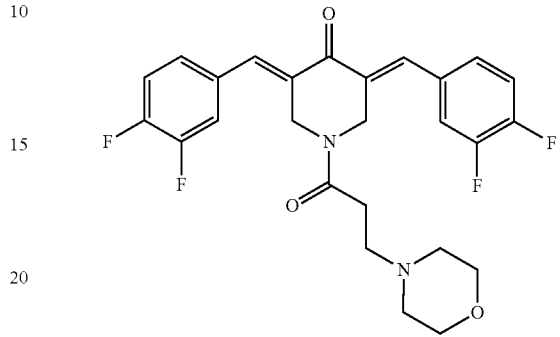

3,5-Bis((E)-3,4-difluorobenzylidene)-1-(3-morpholinopropanoyl)piperidin-4-one (JC047)

$^1$H NMR (400 MHz, CDCl$_3$) δ 7.72 (br s, 2H), 7.18 (m, 6H), 4.85 (s, 2H), 4.69 (s, 2H), 3.60 (t, J=4.8 Hz, 4H), 2.57 (t, J=7.4 Hz, 2H), 2.36 (t, J=7.4 Hz, 2H), 2.29 (t, J=4.8 Hz, 4H).

$^{13}$C NMR (100 MHz, CDCl$_3$) δ 185.8, 170.4, 151.1 (dd, $J_{CF}$=253 Hz, $J_{C\text{—}CF}$=14 Hz, 2C), 150.4 (dd, $J_{CF}$=253 Hz, $J_{C\text{—}CF}$=14 Hz, 2C), 136.4, 135.3, 132.2 (dd, $J_{C\text{—}C\text{—}CF}$=5.8 Hz, $J_{C\text{—}C\text{—}CF}$=4.1 Hz, 2C), 131.4, 127.2 (dd, $J_{C\text{—}C\text{—}CF}$=6.1 Hz, $J_{C\text{—}C\text{—}CF}$=4.1 Hz, 2C), 126.9, 119.2 (d, $J_{C\text{—}CF}$=18 Hz, 2C), 118.0 (d, $J_{C\text{—}CF}$=17 Hz, 2C), 64.0, 51.2, 46.4, 43.1, 31.2, 29.7, 23.4, 22.8.

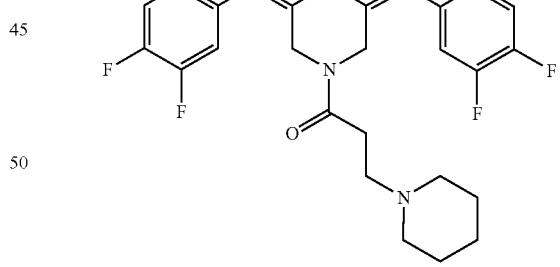

3,5-Bis((E)-3,4-difluorobenzylidene)-1-(3-(piperidin-1-yl)propanoyl)piperidin-4-one (JC048)

$^1$H NMR (400 MHz, CDCl$_3$) δ 7.70 (s, 1H), 7.67 (s, 1H), 7.19 (m, 6H), 4.82 (s, 2H), 4.69 (s, 2H), 2.58 (t, J=7.4 Hz, 2H), 2.40 (t, J=7.4 Hz, 2H), 2.26 (m, 4H), 1.49 (m, 4H), 1.37 (m, 2H).

$^{13}$C NMR (100 MHz, CDCl$_3$) δ 185.9, 170.6, 151.1 (dd, $J_{CF}$=254 Hz, $J_{C\text{—}CF}$=14 Hz, 2C), 150.4 (dd, $J_{CF}$=251 Hz, $J_{C\text{—}CF}$=14 Hz, 2C), 136.2, 135.3, 132.2, 131.5 dd, $J_{C\text{—}C\text{—}CF}$=5.7 Hz, $J_{C\text{—}C\text{—}CF}$=4.1 Hz, 2C), 127.2 (dd, $J_{C-C-CF}$=5.8 Hz, $J_{C-C-CF}$=3.4 Hz, 2C), 126.2, 118.8 (d, $J_{C-CF}$=18 Hz, 2C), 117.4 (d, $J_{C-CF}$=18 Hz, 2C), 54.4, 46.3, 43.1, 30.5, 25.6, 23.9.

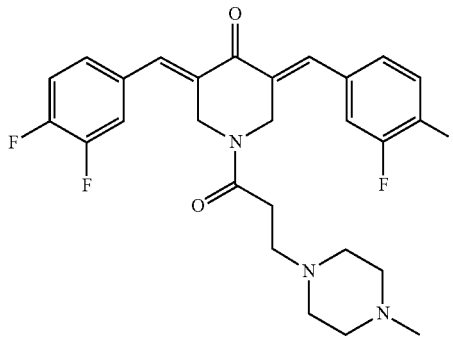

3,5-Bis((E)-3,4-difluorobenzylidene)-1-(3-(4-methylpiperazin-1-yl)propanoyl)piperidin-4-one (JC050)

$^1$H NMR (400 MHz, CDCl$_3$) δ 7.71 (br s, 2H), 7.16 (m, 6H), 4.84 (s, 2H), 4.69 (s, 2H), 2.60 (t, J=7.4 Hz, 2H), 2.37 (m, 10H), 2.25 (s, 3H).

$^{13}$C NMR (100 MHz, CDCl$_3$) δ 186.0, 170.4, 151.1 (dd, $J_{CF}$=254 Hz, $J_{C-CF}$=14 Hz, 2C), 150.4 (dd, $J_{CF}$=251 Hz, $J_{C-CF}$=14 Hz, 2C), 136.4, 135.3, 132.2 (dd, $J_{C-C-CF}$=5.8 Hz, $J_{C-C-CF}$=3.4 Hz, 2C), 131.4, 127.2 (dd, $J_{C-C-CF}$=5.8 Hz, $J_{C-C-CF}$=3.4 Hz, 2C), 126.9, 118.7 (d, $J_{C-CF}$=20 Hz, 2C), 117.6 (d, $J_{C-CF}$=20 Hz, 2C), 54.6, 53.5, 52.6, 46.3, 45.6, 30.5.

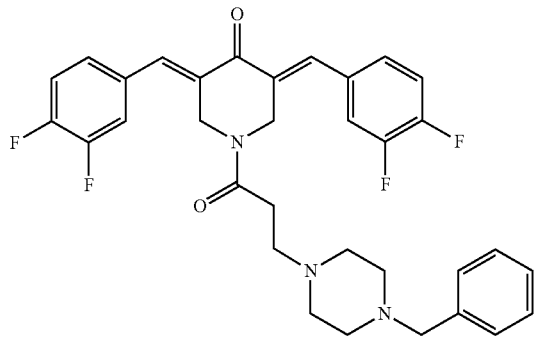 [SMILES: O=C1/C(=C/c2ccc(F)c(F)c2)CN(C(=O)CCN2CCN(Cc3ccccc3)CC2)C/C1=C\c1ccc(F)c(F)c1]

1-(3-(4-Benzylpiperazin-1-yl)propanoyl)-3,5-bis((E)-3,4-difluorobenzylidene)piperidin-4-one (JC051)

$^1$H NMR (400 MHz, CDCl$_3$) δ 7.70 (br s, 2H), 7.23 (m, 11H), 4.83 (s, 2H), 4.68 (s, 2H), 3.45 (s, 2H), 2.58 (t, 0.1=7.4 Hz, 2H), 2.35 (m, 10H).

$^{13}$C NMR (100 MHz, CDCl$_3$) δ 185.9, 170.5, 151.1 (dd, $J_{CF}$=254 Hz, $J_{C-CF}$=13 Hz, 2C), 150.4 (dd, $J_{CF}$=251 Hz, $J_{C-CF}$=13 Hz, 2C), 1$^3$7.9, 136.3, 135.3, 132.2, 131.4 (dd, $J_{C-C-CF}$=5.8 Hz, $J_{C-C-CF}$=3.8 Hz, 2C), 129.2, 128.2, 127.1, 127.2 (dd, $J_{C-C-CF}$=5.8 Hz, $J_{C-C-CF}$=3.4 Hz, 2C), 126.9, 118.6 (d, $J_{C-CF}$=20 Hz, 2C), 117.5 (d, $J_{C-CF}$=20 Hz, 2C), 62.9, 53.7, 53.0, 52.2, 46.3, 43.1, 30.7.

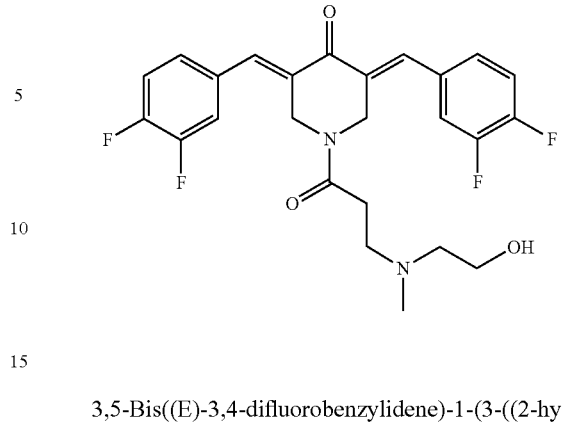

3,5-Bis((E)-3,4-difluorobenzylidene)-1-(3-((2-hydroxyethyl)(methyl)amino)propanoyl) piperidin-4-one (JC052)

$^1$H NMR (400 MHz, CDCl$_3$) δ 7.75 (s, 1H), 7.70 (s, 1H), 7.21 (m, 6H), 4.86 (s, 2H), 4.70 (s, 2H), 3.56 (t, J=5.4 Hz, 2H), 2.79 (s, 1H), 2.67 (t, J=6.7 Hz, 2H), 2.46 (t, J=5.4 Hz, 2H), 2.36 (t, J=6.7 Hz, 2H), 2.16 (s, 3H).

$^{13}$C NMR (100 MHz, CDCl$_3$) δ 185.8, 170.6, 151.1 (dd, $J_{CF}$=254 Hz, $J_{C-CF}$=13 Hz, 2C), 150.4 (dd, $J_{CF}$=255 Hz, $J_{C-CF}$=13 Hz, 2C), 136.3, 135.2, 132.2 (dd, $J_{C-C-CF}$=6.4 Hz, $J_{C-C-CF}$=4.2 Hz, 2C), 131.3, 127.2 (dd, $J_{C-C-CF}$=6.0 Hz, $J_{C-C-CF}$=3.8 Hz, 2C), 126.8, 119.3 (d, $J_{C-CF}$=17 Hz), 118.9 (d, $J_{C-CF}$=17 Hz), 118.2 (d, $J_{C-CF}$=17 Hz), 117.9 (d, $J_{C-CF}$=17 Hz), 60.0, 58.6, 52.1, 46.2, 43.2, 42.0, 30.6.

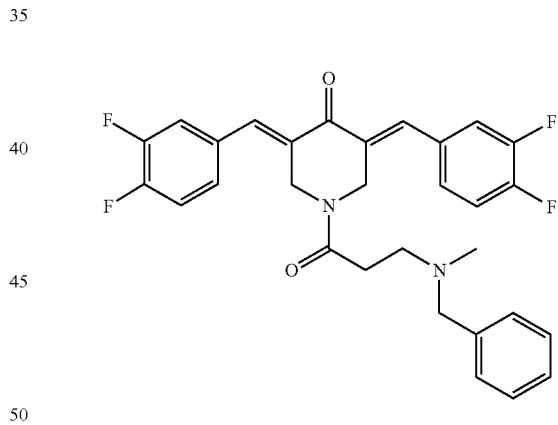

1-(3-(Benzyl(methyl)amino)propanoyl)-3,5-bis((E)-3,4-difluorobenzylidene)piperidin-4-one (JC069)

$^1$H NMR (400 MHz, CDCl$_3$) δ 7.69 (br s, 2H), 7.20 (m, 11H), 4.83 (s, 2H), 4.64 (s, 2H), 3.36 (s, 2H), 2.63 (t, J=7.2 Hz, 2H), 2.37 (t, J=7.2 Hz, 2H), 2.05 (s, 3H).

$^{13}$C NMR (100 MHz, CDCl$_3$) δ 185.9, 170.7, 150.9 (dd, $J_{CF}$=255 Hz, $J_{C-CF}$=13 Hz, 2C), 150.4 (dd, $J_{CF}$=255 Hz, $J_{C-CF}$=13 Hz, 2C), 138.6, 136.2 (2C), 135.2 (2C), 131.8 (dd, $J_{C-C-CF}$=6.4 Hz, $J_{C-C-CF}$=4.2 Hz, 2C), 128.9, 128.3, 127.1, 126.8 (dd, $J_{C-C-CF}$=5.9 Hz, $J_{C-C-CF}$=3.8 Hz, 2C), 119.3 (d, $J_{C-CF}$=17 Hz), 119.0 (d, $J_{C-CF}$=17 Hz), 118.1 (d, $J_{C-CF}$=17 Hz), 117.5 (d, $J_{C-CF}$=18 Hz), 62.4, 53.0, 46.4, 43.1, 42.2, 31.6.

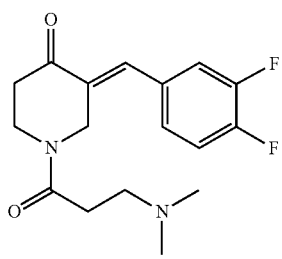

(E)-3-(3,4-Difluorobenzylidene)-1-(3-(dimethyl-amino)propanoyl)piperidin-4-one (JC079)

$^1$H NMR (400 MHz, CDCl$_3$) δ 7.54 (s, 1H), 7.21 (m, 3H), 4.80 (s, 2H), 3.85 (t, J=6.3 Hz, 2H), 2.73 (m, 4H), 2.62 (t, J=6.3 Hz, 2H), 2.31 (s, 6H).
$^{13}$C NMR (126 MHz, CDCl$_3$) δ 196.0, 170.4, 150.9 (dd, $J_{CF}$=254 Hz, $J_{C-CF}$=13 Hz), 150.4 (dd, $J_{CF}$=254 Hz, $J_{C-CF}$=13 Hz), 135.6, 131.7 (dd, $J_{C-C-CF}$=6.4 Hz, $J_{C-C-CF}$=4.2 Hz), 127.3 (dd, $J_{C-C-CF}$=6.4 Hz, $J_{C-C-CF}$=4.2 Hz), 125.5, 118.4 (d, $J_{C-CF}$=17 Hz), 117.6 (d, $J_{C-CF}$=17 Hz), 55.0, 45.4, 42.7, 42.0, 39.2, 29.7.

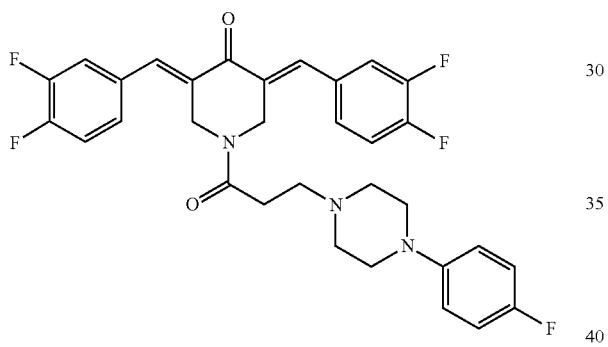

3,5-Bis((E)-3,4-difluorobenzylidene)-1-(3-(4-(4-fluorophenyl)piperazin-1 yl)propanoyl)piperidin-4-one (JC096)

$^1$H NMR (400 MHz, CDCl$_3$) δ 7.77 (br s, 2H), 7.19 (m, 6H), 6.95 (m, 2H), 6.82 (m, 2H), 4.66 (br s, 4H), 3.13 (t, J=6.4 Hz, 2H), 3.03 (m, 4H), 2.80 (t, J=6.4 Hz, 2H), 2.56 (m, 4H).
$^{13}$C NMR (126 MHz, CDCl$_3$) δ 184.8, 170.1, 157.3 (d, $J_{CF}$=240 Hz), 151.2 (dd, $J_{CF}$=255 Hz, $J_{C-CF}$=13 Hz, 2C), 150.5 (dd, $J_{CF}$=251 Hz, $J_{C-CF}$=13 Hz, 2C), 147.6 (d, $J_{C-C-CF}$=11 Hz), 136.5, 134.1 (2C), 133.0 (dd, $J_{C-C-CF}$=6.6 Hz, $J_{C-C-CF}$=3.5 Hz, 2C), 131.2 (2C), 127.2 (dd, $J_{C-C-CF}$=6.6 Hz, $J_{C-C-CF}$=3.5 Hz, 2C), 118.9 (d, $J_{C-CF}$=17 Hz, 2C), 117.8 (d, $J_{C-CF}$=18 Hz, 2C), 115.5 (d, $J_{C-CF}$=20 Hz), 53.0, 51.8, 50.0, 49.9, 46.7.

General Procedure C:

Compounds JC070, JC080 and their analogues were generally prepared by reaction of 3,4-difluoro-benzaldehyde, with tert-butyl (4-oxocyclohexyl)carbamate in the present of 20% aq. sodium hydroxide to give tert-butyl (3,5-bis((E)-3,4-difluorobenzylidene)-4-oxocyclohexyl)carbamate. The Boc protecting group was deprotected with TFA. Acylation of the 4-amino-2,6-bis((E)-3,4-difluorobenzylidene)cyclo-hexan-1-one with acryloyl chloride under basic conditions afforded the N-(3,5-bis((E)-3,4-difluorobenzylidene)-4-oxocyclohexyl)acrylamide. Michael addition of an amine, e.g., dimethylamine, afforded the N-(3,5-bis((E)-3,4-difluorobenzylidene)-4-oxocyclohexyl)-3-(dialkylamino)propanamide, e.g., N-(3,5-bis((E)-3,4-difluorobenzylidene)-4-oxocyclohexyl)-3-(dimethylamino)propanamide

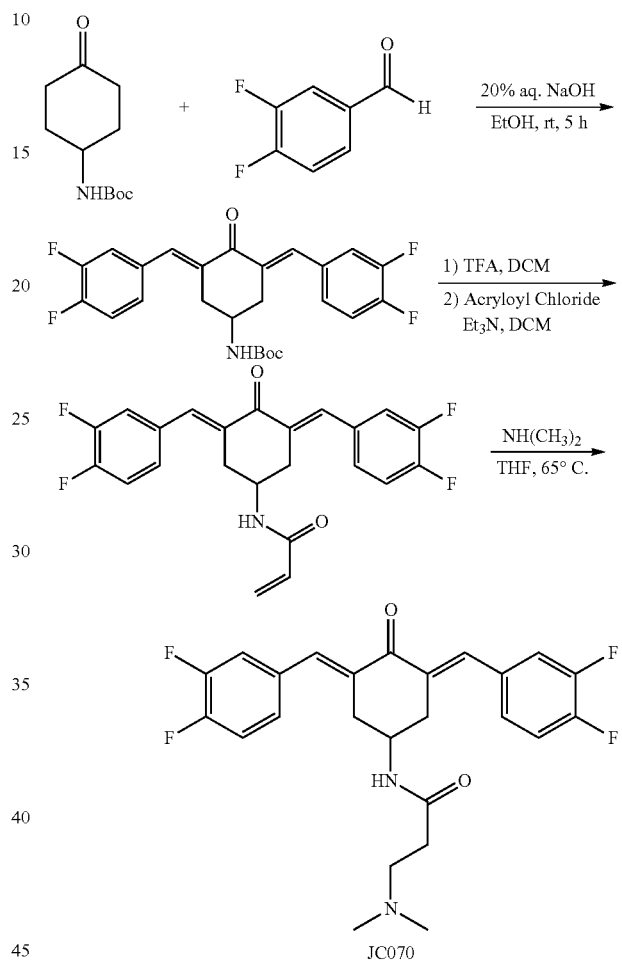

Preparation of JC070

To a mixture of tert-butyl (4-oxocyclohexyl)carbamate (213.28 mg, 1 mmol, 1.0 equiv.) and ethanol (1.0 mL) in a round bottom flask was added dropwise 20% aqueous sodium hydroxide (1.0 mL) and the reaction mixture was stirred for 5 min. To this mixture was added 3,4-difluorobenzaldehyde (355.3 mg, 2.5 mmol, 2.5 equiv.). The reaction mixture was then allowed to stir at 21° C. for 5 h, at which time a yellow solid had precipitated. The precipitate thus obtained was filtered, washed with water and cold ethanol and dried to get the pure bis(arylmethylidene)cyclohexanone product (360 mg, 78% yield).

Trifluoroacetic acid (0.5 ml) was added to a solution of tert-butyl (3,5-bis((E)-3,4-difluorobenzylidene)-4-oxocyclohexyl)carbamate (230.7 mg, 0.5 mmol) in methylene chloride (5.0 ml) at 21° C. and the reaction mixture was stirred overnight at 21° C. The reaction solvent was distilled off under reduced pressure and the resulting residue was poured into a 1N aqueous sodium hydroxide solution and extracted with ethyl acetate and chloroform. The organic layer was washed with a saturated aqueous sodium chloride solution and then dried over anhydrous magnesium sulfate. The solvent was distilled off under reduced pressure to obtain 4-amino-2,6-bis((E)-3,4-difluorobenzylidene)cyclohexan-1-one.

A mixture of 4-amino-2,6-bis((E)-3,4-difluorobenzylidene)cyclohexan-1-one (180.7 mg, 0.5 mmol, 1.0 equiv.) and anhydrous triethylamine (70 μL, 0.5 mmol, 1.0 equiv.) in dichloromethane was maintained at 0° C. (ice bath). To this cooled mixture was added dropwise acryloyl chloride (40 μL, 0.5 mmol, 1.0 equiv.). After the complete addition of the acryloyl chloride, the reaction mixture was slowly warmed up to 21° C. and stirred over night. After completion of the reaction, the solvent was evaporated and the residue thus obtained was washed with water, filtered and dried. The crude amide product was pure enough to be used for the next step.

A mixture of the crude N-(3,5-bis((E)-3,4-difluorobenzylidene)-4-oxocyclohexyl)acrylamide (207.7 mg, 0.5 mmol, 1.0 equiv.), 2,6-bis(1,1-dimethylethyl)-4-methylphenol (1.1 mg, 0.005 mmol, 1%) and dimethylamine (2N in THF) (0.375 mL, 0.75 mmol, 1.5 equiv.) in 1.0 mL anhydrous THF was heated to 65° C. under argon for 12 h. The solvent was evaporated and flash chromatography of the residue (gradient elution 10% methanol/EtOAC-20% methanol/EtOAc) gave the desired compound JC070 (170.4 mg, 74% yield) as a yellow solid.

The following compounds were synthesized by procedure C: JC070, JC080, JC097.

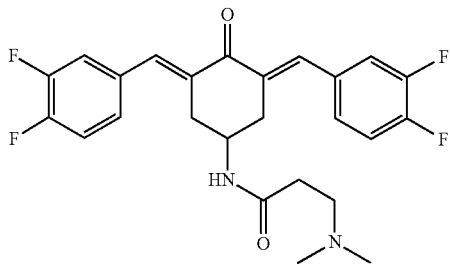 [SMILES: CN(C)CCC(=O)NC1C/C(=C\c2ccc(F)c(F)c2)C(=O)/C(=C/c2ccc(F)c(F)c2)C1]

N-(3,5-Bis((E)-3,4-difluorobenzylidene)-4-oxocyclohexyl)-3-(dimethylamino)propanamide (JC070)

$^1$H NMR (400 MHz, CDCl$_3$) δ 9.21 (s, 1H), 7.80 (s, 2H), 7.22 (m, 6H), 4.39 (m, 1H), 3.14 (dd, J=16.3 Hz, J=5.7 Hz, 2H), 3.01 (bd, J=15.7 Hz, 2H), 2.39 (t, J=5.5 Hz, 2H), 2.23 (t, J=5.5 Hz, 2H), 2.11 (s, 6H).

$^{13}$C NMR (126 MHz, CDCl$_3$) δ 187.9, 172.4, 150.6 (dd, J$_{CF}$=254 Hz, J$_{CF}$=13 Hz, 2C), 150.2 (dd, J$_{CF}$=250 Hz, J$_{CF}$=13 Hz, 2C), 137.6 (2C), 132.9 (2C), 132.3 (dd, J$_{C-C-CF}$=5.7 Hz, J$_{C-C-CF}$=4.3 Hz, 2C), 126.9 (dd, J$_{C-C-CF}$=6.3 Hz, J$_{C-C-CF}$=3.4 Hz, 2C), 118.9 (d, J$_{C-CF}$=18 Hz) (2C), 117.6 (d, J$_{C-CF}$=17 Hz) (2C), 54.9, 53.5, 44.2, 42.8 (2C), 33.3 (2C), 32.4.

$^{19}$F NMR (376 MHz, CDCl$_3$) δ -135.2 (m, 2F), -136.6 (m, 2F).

HR-APCI m/z calcd for C$_{25}$H$_{24}$F$_4$N$_2$O$_2$[M+H]= 461.18522, found 461.18461.

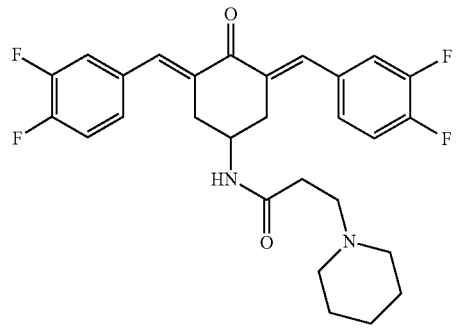 [SMILES: O=C(CCN1CCCCC1)NC1C/C(=C\c2ccc(F)c(F)c2)C(=O)/C(=C/c2ccc(F)c(F)c2)C1]

N-(3,5-Bis((E)-3,4-difluorobenzylidene)-4-oxocyclohexyl)-3-(piperidin-1-yl)propanamide (JC080)

$^1$H NMR (400 MHz, CDCl$_3$) δ 9.11 (s, 1H), 7.79 (s, 2H), 7.22 (m, 6H), 4.37 (m, 1H), 3.12 (bd, J=15.8 Hz, 2H), 3.04 (dd, J=16.2 Hz, J=6.0 Hz, 2H), 2.48 (t, J=5.6 Hz, 2H), 2.39 (m, 4H), 2.31 (t, J=5.8 Hz, 2H), 1.50 (m, 6H).

$^{13}$C NMR (126 MHz, CDCl$_3$) δ 187.8, 172.1, 150.6 (dd, J$_{CF}$=252 Hz, J$_{C-CF}$=13 Hz, 2C), 150.2 (dd, J$_{CF}$=248 Hz, J$_{C-CF}$=13 Hz, 2C), 137.6 (2C), 132.9 (2C), 132.3 (dd, J$_{C-C-CF}$=5.9 Hz, J$_{C-C-CF}$=4.1 Hz, 2C), 127.1 (dd, J$_{C-C-CF}$=6.3 Hz, J$_{C-C-CF}$=3.4 Hz, 2C), 118.8 (d, J$_{C-CF}$=18 Hz, 2C), 117.6 (d, J$_{C-CF}$=18 Hz, 2C), 54.3, 53.7, 43.3, 33.6, 31.5, 25.4, 23.8.

HR-APCI m/z calcd for C$_{28}$H$_{28}$F$_4$N$_2$O$_2$[M+H]= 501.21652, found 501.21594.

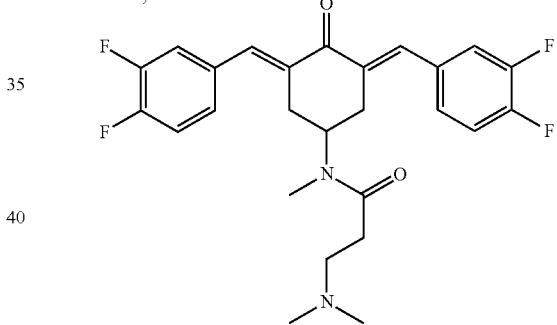

N-(3,5-Bis((E)-3,4-difluorobenzylidene)-4-oxocyclohexyl)-3-(dimethylamino)-N-methylpropanamide (JC097)

$^1$H NMR (500 MHz, CDCl$_3$) δ 7.76 (br s, 2H), 7.20 (m, 6H), 4.77 (m, 1H), 3.04 (s, 3H), 2.98 (dd, J=16.3 Hz, J=5.8 Hz, 2H), 2.92 (bd, J=15.7 Hz, 2H), 2.62 (t, J=5.7 Hz, 2H), 2.51 (t, J=5.8 Hz, 2H), 2.25 (s, 6H).

$^{13}$C NMR (126 MHz, CDCl$_3$) δ 187.8, 171.7, 150.5 (dd, J$_{CF}$=255 Hz, J$_{CF}$=13 Hz, 2C), 150.2 (dd, J$_{CF}$=255 Hz, J$_{CF}$=13 Hz, 2C), 137.4, 136.8, 133.9 (2C), 132.3 (dd, J$_{C-C-CF}$=5.9 Hz, J$_{C-C-CF}$=4.3 Hz, 2C), 127.1 (dd, J$_{C-C-CF}$=6.0 Hz, J$_{C-C-CF}$=3.8 Hz, 2C), 118.8 (d, J$_{C-CF}$=18 Hz, 2C), 117.6 (d, J$_{C-CF}$=17 Hz, 2C), 54.9, 49.1, 45.5, 32.6, 31.2, 30.3.

General Procedure D:

The compounds were generally prepared by reaction of the corresponding aldehydes, e.g., 3,4-difluorobenzaldehyde, with tert-butyl (4-oxocyclohexyl)carbamate in the present of 20% aq. sodium hydroxide to give tert-butyl (3,5-bis((E)-3,4-difluorobenzylidene)-4-oxocyclohexyl)carbamate. TFA deprotected Boc group. Benzoylation of 4-amino-2,6-bis((E)-3,4-difluorobenzylidene)cyclohexan-1-one with 4-(2-(dialkylamino)ethoxy)benzoyl chloride under base condition afforded the N-(3,5-bis((E)-3,4-difluorobenzylidene)-4-oxocyclohexyl)-4-(2-(dimethylamino)ethoxy)benzamide.

Compounds JC081-JC087 and their analogues were generally prepared by reaction of the 3,4-difluorobenzaldehyde, with tert-butyl (4-oxocyclohexyl)carbamate in the present of 20% aq. sodium hydroxide to give tert-butyl (3,5-bis((E)-3,4-difluorobenzylidene)-4-oxocyclohexyl)carbamate. The Boc protecting group was deprotected with TFA. Benzoylation of 4-amino-2,6-bis((E)-3,4-difluoro-benzylidene)cyclohexan-1-one with 4-(2-(dialkylamino)ethoxy)benzoyl chloride under basic conditions afforded the desired N-(3,5-bis((E)-3,4-difluorobenzylidene)-4-oxocyclohexyl)-4-(2-(dimethylamino)-ethoxy)benzamide.

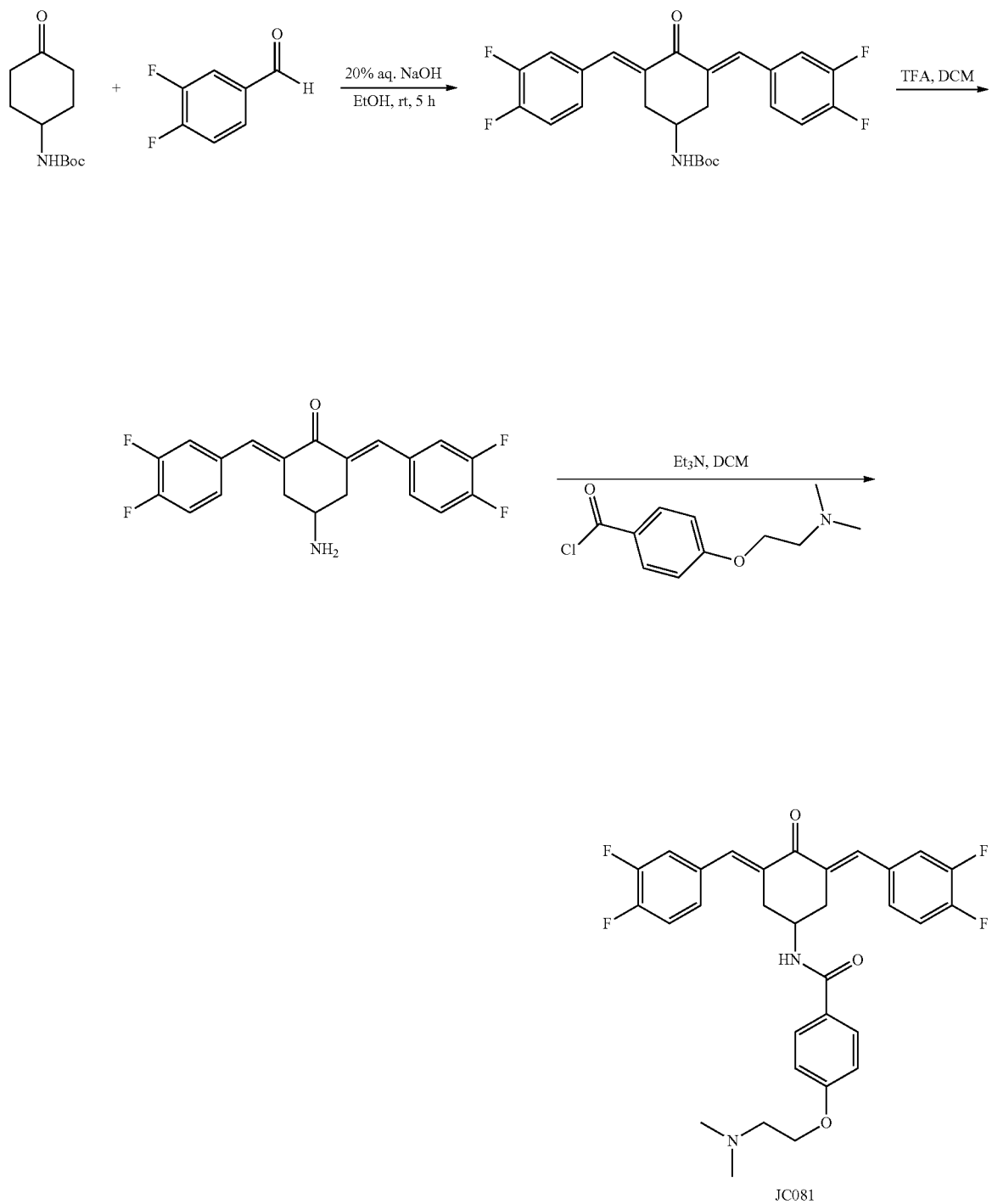

Preparation of JC081

To the mixture of tert-butyl (4-oxocyclohexyl)carbamate (213.28 mg, 1 mmol, 1.0 equiv.) and ethanol (1.0 mL) in a round bottom flask was added dropwise 20% aqueous sodium hydroxide (1.0 mL) and the reaction mixture was stirred for 5 min. To this mixture was added 3,4-difluorobenzaldehyde (355.3 mg, 2.5 mmol, 2.5 equiv.). The reaction mixture was then allowed to stir at 21° C. for 5 h, at which time a yellow solid had precipitated. The precipitate thus obtained was filtered, washed with water, cold ethanol and dried to get the pure bis(arylmethylidene)cyclohexanone product (360 mg, 78% yield).

Trifluoroacetic acid (0.5 ml) was added to a solution of tert-butyl (3,5-bis((E)-3,4-difluorobenzylidene)-4-oxocyclohexyl)carbamate (230.7 mg, 0.5 mmol) in methylene chloride (5.0 ml) at 21° C. and the reaction mixture was stirred overnight at 21° C. The reaction solvent was distilled off under reduced pressure and the resulting residue was poured into a 1N aqueous sodium hydroxide solution and extracted with ethyl acetate and chloroform. The organic layer was washed with a saturated aqueous sodium chloride solution and then dried over anhydrous magnesium sulfate. The solvent was distilled off under reduced pressure to obtain 4-amino-2,6-bis((E)-3,4-difluorobenzylidene)cyclohexan-1-one.

The mixture of 4-amino-2,6-bis((E)-3,4-difluorobenzylidene)cyclohexan-1-one (180.7 mg, 0.5 mmol, 1.0 equiv.) and anhydrous triethylamine (70 µL, 0.5 mmol, 1.0 equiv.) in dichloromethane was maintained at 0° C. (ice bath). To this cooled mixture was added dropwise 4-(2-(dimethylamino)ethoxy)benzoyl chloride (113.8 mg, 0.5 mmol, 1.0 equiv., synthesized as described below) in 2.0 mL dichloromethane. After the complete addition of the 4-(2-(dimethylamino)ethoxy)benzoyl chloride, the reaction mixture was slowly warmed up to 21° C. and stirred overnight. After completion of the reaction, the solvent was evaporated and the residue was stirred in sat. aqueous $K_2CO_3$ for 4 h. The mixture was extracted with ethyl acetate and dichloromethane three times. The organic layer was washed with a saturated aqueous sodium chloride solution and then dried over anhydrous sodium sulfate. The solvent was evaporated and flash chromatography of the residue (gradient elution 5% methanol/EtOAC-10% methanol/EtOAc) gave the desired compound JC081 (226.5 mg, 82% yield) as a yellow solid.

Synthesis of 4-(2-(dimethylamino)ethoxy)benzoyl chloride Method 1

To a round bottom flask with a stir-bar were added methyl 4-hydroxybenzoate (3.043 g, 20 mmol, 1.0 equiv.), 2-chloro-N,N-dimethylethylamine hydrochloride (3.457 g, 24 mmol, 1.2 equiv.), potassium carbonate (6.081 g, 44 mmol, 2.2 equiv.) and 30 mL isopropyl acetate. The mixture was heated at 75° C. for 24 h, at which time all the methyl 4-hydroxybenzoate was consumed. Deionized water (30 mL) was then added to dissolve the potassium carbonate. The organic and aqueous phases were separated. The organic layer was washed with 30 mL water. The organic layer was washed with a saturated aqueous sodium chloride solution and then dried over anhydrous magnesium sulfate. The solvent was evaporated and flash chromatography of the residue (gradient elution 5% methanol/EtOAc-10% methanol/EtOAc) gave the product, methyl 4-(2-(dimethylamino)ethoxy)benzoate (2.0 g, 45% yield), as a light yellow oil.

Methyl 4-(2-(dimethylamino)ethoxy)benzoate (1.116 g, 5.0 mmol, 1.0 equiv.) was dissolved in 2.5 mL ethanol and added to a solution of sodium hydroxide (0.4 g) in 2.5 mL of deionized water. The mixture was heated under reflux for 2 h. The ethanol was removed in vacuo and the aqueous solution was acidified with conc. HCl at 5-6° C. The solid was collected, treated with cold water, filtered and dried at 55-60° C. in vacuo to give 4-(2-(dimethylamino)ethoxy) benzoic acid hydrogen chloride as a white sold (982.8 mg, 80% yield).

To a stirred mixture of 4-(2-(dimethylamino)ethoxy)benzoic acid hydrogen chloride (245.7 mg, 1.0 mmol) was added thionyl chloride (2.5 mL). The mixture was heated under reflux for 4 h. The thionyl chloride was removed in vacuo and the product dried to give 4-(2-(dimethylamino)ethoxy)benzoyl chloride, which was enough pure to be used for the next step.

The following compounds were synthesized by procedure D: JC064, JC065, JC066, JC067, JC081, JC082, JC083, JC084, JC085, JC086, JC087, JC099, JC100, JC102, JC103, JC104, JC105, JC106, JC109, JC110, JC111, JC112, JC113, JC114, JC115, JC116, JC117, JC118, JC122, JC123, JC124, JC125, JC126, JC127, JC128, JC131, JC132, JC133, JC134, JC135, JC144.

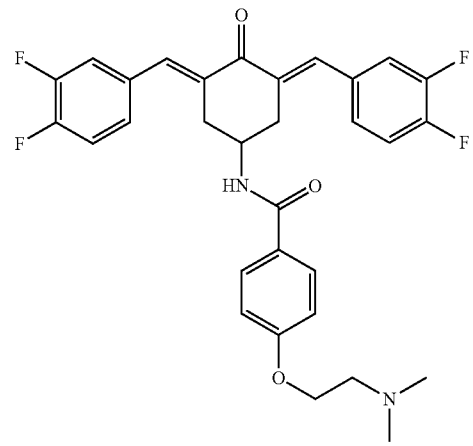 [SMILES: CN(C)CCOc1ccc(C(=O)NC2C/C(=C\c3ccc(F)c(F)c3)C(=O)/C(=C/c3ccc(F)c(F)c3)C2)cc1]

N-(3,5-Bis((E)-3,4-difluorobenzylidene)-4-oxocyclohexyl)-4-(2-(dimethylamino)ethoxy)benzamide (JC081)

$^1$H NMR (400 MHz, CDCl$_3$) δ 7.78 (br s, 2H), 7.63 (d, J=8.8 Hz, 2H), 7.22 (m, 6H), 6.89 (d, J=8.8 Hz, 2H), 6.01 (d, J=7.2 Hz, 1H), 4.48 (m, 1H), 4.10 (t, J=5.6 Hz, 2H), 3.26 (bd, J=15.8 Hz, 2H), 3.07 (dd, J=16.3 Hz, J=5.8 Hz, 2H), 2.78 (t, J=5.6 Hz, 2H), 2.36 (s, 6H).

$^{13}$C NMR (126 MHz, CDCl$_3$) δ 187.9, 166.6, 161.6, 150.7 (dd, $J_{CF}$=254 Hz, $J_{C-CF}$=13 Hz, 2C), 150.3 (dd, $J_{CF}$=250 Hz, $J_{C-CF}$=13 Hz, 2C), 137.9 (2C), 132.7 (2C), 132.2 (dd, $J_{C-C-CF}$=5.7 Hz, $J_{C-C-CF}$=4.1 Hz, 2C), 128.7 (2C), 127.1 (dd, $J_{C-C-CF}$=6.2 Hz, $J_{C-C-CF}$=3.4 Hz, 2C), 126.3, 118.9 (d, $J_{C-CF}$=18 Hz, 2C), 117.7 (d, $J_{C-CF}$=18 Hz, 2C), 114.4 (2C), 65.9, 58.1, 45.8, 44.6, 33.8

HR-APCI m/z calcd for $C_{31}H_{28}F_4N_2O_3$[M+H]= 553.21143, found 553.21034.

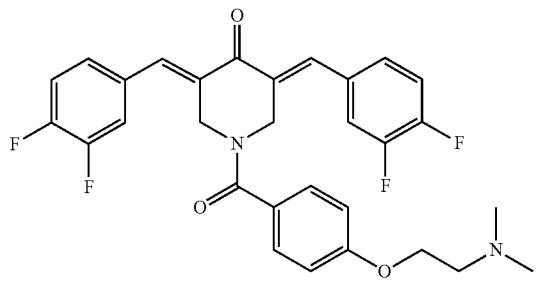 [SMILES: CN(C)CCOc1ccc(C(=O)N2C/C(=C\c3ccc(F)c(F)c3)C(=O)/C(=C/c3ccc(F)c(F)c3)C2)cc1]

3,5-Bis((E)-3,4-difluorobenzylidene)-1-(4-(2-(dimethylamino)ethoxy)benzoyl)piperidin-4-one (JC064)

¹H NMR (400 MHz, CDCl₃) δ 7.74 (br s, 2H), 7.15 (m, 8H), 6.64 (d, J=8.8 Hz, 2H), 4.79 (br s, 4H), 3.98 (t, J=5.7 Hz, 2H), 2.72 (t, J=5.7 Hz, 2H), 2.34 (s, 6H).

¹³C NMR (126 MHz, CDCl₃) δ 186.1, 169.8, 164.2, 151.1 (dd, $J_{CF}$=253 Hz, $J_{C-CF}$=13 Hz, 2C), 150.4 (dd, $J_{CF}$=249 Hz, $J_{C-CF}$=13 Hz, 2C), 132.6, 132.4 (2C), 132.1, 131.9 (2C), 131.3, 128.3, 122.2, 121.8, 121.5, 119.1 (d, $J_{C-CF}$=18 Hz, 2C), 117.9 (d, $J_{C-CF}$=17 Hz, 2C), 114.5, 114.4, 65.9, 65.8, 57.8, 45.5, 29.7.

HR-APCI m/z calcd for C₃₀H₂₆F₄N₂O₃[M+H]= 539.19578, found 539.19473.

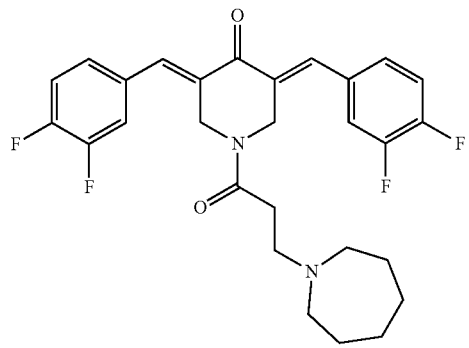

1-(3-(Azepan-1-yl)propanoyl)-3,5-bis((E)-3,4-difluorobenzylidene)piperidin-4-oneone (JC066)

¹H NMR (400 MHz, CDCl₃) δ 7.70 (s, 2H), 7.30 (m, 6H), 4.83 (s, 2H), 4.76 (s, 2H), 3.09 (t, J=7.0 Hz, 2H), 2.89 (m, 4H), 2.76 (t, J=7.0 Hz, 2H), 1.75 (m, 4H), 1.62 (m, 4H).

¹³C NMR (126 MHz, CDCl₃) δ 186.0, 169.5, 150.9 (dd, $J_{CF}$=254 Hz, $J_{C-CF}$=13 Hz, 2C), 150.4 (dd, $J_{CF}$=254 Hz, $J_{C-CF}$=13 Hz, 2C), 136.3, 135.8, 132.2 (dd, $J_{C-C-CF}$=6.2 Hz, $J_{C-C-CF}$=3.4 Hz, 2C), 131.5, 127.2 (dd, $J_{C-C-CF}$=5.8 Hz, $J_{C-C-CF}$=3.6 Hz, 2C), 126.9, 119.3 (d, $J_{C-CF}$=17 Hz, 2C), 118.4 (d, $J_{C-CF}$=17 Hz), 118.0 (d, $J_{C-CF}$=17 Hz), 55.2, 53.2, 46.3, 43.1, 29.7, 26.8, 25.4.

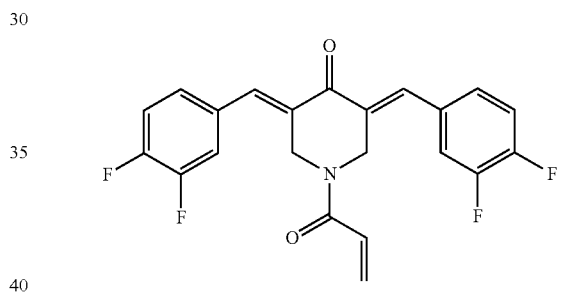

1-Acryloyl-3,5-bis((E)-3,4-difluorobenzylidene)piperidin-4-one (JC067)

¹H NMR (400 MHz, CDCl₃) δ 7.71 (br s, 2H), 7.21 (m, 6H), 6.25 (m, 2H), 5.62 (dd, J=10.0, 2.3 Hz, 1H), 4.84 (br s, 4H).

¹³C NMR (126 MHz, CDCl₃) δ 185.8, 165.5, 150.9 (dd, $J_{CF}$=254 Hz, $J_{C-CF}$=14 Hz, 2C), 150.4 (dd, $J_{CF}$=254 Hz, $J_{C-CF}$=14 Hz, 2C), 136.4, 135.4, 132.0 (dd, $J_{C-C-CF}$=6.2 Hz, $J_{C-C-CF}$=3.4 Hz, 2C), 131.4 (2C), 129.5, 127.1 (dd, $J_{C-C-CF}$=6.2 Hz, $J_{C-C-CF}$=3.4 Hz, 2C), 126.9, 119.0 (d, $J_{C-CF}$=18 Hz, 2C), 117.2 (d, $J_{C-CF}$=18 Hz, 2C), 46.5, 43.6.

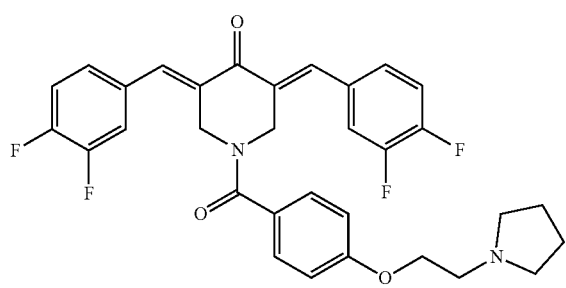 [SMILES: O=C1/C(=C/c2ccc(F)c(F)c2)CN(C(=O)c2ccc(OCCN3CCCC3)cc2)C/C1=C\c1ccc(F)c(F)c1]

3,5-Bis((E)-3,4-difluorobenzylidene)-1-(4-(2-(pyrrolidin-1-yl)ethoxy)benzoyl)piperidin-4-one (JC065)

¹H NMR (400 MHz, CDCl₃) δ 7.75 (br s, 2H), 7.19 (m, 8H), 6.65 (d, J=8.8 Hz, 2H), 4.81 (br s, 4H), 4.03 (t, J=5.9 Hz, 2H), 2.89 (t, J=5.8 Hz, 2H), 2.63 (m, 4H), 1.83 (m, 4H).

¹³C NMR (126 MHz, CDCl₃) δ 186.3, 170.4, 160.5, 150.9 (dd, $J_{CF}$=254 Hz, $J_{C-CF}$=14 Hz, 2C), 150.4 (dd, $J_{CF}$=254 Hz, $J_{C-CF}$=14 Hz, 2C), 135.8 (2C), 132.4 (2C), 131.4 (2C), 129.0, 127.0 (2C), 125.9, 119.0 (d, $J_{C-CF}$=17 Hz, 2C), 117.8 (d, $J_{C-CF}$=17 Hz, 2C), 114.0, 67.0, 54.8, 54.7, 23.5.

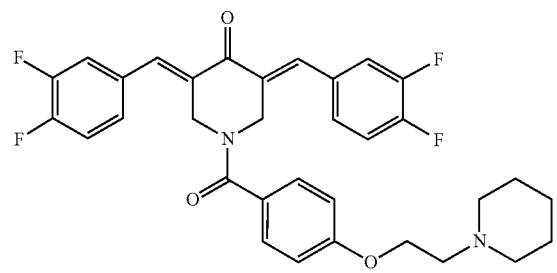 [SMILES: O=C1/C(=C/c2ccc(F)c(F)c2)CN(C(=O)c2ccc(OCCN3CCCCC3)cc2)C/C1=C\c1ccc(F)c(F)c1]

3,5-Bis((E)-3,4-difluorobenzylidene)-1-(4-(2-(piperidin-1-yl)ethoxy)benzoyl)piperidin-4-one (JC082)

$^1$H NMR (500 MHz, CDCl$_3$) δ 7.74 (br s, 2H), 7.12 (m, 8H), 6.62 (d, J=8.6 Hz, 2H), 4.79 (br s, 4H), 4.03 (t, J=5.9 Hz, 2H), 2.77 (t, J=5.8 Hz, 2H), 2.44 (m, 4H), 1.63 (m, 4H), 1.43 (m, 2H).

$^{13}$C NMR (126 MHz, CDCl$_3$) δ 186.2, 170.5, 160.5, 151.0 (dd, J$_{CF}$=255 Hz, J$_{C—CF}$=13 Hz, 2C), 150.3 (dd, J$_{CF}$=250 Hz, J$_{C—CF}$=13 Hz, 2C), 135.9 (2C), 132.4 (2C), 131.4 (dd, J$_{C—C—CF}$=5.4 Hz, J$_{C—C—CF}$=4.2 Hz 2C), 129.0 (2C), 126.9 (2C), 125.9, 118.9 (d, J$_{C—CF}$=18 Hz, 2C), 117.9 (d, J$_{C—CF}$=18 Hz, 2C), 114.1 (2C), 65.9, 57.7, 55.0, 25.8, 24.1.

HR-APCI m/z calcd for C$_{33}$H$_{30}$F$_4$N$_2$O$_3$ [M+H]= 579.22708, found 579.22644.

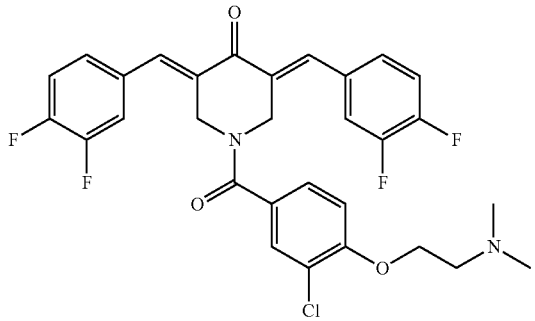 [SMILES: CN(C)CCOc1ccc(C(=O)N2C/C(=C\c3ccc(F)c(F)c3)C(=O)/C(=C/c3ccc(F)c(F)c3)C2)cc1Cl]

1-(3-Chloro-4-(2-(dimethylamino)ethoxy)benzoyl)-3,5-bis((E)-3,4 difluorobenzylidene) piperidin-4-one (JC083)

$^1$H NMR (500 MHz, CDCl$_3$) δ 7.75 (br s, 2H), 7.24 (d, J=2.0 Hz, 1H), 7.17 (m, 6H), 7.10 (dd, J=8.4, 2.0 Hz, 1H), 6.63 (d, J=8.4 Hz, 1H), 4.78 (s, 4H), 4.05 (t, J=5.7 Hz, 2H), 2.79 (t, J=5.7 Hz, 2H), 2.37 (s, 6H).

$^{13}$C NMR (126 MHz, CDCl$_3$) δ 185.9, 168.9, 155.8, 150.9 (dd, J$_{CF}$=254 Hz, J$_{C—CF}$=14 Hz, 2C), 150.4 (dd, J$_{CF}$=254 Hz, J$_{C—CF}$=14 Hz, 2C), 135.9 (2C), 132.1 (2C), 131.3 (2C), 129.3, 127.2, 127.0 (2C), 126.8, 122.8, 118.8 (d, J$_{C—CF}$=17 Hz, 2C), 117.8 (d, J$_{C—CF}$=17 Hz, 2C), 112.2, 67.5, 57.6, 52.1, 45.9.

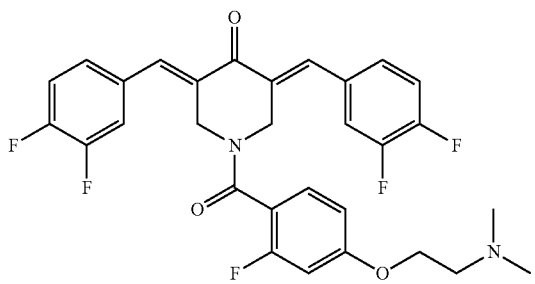 [SMILES: CN(C)CCOc1ccc(C(=O)N2C/C(=C\c3ccc(F)c(F)c3)C(=O)/C(=C/c3ccc(F)c(F)c3)C2)c(F)c1]

3,5-Bis((E)-3,4-difluorobenzylidene)-1-(4-(2-(dimethylamino)ethoxy)-2-fluorobenzoyl)piperidin-4-one (JC084)

$^1$H NMR (500 MHz, CDCl$_3$) δ 7.75 (br s, 2H), 7.24 (d, J=2.0 Hz, 1H), 7.18 (m, 6H), 7.10 (dd, J=8.4, 2.0 Hz, 1H), 6.63 (d, J=8.4 Hz, 1H), 4.78 (br. s, 4H), 4.05 (t, J=5.7 Hz, 2H), 2.79 (t, J=5.7 Hz, 2H), 2.37 (s, 6H).

$^{13}$C NMR (126 MHz, CDCl$_3$) δ 185.9, 169.0, 151.7 (d, J$_{CF}$=252 Hz), 150.9 (dd, J$_{CF}$=254 Hz, J$_{C—CF}$=14 Hz, 2C), 150.4 (dd, J$_{CF}$=254 Hz, J$_{C—CF}$=14 Hz, 2C), 148.6 (d, J$_{C—CF}$=11 Hz), 136.0 (2C), 132.2 (2C), 131.3 (2C), 127.0 (2C), 126.5, 123.7, 119.0 (d, J$_{C—CF}$=17 Hz, 2C), 117.9 (d, J$_{C—CF}$=17 Hz, 2C), 115.6 (d, J$_{C—CF}$=20 Hz), 113.8, 67.5, 57.8, 56.2, 45.8.

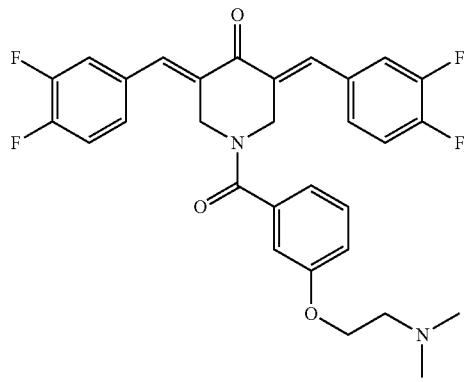 [SMILES: CN(C)CCOc1cccc(C(=O)N2C/C(=C\c3ccc(F)c(F)c3)C(=O)/C(=C/c3ccc(F)c(F)c3)C2)c1]

3,5-Bis((E)-3,4-difluorobenzylidene)-1-(3-(2-(dimethylamino)ethoxy)benzoyl)piperidin-4-one (JC085)

$^1$H NMR (400 MHz, CDCl$_3$) δ 7.72 (s, 1H), 7.59 (s, 1H), 7.34 (m, 1H), 7.22 (m, 3H), 7.09 (m, 1H), 7.03 (m, 1H), 6.83 (m, 3H), 6.72 (m, 1H), 5.09 (s, 1H), 4.93 (s, 1H), 4.48 (s, 2H), 3.99 (m, 2H), 2.72 (m, 2H), 2.33 (s, 6H).

$^{13}$C NMR (126 MHz, CDCl$_3$) δ 186.2, 168.0, 154.1, 151.0 (dd, J$_{CF}$=254 Hz, J$_{C—CF}$=14 Hz), 150.6 (dd, J$_{CF}$=254 Hz, J$_{C—CF}$=14 Hz), 150.4 (dd, J$_{CF}$=254 Hz, J$_{C—CF}$=14 Hz), 150.0 (dd, J$_{CF}$=254 Hz, J$_{C—CF}$=14 Hz), 136.5, 134.6, 132.6, 132.0, 131.5 (dd, J$_{C—C—CF}$=6.0 Hz, J$_{C—C—CF}$=4.2 Hz), 131.2 (dd, J$_{C—C—CF}$=5.2 Hz, J$_{C—C—CF}$=3.8 Hz), 131.0 (2C), 127.8, 127.5 (dd, J$_{C—C—CF}$=5.8 Hz, J$_{C—C—CF}$=3.9 Hz), 126.6 (dd, J$_{C—C—CF}$=6.1 Hz, J$_{C—C—CF}$=3.2 Hz), 124.3, 121.3, 119.4 (d, J$_{C—CF}$=17 Hz), 118.3 (d, J$_{C—CF}$=17 Hz), 117.9 (d, J$_{C—CF}$=17 Hz), 117.6 (d, J$_{C—CF}$=17 Hz), 66.3, 57.4, 46.9, 45.5, 43.0.

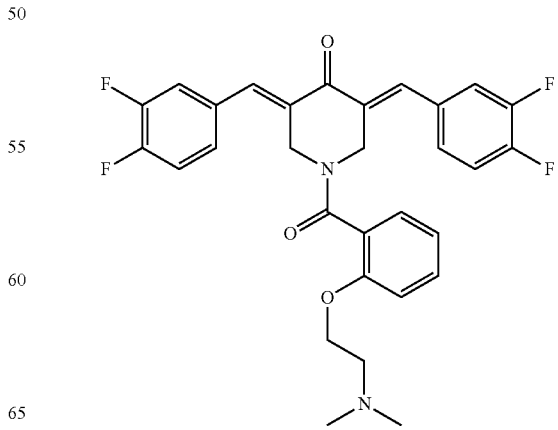

3,5-Bis((E)-3,4-difluorobenzylidene)-1-(2-(2-(dimethylamino)ethoxy)benzoyl)piperidin-4-one (JC086)

$^1$H NMR (400 MHz, CDCl$_3$) δ 7.72 (br s, 2H) 7.15 (m, 6H), 6.99 (m, 1H), 6.83 (m, 1H), 6.81 (m, 1H), 6.71 (m, 1H), 4.78 (br s, 4H), 3.93 (t, J=5.7 Hz, 2H), 2.68 (t, J=5.7 Hz, 2H), 2.31 (s, 6H).

$^{13}$C NMR (100 MHz, CDCl$_3$) δ 186.0, 170.2, 158.7, 151.0 (dd, $J_{CF}$=254 Hz, $J_{C-CF}$=14 Hz, 2C), 150.4 (dd, $J_{CF}$=254 Hz, $J_{C-CF}$=14 Hz, 2C), 136.5 (2C), 135.3, 132.1 (2C), 131.3 (2C), 129.3, 126.8 (2C), 119.0, 118.7 (d, $J_{C-CF}$=18 Hz, 2C), 117.8 (d, $J_{C-CF}$=17 Hz, 2C), 116.3, 113.2, 66.1, 65.6, 58.0, 57.9, 45.7.

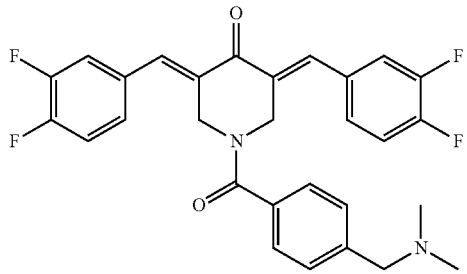 [SMILES: CN(C)Cc1ccc(C(=O)N2C/C(=C\c3ccc(F)c(F)c3)C(=O)/C(=C/c3ccc(F)c(F)c3)C2)cc1]

3,5-Bis((E)-3,4-difluorobenzylidene)-1-(4-((dimethylamino)methyl)benzoyl)piperidin-4-one (JC087)

$^1$H NMR (400 MHz, (CD$_3$)$_2$CO)) δ 7.71 (br s, 2H), 7.38 (m, 6H), 7.15 (d, J=5.7 Hz, 2H), 7.08 (d, J=5.7 Hz, 2H), 4.87 (br s, 4H), 3.27 (s, 2H), 2.06 (s, 6H).

$^{13}$C NMR (126 MHz, CDCl$_3$) δ 186.1, 170.5, 151.0 (dd, $J_{CF}$=254 Hz, $J_{C-CF}$=14 Hz, 2C), 150.4 (dd, $J_{CF}$=254 Hz, $J_{C-CF}$=14 Hz, 2C), 141.5, 136.6 (2C), 132.6, 132.2 (2C), 131.4 (2C), 128.8, 127.0 (2C), 126.8, 118.9 (d, $J_{C-CF}$=18 Hz, 2C), 117.9 (d, $J_{C-CF}$=18 Hz, 2C), 63.7, 56.0, 45.0.

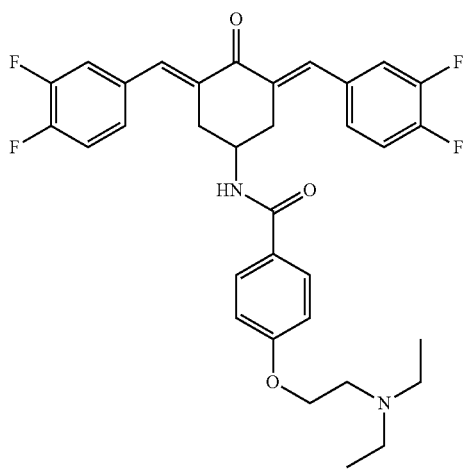 [SMILES: CCN(CC)CCOc1ccc(C(=O)NC2C/C(=C\c3ccc(F)c(F)c3)C(=O)/C(=C/c3ccc(F)c(F)c3)C2)cc1]

N-(3,5-Bis((E)-3,4-difluorobenzylidene)-4-oxocyclohexyl)-4-(2-(diethylamino)ethoxy)benzamide (JC099)

To a mixture of the tert-butyl (4-oxocyclohexyl)carbamate (213.28 mg, 1 mmol, 1.0 equiv) and ethanol (1.0 mL) in a round bottom flask was added dropwise 20% aqueous sodium hydroxide (1.0 mL) and the reaction mixture was stirred for 5 min. To this mixture was added 3,4-difluorobenzaldehyde (355.3 mg, 2.5 mmol, 2.5 equiv). The reaction mixture was then allowed to stir at 21° C. for 5 h. The yellow precipitate thus obtained was filtered, washed with water and cold ethanol and dried to get the pure product (360 mg, 78% yield).

Trifluoroacetic acid (0.5 ml) was added to a solution of tert-butyl (3,5-bis((E)-3,4-difluorobenzylidene)-4-oxocyclohexyl)carbamate (230.7 mg, 0.5 mmol) in methylene chloride (5.0 ml) at 21° C. and the mixture was stirred overnight at 21° C. The reaction solution was distilled off under reduced pressure and the resulting residue was poured into a 1N-aqueous sodium hydroxide solution and extracted with ethyl acetate and chloroform. The organic layer was washed with a saturated aqueous sodium chloride solution and then dried over anhydrous magnesium sulfate. The solvent was distilled off under reduced pressure to obtain 4-amino-2,6-bis((E)-3,4-difluorobenzylidene)cyclohexan-1-one.

A mixture of 4-amino-2,6-bis((E)-3,4-difluorobenzylidene)cyclohexan-1-one (180.7 mg, 0.5 mmol, 1.0 equiv.) and anhydrous triethylamine (70 µL, 0.5 mmol, 1.0 equiv.) in dichloromethane was maintained at 0° C. (ice bath). To this cooled mixture was added dropwise 4-(2-(diethylamino)ethoxy)benzoyl chloride (127.9 mg, 0.5 mmol, 1.0 equiv.) in 2.0 mL dichloromethane. After the complete addition of the acid chloride, the reaction mixture was slowly warmed up to 21° C. and stirred overnight. The reaction solvent was evaporated under reduced pressure and the residue was stirred with satd. aqueous K$_2$CO$_3$ for 4 h. The mixture was extracted three times with ethyl acetate and dichloromethane. The organic layer was washed with a satd. aqueous sodium chloride solution and then dried over anhydrous sodium sulfate. The solvent was evaporated, followed by flash chromatography on silica gel (gradient elution 10% methanol/EtOAc-15% methanol/EtOAc) to give the desired compound JC099 (250 mg, 86% yield) as a yellow solid.

Synthesis of 4-(2-(diethylamino)ethoxy)benzoyl chloride Method 2

Methyl 4-hydroxybenzoate (5.0 g, 32.86 mmol, 10. equiv) was combined with 1,2-dibromoethane (35 mL) and potassium carbonate (6.8 g, 49.23 mmol, 1.5 equiv) then the mixture was heated at reflux for 18 h. The reaction mixture was concentrated under reduced pressure and then the residue was partitioned between ethyl ether (300 mL) and water (200 mL). The ether layer was extracted with 2 N sodium hydroxide (5×30 mL). The solvent was removed to give the desired product as a white solid (8.5 g, 99% yield).

To a round bottom flask equipped with a stir-bar was added a solution of methyl 4-(2-bromoethoxy)-benzoate (2.591 g, 10 mmol, 1.0 equiv), DMF (20 mL), potassium carbonate (4.146 g, 30 mmol, 3.0 equiv) and diethylamine (3.1 mL, 30 mmol, 3.0 equiv). The mixture was heated at 75° C. for 24 h, after which time EtOAc (200 mL) and water (200 mL) were added. The organic layer was washed with water three times and then dried over sodium sulfate. The pure product was obtained by flash chromatography on silica gel (gradient elution 10% methanol/DCM-15% methanol/DCM) to give the desired product, methyl 4-(2-(diethylamino)ethoxy)benzoate (1.281 g, 51% yield), as a light brown oil.

Methyl 4-(2-(diethylamino)ethoxy)benzoate (1.116 g, 5.0 mmol, 1.0 equiv) was dissolved in 2.5 mL ethanol and added to a solution of sodium hydroxide (0.4 g) in 2.5 mL water. The mixture was heated under reflux for 2 h. The ethanol was removed in vacuo and the aqueous solution was acidified with conc. HCl at 5° C. The solid was collected, treated with cold water, filtered and dried at 55-60° C. in vacuo to give 4-(2-(diethylamino)ethoxy)benzoic acid hydrochloride as white sold (1.149 g, 84% yield).

To a stirred mixture of 4-(2-(diethylamino)ethoxy)benzoic acid hydrochloride (273.76 mg, 1.0 mmol) was added thionyl chloride (2.5 mL). The mixture was heated at reflux for 4 h. The thionyl chloride was removed in vacuo and the residue dried to give 4-(2-(diethylamino)ethoxy)benzoyl chloride which was enough pure to be used for next step.

$^1$H NMR (400 MHz, CDCl$_3$) δ 7.81 (s, 2H), 7.63 (d, J=8.9 Hz, 2H), 7.21 (m, 6H), 6.89 (d, J=8.9 Hz, 2H), 6.07 (d, J=7.0 Hz, 1H), 4.50 (m, 1H), 4.14 (t, J=5.5 Hz, 2H), 3.26 (bd, J=15.8 Hz, 2H), 3.07 (dd, J=16.4 Hz, J=5.6 Hz, 2H), 2.96 (t, J=5.0 Hz, 2H), 2.73 (m, 4H), 1.12 (t, J=7.1 Hz, 6H).

$^{13}$C NMR (126 MHz, CDCl$_3$) δ 187.9, 166.6, 161.6, 150.7 (dd, J$_{CF}$=254 Hz, J$_{C-CF}$=13 Hz, 2C), 150.3 (dd, J$_{CF}$=250 Hz, J$_{C-CF}$=13 Hz, 2C), 137.8 (2C), 132.8 (2C), 132.2 (dd, J$_{C-C-CF}$=5.9 Hz, J$_{C-C-CF}$=4.2 Hz, 2C), 128.7 (2C), 127.1 (dd, J$_{C-C-CF}$=6.4 Hz, J$_{C-C-CF}$=3.5 Hz, 2C), 126.3, 118.9 (d, J$_{C-CF}$=18 Hz, 2C), 117.7 (d, J$_{C-CF}$=18 Hz, 2C), 114.4 (2C), 66.5, 51.5, 47.9, 44.6, 33.8, 11.5.

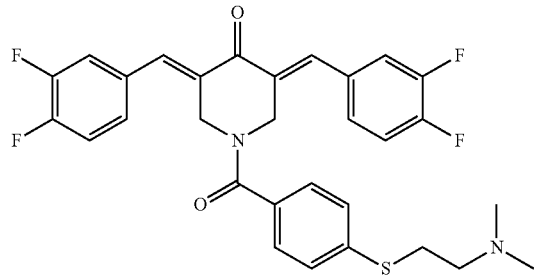 [SMILES: CN(C)CCSc1ccc(C(=O)N2C/C(=C\c3ccc(F)c(F)c3)C(=O)/C(=C/c3ccc(F)c(F)c3)C2)cc1]

3,5-Bis((E)-3,4-difluorobenzylidene)-1-(4-((2-(dimethylamino)ethyl)thio)benzoyl)piperidin-4-one (JC100)

$^1$H NMR (500 MHz, CDCl$_3$) δ 7.74 (br s 2H), 7.23 (m, 6H), 7.13 (d, J=8.3 Hz, 2H), 7.03 (d, J=8.3 Hz, 2H), 4.78 (br s, 4H), 2.99 (t, J=7.5 Hz, 2H), 2.56 (t, J=7.5 Hz, 2H), 2.28 (s, 6H).

$^{13}$C NMR (126 MHz, CDCl$_3$) δ 186.1, 170.1, 151.0 (dd, J$_{CF}$=255 Hz, J$_{C-CF}$=13 Hz, 2C), 150.3 (dd, J$_{CF}$=255 Hz, J$_{C-CF}$=13 Hz, 2C), 140.8, 136.0, 132.2 (2C), 131.9, 131.1 (2C), 130.6 (2C), 127.6, 126.9, 122.4, 119.0 (d, J$_{C-CF}$=18 Hz, 2C), 117.8 (d, J$_{C-CF}$=18 Hz, 2C), 115.2 (2C), 65.6, 58.0, 50.2, 45.2, 30.4.

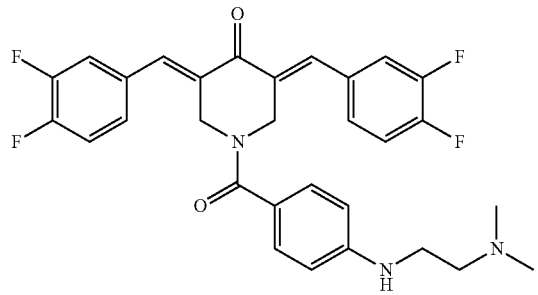 [SMILES: CN(C)CCNc1ccc(C(=O)N2C/C(=C\c3ccc(F)c(F)c3)C(=O)/C(=C/c3ccc(F)c(F)c3)C2)cc1]

3,5-Bis((E)-3,4-difluorobenzylidene)-1-(4-((2-(dimethylamino)ethyl)amino)benzoyl)piperidin-4-one (JC102)

$^1$H NMR (400 MHz, CDCl$_3$) δ 7.76 (br s, 2H), 7.14 (m, 8H), 7.04 (d, J=8.4 Hz, 2H), 6.28 (br s, 1H), 4.80 (br s, 4H), 3.26 (t, J=6.2 Hz, 2H), 2.73 (t, J=6.2 Hz, 2H), 2.42 (s, 6H).

$^{13}$C NMR (126 MHz, CDCl$_3$) δ 186.2, 169.6, 151.1 (dd, J$_{CF}$=255 Hz, J$_{C-CF}$=13 Hz, 2C), 150.4 (dd, J$_{CF}$=250 Hz, J$_{C-CF}$=11 Hz, 2C), 145.0, 135.9, 133.2, 132.4, 131.8 (2C), 129.0, 127.3 (dd, J$_{C-C-CF}$=5.9 Hz, J$_{C-C-CF}$=3.8 Hz, 2C), 126.9 (dd, J$_{C-C-CF}$=6.3 Hz, J$_{C-C-CF}$=4.5 Hz, 2C), 122.3, 119.2 (d, J$_{C-CF}$=18 Hz, 2C), 117.9 (d, J$_{C-CF}$=17 Hz, 2C), 109.0 (2C), 65.9, 56.9, 48.8, 44.7, 29.7.

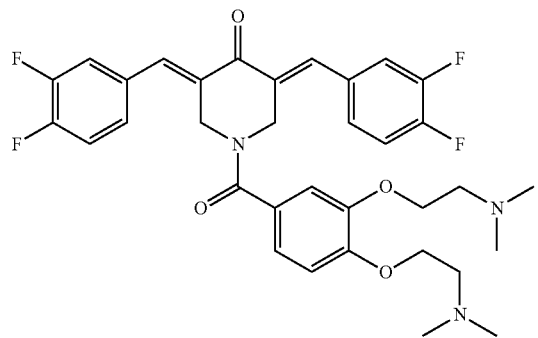 [SMILES: CN(C)CCOc1ccc(C(=O)N2C/C(=C\c3ccc(F)c(F)c3)C(=O)/C(=C/c3ccc(F)c(F)c3)C2)cc1OCCN(C)C]

1-(3,4-Bis(2-(dimethylamino)ethoxy)benzoyl)-3,5-bis((E)-3,4-difluorobenzylidene)piperidin-4-one (JC103)

$^1$H NMR (400 MHz, CDCl$_3$) δ 7.74 (br s, 2H), 7.06 (m, 8H), 6.88 (d, J=7.0 Hz, 1H), 4.81 (br s, 4H), 3.99 (t, J=5.8 Hz, 4H), 2.73 (t, J=5.8 Hz, 4H), 2.35 (br s, 12H).

$^{13}$C NMR (126 MHz, CDCl$_3$) δ 186.2, 170.3, 151.0 (dd, J$_{CF}$=255 Hz, J$_{C-CF}$=13 Hz, 2C), 150.2 (dd, J$_{CF}$=254 Hz, J$_{C-CF}$=13 Hz, 2C), 148.5, 135.9, 132.3 (2C), 131.5 (2C), 127.0, 126.4 (2C), 120.3 (2C), 119.1 (d, J$_{C-CF}$=17 Hz, 2C), 117.9 (d, J$_{C-CF}$=18 Hz, 2C), 113.7 (2C), 68.8, 66.7, 57.8, 56.3, 45.6, 30.2.

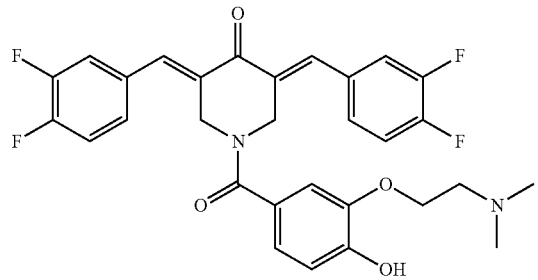 [SMILES: CN(C)CCOc1cc(C(=O)N2C/C(=C\c3ccc(F)c(F)c3)C(=O)/C(=C/c3ccc(F)c(F)c3)C2)ccc1O]

3,5-Bis((E)-3,4-difluorobenzylidene)-1-(3-(2-(dimethylamino)ethoxy)-4-hydroxybenzoyl)piperidin-4-one (JC104)

$^1$H NMR (400 MHz, CDCl$_3$) δ 7.72 (br s, 1H), 7.09 (m, 8H), 6.80 (d, J=6.8 Hz, 1H), 6.62 (br s 1H), 4.78 (br s, 4H), 3.96 (t, J=5.7 Hz, 2H), 2.63 (t, J=5.6 Hz, 2H), 2.40 (s, 6H).

$^{13}$C NMR (126 MHz, CDCl$_3$) δ 186.3, 170.5, 150.9 (dd, J$_{CF}$=254 Hz, J$_{C—CF}$=12 Hz, 2C), 150.6, 150.4 (dd, J$_{CF}$=250 Hz, J$_{C—CF}$=13 Hz, 2C), 148.0, 135.8, 132.4 (2C), 131.5 (2C), 130.2 (2C), 127.1, 126.9, 119.1 (d, J$_{C—CF}$=17 Hz), 118.9 (d, J$_{C—CF}$=18 Hz), 117.9, 117.6 (d, J$_{C—CF}$=18 Hz), 117.0 (d, J$_{C—CF}$=17 Hz), 116.3 (2C), 69.2, 66.8, 57.5, 45.5, 29.7.

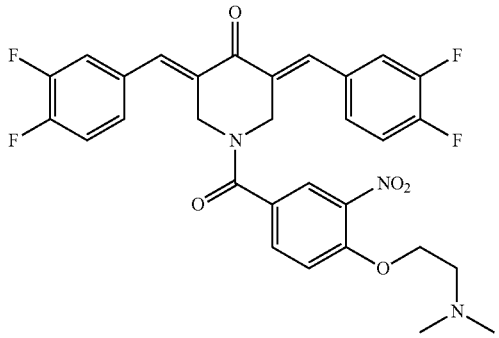 [SMILES: CN(C)CCOc1ccc(C(=O)N2C/C(=C\c3ccc(F)c(F)c3)C(=O)/C(=C/c3ccc(F)c(F)c3)C2)cc1[N+](=O)[O-]]

3,5-Bis((E)-3,4-difluorobenzylidene)-1-(4-(2-(dimethylamino)ethoxy)-3-nitrobenzoyl)piperidin-4-one (JC105)

$^1$H NMR (400 MHz, CDCl$_3$) δ 7.73 (s, 1H), 7.67 (s, 1H), 7.08 (m, 8H), 6.62 (d, J=7.6 Hz, 1H), 4.96 (s, 2H), 4.50 (s, 2H), 4.16 (t, J=5.6 Hz, 2H), 2.78 (t, J=5.6 Hz, 2H), 2.34 (s, 6H).

$^{13}$C NMR (126 MHz, CDCl$_3$) δ 185.7, 165.5, 151.2, 151.0 (dd, J$_{CF}$=250 Hz, J$_{C—CF}$=13 Hz, 2C), 150.3 (dd, J$_{CF}$=255 Hz, J$_{C—CF}$=11 Hz, 2C), 138.3, 137.1, 135.3, 132.2, 131.9 (2C), 131.4 (dd, J$_{C—C—CF}$=5.9 Hz, J$_{C—C—CF}$=3.4 Hz, 2C), 130.9, 127.4, 126.4, 119.2 (d, J$_{C—CF}$=18 Hz), 118.9 (d, J$_{C—CF}$=18 Hz), 118.1 (d, J$_{C—CF}$=18 Hz), 118.0, 117.9 (d, J$_{C—CF}$=17 Hz), 115.2, 68.4, 65.2, 57.4, 45.7, 29.9.

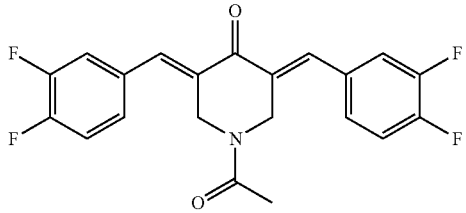 [SMILES: CC(=O)N1C/C(=C\c2ccc(F)c(F)c2)C(=O)/C(=C/c2ccc(F)c(F)c2)C1]

1-Acetyl-3,5-bis((E)-3,4-difluorobenzylidene)piperidin-4-one (JC106)

$^1$H NMR (500 MHz, CDCl$_3$) δ 7.74 (s, 1H), 7.69 (s, 1H), 7.22 (m, 6H), 4.85 (s, 2H), 4.67 (s, 2H), 1.96 (s, 3H)

$^{13}$C NMR (126 MHz, CDCl$_3$) δ 185.9, 169.2, 150.9 (dd, J$_{CF}$=255 Hz, J$_{C—CF}$=13 Hz, 2C), 150.4 (dd, J$_{CF}$=251 Hz, J$_{C—CF}$=11 Hz, 2C), 136.4, 135.3, 132.1, 131.6, 127.3 (dd, J$_{C—C—CF}$=6.2 Hz, J$_{C—C—CF}$=3.4 Hz, 2C), 126.8 (dd, J$_{C—C—CF}$=6.3 Hz, J$_{C—C—CF}$=3.5 Hz, 2C), 119.2 (d, J$_{C—CF}$=18 Hz), 118.9 (d, J$_{C—CF}$=18 Hz), 118.1 (d, J$_{C—CF}$=18 Hz), 117.9 (d, J$_{C—CF}$=17 Hz), 46.9, 43.1, 21.1.

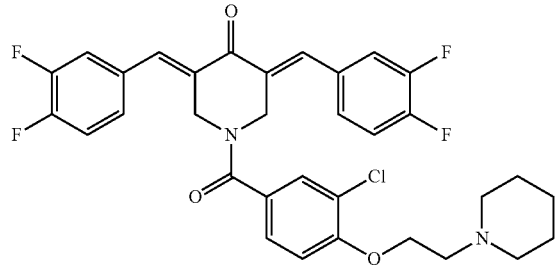

1-(3-Chloro-4-(2-(piperidin-1-yl)ethoxy)benzoyl)-3,5-bis((E)-3,4-difluorobenzylidene)piperidin-4-one (JC109)

$^1$H NMR (400 MHz, CDCl$_3$) δ 7.77 (s, 2H), 7.15 (m, 8H), 6.66 (d, J=8.5 Hz, 1H), 4.80 (br s, 4H), 4.09 (t, J=6.0 Hz, 2H), 2.82 (t, J=6.0 Hz, 2H), 2.54 (m, 4H), 1.61 (m, 4H), 1.45 (m, 2H).

$^{13}$C NMR (126 MHz, CDCl$_3$) δ 185.9, 168.9, 155.8, 151.0 (dd, J$_{CF}$=254 Hz, J$_{C—CF}$=13 Hz, 2C), 150.3 (dd, J$_{CF}$=250 Hz, J$_{C—CF}$=13 Hz, 2C), 132.1 (2C), 131.3 (dd, J$_{C—C—CF}$=5.9 Hz, J$_{C—C—CF}$=4.1 Hz, 2C), 129.3 (2C), 127.2 (2C), 127.0 (dd, J$_{C—C—CF}$=6.3 Hz, J$_{C—C—CF}$=3.7 Hz, 2C), 126.8, 122.8, 118.9 (d, J$_{C—CF}$=18 Hz, 2C), 117.7 (d, J$_{C—CF}$=18 Hz, 2C), 112.2, 67.2, 57.2, 55.0, 25.6, 23.8.

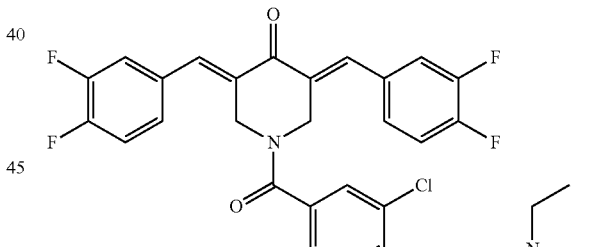

1-(3-Chloro-4-(2-(diethylamino)ethoxy)benzoyl)-3,5-bis((E)-3,4-difluorobenzylidene)piperidin-4-one (JC110)

$^1$H NMR (400 MHz, CDCl$_3$) δ 7.76 (br s, 2H), 7.13 (m, 8H), 6.67 (d, J=8.5 Hz, 1H), 4.79 (br s, 4H), 4.14 (t, J=5.6 Hz, 2H), 3.09 (t, J=5.6 Hz, 2H), 2.83 (q, J=7.1 Hz, 4H), 1.17 (t, J=7.2 Hz, 6H).

$^{13}$C NMR (126 MHz, CDCl$_3$) δ 185.9, 168.9, 155.5, 151.0 (dd, J$_{CF}$=254 Hz, J$_{C—CF}$=13 Hz, 2C), 150.3 (dd, J$_{CF}$=251 Hz, J$_{C—CF}$=13 Hz, 2C), 136.2, 132.1 (2C), 131.3 (dd, J$_{C—C—CF}$=5.9 Hz, J$_{C—C—CF}$=3.8 Hz, 2C), 129.3 (2C), 127.2 (2C), 127.0 (dd, J$_{C—C—CF}$=6.3 Hz, J$_{C—C—CF}$=3.7 Hz, 2C), 122.6, 118.9 (d, J$_{C—CF}$=18 Hz, 2C), 117.7 (d, J$_{C—CF}$=18 Hz, 2C), 112.2, 66.7, 50.9, 47.7, 29.7, 10.7.

101

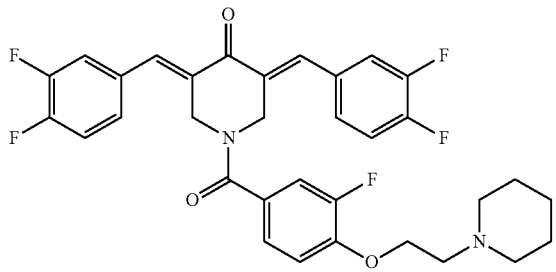 [SMILES: O=C1/C(=C/c2ccc(F)c(F)c2)CN(C(=O)c2ccc(OCCN3CCCCC3)c(F)c2)C/C1=C\c1ccc(F)c(F)c1]

3,5-Bis((E)-3,4-difluorobenzylidene)-1-(3-fluoro-4-(2-(piperidin-1-yl)ethoxy)benzoyl)piperidin-4-one (JC111)

$^1$H NMR (400 MHz, CDCl$_3$) δ 7.75 (br s, 2H), 7.16 (m, 6H), 6.96 (m, 2H), 6.67 (m, 1H), 4.78 (br s, 4H), 4.10 (t, J=6.0 Hz, 2H), 2.82 (t, J=6.0 Hz, 2H), 2.49 (m, 4H), 1.64 (m, 4H), 1.45 (m, 2H).

$^{13}$C NMR (126 MHz, CDCl$_3$) δ 186.0, 169.1, 151.6 (d, $J_{CF}$=252 Hz), 151.1 (dd, $J_{CF}$=255 Hz, $J_{C-CF}$=13 Hz, 2C), 150.3 (dd, $J_{CF}$=251 Hz, $J_{C-CF}$=11 Hz, 2C), 148.6 (d, $J_{C-C-CF}$ 11 Hz), 136.1 (2C), 132.2 (2C), 131.3 (dd, $J_{C-C-CF}$=5.8 Hz, $J_{C-C-CF}$=3.8 Hz, 2C), 126.9 (dd, $J_{C-C-CF}$=5.8 Hz, $J_{C-C-CF}$=3.8 Hz, 2C), 126.4 (d, $J_{C-C-CF}$=5.5 Hz), 123.7 ($J_{C-C-CF}$=3.4 Hz), 118.4 (d, $J_{C-CF}$=18 Hz, 2C), 117.9 (d, $J_{C-CF}$=18 Hz, 2C), 115.5 (d, $J_{C-CF}$=20 Hz), 113.9, 67.2, 57.4, 55.1, 54.9, 25.6, 23.9.

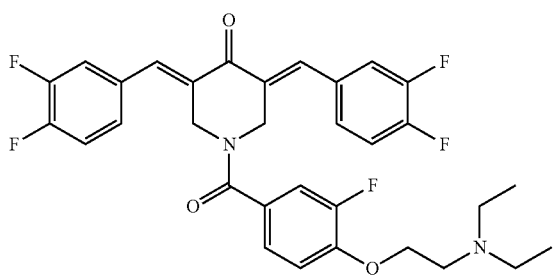 [SMILES: CCN(CC)CCOc1ccc(C(=O)N2C/C(=C\c3ccc(F)c(F)c3)C(=O)/C(=C/c3ccc(F)c(F)c3)C2)cc1F]

1-(4-(2-(Diethylamino)ethoxy)-3-fluorobenzoyl)-3,5-bis((E)-3,4-difluorobenzylidene)piperidin-4-one (JC112)

$^1$H NMR (400 MHz, CDCl$_3$) δ 7.77 (br s, 2H), 7.15 (m, 6H), 6.95 (m, 2H), 6.67 (m, 1H), 4.77 (br s, 4H), 4.03 (t, J=6.2 Hz, 2H), 2.91 (t, J=6.2 Hz, 2H), 2.66 (q, J=7.2 Hz, 4H), 1.08 (t, J=7.2 Hz, 6H).

$^{13}$C NMR (126 MHz, CDCl$_3$) δ 186.0, 169.1, 151.7 (d, $J_{CF}$=250 Hz), 151.0 (dd, $J_{CF}$=255 Hz, $J_{C-CF}$=13 Hz, 2C), 150.4 (dd, $J_{CF}$=251 Hz, $J_{C-CF}$=13 Hz, 2C), 148.7 (d, $J_{C-C-CF}$=11 Hz), 136.1 (2C), 132.2 (2C), 131.3 (dd, $J_{C-C-CF}$=5.9 Hz, $J_{C-C-CF}$=3.8 Hz, 2C), 126.9 (dd, $J_{C-C-CF}$=5.8 Hz, $J_{C-C-CF}$=3.7 Hz, 2C), 126.3 (d, $J_{C-C-CF}$=5.5 Hz), 123.7 ($J_{C-C-CF}$=3.7 Hz), 118.9 (d, $J_{C-CF}$=17 Hz, 2C), 117.8 (d, $J_{C-CF}$=18 Hz, 2C), 115.5 (d, $J_{C-CF}$=20 Hz), 113.6, 67.7, 51.3, 47.9, 11.6.

102

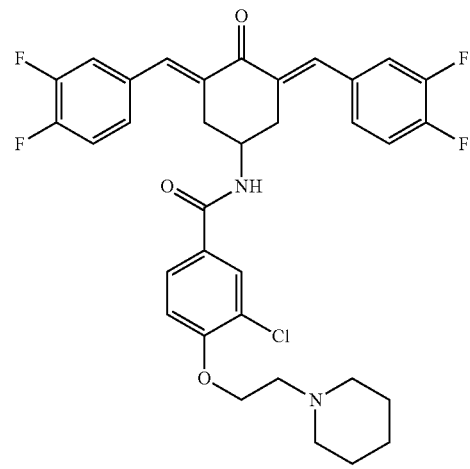 [SMILES: O=C1/C(=C/c2ccc(F)c(F)c2)CC(NC(=O)c2ccc(OCCN3CCCCC3)c(Cl)c2)C/C1=C\c1ccc(F)c(F)c1]

N-(3,5-Bis((E)-3,4-difluorobenzylidene)-4-oxocyclohexyl)-3-chloro-4-(2-(piperidin-1-yl)ethoxy)Benzamide (JC113)

$^1$H NMR (400 MHz, CDCl$_3$) δ 7.70 (br s, 2H), 7.68 (d, J=2.2 Hz, 1H), 7.56 (dd, J=2.2 Hz, J=8.6 Hz, 1H), 7.16 (m, 6H), 6.84 (d, J=8.7 Hz, 1H), 6.64 (d, J=7.4 Hz, 1H), 4.40 (m, 1H), 4.14 (t, J=5.9 Hz, 2H), 3.23 (bd, J=16.1 Hz, 2H), 3.00 (dd, J=5.6 Hz, J=17.0 Hz, 2H), 2.83 (t, J=5.9 Hz, 2H), 2.61 (m, 4H), 1.58 (m, 4H), 1.43 (m, 2H).

$^{13}$C NMR (126 MHz, CDCl$_3$) δ 187.8, 165.6, 156.9, 150.7 (dd, $J_{CF}$=249 Hz, $J_{C-CF}$=11 Hz, 2C), 150.2 (dd, $J_{CF}$=252 Hz, $J_{C-CF}$=13 Hz, 2C), 137.7 (2C), 132.8 (2C), 132.1 (dd, $J_{C-C-CF}$=5.9 Hz, $J_{C-C-CF}$=3.5 Hz, 2C), 129.1 (2C), 127.2 (dd, $J_{C-C-CF}$=5.9 Hz, $J_{C-C-CF}$=3.4 Hz, 2C), 122.9, 118.9 (d, $J_{C-CF}$=18 Hz, 2C), 117.6 (d, $J_{C-CF}$=17 Hz, 2C), 112.3 (2C), 67.4, 57.3, 55.1, 44.9, 33.6, 25.7, 23.9.

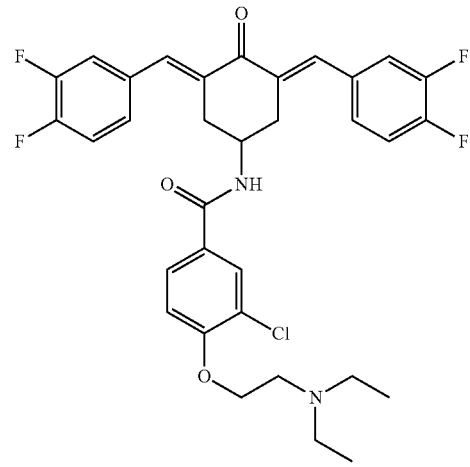 [SMILES: CCN(CC)CCOc1ccc(C(=O)NC2C/C(=C\c3ccc(F)c(F)c3)C(=O)/C(=C/c3ccc(F)c(F)c3)C2)cc1Cl]

N-(3,5-Bis((E)-3,4-difluorobenzylidene)-4-oxocyclohexyl)-3-chloro-4-(2-(diethylamino)ethoxy)Benzamide (JC114)

$^1$H NMR (300 MHz, CDCl$_3$) δ 7.75 (br s, 2H), 7.70 (d, J=2.2 Hz, 1H), 7.56 (dd, J=2.2 Hz, J=8.6 Hz, 1H), 7.19 (m, 6H), 6.86 (d, J=8.7 Hz, 1H), 6.44 (d, J=7.4 Hz, 1H), 4.43 (m, 1H), 4.14 (t, J=5.9 Hz, 2H), 3.25 (bd, J=13.5 Hz, 2H), 3.03 (dd, J=5.6 Hz, J=14.0 Hz, 2H), 2.93 (t, J=5.7 Hz, 2H), 2.71 (q, J=7.1 Hz, 4H), 1.09 (t, J=7.2 Hz, 6H).

$^{13}$C NMR (126 MHz, CDCl$_3$) δ 187.8, 165.6, 156.9, 150.6 (dd, J$_{CF}$=250 Hz, J$_{C-CF}$=13 Hz, 2C), 150.1 (dd, J$_{CF}$=250 Hz, J$_{C-CF}$=13 Hz, 2C), 137.6 (2C), 132.8 (2C), 132.1 (dd, J$_{C-C-CF}$=5.9 Hz, J$_{C-C-CF}$=3.5 Hz, 2C), 129.2 (2C), 127.1 (dd, J$_{C-C-CF}$=5.9 Hz, J$_{C-C-CF}$=3.8 Hz, 2C), 122.9, 118.9 (d, J$_{C-CF}$=18 Hz, 2C), 117.6 (d, J$_{C-CF}$=18 Hz, 2C), 112.4 (2C), 67.4, 57.3, 55.1, 44.9, 33.7, 25.7, 23.9.

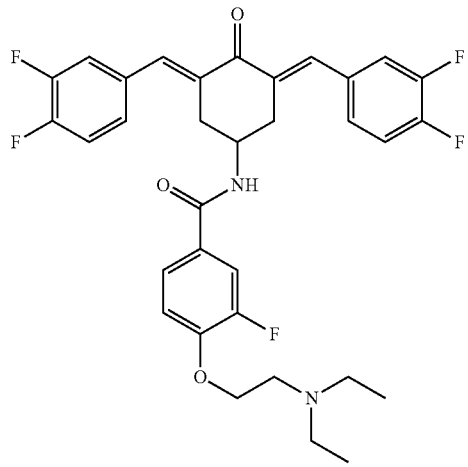

N-(3,5-Bis((E)-3,4-difluorobenzylidene)-4-oxocyclohexyl)-4-(2-(diethylamino)ethoxy)-3-fluorobenzamide (JC116)

$^1$H NMR (400 MHz, CDCl$_3$) δ 7.82 (s, 2H), 7.40 (m, 2H), 7.24 (m, 6H), 6.94 (m, 1H), 5.99 (d, J=7.1 Hz, 1H), 4.50 (m, 1H), 4.13 (t, J=6.2 Hz, 2H), 3.26 (bd, J=15.7 Hz, 2H), 3.06 (dd, J=15.8 Hz, J=6.0 Hz, 2H), 2.92 (t, J=6.2 Hz, 2H), 2.65 (q, J=7.0 Hz, 4H), 1.07 (t, J=7.1 Hz, 6H).

$^{13}$C NMR (126 MHz, CDCl$_3$) δ 187.8, 165.6, 151.9 (d, J$_{CF}$=248 Hz), 150.6 (dd, J$_{CF}$=254 Hz, J$_{C-CF}$=13 Hz, 2C), 150.2 (dd, J$_{CF}$=250 Hz, J$_{C-CF}$=13 Hz, 2C), 149.8 (d, J$_{C-C-CF}$=11 Hz), 137.7, 132.7 (2C), 132.1 (dd, J$_{C-C-CF}$=5.9 Hz, J$_{C-C-CF}$=4.2 Hz, 2C), 127.1 (dd, J$_{C-C-CF}$=6.3 Hz, J$_{C-C-CF}$=3.4 Hz, 2C), 126.7 (d, J$_{C-C-CF}$=5.5 Hz), 123.6 (J$_{C-C-CF}$=3.3 Hz), 123.5, 118.9 (d, J$_{C-CF}$=18 Hz, 2C), 117.6 (d, J$_{C-CF}$=18 Hz, 2C), 115.1 (d, J$_{C-CF}$=20 Hz), 113.7, 67.9, 51.4, 47.9, 44.9, 33.7, 11.6.

N-(3,5-Bis((E)-3,4-difluorobenzylidene)-4-oxocyclohexyl)-3-fluoro-4-(2-(piperidin-1-yl)ethoxy)benzamide (JC115)

$^1$H NMR (300 MHz, CDCl$_3$) δ 7.77 (br s, 2H), 7.49 (m, 2H), 7.22 (m, 6H), 6.94 (m, 1H), 6.54 (d, J=7.2 Hz, 1H), 4.47 (m, 1H), 4.21 (t, J=6.0 Hz, 2H), 3.28 (bd, J=15.6 Hz, 2H), 3.06 (dd, J=7.0 Hz, J=15.3 Hz, 2H), 2.84 (t, J=6.0 Hz, 2H), 2.56 (m, 4H), 1.63 (m, 4H), 1.48 (m, 2H).

$^{13}$C NMR (126 MHz, CDCl$_3$) δ 187.8, 165.6, 151.9 (d, J$_{CF}$=248 Hz), 150.7 (dd, J$_{CF}$=254 Hz, J$_{C-CF}$=13 Hz, 2C), 150.3 (dd, J$_{CF}$=250 Hz, J$_{C-CF}$=13 Hz, 2C), 149.8 (d, J$_{C-C-CF}$=11 Hz), 137.7, 132.8 (2C), 132.1 (dd, J$_{C-C-CF}$=5.9 Hz, J$_{C-C-CF}$=4.2 Hz, 2C), 127.1 (dd, J$_{C-C-CF}$=6.3 Hz, J$_{C-C-CF}$=3.4 Hz, 2C), 126.7 (d, J$_{C-C-CF}$=5.5 Hz), 123.6 (J$_{C-C-CF}$=3.3 Hz), 123.6, 118.9 (d, J$_{C-CF}$=17 Hz, 2C), 117.6 (d, J$_{C-CF}$=18 Hz, 2C), 115.2 (d, J$_{C-CF}$=20 Hz), 113.9, 67.3, 57.5, 55.1, 44.9, 33.7, 25.7, 23.9.

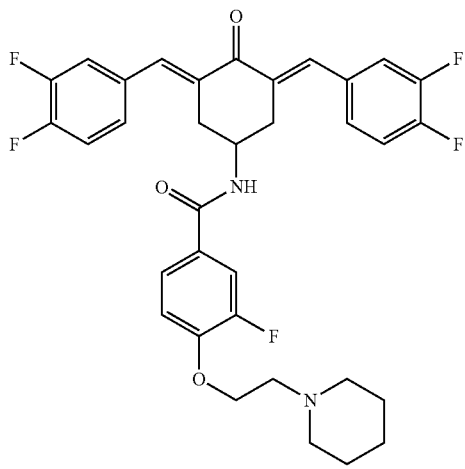 [SMILES: O=C1/C(=C/c2ccc(F)c(F)c2)CC(NC(=O)c2ccc(OCCN3CCCCC3)c(F)c2)C/C1=C\c1ccc(F)c(F)c1]

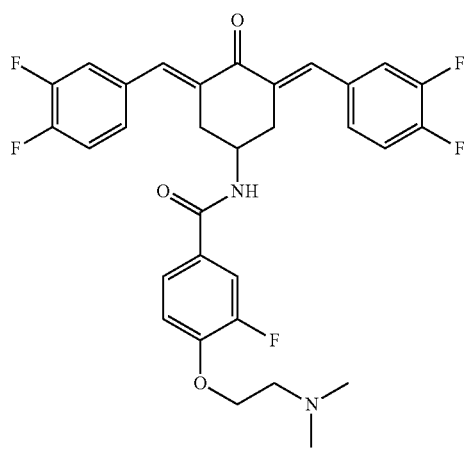 [SMILES: CN(C)CCOc1ccc(C(=O)NC2C/C(=C\c3ccc(F)c(F)c3)C(=O)/C(=C/c3ccc(F)c(F)c3)C2)cc1F]

N-(3,5-Bis((E)-3,4-difluorobenzylidene)-4-oxocyclohexyl)-4-(2-(dimethylamino)ethoxy)-3-fluorobenzamide (JC117)

¹H NMR (300 MHz, CDCl₃) δ 7.76 (br s, 2H), 7.48 (m, 2H), 7.21 (m, 6H), 6.94 (m, 1H), 6.55 (d, J=7.2 Hz, 1H), 4.47 (m, 1H), 4.17 (t, 0.1=5.7 Hz, 2H), 3.28 (bd, J=15.7 Hz, 2H), 3.06 (dd, J=5.7 Hz, J=15.7 Hz, 2H), 2.81 (t, J=5.8 Hz, 2H), 2.38 (s, 6H).

¹³C NMR (126 MHz, CDCl₃) δ 187.8, 165.6, 151.8 (d, $J_{CF}$=248 Hz), 150.6 (dd, $J_{CF}$=254 Hz, $J_{C-CF}$=13 Hz, 2C), 150.2 (dd, $J_{CF}$=256 Hz, $J_{C-CF}$=11 Hz, 2C), 149.7 (d, $J_{C-C-CF}$=11 Hz), 137.6, 132.7 (2C), 132.1 (dd, $J_{C-C-CF}$=5.8 Hz, $J_{C-C-CF}$=4.2 Hz, 2C), 127.1 (dd, $J_{C-C-CF}$=6.0 Hz, $J_{C-C-CF}$=3.4 Hz, 2C), 126.7 (d, $J_{C-C-CF}$=5.5 Hz), 123.6 ($J_{C-C-CF}$=3.4 Hz), 123.5, 118.9 (d, $J_{C-CF}$=18 Hz, 2C), 117.6 (d, $J_{C-CF}$=18 Hz, 2C), 115.1 (d, $J_{C-CF}$=18 Hz), 113.9, 67.5, 57.8, 45.9, 44.9, 33.7.

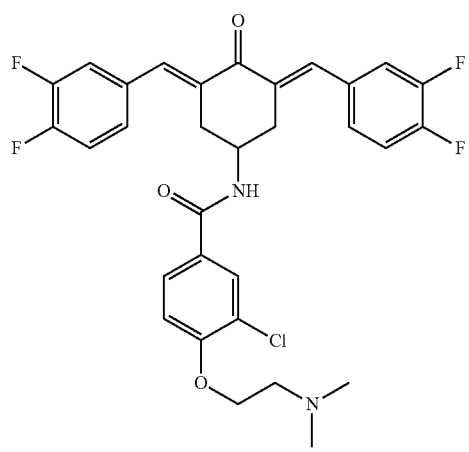 [SMILES: CN(C)CCOc1ccc(C(=O)NC2C/C(=C\c3ccc(F)c(F)c3)C(=O)/C(=C/c3ccc(F)c(F)c3)C2)cc1Cl]

N-(3,5-Bis((E)-3,4-difluorobenzylidene)-4-oxocyclohexyl)-3-chloro-4-(2 (dimethylamino)ethoxy) Benzamide (JC118)

¹H NMR (300 MHz, CDCl₃) δ 7.80 (br s, 2H), 7.75 (d, J=2.2 Hz, 1H), 7.61 (dd, J=2.2 Hz, J=8.6 Hz, 1H), 7.23 (m, 6H), 6.91 (d, J=8.6 Hz, 1H), 6.43 (d, J=7.1 Hz, 1H), 4.49 (m, 1H), 4.23 (t, J=5.5 Hz, 2H), 3.30 (bd, J=13.5 Hz, 2H), 3.08 (dd, J=5.6 Hz, J=14.0 Hz, 2H), 2.93 (t, J=5.5 Hz, 2H), 2.47 (s, 6H).

¹³C NMR (126 MHz, CDCl₃) δ 187.8, 165.5, 155.8, 150.6 (dd, $J_{CF}$=249 Hz, $J_{C-CF}$=13 Hz, 2C), 150.1 (dd, $J_{CF}$=250 Hz, $J_{C-CF}$=13 Hz, 2C), 137.8 (2C), 132.8 (2C), 132.1 (dd, $J_{C-C-CF}$=5.9 Hz, $J_{C-C-CF}$=3.8 Hz, 2C), 129.2 (2C), 127.2 (dd, $J_{C-C-CF}$=5.9 Hz, $J_{C-C-CF}$=3.4 Hz, 2C), 122.9, 118.9 (d, $J_{C-CF}$=18 Hz, 2C), 117.6 (d, $J_{C-CF}$=18 Hz, 2C), 112.4 (2C), 67.4, 57.6, 45.9, 44.9, 33.7.

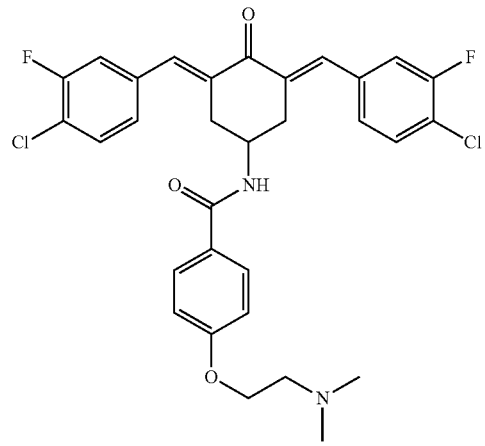 [SMILES: CN(C)CCOc1ccc(C(=O)NC2C/C(=C\c3ccc(Cl)c(F)c3)C(=O)/C(=C/c3ccc(Cl)c(F)c3)C2)cc1]

N-(3,5-Bis((E)-4-chloro-3-fluorobenzylidene)-4-oxocyclohexyl)-4-(2-(dimethylamino)ethoxy)benzamide (JC122)

¹H NMR (400 MHz, CDCl₃) δ 7.80 (br s, 2H), 7.63 (d, J=8.8 Hz, 2H), 7.43 (app. t, J=7.9 Hz, 2H), 7.22 (d, J=10.0 Hz, 2H), 7.17 (d, 1H, J=8.3 Hz, 2H), 6.90 (d, J=8.8 Hz, 2H), 4.49 (m, 1H), 4.13 (t, J=5.5 Hz, 2H), 3.28 (m, 2H), 3.06 (m, 2H), 2.83 (t, J=5.5 Hz, 2H), 2.41 (s, 6H).

¹³C NMR (126 MHz, CDCl₃) δ 187.6, 166.4, 160.0 (d, $J_{CF}$=249 Hz, 2C), 156.8 (2C), 137.6 (2C), 135.4 (d, $J_{C-C-CF}$=7.0 Hz. 2C), 133.3 (2C), 130.7, 128.6, 126.8 (d, $J_{C-C-CF}$=:3.5 Hz, 2C) 126.3, 121.9 (d, $J_{C-CF}$=17 Hz, 2C), 117.8 (d, $J_{C-CF}$=17 Hz, 2C), 114.3, 57.7, 45.4, 44.4, 33.7, 29.6

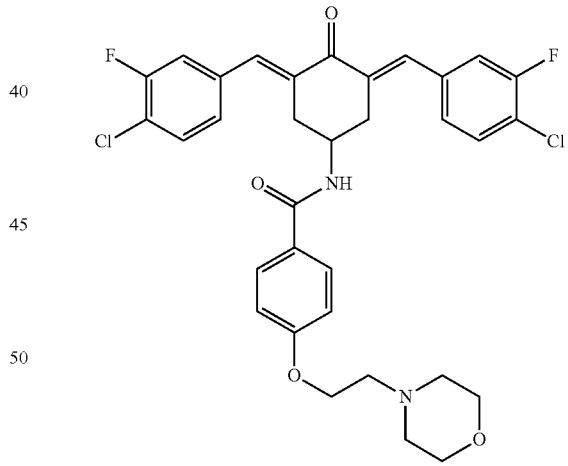

N-(3,5-Bis((E)-4-chloro-3-fluorobenzylidene)-4-oxocyclohexyl)-4-(2-morpholinoethoxy) benzamide (JC123)

¹H NMR (400 MHz, CDCl₃) δ 7.80 (br s, 2H), 7.62 (d, J=8.8 Hz, 2H), 7.42 (m, 2H), 7.21 (m, 2H), 7.16 (m, 2H), 6.89 (d, J=8.8 Hz, 2H), 4.49 (m, 1H), 4.12 (t, J=5.7 Hz, 2H), 3.72 (m, 4H), 3.26 (m, 2H), 3.06 (m, 2H), 2.80 (t, J=5.7 Hz, 2H), 2.56 (m, 4H).

¹³C NMR (100 MHz, CDCl₃) δ 187.6, 166.4, 157.0 (d, $J_{CF}$=252 Hz, 2C), 138.2, 137.7, 137.0, 135.4 (d, $J_{C—C—CF}$=6.9 Hz), 134.3, 133.2, 130.7, 129.9 (2C), 128.7, 128.6 (2C), 126.8 (d, $J_{C—C—CF}$=3.5 Hz 121.8 (d, $J_{C—CF}$=18 Hz, 2C), 117.7 (d, $J_{C—CF}$=18 Hz, 2C), 114.3, 66.6, 57.3, 53.9, 44.4, 40.4, 33.7.

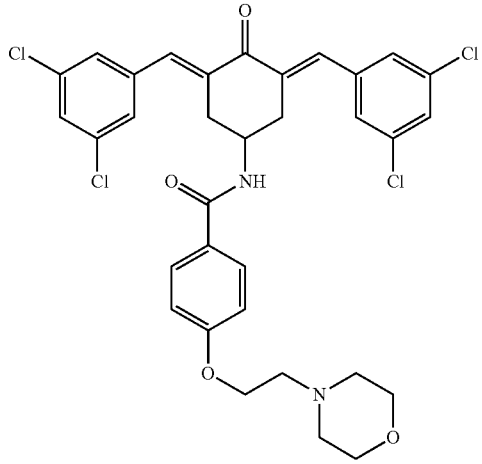 [SMILES: O=C1/C(=C/c2cc(Cl)cc(Cl)c2)CC(NC(=O)c2ccc(OCCN3CCOCC3)cc2)C/C1=C\c1cc(Cl)cc(Cl)c1]

N-(3,5-Bis((E)-3,5-dichlorobenzylidene)-4-oxocyclohexyl)-4-(2-morpholinoethoxy)benzamide (JC124)

$^1$H NMR (400 MHz, CDCl$_3$) δ 7.76 (br s, 2H), 7.63 (d, J=8.9 Hz, 2H), 7.35 (s, 2H), 7.28 (m, 4H), 6.90 (d, J=8.9 Hz, 2H), 4.52 (m, 1H), 4.13 (t, J=5.7 Hz, 2H), 3.73 (m, 4H), 3.22 (m, 2H), 3.08 (m, 2H), 2.80 (t, J=5.7 Hz, 2H), 2.57 (m, 4H).

$^{13}$C NMR (100 MHz, CDCl$_3$) δ 189.9, 188.6, 187.3, 166.4, 138.4, 137.8, 137.5, 137.3, 136.6, 136.0, 135.9, 135.1, 134.6, 135.2, 134.4, 134.0, 128.9, 128.8, 128.7, 128.6, 128.2, 128.1, 128.0, 127.5, 127.4, 114.4, 57.3, 53.8, 40.1, 34.1, 33.6, 29.6.

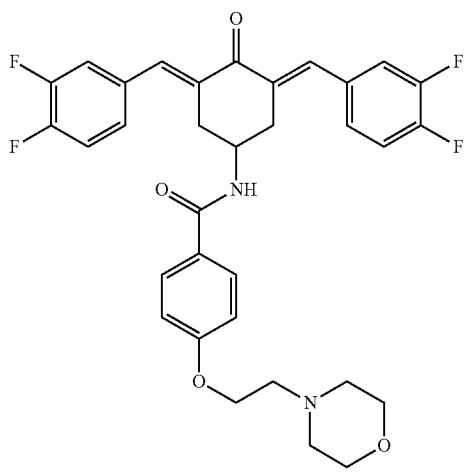 [SMILES: O=C1/C(=C/c2ccc(F)c(F)c2)CC(NC(=O)c2ccc(OCCN3CCOCC3)cc2)C/C1=C\c1ccc(F)c(F)c1]

N-(3,5-Bis((E)-3,4-difluorobenzylidene)-4-oxocyclohexyl)-4-(2-morpholinoethoxy)benzamide (JC125)

$^1$H NMR (400 MHz, CDCl$_3$) δ 7.77 (br s, 2H), 7.63 (d, J=8.9 Hz, 2H), 7.21 (m, 6H), 6.87 (d, J=8.9 Hz, 2H), 4.48 (m, 1H), 4.12 (t, J=5.7 Hz, 2H), 3.72 (m, 4H), 3.25 (m, 2H), 3.04 (m, 2H), 2.80 (t, J=5.7 Hz, 2H), 2.57 (m, 4H).

$^{13}$C NMR (126 MHz, CDCl$_3$) δ 187.7, 166.4, 151.0 (dd, $J_{CF}$=248 Hz, $J_{C—CF}$=13 Hz, 2C), 150.4 (dd, $J_{CF}$=248 Hz, $J_{C—CF}$=13 Hz, 2C), 137.7, 132.6 (2C), 132.0 (dd, $J_{C—C—CF}$=6.2 Hz, $J_{C—C—CF}$=3.4 Hz, 2C), 131.5 (d, $J_{C—CF}$=17 Hz, 2C), 128.6 (2C), 127.0 (dd, $J_{C—C—CF}$=5.9 Hz, $J_{C—C—CF}$=3.8 Hz, 2C), 126.2, 118.8 (d, $J_{C—CF}$=17 Hz, 2C), 117.6 (d, $J_{C—CF}$=17 Hz, 2C), 114.3, 114.1 (d, $J_{C—CF}$=17 Hz, 2C), 66.7, 65.8, 57.3, 54.0, 44.5, 33.6.

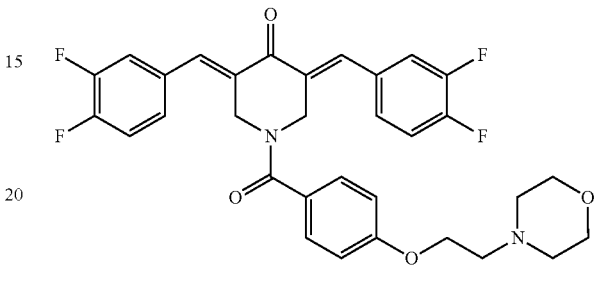

3,5-Bis((E)-3,4-difluorobenzylidene)-1-(4-(2-morpholinoethoxy)benzoyl)piperidin-4-one (JC126)

$^1$H NMR (400 MHz, CDCl$_3$) δ 7.73 (br s, 2H), 7.15 (m, 8H), 6.62 (d, J=8.8 Hz, 2H), 4.78 (br s, 4H), 4.01 (t, J=5.7 Hz, 2H), 3.73 (m, 4H), 2.77 (t, J=5.7 Hz, 2H), 2.55 (m, 4H).

$^{13}$C NMR (126 MHz, CDCl$_3$) δ 186.1, 170.2, 160.2, 151.0 (dd, $J_{CF}$=248 Hz, $J_{C—CF}$=13 Hz, 2C), 150.4 (dd, $J_{CF}$=248 Hz, $J_{C—CF}$=13 Hz, 2C), 135.6 (2C), 132.3 (dd, $J_{C—C—CF}$=5.9 Hz, $J_{C—C—CF}$=3.8 Hz, 2C), 131.3 (2C), 128.9, 126.9 (dd, $J_{C—C—CF}$=6.2 Hz, $J_{C—C—CF}$=3.4 Hz, 2C), 126.0, 118.9 (d, $J_{C—CF}$=17 Hz, 2C), 117.8 (d, $J_{C—CF}$=17 Hz, 2C), 113.9, 66.7, 65.7, 57.3, 53.9, 53.4.

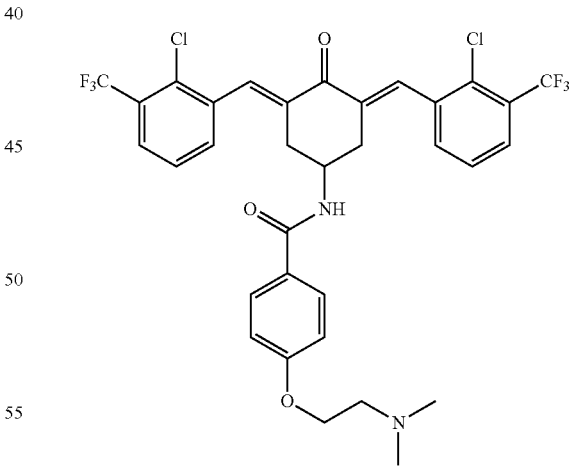

N-(3,5-Bis((E)-2-chloro-3-(trifluoromethyl)benzylidene)-4-oxocyclohexyl)-4-(2 (dimethylamino)ethoxy)benzamide (JC127)

$^1$H NMR (400 MHz, CDCl$_3$) δ 8.00 (br s, 2H), 7.67 (m, 2H), 7.57 (d, J=8.9 Hz, 2H), 7.40 (m, 4H), 6.88 (d, J=8.9 Hz, 2H), 4.46 (m, 1H), 4.08 (t, J=7.0 Hz, 2H), 3.00 (m, 4H), 2.74 (t, J=5.6 Hz, 2H), 2.34 (s, 6H).

$^{13}$C NMR (100 MHz, CDCl$_3$) δ 185.6, 170.3, 161.5, 135.4 (2C), 135.2, 134.9, 134.2, 133.9 (2C), 133.3 (2C), 132.8, 132.7, 130.0 (q, J$_{C-CF}$=38 Hz), 129.4 (q, J$_{C-CF}$=38 Hz), 128.4, 128.1, 128.0, 126.8 (2C), 122.6 (q, J$_{CF}$=272 Hz, 2C), 114.3, 65.8, 57.9, 45.7, 44.3, 33.6.

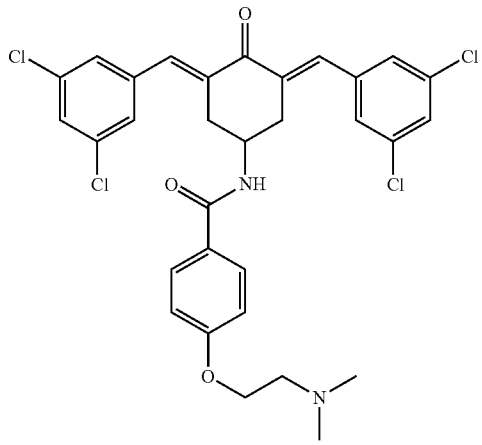 [SMILES: CN(C)CCOc1ccc(C(=O)NC2C/C(=C\c3cc(Cl)cc(Cl)c3)C(=O)/C(=C/c3cc(Cl)cc(Cl)c3)C2)cc1]

N-(3,5-Bis((E)-3,5-dichlorobenzylidene)-4-oxocyclohexyl)-4-(2-(dimethylamino)ethoxy)benzamide (JC128)

$^1$H NMR (400 MHz, CDCl$_3$) δ 7.73 (br s, 2H), 7.63 (d, J=8.8 Hz, 2H), 7.34 (s, 2H), 7.24 (s, 4H), 6.90 (d, J=8.8 Hz, 2H), 4.51 (m, 1H), 4.09 (t, J=5.6 Hz, 2H), 3.21 (m, 2H), 3.06 (m, 2H), 2.75 (t, J=5.6 Hz, 2H), 2.35 (s, 6H).
$^{13}$C NMR (100 MHz, CDCl$_3$) δ 187.4, 166.4, 161.5, 137.8 (2C), 137.3 (2C), 135.2, 134.0 (2C), 128.9 (2C), 128.7 (2C), 128.0, 126.2 (2C), 114.3, 65.8, 57.9, 45.7, 44.3, 33.6.

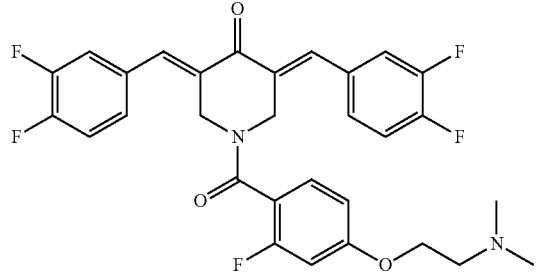 [SMILES: CN(C)CCOc1ccc(C(=O)N2C/C(=C\c3ccc(F)c(F)c3)C(=O)/C(=C/c3ccc(F)c(F)c3)C2)c(F)c1]

3,5-Bis((E)-3,4-difluorobenzylidene)-1-(4-(2-(dimethylamino)ethoxy)-2-fluorobenzoyl)piperidin-4-one (JC131)

$^1$H NMR (400 MHz, CDCl$_3$) δ 7.68 (br s, 2H), 7.09 (br m, 7H), 6.56 (dd, J=8.6, 2.3 Hz, 1H), 6.41 (dd, J=11.6, 2.3 Hz, 1H), 5.01 (br n, 2H), 4.54 (br m, 2H), 3.98 (t, J=5.6 Hz, 2H), 2.75 (t, J=5.6 Hz, 2H), 2.35 (s, 6H).
$^{13}$C NMR (100 MHz, CDCl$_3$) δ 185.6, 165.6, 161.4 (d, J$_{C-CF}$=10 Hz), 158.9 (d, J$_{CF}$=252 Hz), 151.0 (dd, J$_{C-CF}$=248 Hz, J$_{C-CF}$=13 Hz, 2C), 150.4 (dd, J$_{CF}$=248 Hz, J$_{C-CF}$=13 Hz, 2C), 136.6 (2C), 134.9 (2C), 131.3, 129.8, 127.3 (2C), 126.3 (2C), 118.7 (d, J$_{C-CF}$=18 Hz, 2C), 117.4 (d, J$_{C-CF}$=18 Hz, 2C), 110.8, 101.7 (d, J$_{C-CF}$=20 Hz), 66.1, 57.6, 46.9, 45.5, 43.5.

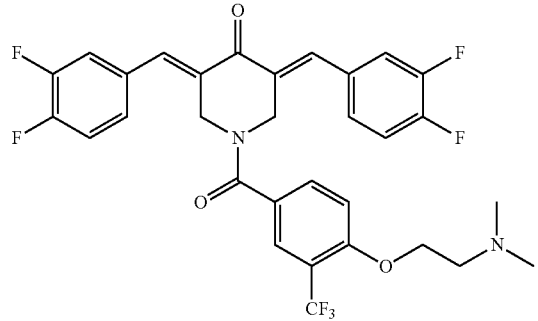 [SMILES: CN(C)CCOc1ccc(C(=O)N2C/C(=C\c3ccc(F)c(F)c3)C(=O)/C(=C/c3ccc(F)c(F)c3)C2)cc1C(F)(F)F]

3,5-Bis((E)-3,4-difluorobenzylidene)-1-(4-(2-(dimethylamino)ethoxy)-3-(trifluoromethyl)Benzoyl)piperidin-4-one (JC132)

$^1$H NMR (400 MHz, CDCl$_3$) δ 7.77 (br s, 2H), 7.44 (m, 2H), 7.11 (m, 6H), 6.76 (d, J=8.6 Hz, 1H), 4.81 (br s, 4H), 4.11 (t, J=5.7 Hz, 2H), 2.79 (t, J=5.7 Hz, 2H), 2.35 (s, 6H).
$^{13}$C NMR (126 MHz, CDCl$_3$) δ 185.8, 169.0, 158.1, 151.0 (dd, J$_{CF}$=255 Hz, J$_{C-CF}$=13 Hz, 2C), 150.3 (dd, J$_{CF}$=255 Hz, J$_{C-CF}$=13 Hz, 2C), 136.1 (2C), 132.9 (2C), 131.9 (2C), 131.2, 126.9 (2C), 126.5, 126.4, 125.6, 122.7 (q, J$_{CF}$=272 Hz), 119.0 (d, J$_{C-CF}$=18 Hz), 118.9 (d, J$_{C-CF}$=18 Hz), 117.8 (d, J$_{C-CF}$=18 Hz, 2C), 112.3, 67.8, 57.5, 45.9, 29.7.

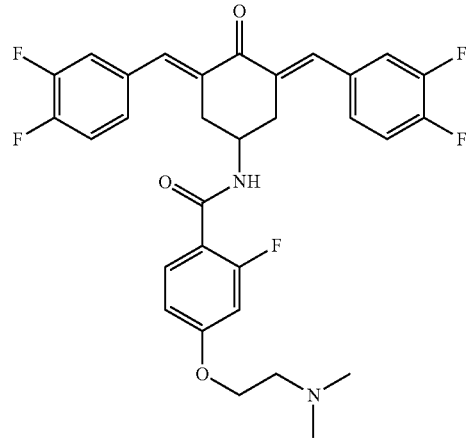 [SMILES: CN(C)CCOc1ccc(C(=O)NC2C/C(=C\c3ccc(F)c(F)c3)C(=O)/C(=C/c3ccc(F)c(F)c3)C2)c(F)c1]

N-(3,5-Bis((E)-3,4-difluorobenzylidene)-4-oxocyclohexyl)-4-(2-(dimethylamino)ethoxy)-2-fluorobenzamide (JC133)

$^1$H NMR (400 MHz, CDCl$_3$) δ 7.96 (m, 1H), 7.81 (br s, 2H), 7.20 (m, 6H), 6.76 (dd, J=8.9, 2.4 Hz, 1H), 6.71 (m, 1H), 6.61 (dd, J=8.8, 2.3 Hz, 1H), 4.54 (m, 1H), 4.15 (t, J=5.4 Hz, 2H), 3.23 (bd, J=15.7 Hz, 2H), 3.09 (dd, J=15.7, 7.0 Hz, 2H), 2.85 (t, J=5.3 Hz, 2H), 2.42 (s, 6H).
$^{13}$C NMR (126 MHz, CDCl$_3$) δ 189.8, 187.9, 162.6, 161.5 (d, J$_{CF}$=247 Hz), 150.7 (dd, J$_{CF}$=255 Hz, J$_{C-CF}$=13 Hz, 2C), 150.2 (dd, J$_{CF}$=251 Hz, J$_{C-CF}$=13 Hz, 2C), 138.3, 137.9, 137.4, 134.8, 133.9, 133.3, 133.2, 132.7, 132.2 (2C), 127.0 (dd, J$_{C-C-CF}$=6.2 Hz, J$_{C-C-CF}$=3.2 Hz), 126.3 (dd, J$_{C-C-CF}$=6.0 Hz, J$_{C-C-CF}$=3.7 Hz), 118.9 (d, J$_{C-CF}$=18 Hz), 118.5 (d, J$_{C-CF}$=19 Hz), 117.6 (d, J$_{C-CF}$=19 Hz), 116.7 (d, J$_{C-CF}$=17 Hz), 113.1 (d, J$_{C-CF}$=11 Hz), 111.3, 111.2, 102.4, 102.1, 65.9, 57.6, 45.1, 44.6, 40.4, 34.2, 33.6.

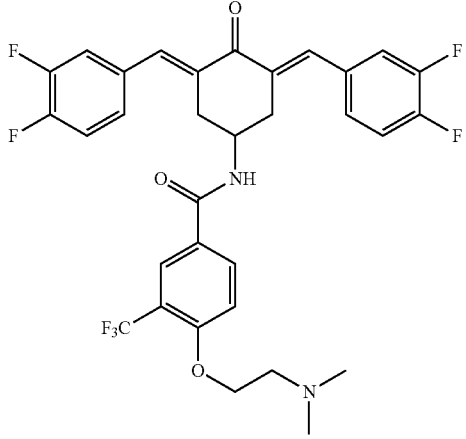 [SMILES: CN(C)CCOc1ccc(C(=O)NC2C/C(=C\c3ccc(F)c(F)c3)C(=O)/C(=C/c3ccc(F)c(F)c3)C2)cc1C(F)(F)F]

N-(3,5-Bis((E)-3,4-difluorobenzylidene)-4-oxocyclohexyl)-4-(2-(dimethylamino)ethoxy)-3-(trifluoromethyl)benzamide (JC134)

$^1$H NMR (400 MHz, CDCl$_3$) δ 7.88 (m, 1H), 7.72 (br s, 2H), 7.16 (m, 7H), 6.95 (d, J=8.7 Hz, 1H), 6.65 (d, J=7.3 Hz, 1H), 4.45 (m, 1H), 4.18 (t, J=5.6 Hz, 2H), 3.26 (bd, J=15.9 Hz, 2H), 3.03 (dd, J=15.8 Hz, J=5.8 Hz, 2H), 2.81 (t, J=5.6 Hz, 2H), 2.35 (s, 6H).

$^{13}$C NMR (126 MHz, CDCl$_3$) δ 187.8, 165.5, 159.1, 150.7 (dd, $J_{CF}$=255 Hz, $J_{C-CF}$=11 Hz, 2C), 150.1 (dd, $J_{CF}$=255 Hz, $J_{C-CF}$=13 Hz, 2C), 137.7 (2C), 134.5, 132.8 (2C), 132.7 (2C), 132.1 (dd, $J_{C-C-CF}$=5.7 Hz, $J_{C-C-CF}$=3.5 Hz, 2C), 129.2 (q, $J_{C-C-CF}$=38 Hz), 127.1 (dd, $J_{C-C-CF}$=5.9 Hz, $J_{C-C-CF}$=4.2 Hz, 2C), 125.8, 122.6 (q, $J_{CF}$=272 Hz), 118.8 (d, $J_{C-CF}$=18 Hz, 2C), 117.6 (d, $J_{C-CF}$=18 Hz, 2C), 112.5, 67.8, 57.5, 45.8, 45.0, 33.6.

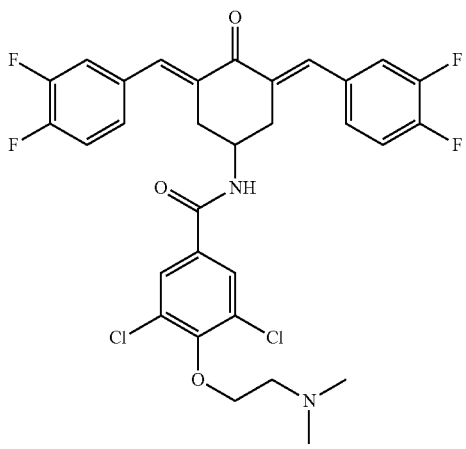 [SMILES: CN(C)CCOc1c(Cl)cc(C(=O)NC2C/C(=C\c3ccc(F)c(F)c3)C(=O)/C(=C/c3ccc(F)c(F)c3)C2)cc1Cl]

N-(3,5-Bis((E)-3,4-difluorobenzylidene)-4-oxocyclohexyl)-3,5-dichloro-4-(2-(dimethylamino)ethoxy)benzamide (JC135)

$^1$H NMR (400 MHz, CDCl$_3$) δ 7.74 (br s, 2H), 7.62 (s, 2H), 7.18 (m, 6H), 6.61 (d, J=7.2 Hz, 1H), 4.42 (m, 1H), 4.11 (t, J=5.7 Hz, 2H), 3.26 (bd, J=16.1 Hz, 2H), 3.03 (dd, J=15.9 Hz, J=5.8 Hz, 2H), 2.84 (t, J=5.7 Hz, 2H), 2.40 (s, 6H).

$^{13}$C NMR (126 MHz, CDCl$_3$) δ 187.6, 164.4, 154.2, 150.7 (dd, $J_{CF}$=255 Hz, $J_{C-CF}$=13 Hz, 2C), 150.2 (dd, $J_{CF}$=255 Hz, $J_{C-CF}$=13 Hz, 2C), 137.9 (2C), 132.6 (2C), 132.1 (dd, $J_{C-C-CF}$=5.9 Hz, $J_{C-C-CF}$=3.8 Hz, 2C), 131.1, 129.8, 127.8, 127.2 (dd, $J_{C-C-CF}$=6.1 Hz, $J_{C-C-CF}$=4.2 Hz, 2C), 118.9 (d, $J_{C-CF}$=18 Hz, 2C), 117.7 (d, $J_{C-CF}$=18 Hz, 2C), 70.9, 58.6, 45.5, 45.2, 33.6.

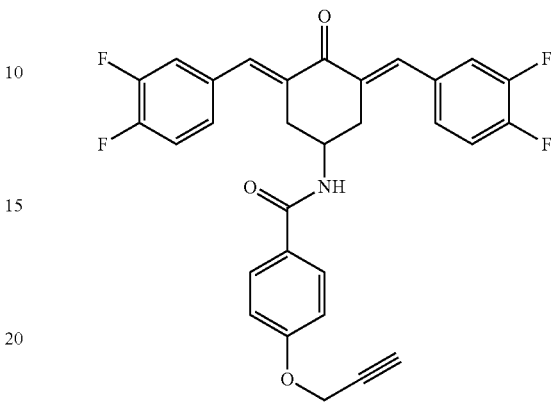

N-(3,5-Bis((E)-3,4-difluorobenzylidene)-4-oxocyclohexyl)-4-(prop-2-yn-1-yloxy)benzamide (JC144)

$^1$H NMR (400 MHz, DMSO-d$_6$) δ 8.42 (d, J=6.5 Hz, 1H), 7.80 (s, 1H), 7.78 (s, 1H), 7.60 (m, 4H), 7.47 (m, 2H), 7.37 (m, 2H), 7.00 (d, J=8.9 Hz, 2H), 4.83 (s, 2H), 4.82 (s, 2H), 4.06 (m, 1H), 3.31 (s, 1H), 3.15 (bd, J=15.8 Hz, 2H), 2.98 (dd, J=15.8 Hz, J=5.6 Hz, 2H).

$^{13}$C NMR (126 MHz, DMSO-d$_6$) δ 188.0, 166.1, 159.9, 150.1 (dd, $J_{CF}$=248 Hz, $J_{C-CF}$=12 Hz, 2C), 149.7 (dd, $J_{CF}$=244 Hz, $J_{C-CF}$=13 Hz, 2C), 135.7, 135.1 (2C), 133.2 (dd, $J_{C-C-CF}$=6.4 Hz, $J_{C-C-CF}$=3.9 Hz, 2C), 129.6, 128.0 (dd, $J_{C-C-CF}$=6.4 Hz, $J_{C-C-CF}$=3.1 Hz, 2C), 127.6, 119.6 (d, $J_{C-CF}$=17 Hz, 2C), 118.2 (d, $J_{C-CF}$=17 Hz, 2C), 114.8 (2C), 79.3, 78.9, 56.0, 45.5, 45.4, 33.5.

General Procedure E: The compounds were generally prepared by reaction of the 3,4-difluorobenzaldehyde, with piperidin-4-one hydrogen chloride in the present of 40% aq. sodium hydroxide to give 3,5-Bis((E)-3,4-difluorobenzylidene)piperidin-4-one, Acylation of 3,5-Bis((E)-3,4-difluorobenzylidene)piperidin-4-one with 2-chloroethanesulfonyl chloride under base condition afforded the 3,5-bis((E)-3,4-difluorobenzylidene)-1-(vinylsulfonyl)piperidin-4-one. Michael addition with amine afforded 3,5-bis((E)-3,4-difluorobenzylidene)-1-((2-(dimethylamino)ethyl)sulfonyl)piperidin-4-one.

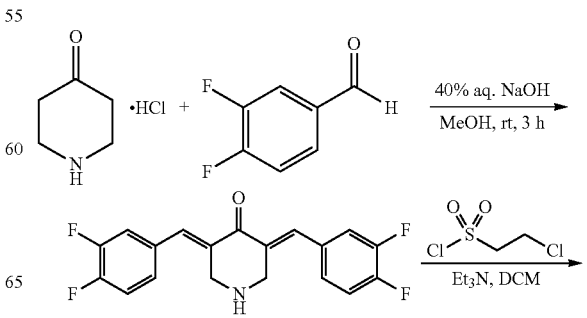

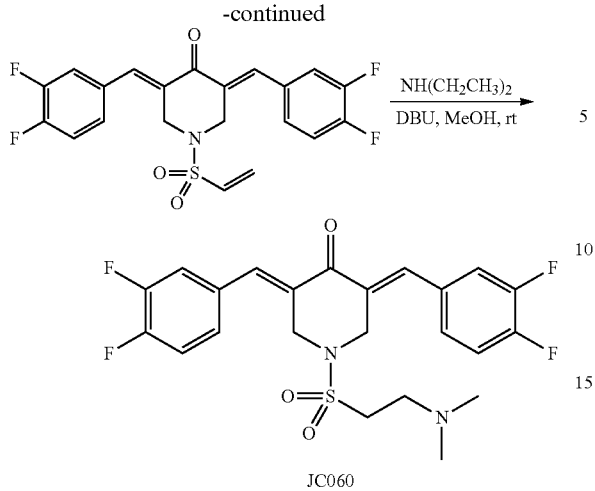

Example JC060

To the mixture of the piperidin-4-one hydrogen chloride (135.59 mg, 1 mmol, 1.0 equiv.) and methanol (2.0 mL) in a round bottom flask added drop-wise 40% aqueous sodium hydroxide (1.0 mL) and stirred for five minutes. To this mixture was added 3,4-difluorobenzaldehyde (355.3 mg, 2.5 mmol, 2.5 equiv.). The reaction mixture was then allowed to stir at room temperature for 3 h. After 3 h the yellow precipitate thus obtained was filtered, washed with water, cold methanol and dried to get pure product (285 mg, 80% yield).

The mixture of 3,5-Bis((E)-3,4-difluorobenzylidene)piperidin-4-one (173.7 mg, 0.5 mmol, 1.0 equiv.) and anhydrous triethylamine (210 μL, 1.5 mmol, 3.0 equiv.) in dry dichloromethane was maintained at 0° C. (ice bath). After stir at 0° C. for 20 minutes, to this cooled mixture, 2-chloroethanesulfonyl chloride (63 μL, 0.6 mmol, 1.2 equiv.) was added drop wise cautiously (exothermic). The reaction mixture was stirred for an addition 20 minutes before being warmed to room temperature and stirred for 4 hours. After such time, the reaction was quenched with 10% aq. HCl (2 mL). The organic layer was separated and washed with water (10 mL) and brine (10 mL). The combined organic solvent was dried over $Na_2SO_4$, filtered and concentrated under pressure. The crude product 3,5-bis((E)-3,4-difluorobenzylidene)-1-(vinylsulfonyl)piperidin-4-one was pure enough to be used for the next step.

Into a round bottom flask was added crude 3,5-bis((E)-3,4-difluorobenzylidene)-1-(vinylsulfonyl)piperidin-4-one (218.7 mg, 0.5 mmol, 1.0 equiv.), dry MeOH (0.5 mL, 1M), dimethylamine (2N in THF) (0.25 mL, 0.5 mmol, 1.0 equiv.) and DBU (7.5 μL, 0.05 mmol, 0.1 equiv.) under Ar. The reaction was stirred for 16 hour at room temperature, after which the crude reaction mixture was concentrated, followed by flash chromatography (gradient elution 50% DCM/EtOAc) to give yellow solid, dried the solvent by vacuum and added dry DCM (20 mL), filtered by cotton to get compound JC060 (139.9 mg, 58% yield).

The following compounds were synthesized by procedure E: JC060, JC088, JC094, JC098, JC107, JC108, JC121.

3,5-Bis((E)-3,4-difluorobenzylidene)-1-((2-(dimethylamino)ethyl)sulfonyl)piperidin-4-one (JC060)

$^1$H NMR (400 MHz, $CDCl_3$) δ 7.76 (br s, 2H), 7.30 (m, 6H), 4.65 (br s, 4H), 3.06 (t, J=6.8 Hz, 2H), 2.67 (t, J=6.8 Hz, 2H), 2.15 (s, 6H).

$^{13}$C NMR (100 MHz, $CDCl_3$) δ 184.7, 151.1 (dd, $J_{CF}$=252 Hz, $J_{C-CF}$=13 Hz, 2C), 150.5 (dd, $J_{CF}$=249 Hz, $J_{C-CF}$=13 Hz, 2C), 136.1 (2C), 131.4 (2C), 131.3 (dd, $J_{C-C-CF}$=5.7 Hz, $J_{C-C-CF}$=4.0 Hz, 2C), 127.1 (dd, $J_{C-C-CF}$=6.5 Hz, $J_{C-C-CF}$=3.5 Hz, 2C), 119.0 (d, $J_{C-CF}$=18 Hz, 2C), 118.2 (d, $J_{C-CF}$=17 Hz, 2C), 53.1, 50.7, 46.5, 45.1, 30.6.

HR-APCI m/z calcd for $C_{23}H_{22}F_4N_2O_3S$ [M+H]= 483.13655, found 483.13541.

N-(3,5-Bis((E)-3,4-difluorobenzylidene)-4-oxocyclohexyl)-2-(dimethylamino)ethane-1-sulfonamide (JC088)

$^1$H NMR (400 MHz, $CDCl_3$) δ 7.81 (br s, 2H), 7.21 (m, 6H), 3.99 (m, 1H), 3.13 (m, 4H), 3.00 (t, J=6.0 Hz, 2H), 2.69 (t, J=6.0 Hz, 2H), 2.07 (s, 6H).

$^{13}$C NMR (100 MHz, DMSO-$d_6$) δ 187.5, 151.0 (dd, $J_{CF}$=254 Hz, $J_{C-CF}$=14 Hz, 2C), 150.4 (dd, $J_{CF}$=254 Hz, $J_{C-CF}$=14 Hz, 2C), 135.9 (2C), 134.5 (2C), 133.2 (dd, $J_{C-C-CF}$=5.7 Hz, $J_{C-C-CF}$=4.0 Hz, 2C), 128.1 (dd, $J_{C-C-CF}$=5.7 Hz, $J_{C-C-CF}$=4.0 Hz, 2C), 119.5 (d, $J_{C-CF}$=20 Hz, 2C), 118.3 (d, $J_{C-CF}$=18 Hz, 2C), 53.4, 49.7, 47.9, 45.1, 34.7.

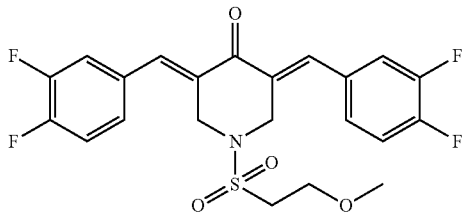 [SMILES: COCCS(=O)(=O)N1C/C(=C\c2ccc(F)c(F)c2)C(=O)/C(=C/c2ccc(F)c(F)c2)C1]

3,5-Bis((E)-3,4-difluorobenzylidene)-1-((2-methoxyethyl)sulfonyl)piperidin-4-one (JC094)

To a mixture of the piperidin-4-one hydrochloride (135.59 mg, 1 mmol, 1.0 equiv.) and methanol (2.0 mL) in a round bottom flask added dropwise 40% aqueous sodium hydroxide (1.0 mL) and the reaction mixture was stirred for 5 min. To this mixture was added 3,4-difluorobenzaldehyde (355.3 mg, 2.5 mmol, 2.5 equiv). The reaction mixture was then allowed to stir at 21° C. for 3 h. The yellow precipitate thus obtained was filtered, washed with water and cold methanol and dried to get the pure piperidone product (285 mg, 80% yield).

A mixture of 3,5-bis((E)-3,4-difluorobenzylidene)piperidin-4-one (173.7 mg, 0.5 mmol, 1.0 equiv.) and anhydrous triethylamine (105 µL, 0.75 mmol, 1.5 equiv.) in dichloromethane was maintained at 0° C. (ice bath). To this cooled mixture was added dropwise 2-methoxyethane-1-sulfonyl chloride (95.16 mg, 0.6 mmol, 1.2 equiv). After the addition was complete, the reaction mixture was slowly warmed up to 21° C. and it was stirred for a further 4 h. The reaction solvent was evaporated and the residue thus obtained was washed with water, filtered and dried. The crude product was purified by flash chromatography on silica gel (gradient elution 20% EtOAc/Hexane-50% EtOAc/Hexane) to give the desired compound JC094 (209 mg, 89%) as a light yellow powder.

$^1$H NMR (400 MHz, CDCl$_3$) δ 7.74 (br s, 2H), 7.19 (m, 6H), 4.62 (br s, 4H), 3.71 (t, J=5.5 Hz, 2H), 3.29 (s, 3H), 3.21 (t, J=5.5 Hz, 2H).

$^{13}$C NMR (126 MHz, CDCl$_3$) δ 185.0, 151.1 (dd, $J_{CF}$=255 Hz, $J_{C-CF}$=13 Hz, 2C), 150.4 (dd, $J_{CF}$=250 Hz, $J_{C-CF}$=13 Hz, 2C), 135.8 (2C), 131.5 (2C), 131.3 (dd, $J_{C-C-CF}$=5.8 Hz, $J_{C-C-CF}$=4.2 Hz, 2C), 127.1 (dd, $J_{C-C-CF}$=6.6 Hz, $J_{C-C-CF}$=3.5 Hz, 2C), 119.1 (d, $J_{C-CF}$=18 Hz, 2C), 118.0 (d, $J_{C-CF}$=18 Hz, 2C), 66.3, 58.7, 56.3, 52.6, 46.6.

HR-APCI m/z calcd for C$_{22}$H$_{19}$F$_4$NO$_4$S [M+H]= 470.10492, found 470.11597.

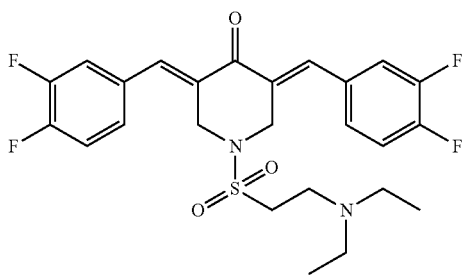 [SMILES: CCN(CC)CCS(=O)(=O)N1C/C(=C\c2ccc(F)c(F)c2)C(=O)/C(=C/c2ccc(F)c(F)c2)C1]

1-((2-(Diethylamino)ethyl)sulfonyl)-3,5-bis((E)-3,4-difluorobenzylidene)piperidin-4-one (JC098)

$^1$H NMR (400 MHz, CDCl$_3$) δ 7.75 (br s, 2H), 7.18 (m, 6H), 4.62 (br s, 4H), 3.04 (t, J=6.5 Hz, 2H), 2.83 (t, J=6.5 Hz, 2H), 2.45 (q, J=7.1 Hz, 4H), 0.95 (t, J=7.2 Hz, 6H).

$^{13}$C NMR (126 MHz, CDCl$_3$) δ 184.8, 151.0 (dd, $J_{CF}$=254 Hz, $J_{C-CF}$=13 Hz, 2C), 150.4 (dd, $J_{C-CF}$=254 Hz, $J_{C-CF}$=13 Hz, 2C), 136.4 (2C), 131.2 (2C), 131.1 (dd, $J_{C-C-CF}$=5.9 Hz, $J_{C-C-CF}$=3.8 Hz, 2C), 127.1 (dd, $J_{C-C-CF}$=6.7 Hz, $J_{C-C-CF}$=3.7 Hz, 2C), 119.1 (d, $J_{C-CF}$=18 Hz, 2C), 118.1 (d, $J_{C-CF}$=18 Hz, 2C), 50.0, 46.8, 46.6, 46.5, 29.7, 11.6.

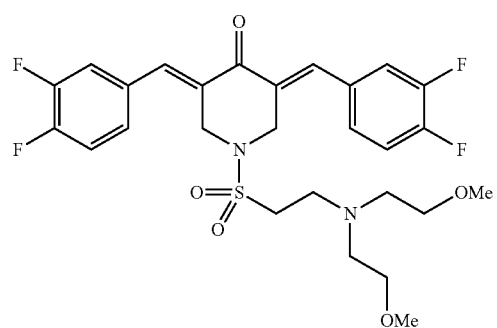 [SMILES: COCCN(CCOC)CCS(=O)(=O)N1C/C(=C\c2ccc(F)c(F)c2)C(=O)/C(=C/c2ccc(F)c(F)c2)C1]

1-((2-(Bis(2-methoxyethyl)amino)ethyl)sulfonyl)-3,5-bis((E)-3,4-difluorobenzylidene)piperidin-4-one (JC107)

$^1$H NMR (400 MHz, CDCl$_3$) δ 7.77 (br s, 2H), 7.20 (m, 6H), 4.63 (br s, 4H), 3.40 (t, J=5.5 Hz, 4H), 3.28 (s, 6H), 3.14 (dd, J=5.3 Hz, J=9.6 Hz, 2H), 3.01 (dd, J=5.0 Hz, J=9.2 Hz, 2H), 2.69 (t, J=5.5 Hz, 4H).

$^{13}$C NMR (126 MHz, CDCl$_3$) δ 184.9, 151.2 (dd, $J_{CF}$=250 Hz, $J_{C-CF}$=13 Hz, 2C), 150.4 (dd, $J_{CF}$=254 Hz, $J_{C-CF}$=11 Hz, 2C), 136.4 (2C), 131.2 (2C), 131.3 (dd, $J_{C-C-CF}$=5.8 Hz, $J_{C-C-CF}$=3.9 Hz, 2C), 127.1 (dd, $J_{C-C-CF}$=6.0 Hz, $J_{C-C-CF}$=3.8 Hz, 2C), 119.2 (d, $J_{C-CF}$=18 Hz, 2C), 118.1 (d, $J_{C-CF}$=17 Hz, 2C), 70.7, 58.8, 53.9, 49.5, 48.7, 46.6.

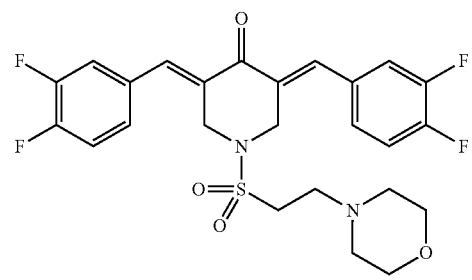 [SMILES: O=C1/C(=C/c2ccc(F)c(F)c2)CN(S(=O)(=O)CCN2CCOCC2)C/C1=C\c1ccc(F)c(F)c1]

3,5-Bis((E)-3,4-difluorobenzylidene)-1-((2-morpholinoethyl)sulfonyl)piperidin-4-one (JC108)

$^1$H NMR (400 MHz, CDCl$_3$) δ 7.78 (br s, 2H), 7.19 (m, 6H), 4.66 (br s, 4H), 3.63 (m, 4H), 3.08 (t, J=6.8 Hz, 2H), 2.73 (t, J=6.8 Hz, 2H), 2.39 (m, 4H).

$^{13}$C NMR (100 MHz, CDCl$_3$) δ 184.8, 151.1 (dd, $J_{CF}$=255 Hz, $J_{C-CF}$=13 Hz, 2C), 150.5 (dd, $J_{CF}$=251 Hz, $J_{C-CF}$=13 Hz, 2C), 136.6 (2C), 131.4 (2C), 131.3 (dd, $J_{C-C-CF}$=5.9

Hz, $J_{C-C-CF}$=3.8 Hz, 2C), 127.1 (dd, $J_{C-C-CF}$=6.0 Hz, $J_{C-C-CF}$=3.5 Hz, 2C), 119.0 (d, $J_{C-CF}$=18 Hz, 2C), 118.2 (d, $J_{C-CF}$=17 Hz, 2C), 66.5, 56.0, 53.4, 52.1, 46.7, 29.7.

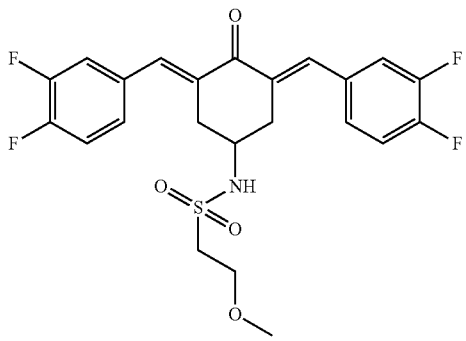 [SMILES: COCCS(=O)(=O)NC1C/C(=C\c2ccc(F)c(F)c2)C(=O)/C(=C/c2ccc(F)c(F)c2)C1]

N-(3,5-Bis((E)-3,4-difluorobenzylidene)-4-oxocyclohexyl)-2-methoxyethane-1-sulfonamide (JC121)

$^1$H NMR (400 MHz, CDCl$_3$) δ 7.58 (br s, 2H), 7.45 (m, 6H), 3.60 (m, 1H), 3.53 (t, J=6.0 Hz, 4H), 3.23 (t, J=6.0 Hz, 4H), 3.13 (m, 2H), 3.06 (s, 3H), 2.91 (in, 2H).

$^{13}$C NMR (100 MHz, CDCl$_3$) δ 187.4, 151.0 (dd, $J_{CF}$=248 Hz, $J_{C-CF}$=13 Hz, 2C), 150.4 (dd, $J_{CF}$=248 Hz, $J_{C-CF}$=13 Hz, 2C), 135.9 (2C), 134.4 (2C), 133.2 (2C), 128.1 (2C), 119.5 (d, $J_{C-CF}$ 17 Hz, 2C), 118.3 (d, $J_{C-CF}$ 17 Hz, 2C), 66.5, 58.2, 51.7, 48.0, 34.7.

General Procedure F: The compounds were generally prepared by reaction of the 3,4-difluorobenzaldehyde, with 4-oxocyclohexane-1-carboxylic acid in the present of 20% a aq. sodium hydroxide (1.5 mL) to give 3,5-bis((E)-3,4-difluorobenzylidene)-4-oxocyclohexane-1-carboxylic acid. 3,5-bis((E)-3,4-difluorobenzylidene)-4-oxocyclohexane-h-carboxylic acid coupling with amine afforded 3,5-bis((E)-3,4-difluorobenzylidene)-N-(2-(dimethylamino)ethyl)-4-oxocycloexane-1-carboxamide.

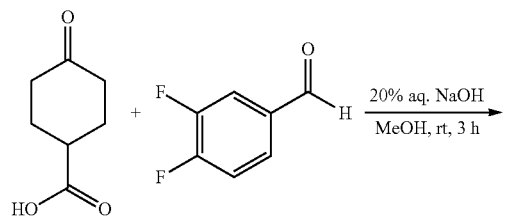

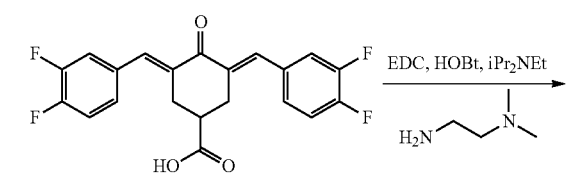

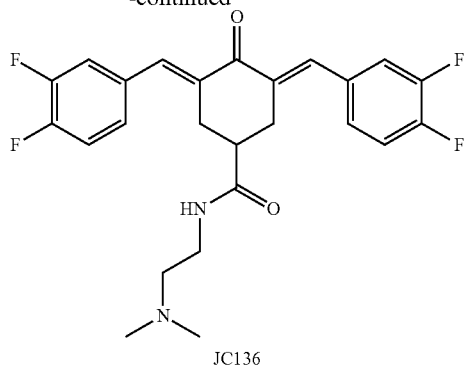

JC136

Example JC136

To the mixture of the 4-oxocyclohexane-1-carboxylic acid (142.15 mg, 1 mmol, 1.0 equiv.) and ethanol (1.0 mL) in a round bottom flask added drop-wise 20% aqueous sodium hydroxide (1.0 mL) and stirred for five minutes. To this mixture was added 3,4-difluorobenzaldehyde (355.3 mg, 2.5 mmol, 2.5 equiv.). The reaction mixture was then allowed to stir at room temperature for 3 h. After such time, remove MeOH under vacuum, added 1 N HCl (1 mL), the yellow precipitate thus obtained was filtered, washed with water and cold methanol, dried to get pure product (273 mg, 70% yield).

To mixture of crude 3,5-bis((E)-3,4-difluorobenzylidene)-4-oxocyclohexane-1-carboxylic acid (195.2 mg, 0.5 mmol, 1.0 equiv.), $N^1,N^1$-dimethylethane-1,2-diamine (65.5 μL, 0.6 mmol, 1.2 equiv.), N-(3-dimethylaminopropyl)-N'-ethylcarbodiimide hydrochloride (143.8 mg, 0.75 mmol, 1.5 equiv.), hydroxybenzotriazole (101.3 mg, 0.75 mmol, 1.5 equiv.) in 1.0 mL anhydrous dichloromethane (2.0 mL) drop wise N,N-diisopropylethylamine (135 μL, 0.775 mmol, 1.55 equiv.) at room temperature. The mixture was stirred for 16 h. The reaction mixture was diluted with DCM (10 mL) then washed with sat. NaHCO$_3$ (2×10 mL), water (2×10 mL), brine the dried over Na$_2$SO$_4$, filtered. The solvent was evaporated, followed by flash chromatography (gradient elution 20% methanol/EtOAC-25% methanol/EtOAC) to give yellow solid, dried the solvent by vacuum and added dry DCM (10 mL), filtered by cotton to get compound JC136 (188.8 mg, 82% yield).

The following compounds were synthesized by procedure F: JC136, JC137, JC138, JC139, JC143.

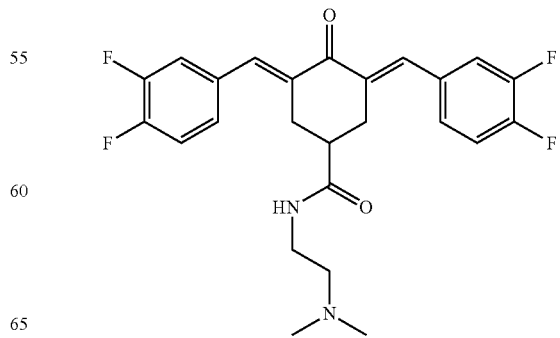

3,5-Bis((E)-3,4-difluorobenzylidene)-N-(2-(dimethylamino)ethyl)-4-oxocyclohexane-1-carboxamide (JC136)

$^1$H NMR (400 MHz, CDCl$_3$) δ 7.69 (br s, 2H), 7.24 (m, 2H), 7.15 (m, 4H), 6.32 (t, J=4.4 Hz, 1H), 3.33 (m, 2H), 3.05 (m, 4H), 2.46 (m, 1H), 2.40 (t, J=5.8 Hz, 2H), 2.15 (s, 6H).

$^{13}$C NMR (100 MHz, CDCl$_3$) δ 188.8, 173.3, 150.6 (dd, J$_{CF}$=251 Hz, J$_{C-CF}$=13 Hz, 2C), 150.1 (dd, J$_{CF}$=248 Hz, J$_{C-CF}$=14 Hz, 2C), 136.2 (2C), 134.1 (2C), 132.4 (dd, J$_{C-C-CF}$=6.0 Hz, J$_{C-C-CF}$=3.1 Hz, 2C), 127.1 (dd, J$_{C-C-CF}$=5.8 Hz, J$_{C-C-CF}$=3.2 Hz, 2C), 118.9 (d, J$_{C-CF}$=18 Hz, 2C), 117.5 (d, J$_{C-CF}$=18 Hz, 2C), 57.5, 45.0, 41.3, 36.8, 31.3.

3,5-Bis((E)-3,5-dichlorobenzylidene)-N-(2-(dimethylamino)ethyl)-4-oxocyclohexane-1-carboxamide (JC137)

$^1$H NMR (400 MHz, CDCl$_3$) δ 7.60 (br s, 2H), 7.27 (m, 2H), 7.22 (m, 4H), 6.47 (t, J=4.7 Hz, 1H), 3.30 (m, 2H), 3.01 (m, 4H), 2.48 (m, 1H), 2.40 (t, J=5.8 Hz, 2H), 2.17 (s, 6H).

$^{13}$C NMR (126 MHz, CDCl$_3$) δ 187.4, 173.0, 138.2 (2C), 135.5 (2C), 135.4 (2C), 135.1 (2C), 128.7 (2C), 128.2 (2C), 57.5, 44.9, 40.9, 36.7, 31.2.

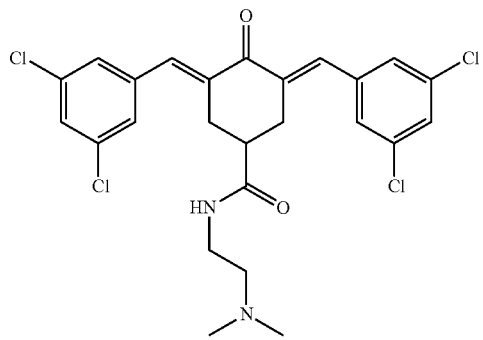 [SMILES: CN(C)CCNC(=O)C1C/C(=C\c2cc(Cl)cc(Cl)c2)C(=O)/C(=C/c2cc(Cl)cc(Cl)c2)C1]

3,5-Bis((E)-3,5-dichlorobenzylidene)-N-(4-(2-(dimethylamino)ethoxy)phenyl)-4-oxocyclohexane-1-carboxamide (JC138)

$^1$H NMR (400 MHz, CDCl$_3$) δ 7.72 (br s, 2H), 7.49 (s, 1H), 7.37 (d, J=9.0 Hz, 2H), 7.20 (m, 6H), 6.87 (d, J=9.0 Hz, 2H), 4.05 (t, J=5.7 Hz, 2H), 3.15 (m, 2H), 2.98 (m, 2H), 2.74 (t, J=5.6 Hz, 2H), 2.58 (m, 1H), 2.35 (s, 6H).

$^{13}$C NMR (126 MHz, CDCl$_3$) δ 187.6, 171.2, 155.6, 138.0 (2C), 135.9 (2C), 135.3 (2C), 135.2 (2C), 130.9, 128.9 (2C), 128.2 (2C), 121.8, 114.9, 65.7, 57.8, 45.4, 41.8, 31.2.

3,5-Bis((E)-3,4-difluorobenzylidene)-N-(4-(2-(dimethylamino)ethoxy)phenyl)-4-oxocyclohexane-1-carboxamide (JC139)

$^1$H NMR (400 MHz, CDCl$_3$) δ 7.74 (br s, 2H), 7.43 (s, 1H), 7.41 (d, J=9.0 Hz, 2H), 7.21 (m, 6H), 6.85 (d, J=9.0 Hz, 2H), 4.06 (t, J=5.6 Hz, 2H), 3.35 (m, 2H), 3.17 (m, 2H), 2.79 (t, J=5.6 Hz, 2H), 2.55 (m, 1H), 2.37 (s, 6H).

$^{13}$C NMR (126 MHz, CDCl$_3$) δ 188.8, 171.1, 155.6, 150.9 (dd, J$_{CF}$=255 Hz, J$_{C-CF}$=13 Hz, 2C), 150.4 (dd, J$_{CF}$=255 Hz, J$_{C-CF}$=13 Hz, 2C), 136.4 (2C), 134.8, 133.7 (2C), 132.1 (dd, J$_{C-C-CF}$=5.9 Hz, J$_{C-C-CF}$=3.8 Hz, 2C), 126.9 (dd, J$_{C-C-CF}$=6.4 Hz, J$_{C-C-CF}$=4.2 Hz, 2C), 121.5, 118.9 (d, J$_{C-CF}$=18 Hz, 2C), 117.5 (d, J$_{C-CF}$=18 Hz, 2C), 114.8, 65.7, 57.8, 45.3, 42.3, 31.3.

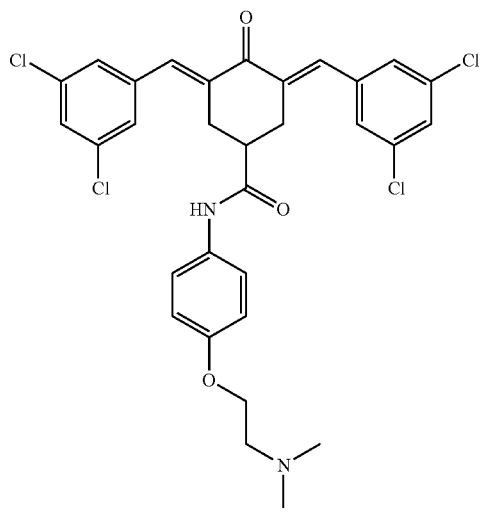 [SMILES: CN(C)CCOc1ccc(NC(=O)C2C/C(=C\c3cc(Cl)cc(Cl)c3)C(=O)/C(=C/c3cc(Cl)cc(Cl)c3)C2)cc1]

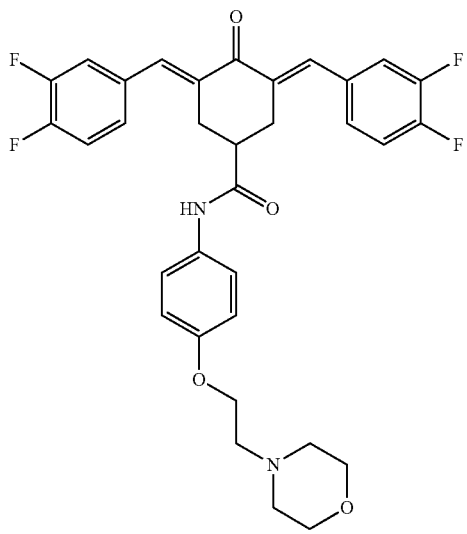 [SMILES: O=C1/C(=C/c2ccc(F)c(F)c2)CC(C(=O)Nc2ccc(OCCN3CCOCC3)cc2)C/C1=C\c1ccc(F)c(F)c1]

3,5-Bis((E)-3,4-difluorobenzylidene)-N-(4-(2-morpholinoethoxy)phenyl)-4-oxocyclohexane-1-carboxamide (JC143)

¹H NMR (400 MHz, CDCl₃) δ 7.76 (s, 1H), 7.68 (br s 2H), 7.42 (d, J=9.0 Hz, 2H), 7.15 (m, 6H), 6.83 (d, J=9.0 Hz, 2H), 4.07 (t, J=5.7 Hz, 2H), 3.71 (m, 4H), 3.11 (m, 4H), 2.94 (m, 1H), 2.78 (t, J=5.7 Hz, 2H), 2.61 (m, 4H).

¹³C NMR (100 MHz, CDCl₃) δ 188.1, 171.3, 155.6, 150.7 (dd, $J_{CF}$=252 Hz, $J_{C-CF}$=13 Hz, 2C), 150.1 (dd, $J_{CF}$=248 Hz, $J_{C-CF}$=13 Hz, 2C), 136.6, 133.4 (2C), 132.1 (dd, $J_{C-C-CF}$=5.8 Hz, $J_{C-C-CF}$=4.2 Hz, 2C), 130.9, 127.1 (dd, $J_{C-C-CF}$=6.3 Hz, $J_{C-C-CF}$=3.6 Hz, 2C), 121.6, 119.1 (d, $J_{C-CF}$=18 Hz, 2C), 117.6 (d, $J_{C-CF}$=18 Hz, 2C), 115.0 (2C), 66.8, 66.0, 57.6, 54.1, 42.2, 31.4.

General Procedure G: The compounds were generally prepared by reaction of the 3,4-difluorobenzaldehyde, with tert-butyl (4-(4-oxocyclohexyl)phenyl)carbamate in the present of 20% aq. sodium hydroxide to give tert-butyl (4-(3,5-bis((E)-3,4-difluorobenzylidene)-4-oxocyclohexyl) phenyl)-carbamate. TFA deprotected Boc group. Acylation of 4-(4-aminophenyl)-2,6-bis((E)-3,4-difluorobenzylidene) cyclohexan-1-one with 3-(dimethylamino)propanoyl chloride under basic conditions afforded the N-(4-(3,5-bis((E)-3,4-difluorobenzylidene)-4-oxocyclohexyl)phenyl)-3-(dimethylamino)-propanamide.

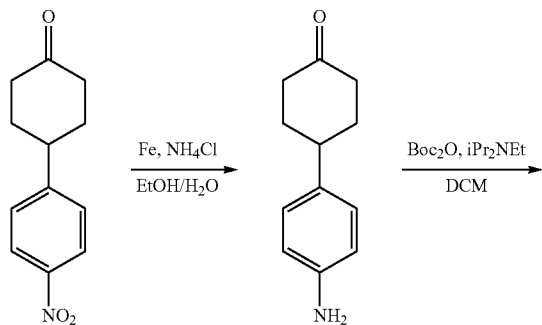

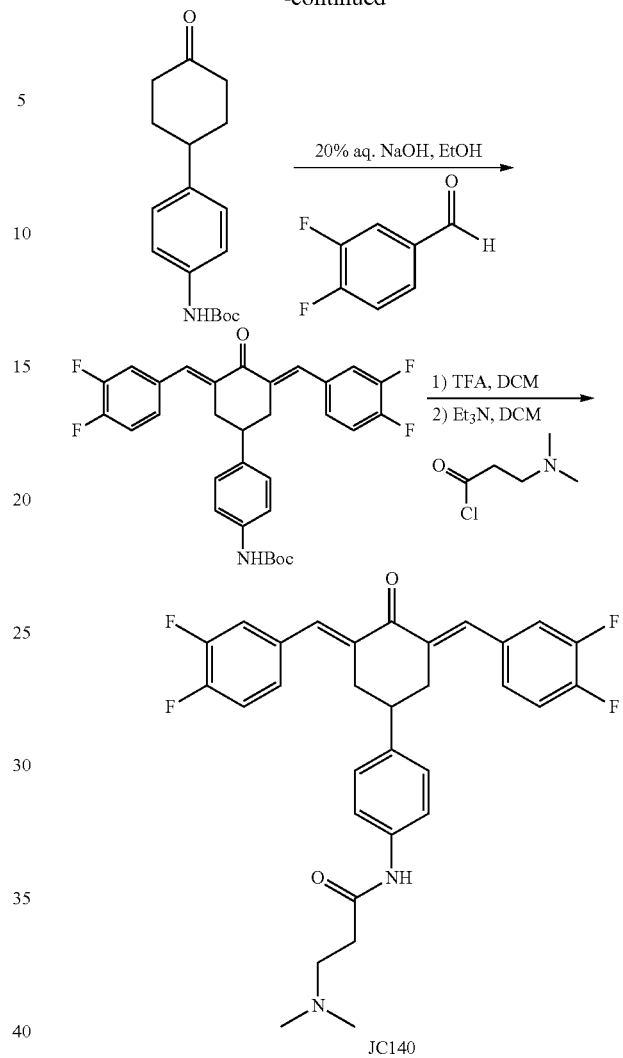

Example JC140

To a solution of 4-(4-nitrophenyl)cyclohexanone (892 mg, 4.07 mmol, 1.0 equiv.) in Ethanol (16 mL) at 60° C. was added a solution of ammonium chloride (2.18 g, 40.7 mmol, 10.0 equiv.) in water (5.0 mL) followed by Iron powder (682 mg, 12.2 mmol, 3.0 equiv.) portion wise. The reaction mixture was refluxed for 3 h, cooling to room temperature, filtered and exacted with EtOAc (2×10 mL). The combined organic layers were washed with brine and dried over MgSO₄, removal of the solvent followed by flash chromatography (gradient elution 25% EtOAC/DCM) to give light yellow solid (385.1 mg, 50% yield).

To a solution of 4-(4-aminophenyl)cyclohexan-1-one (378.5 mg, 2 mmol, 1.0 equiv.) in THF (3.0 mL) cooled in an ice bath was added (Boc)₂O (436.5 mg, 2 mmol, 1.0 equiv.) followed by diisopropylethylamine (348.4 µL, 2 mmol, 1.0 equiv.). The mixture was stirred at room temperature for 20 h and concentrated. The residue was taken up in ethyl acetate, washed with brine, dried over Na₂SO₄ and concentrated to get product which is enough pure to be used for next step.

To the mixture of tert-butyl (4-(4-oxocyclohexyl)phenyl) carbamate (289.38 mg, 1 mmol, 1.0 equiv.) and ethanol (1.0 mL) in a round bottom flask added drop-wise 20% aqueous sodium hydroxide (1.5 mL) and stirred for five minutes. To this mixture was added 3,4-difluorobenzaldehyde (355.3 mg, 2.5 mmol, 2.5 equiv.). The reaction mixture was then allowed to stir at room temperature for 5 h. After 5 h the yellow precipitate thus obtained was filtered, washed with water, cold ethanol and dried to get pure product (430 mg, 80% yield).

Trifluoroacetic acid (0.5 ml) was added to a solution of tert-butyl (4-(3,5-bis((E)-3,4-difluorobenzylidene)-4-oxocyclohexyl)phenyl)carbamate (268.8 mg, 0.5 mmol) in methylene chloride (5.0 ml) at room temperature and stirred for 3 h at room temperature. Then, the solvent of the reaction solution was distilled off under reduced pressure and the resulting residue was poured into a 1N-aqueous sodium hydroxide solution and extracted with ethyl acetate and chloroform. The organic layer was washed with a saturated aqueous sodium chloride solution and then dried over anhydrous magnesium sulfate. The solvent was distilled off under reduced pressure to obtain 4-(4-aminophenyl)-2,6-bis((E)-3,4-difluorobenzylidene)cyclohexan-1-one.

The mixture of 4-(4-aminophenyl)-2,6-bis((E)-3,4-difluorobenzylidene)cyclohexan-1-one (218.7 mg, 0.5 mmol, 1.0 equiv.) and anhydrous triethylamine (70 μL, 0.5 mmol, 1.0 equiv.) in dichloromethane was maintained at 0° C. (ice bath). To this cooled mixture, 3-(dimethylamino)propanoyl chloride (67.8 mg, 0.5 mmol, 1.0 equiv.) in 2.0 mL dichloromethane was added drop wise. After the complete addition of 3-(dimethylamino)propanoyl chloride the reaction mixture was slowly warmed up to room temperature and stirred over night. The mixture was extracted with ethyl acetate and dichloromethane three times. The organic layer was washed with a saturated aqueous sodium chloride solution and then dried over anhydrous sodium sulfate. The solvent was evaporated, followed by flash chromatography (gradient elution 25% methanol/EtOAC-30% methanol/EtOAC) to give yellow solid, dried the solvent by vacuum and added dry DCM (10 mL), filtered by cotton to get compound JC140 (169 mg, 63% yield).

The following compounds were synthesized by procedure G: JC140, JC141.

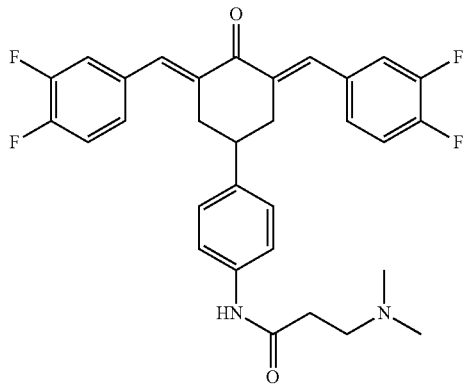 [SMILES: CN(C)CCC(=O)Nc1ccc(C2C/C(=C\c3ccc(F)c(F)c3)C(=O)/C(=C/c3ccc(F)c(F)c3)C2)cc1]

N-(4-(3,5-Bis((E)-3,4-difluorobenzylidene)-4-oxocyclohexyl)phenyl)-3-(dimethylamino) propanamide (JC140)

$^{1}$H NMR (400 MHz, CDCl$_{3}$) δ 10.9 (s, 1H), 7.73 (br s, 2H), 7.49 (d, J=8.5 Hz, 2H), 7.22 (m, 4H), 7.16 (m, 4H), 3.20 (m, 2H), 2.94 (m, 3H), 2.68 (t, J=5.6 Hz, 2H), 2.52 (t, J=5.6 Hz, 2H), 2.38 (s, 6H).

$^{13}$C NMR (126 MHz, CDCl$_{3}$) δ 188.7, 170.5, 150.9 (dd, J$_{CF}$=255 Hz, J$_{C—CF}$=13 Hz, 2C), 150.2 (dd, J$_{CF}$=255 Hz, J$_{C—CF}$=13 Hz, 2C), 139.1, 137.5 (2C), 135.6, 135.3 (2C), 132.4 (dd, J$_{C—C—CF}$=5.9 Hz, J$_{C—C—CF}$=4.3 Hz, 2C), 127.0, 126.9 (dd, J$_{C—C—CF}$=6.4 Hz, J$_{C—C—CF}$=3.5 Hz, 2C), 120.3, 118.9 (d, J$_{C—CF}$=18 Hz, 2C), 117.4 (d, J$_{C—CF}$=18 Hz, 2C), 55.0, 44.3, 39.8, 35.7, 33.3.

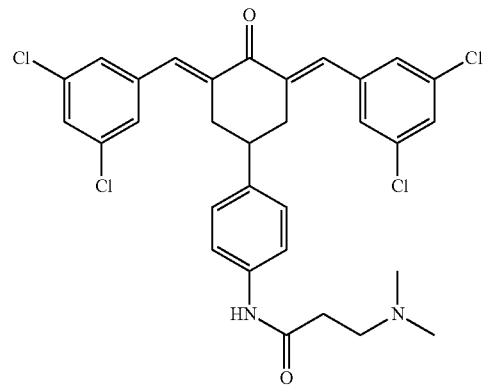 [SMILES: CN(C)CCC(=O)Nc1ccc(C2C/C(=C\c3cc(Cl)cc(Cl)c3)C(=O)/C(=C/c3cc(Cl)cc(Cl)c3)C2)cc1]

N-(4-(3,5-Bis((E)-3,5-dichlorobenzylidene)-4-oxocyclohexyl)phenyl)-3-(dimethylamino)-Propanamide (JC141)

$^{1}$H NMR (400 MHz, CDCl$_{3}$) δ 10.9 (s, 1H), 7.68 (br m, 2H), 7.29 (m, 10H), 2.67 (m, 2H), 2.53 (m, 2H), 2.37 (s, 6H).

$^{13}$C NMR (100 MHz, CDCl$_{3}$) δ 188.3, 170.3, 138.7, 138.2, 135.4 (2C), 135.2 (2C), 135.0 (2C), 128.6, 128.5, 128.1, 128.0, 127.3, 127.0, 120.3 (2C), 54.9, 44.3, 39.6, 35.4, 33.2, 29.6.

General Procedure H: The compounds were generally prepared by reaction of the 3,4-difluorobenzaldehyde, with piperidin-4-one hydrogen chloride in the present of 40% aq. sodium hydroxide to give 3,5-bis((E)-3,4-difluorobenzylidene)piperidin-4-one, Acylation or alkylation of 3,5-bis ((E)-3,4-difluorobenzylidene)piperidin-4-one with chloride under base condition afforded the 1-acryloyl 3,5-bis((E)-3, 4-difluorobenzylidene)piperidin-4-one or 1-alkyl 3,5-bis ((E)-3,4-difluorobenzyl-idene)piperidin-4-one.

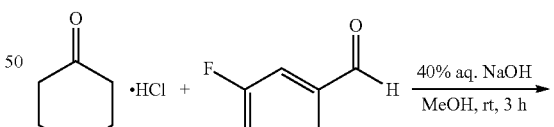

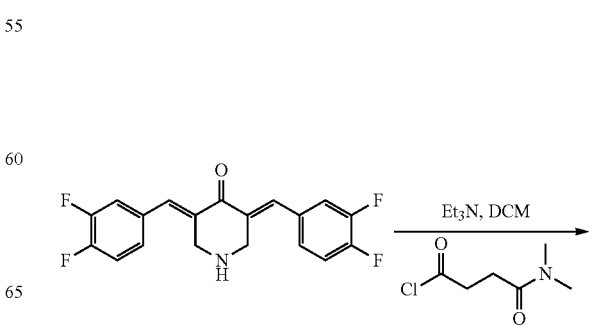

-continued

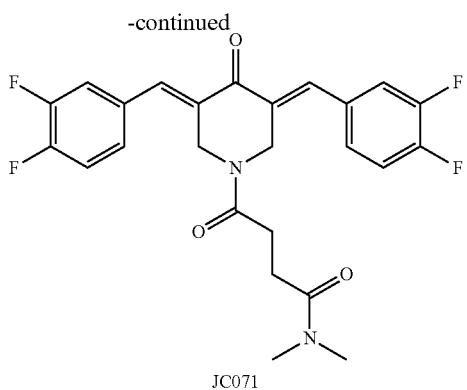

JC071

Example JC071

To the mixture of the piperidin-4-one hydrogen chloride (135.59 mg, 1 mmol, 1.0 equiv.) and methanol (2.0 mL) in a round bottom flask added drop-wise 40% aqueous sodium hydroxide (1.0 mL) and stirred for five minutes. To this mixture was added 3,4-difluorobenzaldehyde (355.3 mg, 2.5 mmol, 2.5 equiv.). The reaction mixture was then allowed to stir at room temperature for 3 h. After 3 h the yellow precipitate thus obtained was filtered, washed with water, cold methanol and dried to get pure product (285 mg, 80% yield).

The mixture of 3,5-Bis((E)-3,4-difluorobenzylidene)piperidin-4-one (173.7 mg, 0.5 mmol, 1.0 equiv.) and anhydrous triethylamine (105 μL, 0.75 mmol, 1.5 equiv.) in dichloromethane was maintained at 0° C. (ice bath). To this cooled mixture, 4-(dimethylamino)-4-oxobutanoyl chloride (122.7 mg, 0.75 mmol, 1.5 equiv.) was added drop wise. After the complete addition of 4-(dimethylamino)-4-oxobutanoyl chloride the reaction mixture was slowly warmed up to room temperature and stirred further for 4 h. After completion of the reaction solvent was evaporated and the residue thus obtained was washed with water, filtered and dried. The crude product was purified by flash chromatography (gradient elution 10% methanol/EtOAc-20% methanol/EtOAc) to give yellow solid, dried the solvent by vacuum and added dry DCM (10 mL), filtered by cotton to get compound JC071 (142.3 mg, 60% yield).

The following compounds were synthesized by procedure H: JC007, JC008, JC009, JC010, JC011, JC053, JC054, JC055, JC056, JC057, JC058, JC059, JC061, JC062, JC063, JC068, JC071, JC072, JC073, JC074, JC075, JC076, JC077, JC078, JC089, JC090, JC091, JC092, JC093, JC101, JC119, JC120, JC129, JC130.

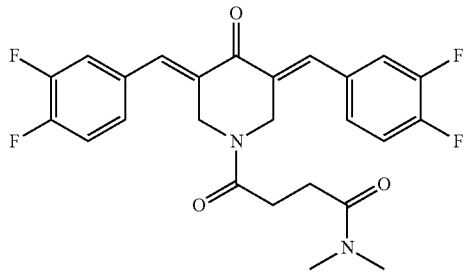 [SMILES: CN(C)C(=O)CCC(=O)N1C/C(=C\c2ccc(F)c(F)c2)C(=O)/C(=C/c2ccc(F)c(F)c2)C1]

4-(3,5-Bis((E)-3,4-difluorobenzylidene)-4-oxopiperidin-1-yl)-N,N-dimethyl-4-oxobutan amide (JC071)

$^1$H NMR (400 MHz, CDCl$_3$) δ 7.73 (br s, 2H), 7.21 (m, 6H), 4.86 (s, 2H), 4.81 (s, 2H), 2.99 (s, 3H), 2.91 (s, 3H), 2.59 (t, J=7.2 Hz, 2H), 2.54 (t, J=7.2 Hz, 2H).

$^{13}$C NMR (100 MHz, CDCl$_3$) δ 186.1, 171.0, 170.0, 150.9 (dd, J$_{CF}$=252 Hz, J$_{C-CF}$=13 Hz, 2C), 150.4 (dd, J$_{CF}$=252 Hz, J$_{C-CF}$=13 Hz, 2C), 136.1, 135.5, 132.1 (dd, J$_{C-C-CF}$=6.1 Hz, J$_{C-C-CF}$=3.5 Hz, 2C), 131.5, 127.2 (dd, J$_{C-C-CF}$=6.4 Hz, J$_{C-C-CF}$=4.2 Hz, 2C), 119.2 (d, J$_{C-CF}$=17 Hz), 119.0 (d, J$_{C-CF}$=17 Hz), 118.1 (d, J$_{C-CF}$=17 Hz), 117.8 (d, J$_{C-CF}$=17 Hz), 46.0, 37.2, 35.7, 29.8, 28.2, 27.8.

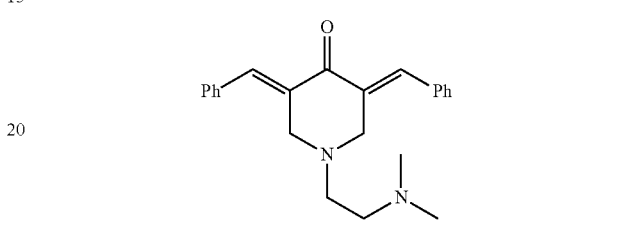

3,5-Di((E)-benzylidene)-1-(2-(dimethylamino)ethyl)piperidin-4-one (JC007)

$^1$HNMR (400 MHz, CDCl$_3$) δ 7.83 (br s, 2H), 7.39 (m, 10H), 3.91 (br s, 4H), 2.71 (t, J=6.8 Hz, 2H), 2.42 (t, J=6.8 Hz, 2H), 2.21 (s, 6H).

$^{13}$C NMR (100 MHz, CDCl$_3$) δ 187.3, 136.9 (2C), 135.2 (2C), 133.1 (2C), 130.4 (2C), 129.1 (2C), 128.6 (2C), 56.7, 54.9, 54.3, 45.3.

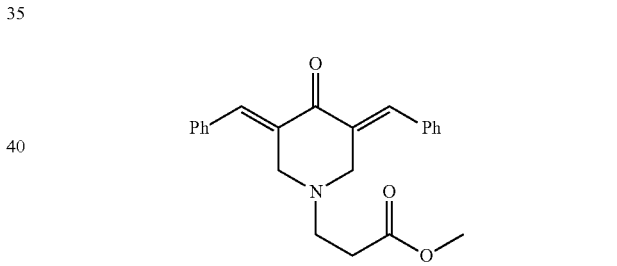

Methyl 3-(3,5-di((E)-benzylidene)-4-oxopiperidin-1-yl)propanoate (JC008)

$^1$H NMR (400 MHz, CDCl$_3$) δ 7.82 (br s, 2H), 7.38 (m, 10H), 3.86 (br s, 4H), 3.59 (s, 3H), 2.89 (t, J=7.2 Hz, 2H), 2.45 (t, J=7.2 Hz, 2H).

$^{13}$C NMR (100 MHz, CDCl$_3$) δ 187.1, 172.5, 136.8 (2C), 135.2 (2C), 132.9 (2C), 130.4 (2C), 129.1 (2C), 128.6 (2C), 54.6, 52.2, 51.7, 32.6.

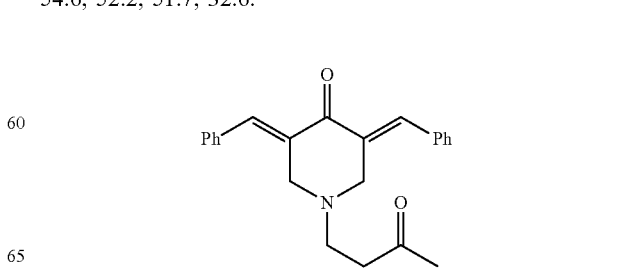

3,5-Di((E)-benzylidene)-1-(3-oxobutyl)piperidin-4-one (JC009)

$^1$H NMR (400 MHz, CDCl$_3$) δ 7.84 (br s, 2H), 7.41 (m, 10H), 3.85 (br s, 4H), 2.86 (t, J=7.1 Hz, 2H), 2.57 (t, J=7.1 Hz, 2H), 2.07 (s, 3H).
$^{13}$C NMR (100 MHz, CDCl$_3$) δ 207.3, 187.0, 136.7 (2C), 135.1 (2C), 133.0 (2C), 129.2 (2C), 128.7 (2C), 54.9, 51.5, 41.6, 30.3.

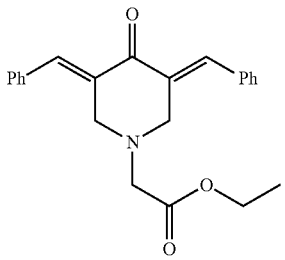

Ethyl 2-(3,5-di((E)-benzylidene)-4-oxopiperidin-1-yl)acetate (JC010)

$^1$H NMR (400 MHz, CDCl$_3$) δ 7.82 (s, 2H), 7.37 (m, 10H), 4.11 (q, J=7.1 Hz, 2H), 4.04 (br s, 4H), 3.41 (s, 2H), 1.15 (t, J=7.1 Hz, 3H).
$^{13}$C NMR (100 MHz, CDCl$_3$) δ 186.9, 170.0, 136.9 (2C), 135.2 (2C), 132.9 (2C), 130.4 (2C), 129.1 (2C), 128.6 (2C), 60.7, 57.8, 54.1, 14.1.

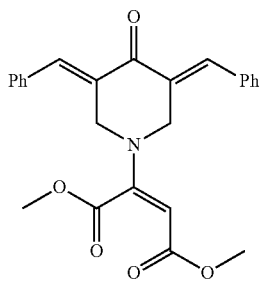 [SMILES: COC(=O)/C=C(\C(=O)OC)N1C/C(=C\c2ccccc2)C(=O)/C(=C/c2ccccc2)C1]

Dimethyl 2-(3,5-di((E)-benzylidene)-4-oxopiperidin-1-yl)maleate (JC011)

$^1$H NMR (400 MHz, DMSO-d$_6$) δ 7.73 (s, 2H), 7.46 (m, 10H), 4.51 (s, 4H), 4.43 (s, 1H), 3.37 (s, 3H), 3.09 (s, 3H).
$^{13}$C NMR (100 MHz, DMSO-d$_6$) δ 186.0, 166.8, 165.0, 153.7, 137.7 (2C), 134.4 (2C), 132.1 (2C), 130.9 (2C), 130.2 (2C), 129.3 (2C), 87.7, 52.4, 50.9, 48.7.

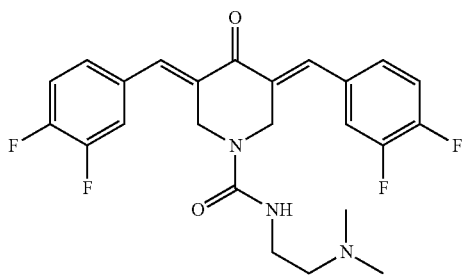 [SMILES: CN(C)CCNC(=O)N1C/C(=C\c2ccc(F)c(F)c2)C(=O)/C(=C/c2ccc(F)c(F)c2)C1]

3,5-Bis((E)-3,4-difluorobenzylidene)-N-(2-(dimethylamino)ethyl)-4-oxopiperidine-1-carboxamide (JC053)

$^1$H NMR (400 MHz, CDCl$_3$) δ 7.68 (br s, 2H), 7.25 (m, 6H), 4.68 (br s, 4H), 3.27 (t, J=7.4 Hz, 2H), 2.48 (t, J=7.4 Hz, 2H), 2.23 (s, 6H).
$^{13}$C NMR (126 MHz, CDCl$_3$) δ 187.2, 156.8, 151.1 (dd, $J_{CF}$=254 Hz, $J_{C-CF}$=14 Hz, 2C), 150.4 (dd, $J_{CF}$=251 Hz, $J_{C-CF}$=14 Hz, 2C), 135.3 (2C), 132.4 (2C), 131.5 (dd, $J_{C-C-CF}$ 5.6 Hz, $J_{C-C-CF}$=3.5 Hz, 2C), 127.4 (dd, $J_{C-C-CF}$=5.8 Hz, $J_{C-C-CF}$=4.2 Hz, 2C), 119.6 (d, $J_{C-CF}$=17 Hz, 2C), 117.9 (d, $J_{C-CF}$=17 Hz, 2C), 59.7, 44.8, 43.9, 36.3.

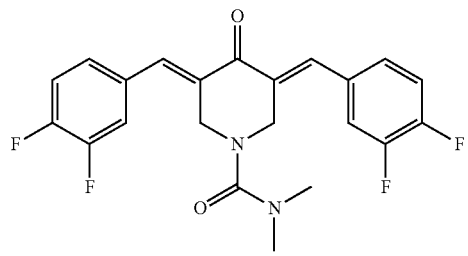 [SMILES: CN(C)C(=O)N1C/C(=C\c2ccc(F)c(F)c2)C(=O)/C(=C/c2ccc(F)c(F)c2)C1]

3,5-Bis((E)-3,4-difluorobenzylidene)-N,N-dimethyl-4-oxopiperidine-1-carboxamide (JC054)

$^1$H NMR (400 MHz, CDCl$_3$) δ 7.72 (br s, 2H), 7.21 (m, 6H), 4.43 (br s, 4H), 2.67 (s, 6H).
$^{13}$C NMR (126 MHz, CDCl$_3$) δ 188.4, 163.6, 151.1 (dd, $J_{CF}$=254 Hz, $J_{C-CF}$=14 Hz, 2C), 150.4 (dd, $J_{CF}$=251 Hz, $J_{C-CF}$=14 Hz, 2C), 135.1 (2C), 132.7 (dd, $J_{C-C-CF}$=5.9 Hz, $J_{C-C-CF}$=3.5 Hz, 2C), 126.9 (dd, $J_{C-C-CF}$=6.1 Hz, $J_{C-C-CF}$=3.5 Hz, 2C), 128.9 (2C), 119.1 (d, $J_{C-CF}$=17 Hz, 2C), 117.5 (d, $J_{C-CF}$=17 Hz, 2C), 48.4, 38.1.

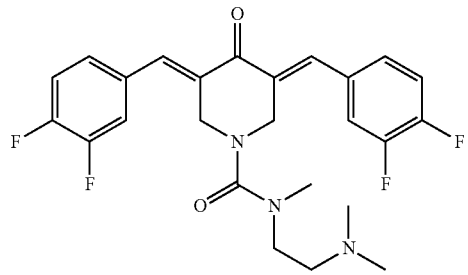 [SMILES: CN(C)CCN(C)C(=O)N1C/C(=C\c2ccc(F)c(F)c2)C(=O)/C(=C/c2ccc(F)c(F)c2)C1]

3,5-Bis((E)-3,4-difluorobenzylidene)-N-(2-(dimethylamino)ethyl)-N-methyl-4-oxopiperidine-1-carboxamide (JC055)

$^1$H NMR (400 MHz, CDCl$_3$) δ 7.72 (br s, 2H), 7.22 (m, 6H), 4.43 (br s, 4H), 3.21 (t, J=6.7 Hz, 2H), 2.67 (s, 3H), 2.32 (t, J=6.7 Hz, 2H), 2.14 (s, 6H).
$^{13}$C NMR (126 MHz, CDCl$_3$) δ 186.3, 163.6, 151.1 (dd, $J_{CF}$=254 Hz, $J_{C-CF}$=14 Hz, 2C), 150.4 (dd, $J_{CF}$=251 Hz, $J_{C-CF}$=14 Hz, 2C), 135.0 (2C), 133.0 (2C), 131.8 (dd, $J_{C-C-CF}$ 5.9 Hz, $J_{C-C-CF}$=3.5 Hz, 2C), 127.0 (dd, $J_{C-C-CF}$=5.9 Hz, $J_{C-C-CF}$=3.5 Hz, 2C), 118.8 (d, $J_{C-CF}$=17 Hz, 2C), 117.5 (d, $J_{C-CF}$=17 Hz, 2C), 56.6, 48.5, 47.8, 45.6, 36.3.

129

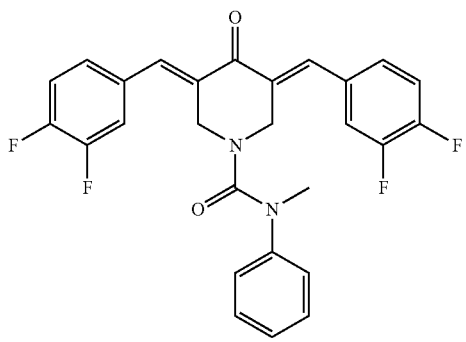 [SMILES: CN(C(=O)N1C/C(=C\c2ccc(F)c(F)c2)C(=O)/C(=C/c2ccc(F)c(F)c2)C1)c1ccccc1]

3,5-Bis((E)-3,4-difluorobenzylidene)-N-methyl-4-oxo-N-phenylpiperidine-1-carboxamide (JC056)

$^1$H NMR (400 MHz, CDCl$_3$) δ 7.55 (s, 2H), 7.2-6.8 (m, 11H), 4.44 (s, 4H), 3.16 (s, 3H).

$^{13}$C NMR (126 MHz, CDCl$_3$) δ 186.0, 160.2, 151.1 (dd, $J_{CF}$=254 Hz, $J_{C-CF}$=14 Hz, 2C), 150.4 (dd, $J_{CF}$=251 Hz, $J_{C-CF}$=14 Hz, 2C), 145.7, 135.1, 132.3 (2C), 131.6 (dd, $J_{C-C-CF}$=6.2 Hz, $J_{C-C-CF}$=3.8 Hz, 2C), 129.5, 127.2 (dd, $J_{C-C-CF}$=5.9 Hz, $J_{C-C-CF}$=3.5 Hz, 2C), 125.3 (2C), 124.2, 119.1 (d, $J_{C-CF}$=17 Hz, 2C), 117.5 (d, $J_{C-CF}$=17 Hz, 2C), 56.6, 48.5, 47.8, 45.6, 36.3.

130

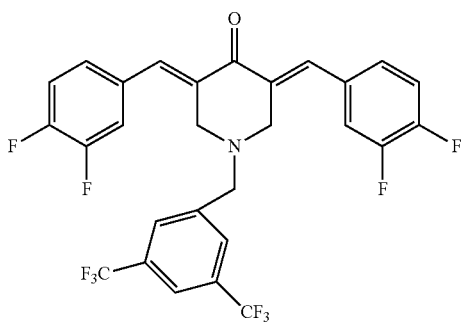

1-(3,5-Bis(trifluoromethyl)benzyl)-3,5-bis((E)-3,4-difluorobenzylidene)piperidin-4-one (JC058)

$^1$H NMR (400 MHz, CDCl$_3$) δ 7.78 (br. s, 3H), 7.73 (s, 2H), 7.17 (m, 6H), 3.87 (br s, 4H), 3.86 (s, 2H).

$^{13}$C NMR (126 MHz, CDCl$_3$) δ 186.4, 151.1 (dd, $J_{CF}$=254 Hz, $J_{C-CF}$=14 Hz, 2C), 150.4 (dd, $J_{CF}$=251 Hz, $J_{C-CF}$=14 Hz, 2C), 139.9, 135.3 (2C), 132.9 (2C), 131.8 (q, $J_{C-CF}$=33.4 Hz, 2C), 131.7 (dd, $J_{C-C-CF}$=6.2 Hz, $J_{C-C-CF}$=3.8 Hz, 2C), 128.7 (2C), 126.9 (dd, $J_{C-C-CF}$=5.8 Hz, $J_{C-C-CF}$=3.8 Hz, 2C), 123.1 (q, $J_{CF}$=272 Hz), 121.6, 118.7 (d, $J_{C-CF}$=17 Hz, 2C), 117.6 (d, $J_{C-CF}$=17 Hz, 2C), 59.8, 53.9.

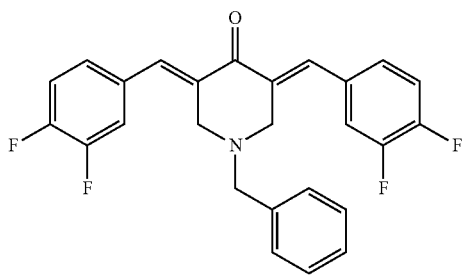 [SMILES: O=C1/C(=C/c2ccc(F)c(F)c2)CN(Cc2ccccc2)C/C1=C\c1ccc(F)c(F)c1]

1-Benzyl-3,5-bis((E)-3,4-difluorobenzylidene)piperidin-4-one (JC057)

$^1$H NMR (400 MHz, CDCl$_3$) δ 7.71 (br s, 2H), 7.3-7.0 (m, 11H), 3.83 (br s, 4H), 3.76 (s, 2H).

$^{13}$C NMR (126 MHz, CDCl$_3$) δ 187.0, 151.1 (dd, $J_{CF}$=254 Hz, $J_{C-CF}$=14 Hz, 2C), 150.4 (dd, $J_{CF}$=251 Hz, $J_{C-CF}$=14 Hz, 2C), 136.9, 134.4 (2C), 133.7 (2C), 132.1 (dd, $J_{C-C-CF}$=6.2 Hz, $J_{C-C-CF}$=3.8 Hz, 2C), 128.9, 128.5, 127.6 (2C), 126.9 (dd, $J_{C-C-CF}$=6.2 Hz, $J_{C-C-CF}$=3.8 Hz, 2C), 118.9 (d, $J_{C-CF}$=17 Hz, 2C), 117.6 (d, $J_{C-CF}$=17 Hz, 2C), 61.5, 54.1.

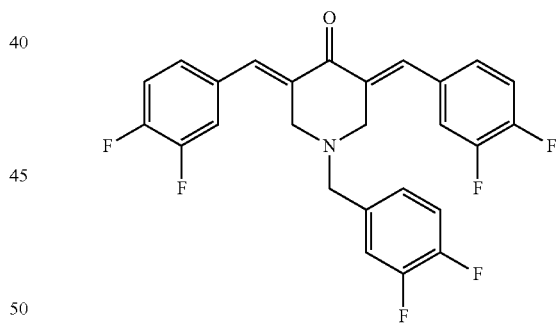

1-(3,4-Difluorobenzyl)-3,5-bis((E)-3,4-difluorobenzylidene)piperidin-4-one (JC059)

$^1$H NMR (400 MHz, CDCl$_3$) δ 7.72 (br s, 2H), 7.2-7.0 (m, 9H), 3.82 (br s, 4H), 3.69 (s, 2H).

$^{13}$C NMR (126 MHz, CDCl$_3$) δ 186.7, 151.1 (dd, $J_{CF}$=254 Hz, $J_{C-CF}$=14 Hz, 2C), 150.4 (dd, $J_{CF}$=254 Hz, $J_{C-CF}$=14 Hz, 2C), 150.2 (dd, $J_{CF}$=254 Hz, $J_{C-CF}$=14 Hz, 2C), 149.7 (dd, $J_{CF}$=254 Hz, $J_{C-CF}$=14 Hz), 134.7, 134.3, 133.4 (2C), 132.0 (dd, $J_{C-C-CF}$=5.8 Hz, $J_{C-C-CF}$=3.8 Hz, 2C), 127.0 (dd, $J_{C-C-CF}$=5.8 Hz, $J_{C-C-CF}$=3.8 Hz, 2C), 124.4 (dd, $J_{C-C-CF}$=6.1 Hz, $J_{C-C-CF}$=3.8 Hz, 2C), 118.8 (d, $J_{C-CF}$=17 Hz, 2C), 117.6 (d, $J_{C-CF}$=17 Hz, 2C), 117.3 (d, $J_{C-CF}$=17 Hz), 117.1 (d, $J_{C-CF}$=17 Hz), 60.2, 54.1.

131

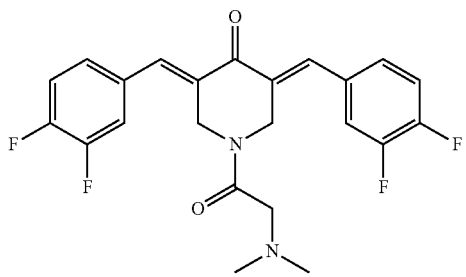 [SMILES: CN(C)CC(=O)N1C/C(=C\c2ccc(F)c(F)c2)C(=O)/C(=C/c2ccc(F)c(F)c2)C1]

3,5-Bis((E)-3,4-difluorobenzylidene)-1-(dimethylglycyl)piperidin-4-one (JC061)

$^1$H NMR (400 MHz, CDCl$_3$) δ 7.74 (br s, 1H), 7.70 (s, 1H), 7.22 (m, 6H), 4.97 (s, 2H), 4.86 (s, 2H), 2.96 (s, 2H), 1.99 (s, 6H).

$^{13}$C NMR (126 MHz, CDCl$_3$) δ 186.2, 168.9, 151.1 (dd, $J_{CF}$=254 Hz, $J_{C-CF}$=14 Hz, 2C), 150.4 (dd, $J_{CF}$=254 Hz, $J_{C-CF}$=14 Hz, 2C), 136.5, 135.0, 132.8, 132.2 (dd, $J_{C-C-CF}$=5.8 Hz, $J_{C-C-CF}$=3.8 Hz, 2C), 127.3 (dd, $J_{C-C-CF}$=5.8 Hz, $J_{C-C-CF}$=3.8 Hz, 2C), 126.9, 119.3 (d, $J_{C-CF}$=17 Hz), 118.8 (d, $J_{C-CF}$=17 Hz), 117.9 (d, $J_{C-CF}$=17 Hz, 2C), 63.0, 45.8, 44.9, 43.7.

132

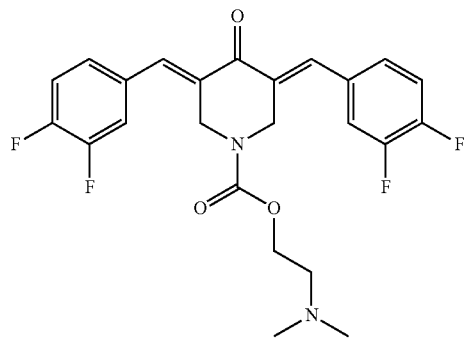

2-(Dimethylamino)ethyl 3,5-bis((E)-3,4-difluorobenzylidene)-4-oxopiperidine-1-carboxylate (JC063)

$^1$H NMR (400 MHz, CDCl$_3$) δ 7.69 (br s, 2H), 7.23 (m, 6H), 4.73 (br s, 4H), 4.13 (t, J=5.7 Hz, 2H), 2.45 (t, J=5.7 Hz, 2H), 2.15 (s, 6H).

$^{13}$C NMR (126 MHz, CDCl$_3$) δ 186.2, 155.0, 150.9 (dd, $J_{CF}$=254 Hz, $J_{C-CF}$=14 Hz, 2C), 150.4 (dd, $J_{C-CF}$=254 Hz, $J_{C-CF}$=14 Hz, 2C), 135.9, 135.4 (2C), 132.3 (dd, $J_{C-C-CF}$=5.8 Hz, $J_{C-C-CF}$=3.8 Hz, 2C), 131.6, 127.1 (dd, $J_{C-C-CF}$=5.8 Hz, $J_{C-C-CF}$=3.8 Hz, 2C), 118.9 (d, $J_{C-CF}$=17 Hz, 2C), 117.9 (d, $J_{C-CF}$=17 Hz, 2C), 64.2, 57.8, 45.6, 45.0.

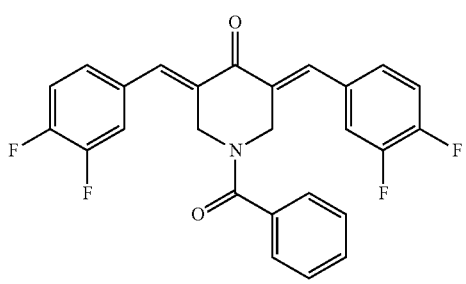 [SMILES: O=C1/C(=C/c2ccc(F)c(F)c2)CN(C(=O)c2ccccc2)C/C1=C\c1ccc(F)c(F)c1]

1-Benzoyl-3,5-bis((E)-3,4-difluorobenzylidene)piperidin-4-one (JC062)

$^1$H NMR (400 MHz, CDCl$_3$) δ 7.75 (s, 2H), 7.21 (m, 11H), 4.76 (br. s, 4H).

$^{13}$C NMR (126 MHz, CDCl$_3$) δ 186.1, 170.5, 151.1 (dd, $J_{CF}$=254 Hz, $J_{C-CF}$=14 Hz, 2C), 150.4 (dd, $J_{CF}$=254 Hz, $J_{C-CF}$=14 Hz, 2C), 134.0, 132.2 (dd, $J_{C-C-CF}$=5.8 Hz, $J_{C-C-CF}$=3.8 Hz, 2C), 131.4 (2C), 130.3, 128.3, 127.0 (dd, $J_{C-C-CF}$=5.8 Hz, $J_{C-C-CF}$=3.8 Hz, 2C), 126.8, 125.3 (2C), 119.0 (d, $J_{C-CF}$=18 Hz, 2C), 117.9 (d, $J_{C-CF}$=18 Hz, 2C).

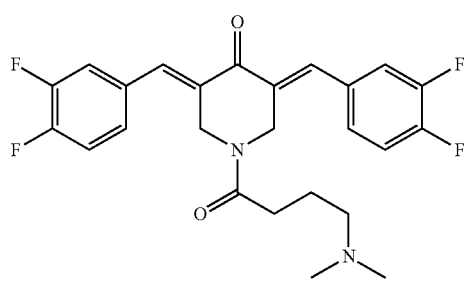 [SMILES: CN(C)CCCC(=O)N1C/C(=C\c2ccc(F)c(F)c2)C(=O)/C(=C/c2ccc(F)c(F)c2)C1]

3,5-Bis((E)-3,4-difluorobenzylidene)-1-(4-(dimethylamino)butanoyl)piperidin-4-one (JC068)

$^1$H NMR (400 MHz, CDCl$_3$) δ 7.71 (br s, 1H), 7.69 (s, 1H), 7.22 (m, 6H), 4.85 (s, 2H), 4.73 (s, 2H), 2.22 (t, J=7.3 Hz, 2H), 2.15 (t, J=7.0 Hz, 2H), 2.09 (s, 6H), 1.68 (m, 2H).

$^{13}$C NMR (126 MHz, CDCl$_3$) δ 186.1, 171.1, 150.9 (dd, $J_{CF}$=254 Hz, $J_{C-CF}$=14 Hz, 2C), 150.4 (dd, $J_{CF}$=254 Hz, $J_{C-CF}$=14 Hz, 2C), 136.2, 135.3, 132.3 (dd, $J_{C-C-CF}$=5.8 Hz, $J_{C-C-CF}$=3.8 Hz, 2C), 131.5, 127.3 (dd, $J_{C-C-CF}$=5.8 Hz, $J_{C-C-CF}$=3.8 Hz, 2C), 126.7, 119.3 (d, $J_{C-CF}$=13.7 Hz), 119.0 (d, $J_{C-CF}$=14.0 Hz), 118.1 (d, $J_{C-CF}$=17 Hz), 117.8 (d, $J_{C-CF}$=17 Hz), 58.6, 46.3, 45.1, 43.1, 30.2, 22.8.

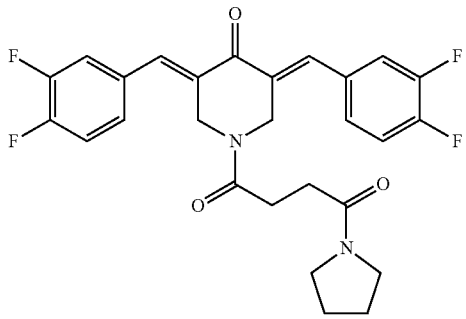 [SMILES: O=C1/C(=C/c2ccc(F)c(F)c2)CN(C(=O)CCC(=O)N2CCCC2)C/C1=C\c1ccc(F)c(F)c1]

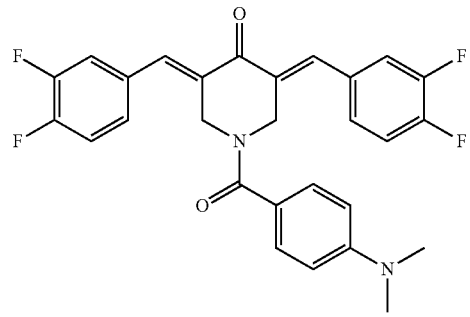

1-(3,5-Bis((E)-3,4-difluorobenzylidene)-4-oxopiperidin-1-yl)-4-(pyrrolidin-1-yl)butane-1,4-dione (JC072)

$^1$H NMR (400 MHz, CDCl$_3$) δ 7.73 (s, 1H), 7.69 (s, 1H), 7.21 (m, 6H), 4.86 (br s, 2H), 4.80 (s, 2H), 3.41 (m, 4H), 2.54 (m, 4H), 1.92 (m, 2H), 1.81 (m, 2H).
$^{13}$C NMR (126 MHz, CDCl$_3$) δ 186.1, 171.0, 170.0, 150.9 (dd, J$_{CF}$=252 Hz, J$_{C-CF}$=13 Hz, 2C), 150.4 (dd, J$_{CF}$=252 Hz, J$_{C-CF}$=13 Hz, 2C), 136.1, 135.5, 132.1 (dd, J$_{C-C-CF}$=5.9 Hz, J$_{C-C-CF}$=4.2 Hz, 2C), 131.5, 127.2 (dd, J$_{C-C-CF}$=6.1 Hz, J$_{C-C-CF}$=3.8 Hz, 2C), 126.9, 119.2 (d, J$_{C-CF}$=17 Hz), 119.0 (d, J$_{C-CF}$=17 Hz), 118.1 (d, J$_{C-CF}$=17 Hz), 117.8 (d, J$_{C-CF}$=17 Hz), 46.5, 46.2, 45.7, 43.2, 29.3, 27.4, 26.0, 24.4.

3,5-Bis((E)-3,4-difluorobenzylidene)-1-(4-(dimethylamino)benzoyl)piperidin-4-one (JC074)

$^1$H NMR (400 MHz, CDCl$_3$) δ 7.74 (br s, 2H), 7.17 (m, 8H), 6.34 (d, J=8.8 Hz, 2H), 4.80 (br s, 4H), 2.91 (s, 6H).
$^{13}$C NMR (126 MHz, CDCl$_3$) δ 186.6, 171.2, 151.7, 150.9 (dd, J$_{CF}$=254 Hz, J$_{C-CF}$=14 Hz, 2C), 150.4 (dd, J$_{CF}$=254 Hz, J$_{C-CF}$=14 Hz, 2C), 135.4 (2C), 132.2, 131.6 (dd, J$_{C-C-CF}$=5.9 Hz, J$_{C-C-CF}$=4.2 Hz, 2C), 129.2, 127.0 (dd, J$_{C-C-CF}$=5.9 Hz, J$_{C-C-CF}$=4.2 Hz, 2C), 120.0 (2C), 119.0 (d, J$_{C-CF}$=17 Hz, 2C), 117.8 (d, J$_{C-CF}$=17 Hz, 2C), 110.6, 46.4, 39.9.

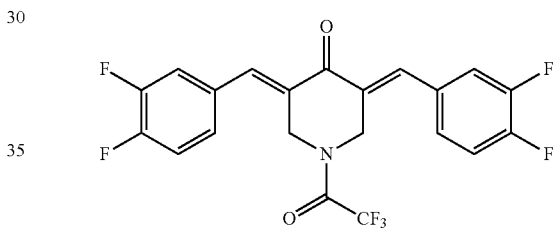

3,5-Bis((E)-3,4-difluorobenzylidene)-1-(2,2,2-trifluoroacetyl)piperidin-4-one (JC075)

$^1$H NMR (400 MHz, CDCl$_3$) δ 7.83 (s, 1H), 7.80 (s, 1H), 7.19 (m, 6H), 4.91 (s, 2H), 4.82 (s, 2H).
$^{13}$C NMR (126 MHz, CDCl$_3$) δ 184.4, 155.6 (q, J=37 Hz), 150.9 (dd, J$_{CF}$=254 Hz, J$_{C-CF}$=14 Hz, 2C), 150.4 (dd, J$_{CF}$=254 Hz, J$_{C-CF}$=14 Hz, 2C), 137.6, 137.0, 131.0 (dd, J$_{C-C-CF}$=5.9 Hz, J$_{C-C-CF}$=4.2 Hz, 2C), 130.5, 127.2 (dd, J$_{C-C-CF}$=5.9 Hz, J$_{C-C-CF}$=4.2 Hz, 2C), 126.6, 119.2 (d, J$_{C-CF}$=17 Hz), 118.8 (d, J$_{C-CF}$=17 Hz), 118.2 (d, J$_{C-CF}$=17 Hz), 118.8 (d, J$_{C-CF}$=17 Hz), 116.0 (q, J=288 Hz), 44.6.

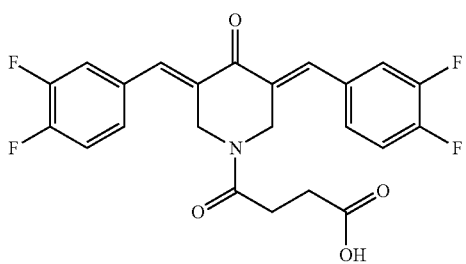 [SMILES: O=C(O)CCC(=O)N1C/C(=C\c2ccc(F)c(F)c2)C(=O)/C(=C/c2ccc(F)c(F)c2)C1]

4-(3,5-Bis((E)-3,4-difluorobenzylidene)-4-oxopiperidin-1-yl)-4-oxobutanoic acid (JC073)

$^1$H NMR (400 MHz, CDCl$_3$) δ 7.72 (s, 1H), 7.69 (s, 1H), 7.39 (m, 6H), 4.86 (br s, 4H), 2.45 (m, 4H).
$^{13}$C NMR (100 MHz, CDCl$_3$) δ 186.1, 174.2, 170.7, 150.9 (dd, J$_{CF}$=252 Hz, J$_{C-CF}$=13 Hz, 2C), 150.4 (dd, J$_{CF}$=252 Hz, J$_{C-CF}$=13 Hz, 2C), 134.7, 134.6, 1$^3$3.8, 133.6, 132.4 (dd, J$_{C-C-CF}$=5.9 Hz, J$_{C-C-CF}$=4.2 Hz, 2C), 128.5 (dd, J$_{C-C-CF}$=5.9 Hz, J$_{C-C-CF}$=4.2 Hz, 2C), 120.0 (d, J$_{C-CF}$=17 Hz), 119.7 (d, J$_{C-CF}$=17 Hz), 118.5 (d, J$_{C-CF}$=17 Hz, 2C), 46.6, 42.7, 29.1, 27.5.

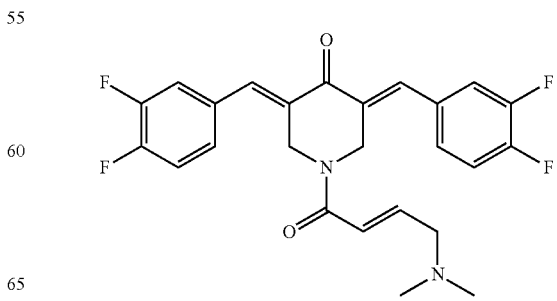

3,5-Bis((E)-3,4-difluorobenzylidene)-1-((E)-4-(dimethylamino)but-2-enoyl)piperidin-4-one (JC076)

¹H NMR (400 MHz, CDCl₃) δ 7.72 (br s, 2H), 7.18 (m, 6H), 6.74 (dt, J=15.2, 6.1 Hz, 1H), 6.15 (d, J=15.2 Hz, 1H), 4.84 (br s, 4H), 2.99 (d, J=6.1 Hz, 1H), 2.16 (s, 6H).

¹³C NMR (100 MHz, CDCl₃) δ 185.9, 165.5, 150.9 (dd, $J_{CF}$=254 Hz, $J_{C-CF}$=14 Hz, 2C), 150.4 (dd, $J_{CF}$=254 Hz, $J_{C-CF}$=14 Hz, 2C), 143.8, 136.3 (2C), 135.2 (2C), 132.3, 131.4, 120.9, 127.0 (2C), 119.2 (d, $J_{C-CF}$=17 Hz, 2C), 118.0 (d, $J_{C-CF}$=17 Hz, 2C), 60.4, 45.2, 29.7.

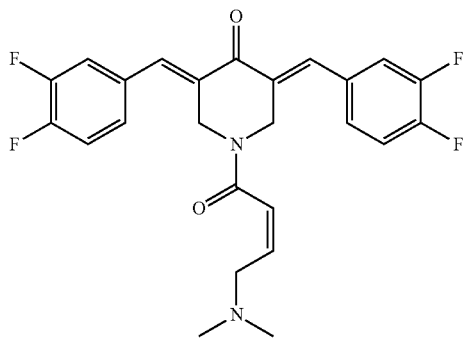 [SMILES: CN(C)C/C=C\C(=O)N1C/C(=C\c2ccc(F)c(F)c2)C(=O)/C(=C/c2ccc(F)c(F)c2)C1]

3,5-Bis((E)-3,4-difluorobenzylidene)-1-((Z)-4-(dimethylamino)but-2-enoyl)piperidin-4-one (JC077)

¹H NMR (400 MHz, CDCl₃) δ 7.74 (br s, 2H), 7.21 (m, 6H), 6.08 (dt, J=11.7, 5.4 Hz, 1H), 5.96 (d, J=11.7 Hz, 1H), 4.89 (s, 2H), 4.74 (s, 2H), 3.35 (d, J=5.4 Hz, 2H), 2.27 (s, 6H).

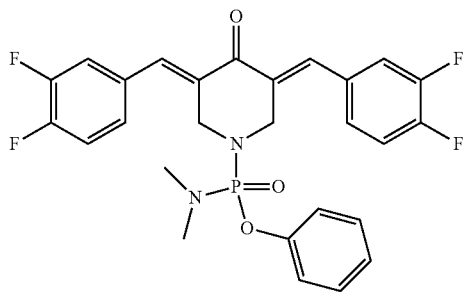 [SMILES: CN(C)P(=O)(Oc1ccccc1)N1C/C(=C\c2ccc(F)c(F)c2)C(=O)/C(=C/c2ccc(F)c(F)c2)C1]

Phenyl p-(3,5-bis((E)-3,4-difluorobenzylidene)-4-oxopiperidin-1-yl)-N,N-dimethylphosphonamidate (JC078)

¹H NMR (400 MHz, CDCl₃) δ 7.68 (br s, 2H), 7.11 (m, 6H), 4.42 (br s, 4H), 2.58 (s, 3H), 2.56 (s, 3H).

¹³C NMR (126 MHz, CDCl₃) δ 186.0, 150.9 (dd, $J_{CF}$=254 Hz, $J_{C-CF}$=14 Hz, 2C), 150.8, 150.4 (dd, $J_{CF}$=254 Hz, $J_{C-CF}$=14 Hz, 2C), 134.6, 133.2 (2C), 131.7 (2C), 129.7, 127.0 (2C), 124.6 (2C), 119.7, 119.0 (d, $J_{C-CF}$=17 Hz, 2C), 117.8 (d, $J_{C-CF}$=17 Hz, 2C), 46.1, 36.7.

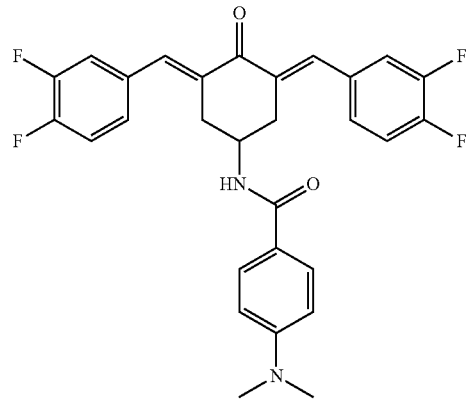 [SMILES: CN(C)c1ccc(C(=O)NC2C/C(=C\c3ccc(F)c(F)c3)C(=O)/C(=C/c3ccc(F)c(F)c3)C2)cc1]

N-(3,5-Bis((E)-3,4-difluorobenzylidene)-4-oxocyclohexyl)-4-(dimethylamino)benzamide (JC089)

¹H NMR (400 MHz, DMSO-d₆) δ 8.17 (s, 1H), 8.15 (s, 1H), 7.53 (m, 8H), 6.65 (d, J=9.0 Hz, 2H), 4.03 (m, 1H), 3.14 (m, 2H), 2.97 (m, 2H), 2.92 (s, 6H).

¹³C NMR (126 MHz, CDCl₃) δ 188.1, 166.9, 152.6, 151.0 (dd, $J_{CF}$=254 Hz, $J_{C-CF}$=14 Hz, 2C), 150.4 (dd, $J_{CF}$=254 Hz, $J_{C-CF}$=14 Hz, 2C), 137.7, 132.9 (2C), 132.2 (dd, $J_{C-C-CF}$=5.9 Hz, $J_{C-C-CF}$=4.2 Hz, 2C), 128.4, 127.1 (dd, $J_{C-C-CF}$=5.9 Hz, $J_{C-C-CF}$=4.2 Hz, 2C), 120.5 (2C), 119.0 (d, $J_{C-CF}$=17 Hz, 2C), 117.7 (d, $J_{C-CF}$=17 Hz, 2C), 111.0, 44.3, 40.1, 33.9.

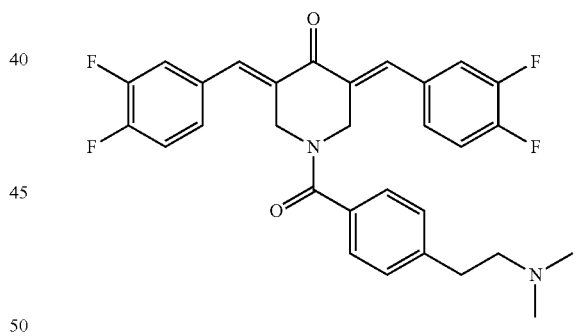

3,5-Bis((E)-3,4-difluorobenzylidene)-1-(4-(2-(dimethylamino)ethyl)benzoyl)piperidin-4-one (JC090)

¹H NMR (400 MHz, CDCl₃) δ 7.74 (br s, 2H), 7.16 (m, 6H), 7.11 (d, J=8.1 Hz, 2H), 6.94 (d, J=8.1 Hz, 2H), 4.77 (br. s, 4H), 2.68 (t, J=8.0 Hz, 2H), 2.40 (t, J=8.0 Hz, 2H), 2.29 (s, 6H).

¹³C NMR (100 MHz, CDCl₃) δ 186.2, 170.5, 151.0 (dd, $J_{CF}$=254 Hz, $J_{C-CF}$=14 Hz, 2C), 150.4 (dd, $J_{CF}$=254 Hz, $J_{C-CF}$=14 Hz, 2C), 143.0, 139.5 (2C), 132.3 (dd, $J_{C-C-CF}$=5.9 Hz, $J_{C-C-CF}$=4.2 Hz, 2C), 131.7, 131.5 (2C), 128.5, 127.0, 126.9 (dd, $J_{C-C-CF}$=5.9 Hz, $J_{C-C-CF}$=4.2 Hz, 2C), 119.0 (d, $J_{C-CF}$=17 Hz, 2C), 117.9 (d, $J_{C-CF}$=17 Hz, 2C), 60.9, 50.8, 45.1, 33.9.

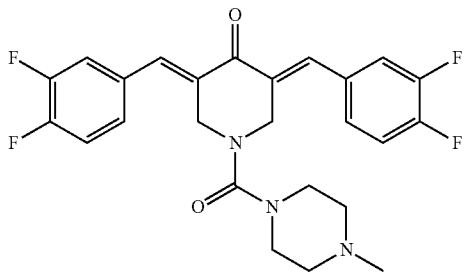 [SMILES: CN1CCN(C(=O)N2C/C(=C\c3ccc(F)c(F)c3)C(=O)/C(=C/c3ccc(F)c(F)c3)C2)CC1]

3,5-Bis((E)-3,4-difluorobenzylidene)-1-(4-methylpiperazine-1-carbonyl)piperidin-4-one (JC091)

¹H NMR (400 MHz, CDCl₃) δ 7.73 (br s, 2H), 7.20 (m, 6H), 4.44 (br s, 4H), 3.12 (t, J=8.0 Hz, 4H), 2.16 (s, 3H), 2.11 (t, J=8.0 Hz, 4H).
¹³C NMR (126 MHz, CDCl₃) δ 186.2, 162.8, 151.0 (dd, $J_{CF}$=254 Hz, $J_{C-CF}$=14 Hz, 2C), 150.4 (dd, $J_{CF}$=254 Hz, $J_{C-CF}$=14 Hz, 2C), 135.4 (2C), 132.8 (dd, $J_{C-C-CF}$=5.9 Hz, $J_{C-C-CF}$=4.2 Hz, 2C), 131.6 (2C), 127.0 (dd, $J_{C-C-CF}$=5.9 Hz, $J_{C-C-CF}$=4.2 Hz, 2C), 119.1 (d, $J_{C-CF}$=17 Hz, 2C), 118.0 (d, $J_{C-CF}$=17 Hz, 2C), 54.4, 48.4, 46.3, 45.9.

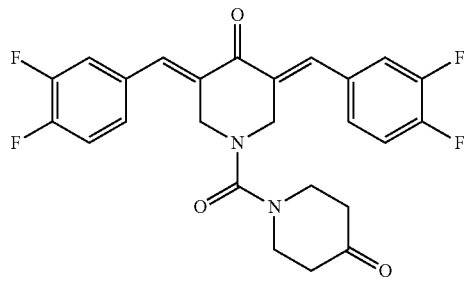

3,5-Bis((E)-3,4-difluorobenzylidene)-1-(4-oxopiperidine-1-carbonyl)piperidin-4-one (JC093)

¹H NMR (400 MHz, CDCl₃) δ 7.76 (br s, 2H), 7.21 (m, 6H), 4.53 (br s, 4H), 3.37 (m, 4H), 2.25 (m, 4H).
¹³C NMR (126 MHz, CDCl₃) δ 206.7, 185.9, 162.6, 151.0 (dd, $J_{CF}$=255 Hz, $J_{C-CF}$=13 Hz, 2C), 150.3 (dd, $J_{CF}$=251 Hz, $J_{C-CF}$=13 Hz, 2C), 135.7 (2C), 132.4 (2C), 131.4 (dd, $J_{C-C-CF}$=5.5 Hz, $J_{C-C-CF}$=4.2 Hz, 2C), 127.0 (dd, $J_{C-C-CF}$=6.3 Hz, $J_{C-C-CF}$=3.5 Hz, 2C), 119.1 (d, $J_{C-CF}$=18 Hz, 2C), 118.0 (d, $J_{C-CF}$=17 Hz, 2C), 50.9, 48.4, 45.9, 40.8.

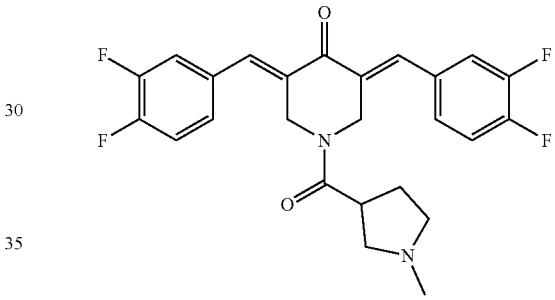

3,5-Bis((E)-3,4-difluorobenzylidene)-1-(1-methylpyrrolidine-3-carbonyl)piperidin-4-one (JC101)

¹H NMR (500 MHz, CDCl₃) δ 7.76 (s, 1H), 7.71 (s, 1H), 7.17 (m, 6H), 4.76 (br s, 4H), 3.20 (m, 1H), 2.95 (m, 1H), 2.88 (m, 1H), 2.69 (m, 1H), 2.45 (m, 1H), 2.40 (s, 3H), 1.91 (m, 2H).
¹³C NMR (126 MHz, CDCl₃) δ 185.7, 172.6, 151.2 (dd, $J_{CF}$=255 Hz, $J_{C-CF}$=14 Hz, 2C), 150.5 (dd, $J_{CF}$=255 Hz, $J_{C-CF}$=13 Hz, 2C), 136.5, 135.7, 132.0 (2C), 131.5 (dd, $J_{C-C-CF}$=5.9 Hz, $J_{C-C-CF}$=3.4 Hz), 131.0 (dd, $J_{C-C-CF}$=6.0 Hz, $J_{C-C-CF}$=3.8 Hz), 127.2 (d, $J_{C-C-CF}$=6.1 Hz), 126.8 (d, $J_{C-C-CF}$=5.5 Hz), 119.2 (d, $J_{C-CF}$=18 Hz), 118.9 (d, $J_{C-CF}$=18 Hz), 118.2 (d, $J_{C-CF}$=18 Hz), 117.9 (d, $J_{C-CF}$=18 Hz), 58.4, 55.4, 46.2, 43.5, 41.3, 40.1, 28.6.

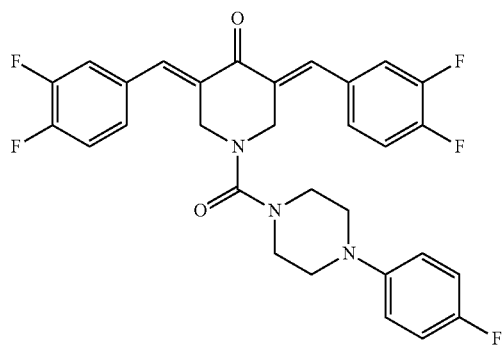 [SMILES: O=C1/C(=C/c2ccc(F)c(F)c2)CN(C(=O)N2CCN(c3ccc(F)cc3)CC2)C/C1=C\c1ccc(F)c(F)c1]

3,5-Bis((E)-3,4-difluorobenzylidene)-1-(4-(4-fluorophenyl)piperazine-1-carbonyl)piperidin-4-one (JC092)

¹H NMR (400 MHz, CDCl₃) δ 7.75 (br s, 2H), 7.24 (m, 4H), 7.16 (m, 2H), 6.94 (m, 2H), 6.72 (m, 2H), 4.49 (br s, 4H), 3.24 (m, 4H), 2.76 (m, 4H).
¹³C NMR (100 MHz, CDCl₃) δ 186.1, 162.7, 157.5 (dd, $J_{CF}$=254 Hz, $J_{C-CF}$=14 Hz), 151.0 (dd, $J_{CF}$=254 Hz, $J_{C-CF}$=14 Hz, 2C), 150.4 (dd, $J_{CF}$=254 Hz, $J_{C-CF}$=14 Hz, 2C), 147.5, 135.4 (2C), 132.8 (dd, $J_{C-C-CF}$=5.9 Hz, $J_{C-C-CF}$=4.2 Hz, 2C), 131.6 (2C), 127.0 (dd, $J_{C-C-CF}$=5.9 Hz, $J_{C-C-CF}$=4.2 Hz, 2C), 119.1 (d, $J_{C-CF}$=17 Hz, 2C), 118.4 (d, $J_{C-CF}$=7.8 Hz), 117.9 (d, $J_{C-CF}$=17 Hz, 2C), 115.7 (d, $J_{C-CF}$=22 Hz), 50.0, 48.3, 46.5.

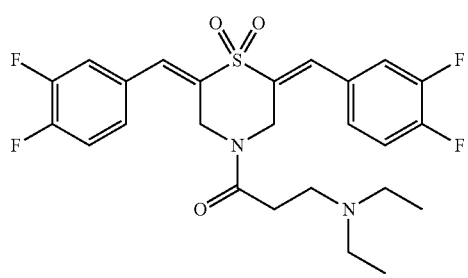 [SMILES: CCN(CC)CCC(=O)N1C/C(=C\c2ccc(F)c(F)c2)S(=O)(=O)/C(=C/c2ccc(F)c(F)c2)C1]

1-(2,6-Bis((E)-3,4-difluorobenzylidene)-1,1-dioxido-thiomorpholino)-3-(diethylamino)propan-1-one (JC119)

$^1$H NMR (300 MHz, CDCl$_3$) δ 7.61 (s, 1H), 7.54 (s, 1H), 7.46 (m, 2H), 7.28 (m, 4H), 4.94 (s, 2H), 4.90 (s, 2H), 2.83 (t, J=7.5 Hz, 2H), 2.50 (q, J=7.1 Hz, 4H), 2.35 (t, J=7.4 Hz, 2H), 1.03 (t, J=7.1 Hz, 6H).

$^{13}$C NMR (126 MHz, CDCl$_3$) δ 170.5, 151.4 (dd, J$_{CF}$=255 Hz, J$_{C-CF}$=10 Hz, 2C), 150.5 (dd, J$_{CF}$=251 Hz, J$_{C-CF}$=13 Hz, 2C), 137.6, 137.1, 133.1, 132.8, 129.1, 128.9, 126.5, 126.0, 118.7 (d, J$_{C-CF}$=18 Hz), 118.6 (d, J$_{C-CF}$=17 Hz), 118.4 (d, J$_{C-CF}$=18 Hz), 118.2 (d, J$_{C-CF}$=18 Hz), 48.2, 46.7, 45.4, 42.2, 30.2, 10.7.

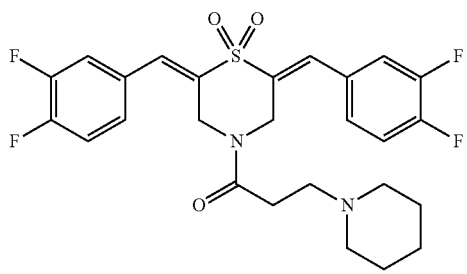 [SMILES: O=C(CCN1CCCCC1)N1C/C(=C\c2ccc(F)c(F)c2)S(=O)(=O)/C(=C/c2ccc(F)c(F)c2)C1]

1-(2,6-Bis((E)-3,4-difluorobenzylidene)-1,1-dioxido-thiomorpholino)-3-(piperidin-1-yl)propan-1-one (JC120)

$^1$H NMR (300 MHz, CDCl$_3$) δ 7.61 (s, 1H), 7.53 (s, 1H), 7.51 (m, 2H), 7.28 (m, 4H), 4.93 (s, 2H), 4.86 (s, 2H), 2.55 (t, J=6.4 Hz, 2H), 2.19 (m, 4H), 1.56 (m, 4H), 1.43 (t, J=6.4 Hz, 2H), 1.28 (m, 2H).

$^{13}$C NMR (126 MHz, CDCl$_3$) δ 170.8, 151.5 (dd, J$_{CF}$=255 Hz, J$_{C-CF}$=11 Hz, 2C), 150.4 (dd, J$_{CF}$=253 Hz, J$_{C-CF}$=13 Hz, 2C), 138.2, 137.2, 133.1, 132.5, 129.2, 128.9, 126.4, 125.9, 118.8 (d, J$_{C-CF}$=18 Hz), 118.5 (d, J$_{C-CF}$=16 Hz), 118.4 (d, J$_{C-CF}$=16 Hz), 118.1 (d, J$_{C-CF}$=18 Hz), 54.2, 53.9, 45.2, 42.1, 30.6, 25.6, 23.9.

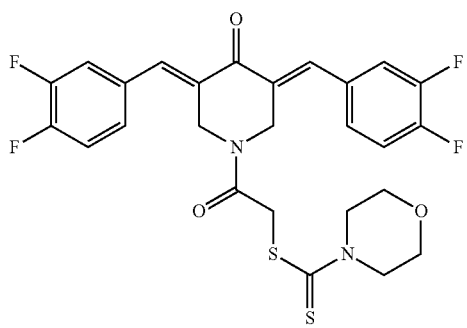 [SMILES: O=C1/C(=C/c2ccc(F)c(F)c2)CN(C(=O)CSC(=S)N2CCOCC2)C/C1=C\c1ccc(F)c(F)c1]

2-(3,5-Bis((E)-3,4-difluorobenzylidene)-4-oxopiperidin-1-yl)-2-oxoethyl morpholine-4-carbodithioate (JC129)

$^1$H NMR (500 MHz, CDCl$_3$) δ 7.75 (s, 1H), 7.70 (s, 1H), 7.21 (m, 6H), 4.90 (s, 2H), 4.87 (s, 2H), 4.18 (m, 4H), 1.87 (s, 2H), 3.71 (m, 4H).

$^{13}$C NMR (126 MHz, CDCl$_3$) δ 195.0, 185.6, 166.4, 151.0 (dd, J$_{CF}$=248 Hz, 2C), 150.4 (dd, J$_{CF}$=248 Hz, 2C), 136.2, 135.7, 131.7 (d, J$_{C-C-CF}$=6.7 Hz), 131.2 (dd, J$_{C-C-CF}$=6.7 Hz), 127.0 (dd, J$_{C-C-CF}$=5.9 Hz, J$_{C-C-CF}$=3.4 Hz, 2C), 126.9, 119.2 (d, J$_{C-CF}$=17 Hz), 118.9 (d, J$_{C-CF}$=17 Hz), 118.0 (dd, J$_{C-CF}$=17 Hz), 117.8 (d, J$_{C-CF}$=17 Hz), 46.9, 43.6, 39.1, 29.6.

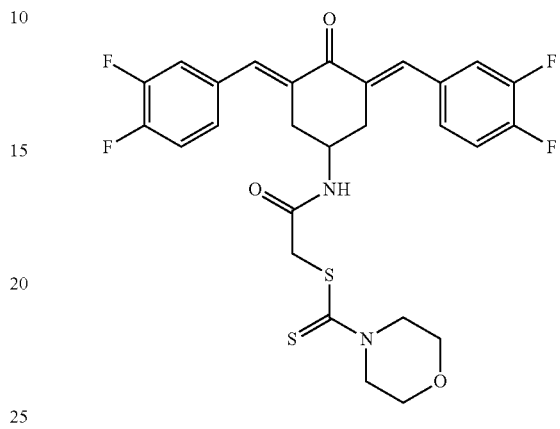

2-((3,5-Bis((E)-3,4-difluorobenzylidene)-4-oxocyclohexyl)amino)-2-oxoethyl morpholine-4-carbodithioate (JC130)

$^1$H NMR (400 MHz, CDCl$_3$) δ 7.76 (br s, 2H), 7.17 (m, 6H), 4.28 (m, 3H), 3.85 (m, 4H), 3.74 (m, 4H), 3.04 (m, 4H).

$^{13}$C NMR (126 MHz, CDCl$_3$) δ 195.8, 187.5, 168.4, 151.0 (dd, J$_{CF}$=248 Hz, J$_{C-CF}$=13 Hz, 2C), 150.4 (dd, J$_{CF}$=248 Hz, J$_{C-CF}$=13 Hz, 2C), 137.9 (2C), 132.4 (2C), 132.0 (dd, J$_{C-C-CF}$=5.9 Hz, J$_{C-C-CF}$=3.6 Hz, 2C), 127.0 (dd, J$_{C-C-CF}$=6.3 Hz, J$_{C-C-CF}$=3.8 Hz, 2C), 118.8 (d, J$_{C-CF}$=17 Hz, 2C), 117.5 (d, J$_{C-CF}$=17 Hz, 2C), 65.9 (b, 1C), 51.5 (b, 1C), 44.3, 39.0, 32.8.

Example 2: Biological Data

Figure 5A:
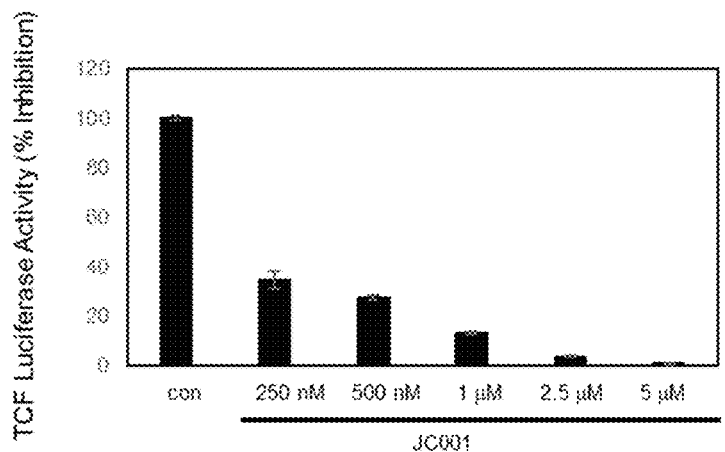
FIG. 5A. Screening of JC inhibitors for Wnt/β-catenin-mediated transcription. 293T/Top cells were treated with 20 mM of LiCl and increasing concentration of JC001 as indicated. JC001 was shown to inhibit Topflash reporter activities induced by LiCl in 293T/Top cells.
Figure 5B:
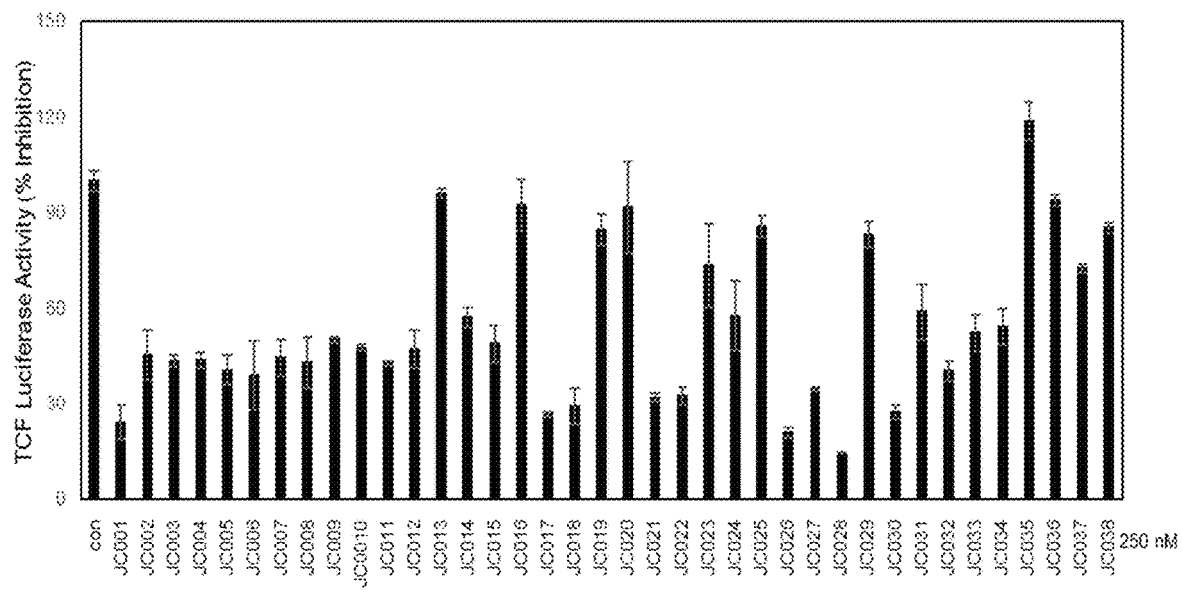
FIG. 5B. Analysis of luciferase activity of 293T/Top cells treated with the indicated JC inhibitors relative to control (con). 293T/Top cells were treated with 20 mM of LiCl and 250 nM of Wnt inhibitors as indicated. Luciferase activities were measured 15 hours post treatment. Values are mean±s.d. for triplicate samples from a representative experiment. Several compounds were found to possess inhibitory activity.
Figure 6A:
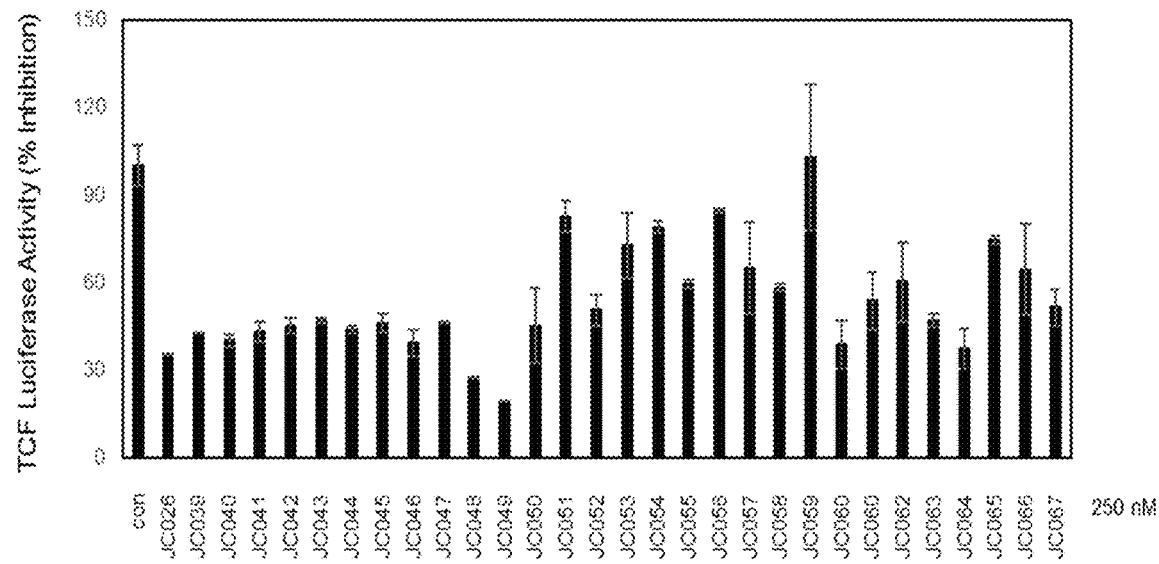
FIG. 6A. Screening of JC inhibitors for Wnt/β-catenin-mediated transcription. Analysis of luciferase activity of 293T/Top/β-cat* cells treated with the indicated inhibitors (JC039-JC067) relative to control (con). Several compounds were found to possess inhibitory activity.
Figure 6B:
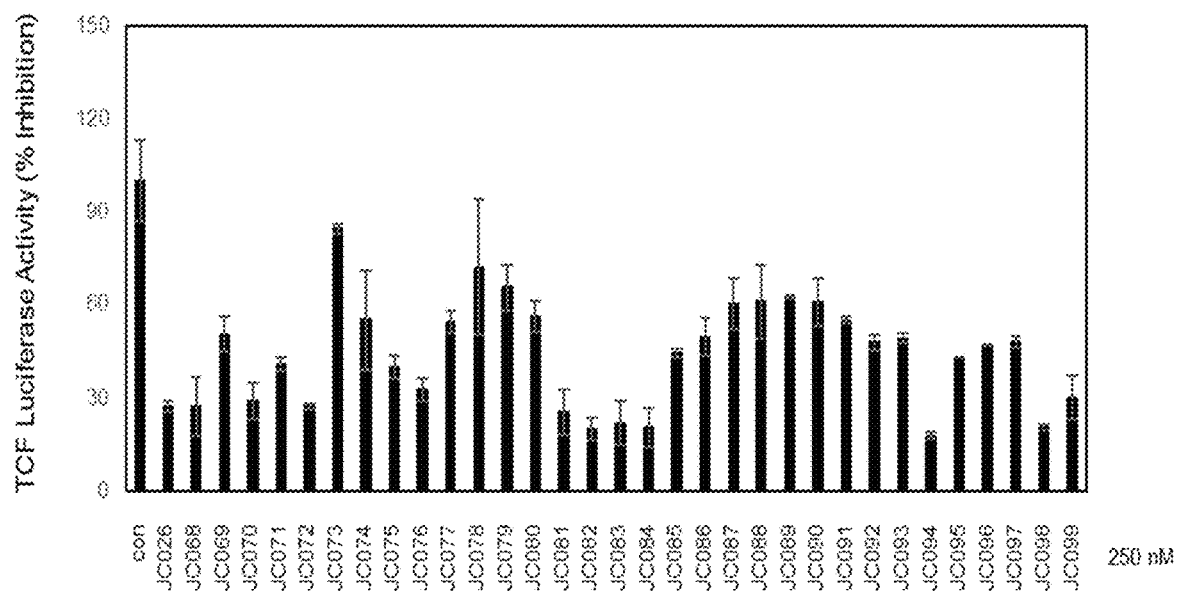
FIG. 6B. Screening of JC inhibitors for Wnt/β-catenin-mediated transcription. Analysis of luciferase activity of 293T/Top/β-cat* cells treated with the indicated inhibitors (JC068-JC099) relative to control (con). Several compounds were found to possess inhibitory activity.
Figure 6C:
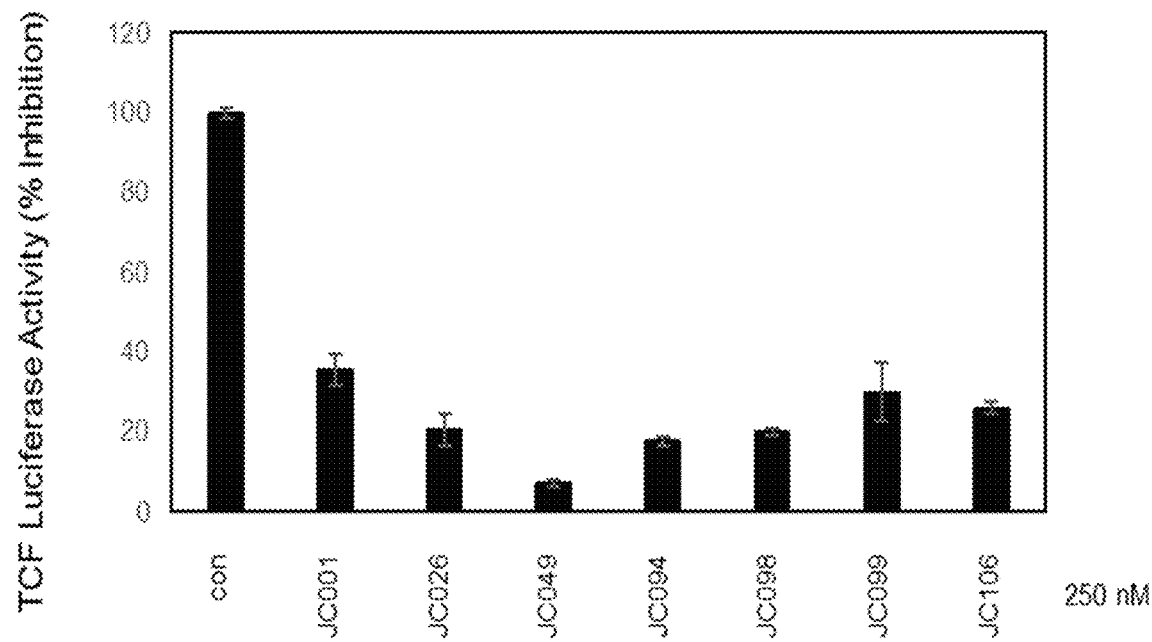
FIG. 6C. Inhibitory activities of JC001, JC026, JC049, JC094, JC098, JC099 and JC106 measured with Topflash reporter. 293T/Top/β-cat* cells were treated with 250 nM of inhibitors as indicated. Luciferase activities were measured 15 hours post treatment. Values are mean±s.d. for triplicate samples from a representative experiment. Several compounds were found to possess inhibitory activity.
Figure 7A:
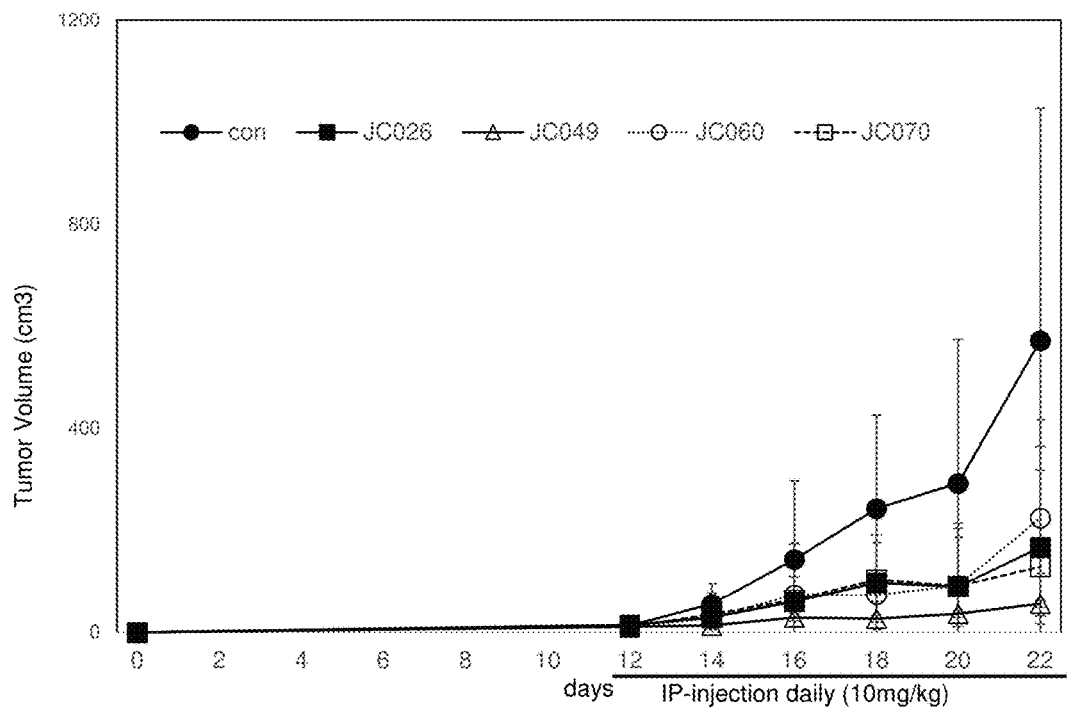
FIG. 7A. JC Wnt inhibitors suppress CRC cells growth in vivo. The growth of SW480 tumor xenografts are inhibited by JC inhibitors as indicated. Animals were treated with 10 mg/kg of the indicated drug on day 12 to 22. JC026, JC049, JC060, and JC070 significantly reduced tumor volumes.
Figure 7B:
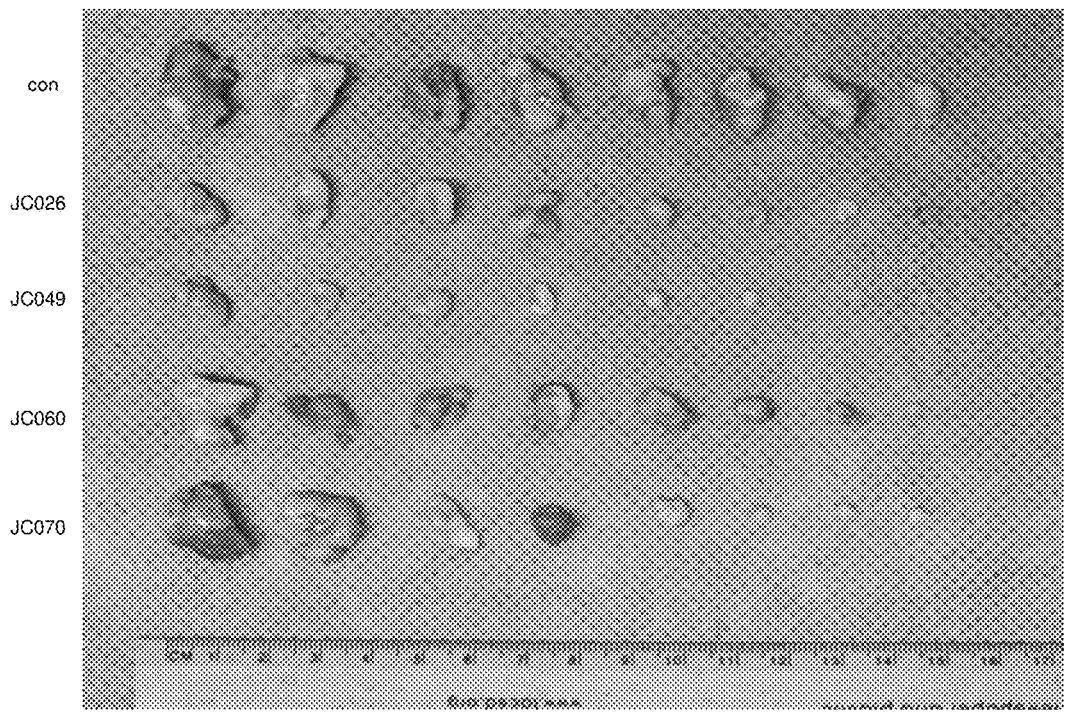
FIG. 7B. Comparisons of tumor sizes at the end of treatment. Treatment with JC026, JC049, JC060, and JC070 significantly reduced the size of tumors recovered.
Figure 7C:
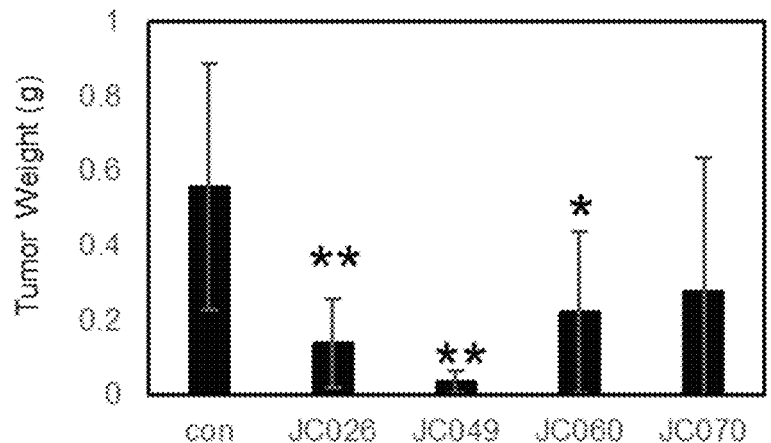
FIG. 7C. Comparisons of tumor weights at the end of treatment. Tumors from nude mice were dissected and weighed. *P<0.05; **P<0.01, unpaired 2-tailed Student's t-Test. Treatment with JC026, JC049, JC060, and JC070 significantly reduced the weight of tumors recovered.
Figure 7D:
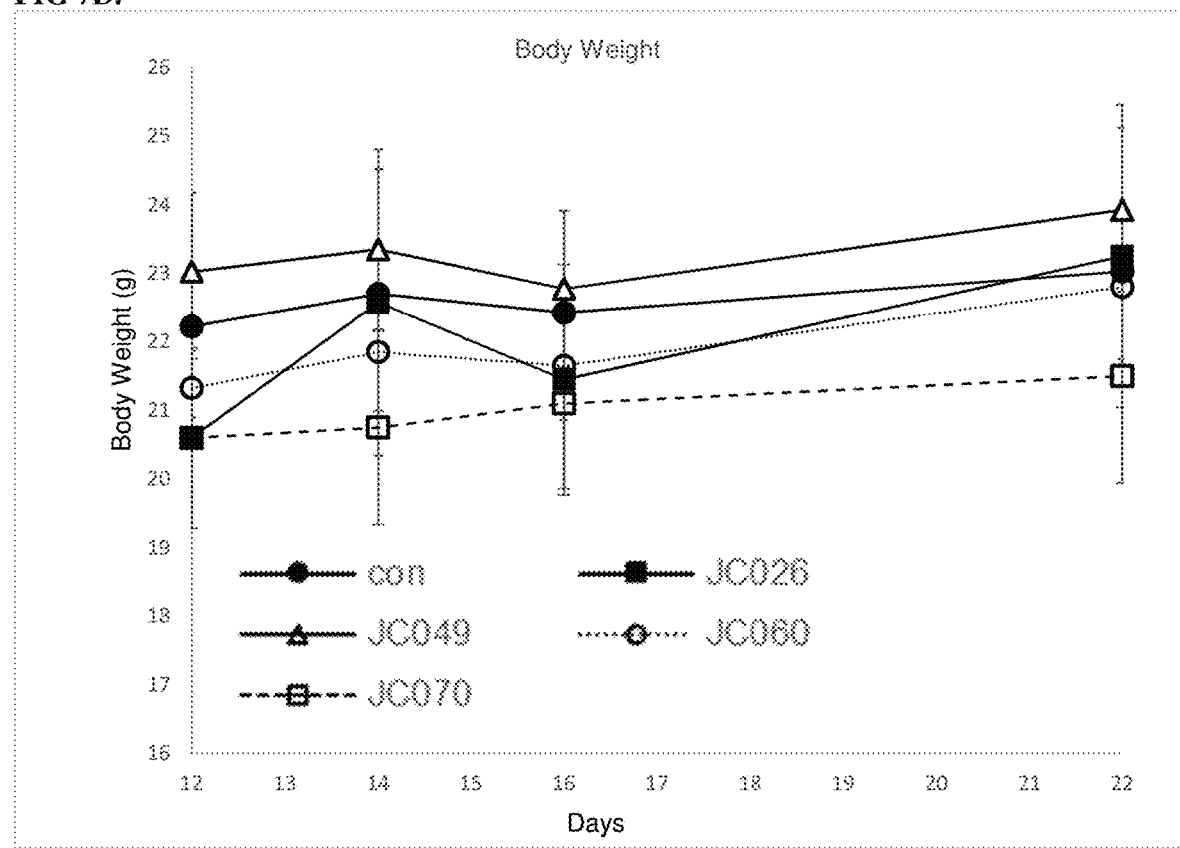
FIG. 7D. Treatment with JC Wnt inhibitors has no effect on nude mice body weight.
Figure 8A:
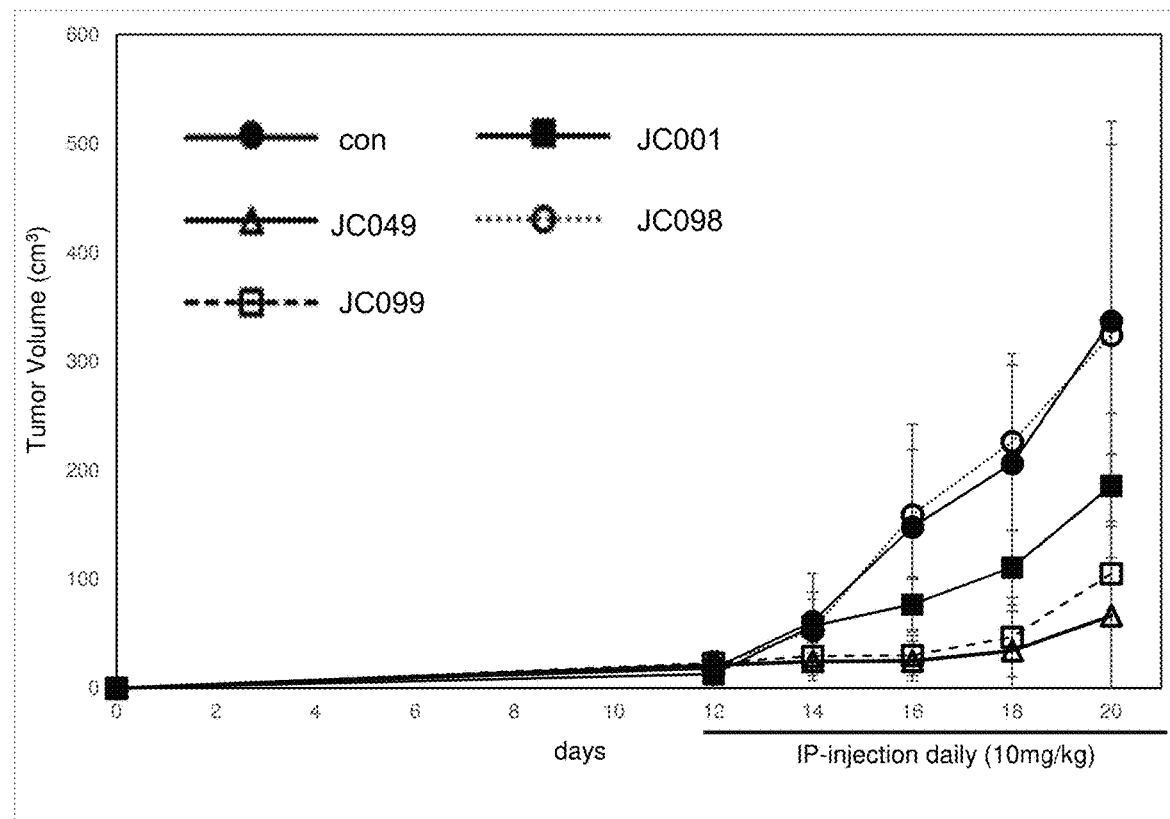
FIG. 8A. Treatment with JC Wnt inhibitors suppress CRC cells growth in vivo. The growth of SW480 tumor xenografts are inhibited by JC inhibitors as indicated Animals were treated with 10 mg/kg of the indicated drug on day 12 to day 20. Treatment with JC001, JC049, and JC099 significantly reduced tumor volumes.
Figure 8B:
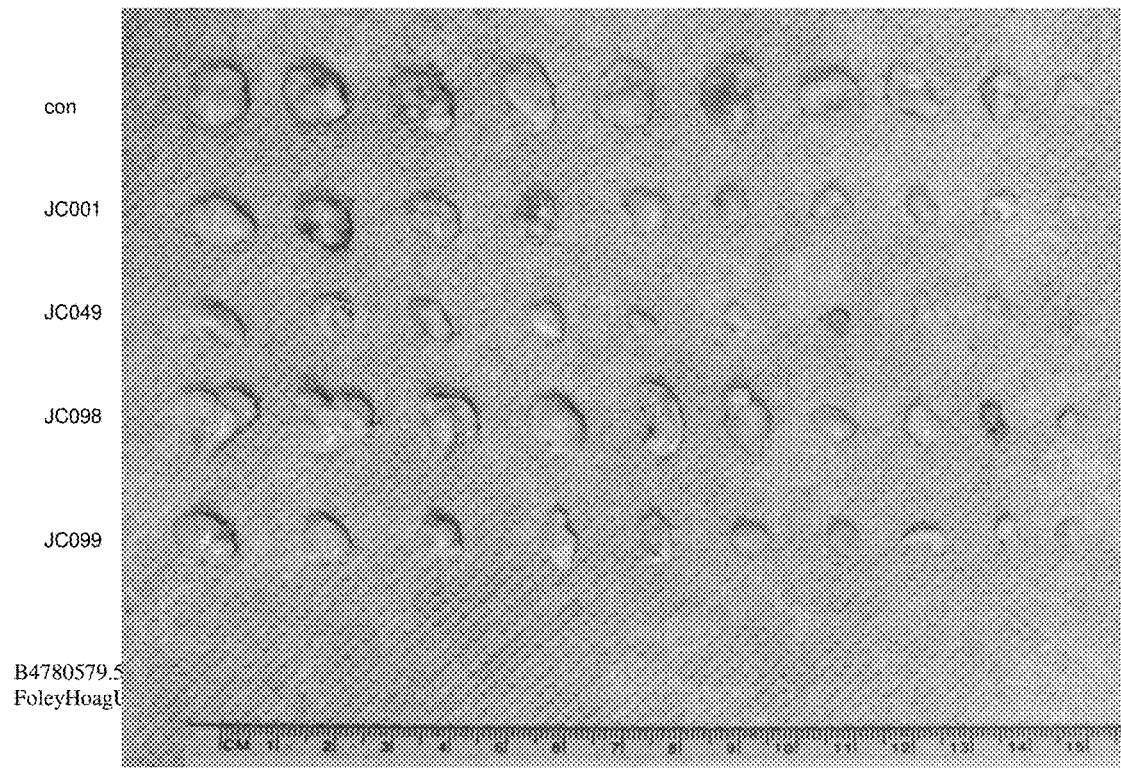
FIG. 8B. Comparisons of actual tumor sizes at the end of treatment. Treatment with JC001, JC049, JC098, and JC099 reduced the size of tumors recovered.
Figure 8C:
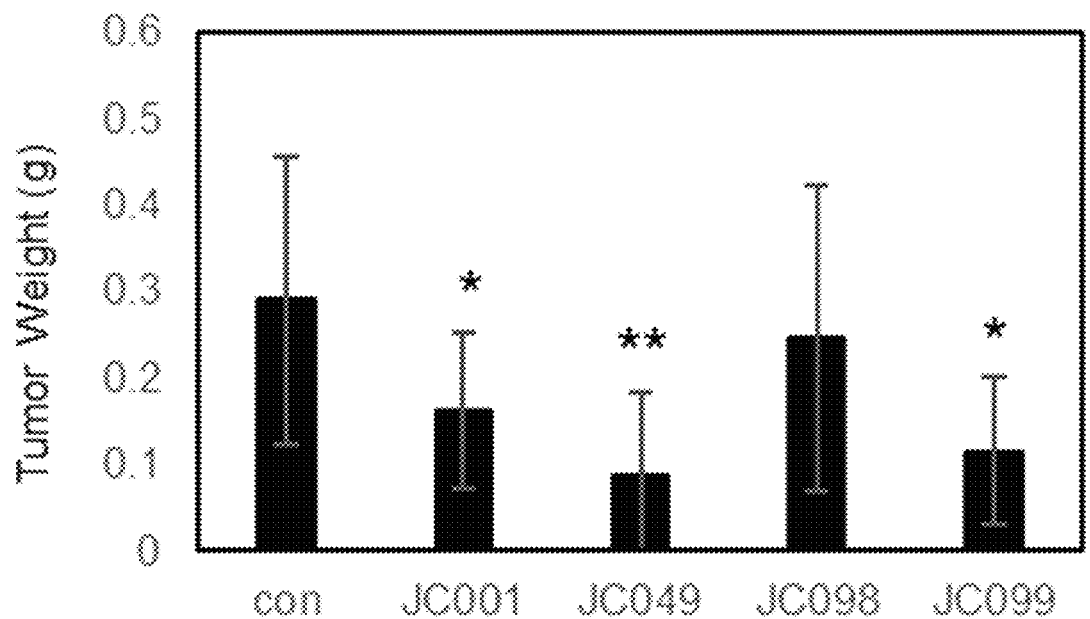
FIG. 8C. Comparisons of actual tumor weights at the end of treatment. Tumors from nude mice were dissected and weighed. *P<0.05; **P<0.01, unpaired 2-tailed Student's t-Test. Treatment with JC001, JC049, and JC099 significantly reduced the weight of tumors recovered.
Figure 9A:
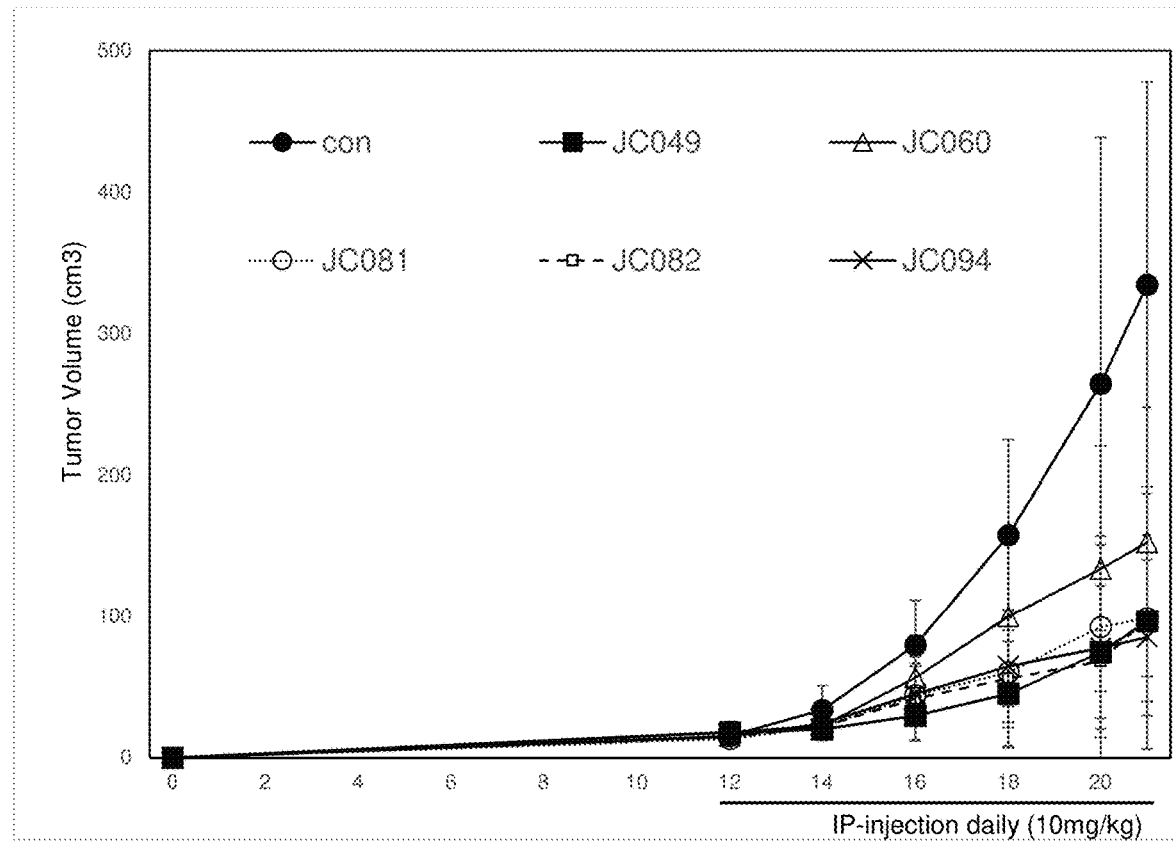
FIG. 9A. Treatment with JC Wnt inhibitors suppress CRC cells growth in vivo. The growth of SW480 tumor xenografts are inhibited by JC inhibitors as indicated. Animals were treated with 10 mg/kg of the indicated drug treatment on day 12 to day 21. Treatment with JC049, JC060, JC081, JC082, and JC094 was found to significantly reduce tumor volume.
Figure 9B:
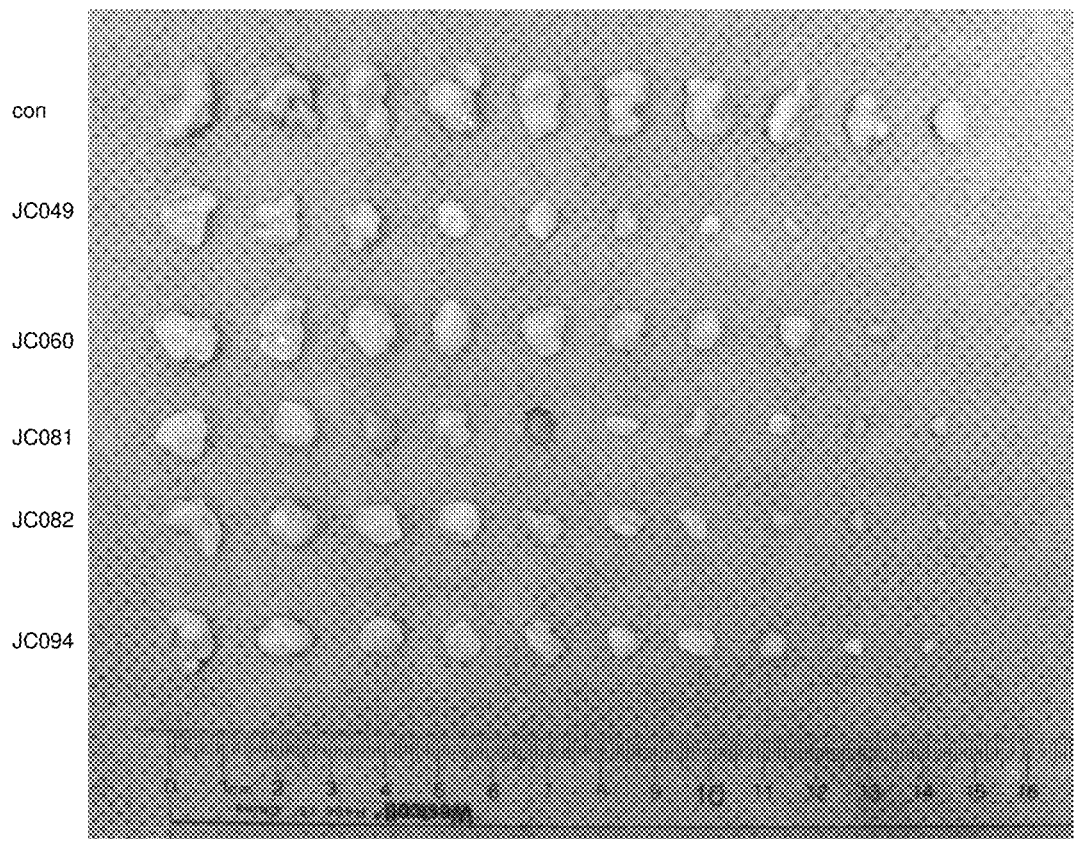
FIG. 9B. Comparisons of tumor sizes at the end of treatment. Tumors from nude mice were dissected and weighed. Treatment with JC049, JC060, JC081, JC082, and JC094 were found to significantly reduced the size of the tumors recovered.
Figure 9C:
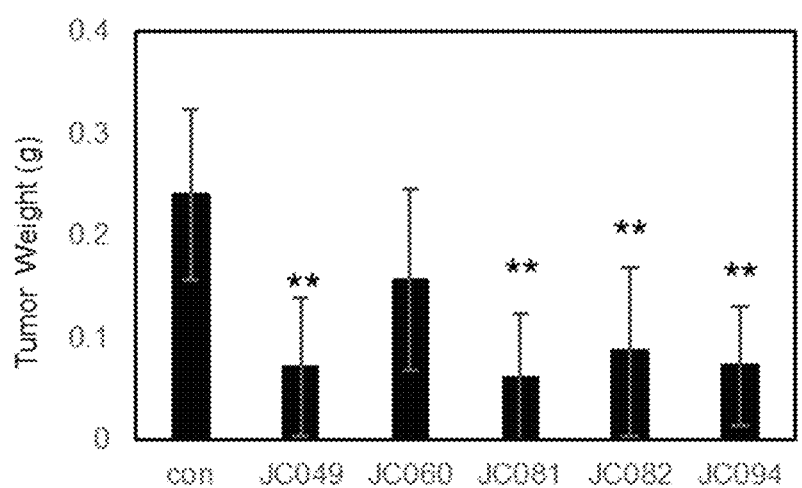
FIG. 9C. Comparisons of tumor weights at the end of treatment. Tumors from nude mice were dissected and weighed. *P<0.05; **P<0.01, unpaired 2-tailed Student's t-Test. Treatment with JC049, JC060, JC081, JC082, and JC094 was found to significantly reduce the weight of tumors recovered.
Figure 10:
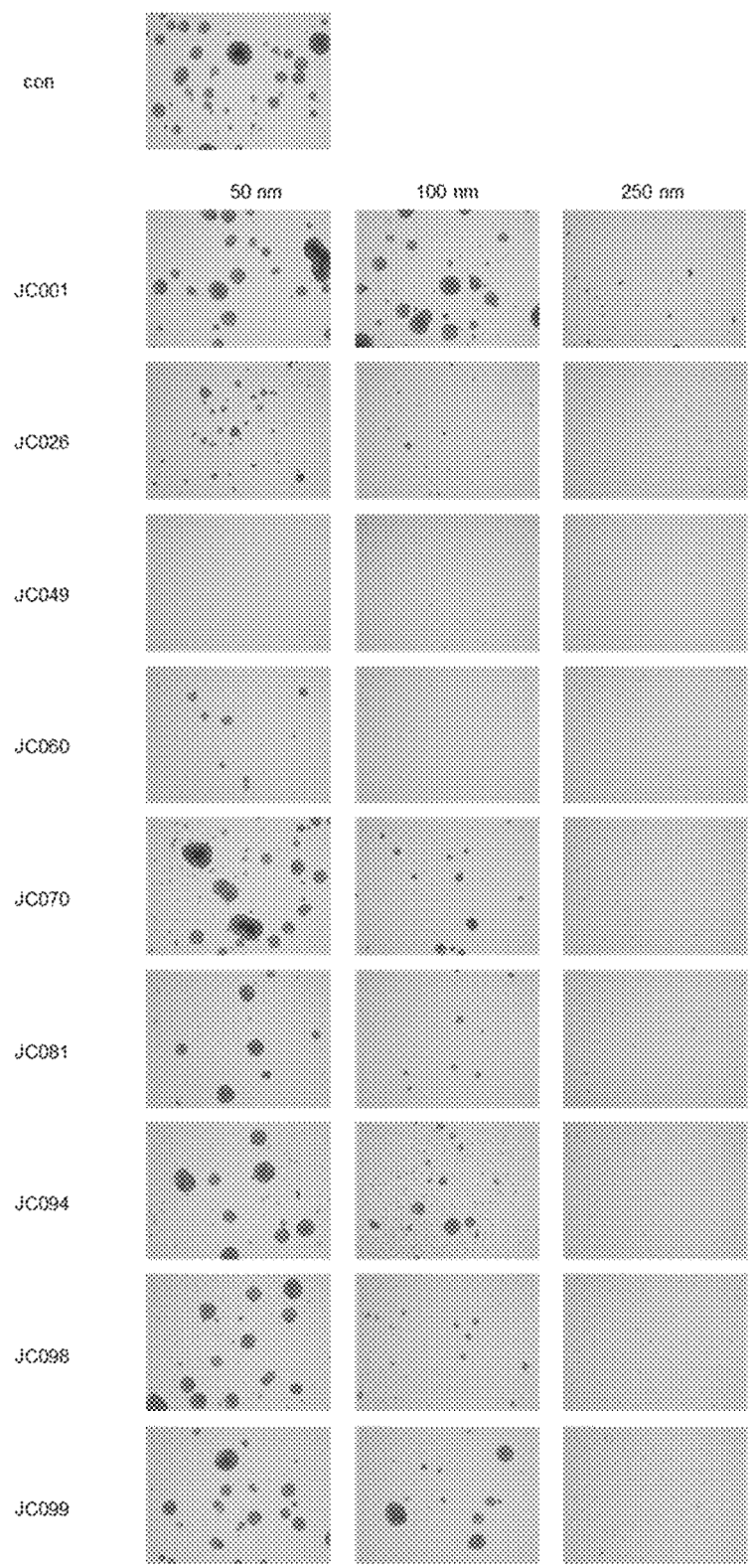
FIG. 10. Treatment with JC Wnt inhibitors suppress the tumor sphere formation of colorectal cancer stem cells. ALDH⁺HCT116 cells were treated with JC Wnt inhibitors as indicated. Tumor spheres were observed under a microscope 2 weeks later. All of the tested compounds showed a reduction in tumor sphere formation.
Figure 11:
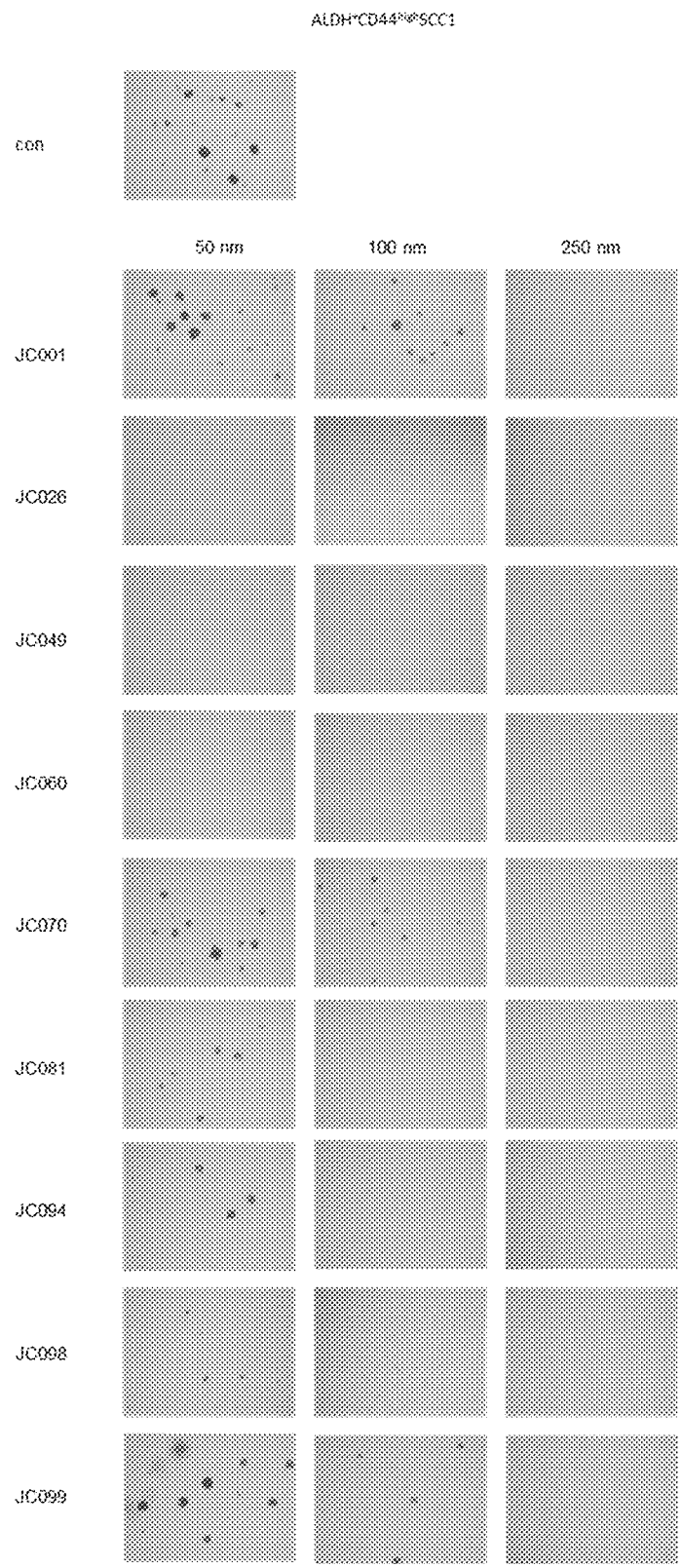
FIG. 11. JC Wnt inhibitors suppress the tumor sphere formation of HNSCC cancer stem cells. ALDH⁺ CD44$^{high}$SCC1 cells were treated with JC Wnt inhibitors as indicated. Tumor spheres were observed under a microscope 2 weeks later. All of the tested compounds showed a reduction in tumor sphere formation.
Figure 12:
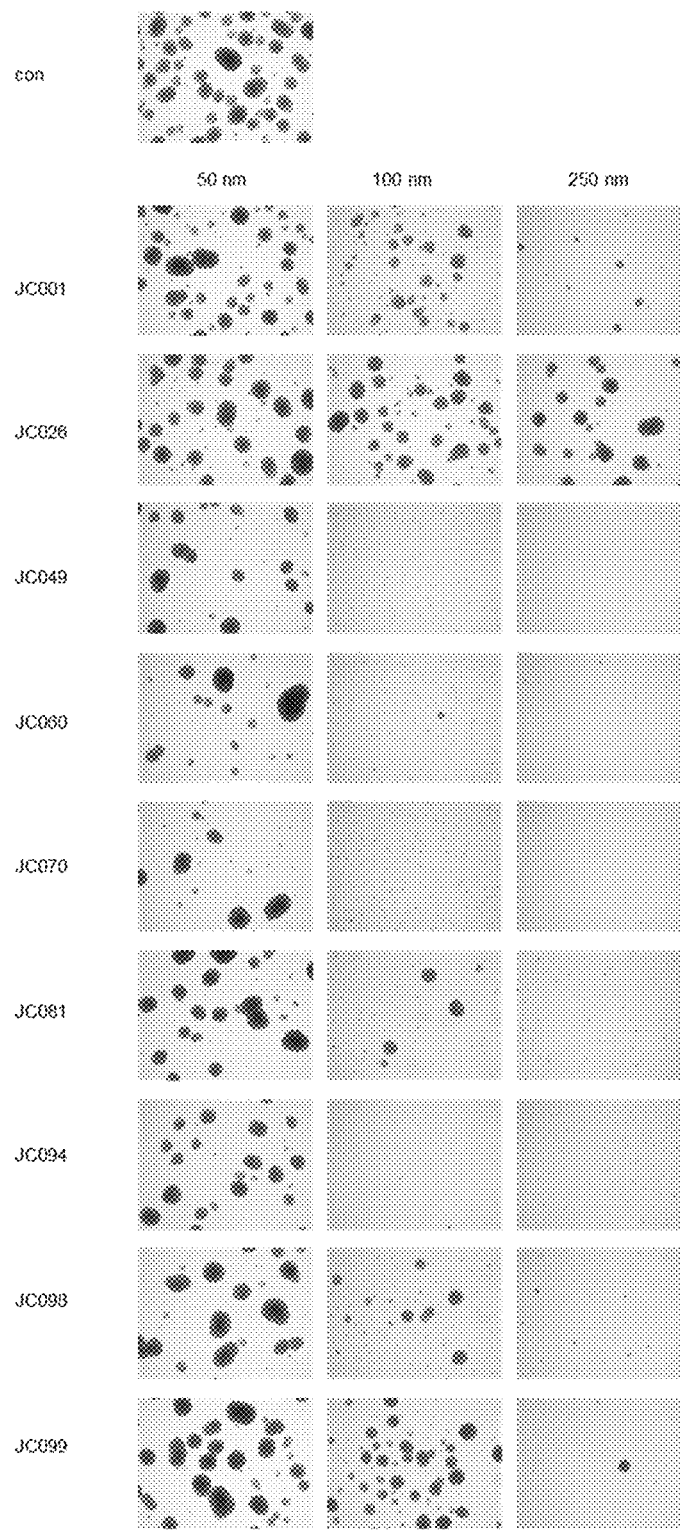
FIG. 12. JC Wnt inhibitors suppress the tumorsphere formation of liver cancer stem cells. CD13highCD133highHep3B cells were treated with JC Wnt inhibitors as indicated. Tumorspheres were observed under the microscope 2 weeks later. All of the tested compounds showed a reduction in tumor sphere formation.
Figure 13:
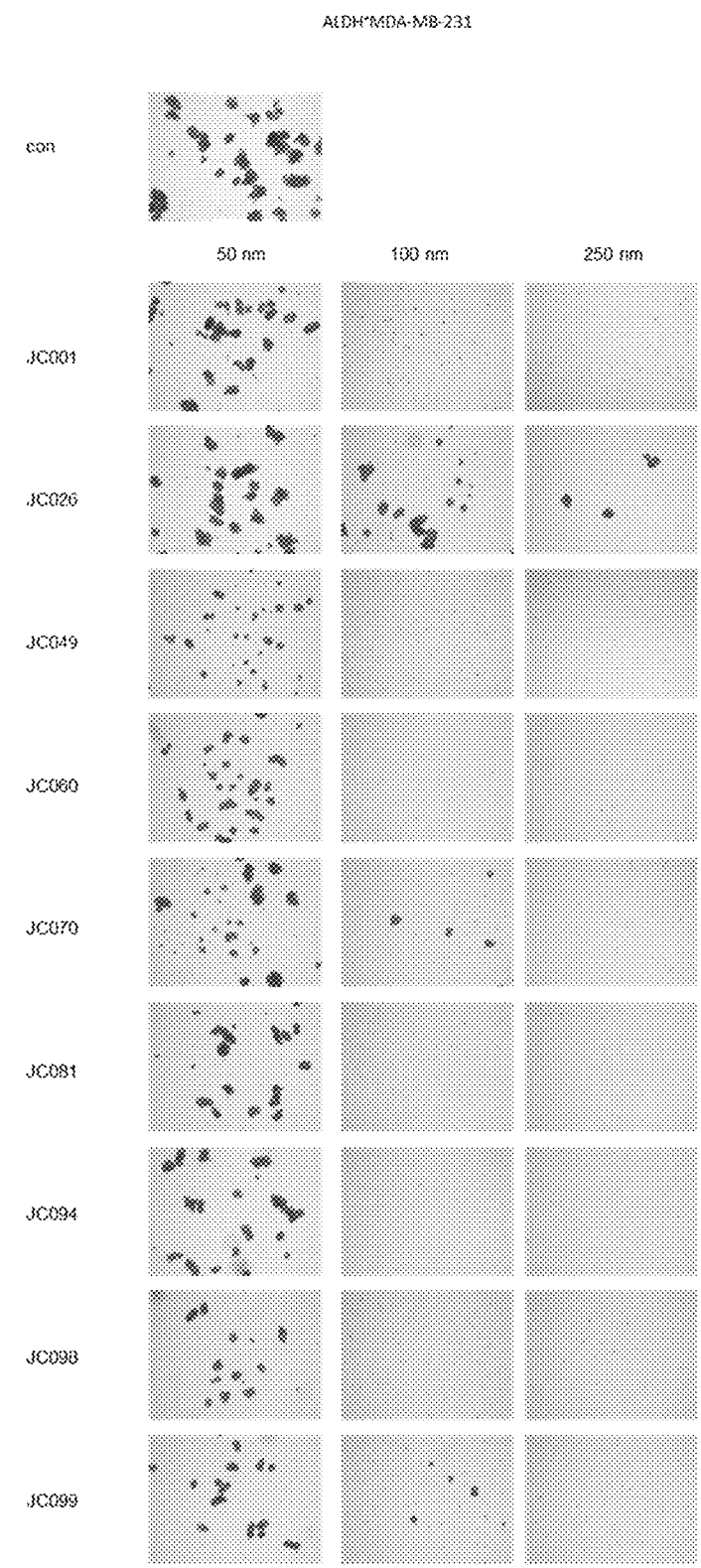
FIG. 13. JC Wnt inhibitors suppress the tumorsphere formation of HNSCC cancer stem cells. ALDH+MDA-MB-231 cells were treated with JC Wnt inhibitors as indicated. Tumorspheres were observed under the microscope 2 weeks later. All of the tested compounds showed a reduction in tumor sphere formation.
Figure 14A:
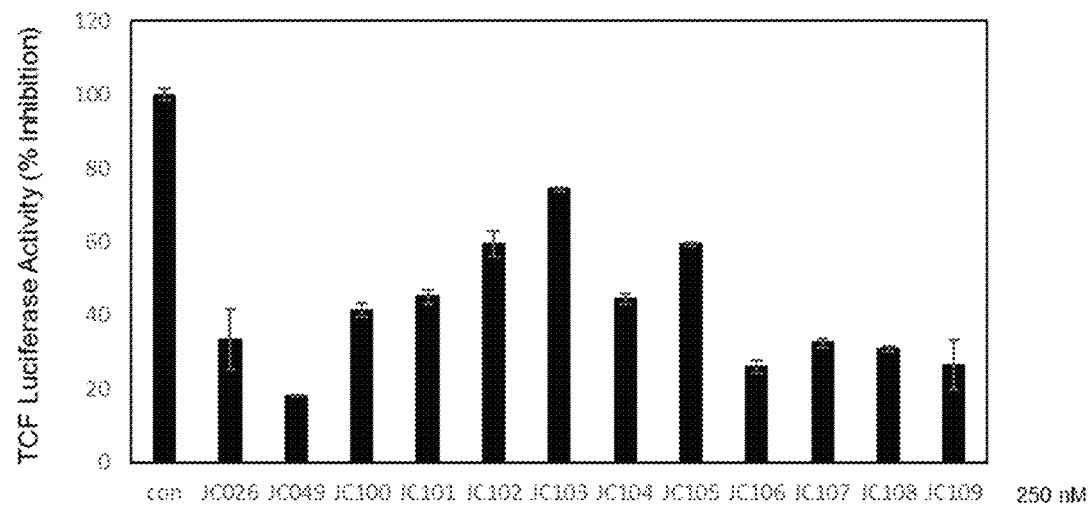
FIG. 14A. depicts the screening of JC inhibitors for Wnt/β-catenin-mediated transcription. Analysis of luciferase activity of 293 T/Top/β-cat* cells treated with the indicated inhibitors (JC100-JC109) relative to control (con). Several compounds were found to possess inhibitory activity. JC049 as a positive control.
Figure 14B:
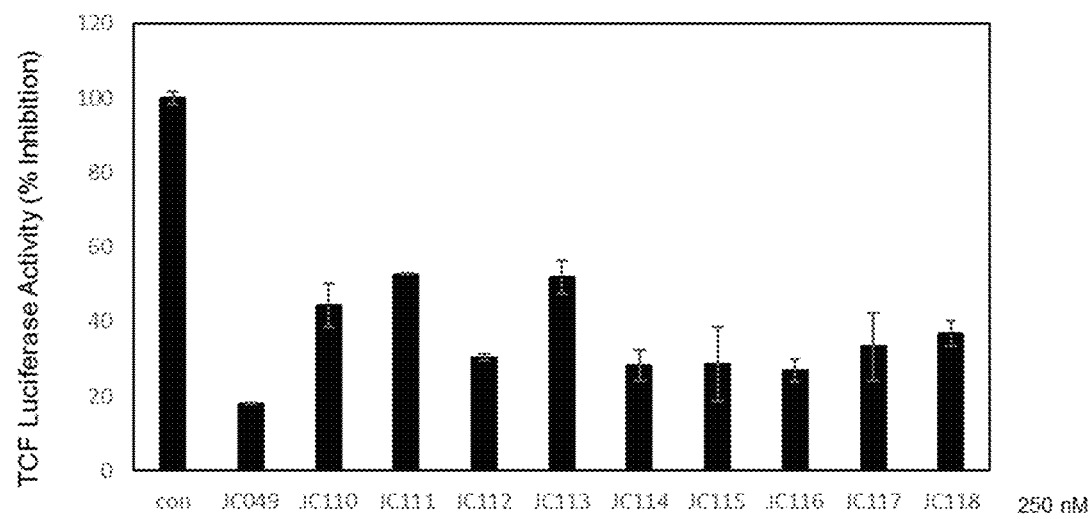
FIG. 14B. depicts the screening of JC inhibitors for Wnt/β-catenin-mediated transcription. Analysis of luciferase activity of 293T/Top/β-cat* cells treated with the indicated inhibitors (JC110-JC118) relative to control (con). Several compounds were found to possess inhibitory activity.
Figure 14C:
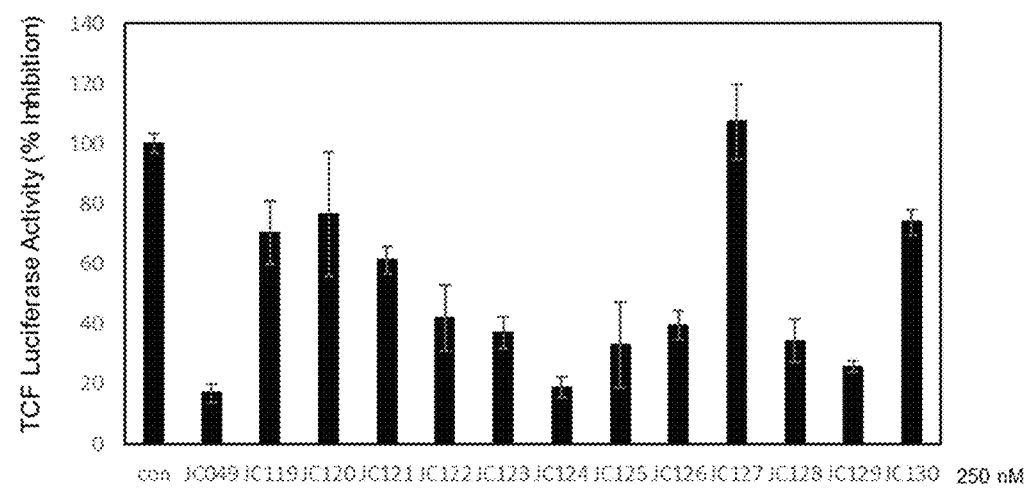
FIG. 14C. depicts the screening of JC inhibitors for Wnt/β-catenin-mediated transcription. Analysis of luciferase activity of 293T/Top/β-cat* cells treated with the indicated inhibitors (JC119-JC130) relative to control (con). Several compounds were found to possess inhibitory activity.
Figure 15A:
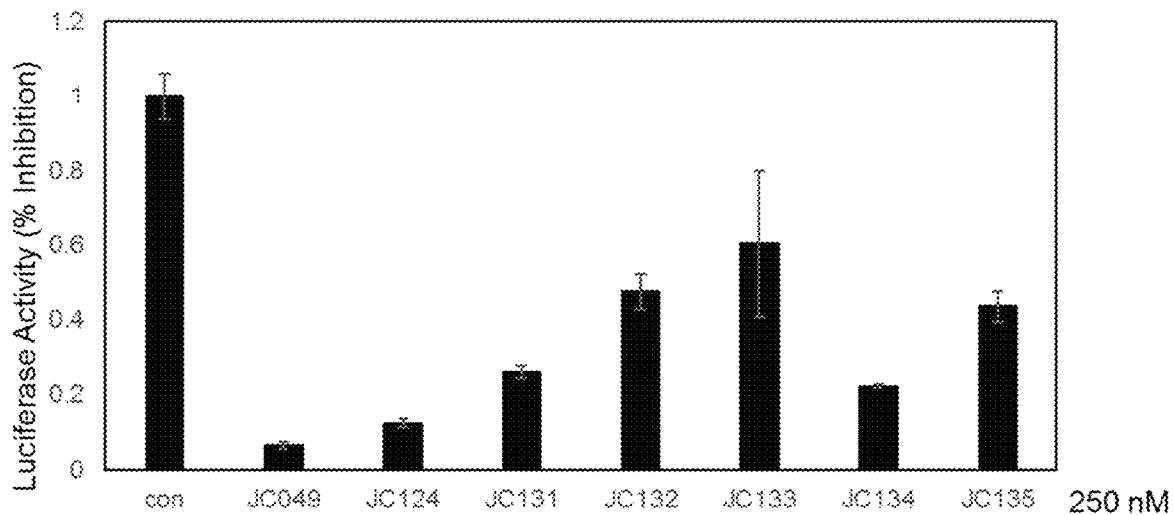
FIG. 15A. depicts the screening of JC inhibitors for Wnt/β-catenin-mediated transcription. Analysis of luciferase activity of 293T/Top/β-cat* cells treated with the indicated inhibitors (JC131-JC135) relative to control (con). Several compounds were found to possess inhibitory activity.
Figure 15B:
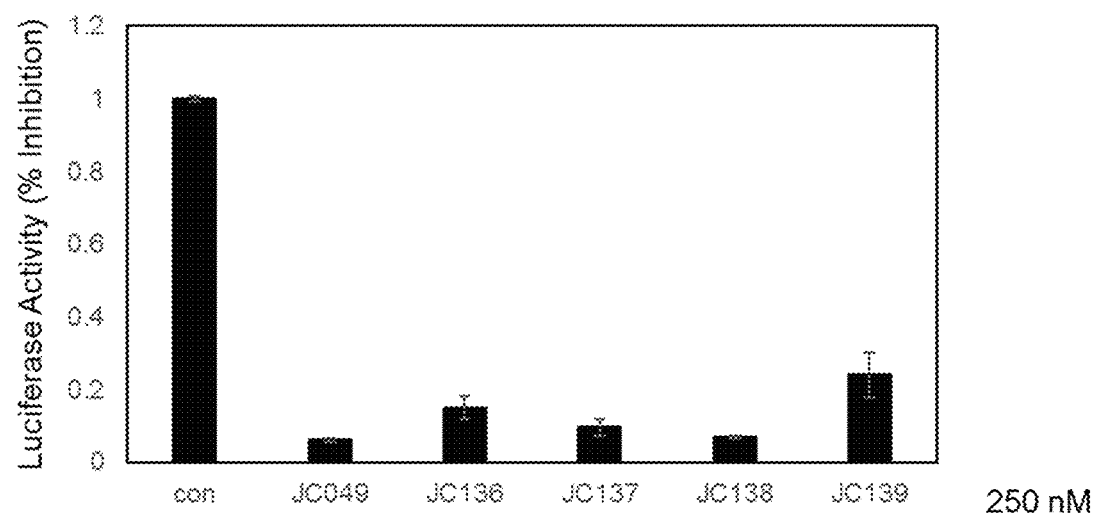
FIG. 15B. depicts the screening of JC inhibitors for Wnt/β-catenin-mediated transcription. Analysis of luciferase activity of 293T/Top/β-cat* cells treated with the indicated inhibitors (JC136-JC139) relative to control (con). Several compounds were found to possess inhibitory activity.
Figure 15C:
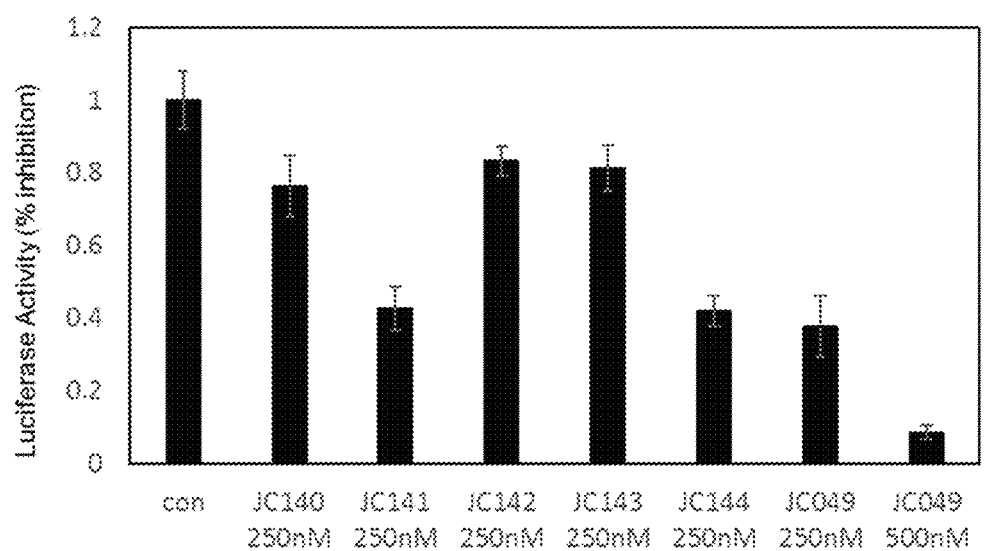
FIG. 15C. depicts the screening of JC inhibitors for Wnt/β-catenin-mediated transcription. Analysis of luciferase activity of 293T/Top/β-cat* cells treated with the indicated inhibitors (JC140-JC144) relative to control (con). Several compounds were found to possess inhibitory activity.
Figure 16A:
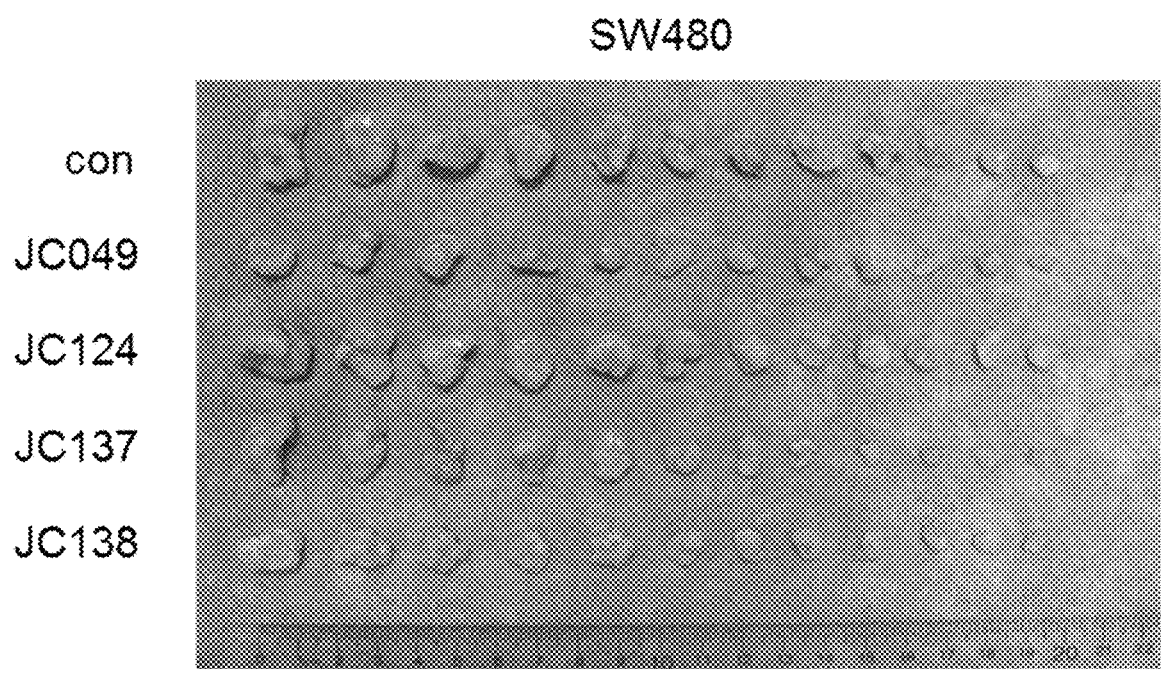
FIG. 16A. depicts the comparisons of actual tumor sizes at the end of treatment. Treatment with JC049, JC137, and JC138 reduced the size of tumors recovered.
Figure 16B:
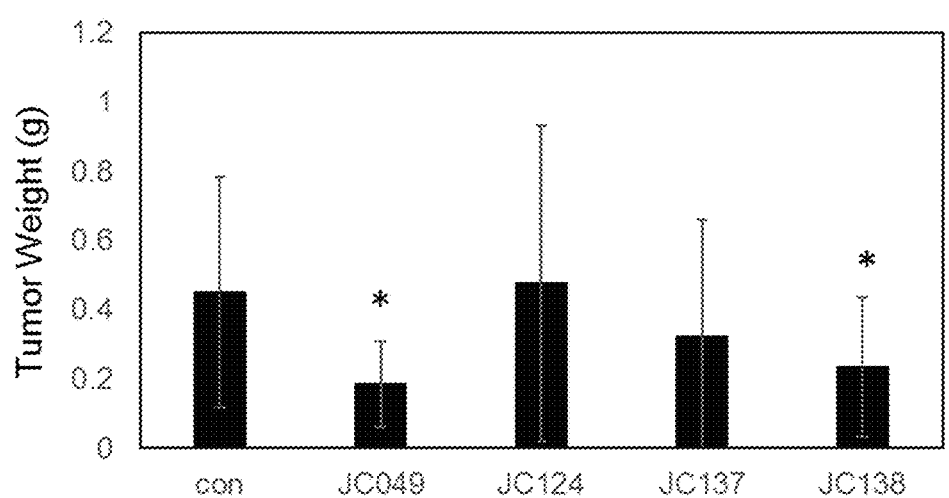
FIG. 16B. depicts the comparisons of tumor weights at the end of treatment. Tumors from nude mice were dissected and weighed. *P<0.05; unpaired 2-tailed Student's t-Test. Treatment with JC049 and JC138 significantly reduced the weight of tumors recovered.
Figure 16C:
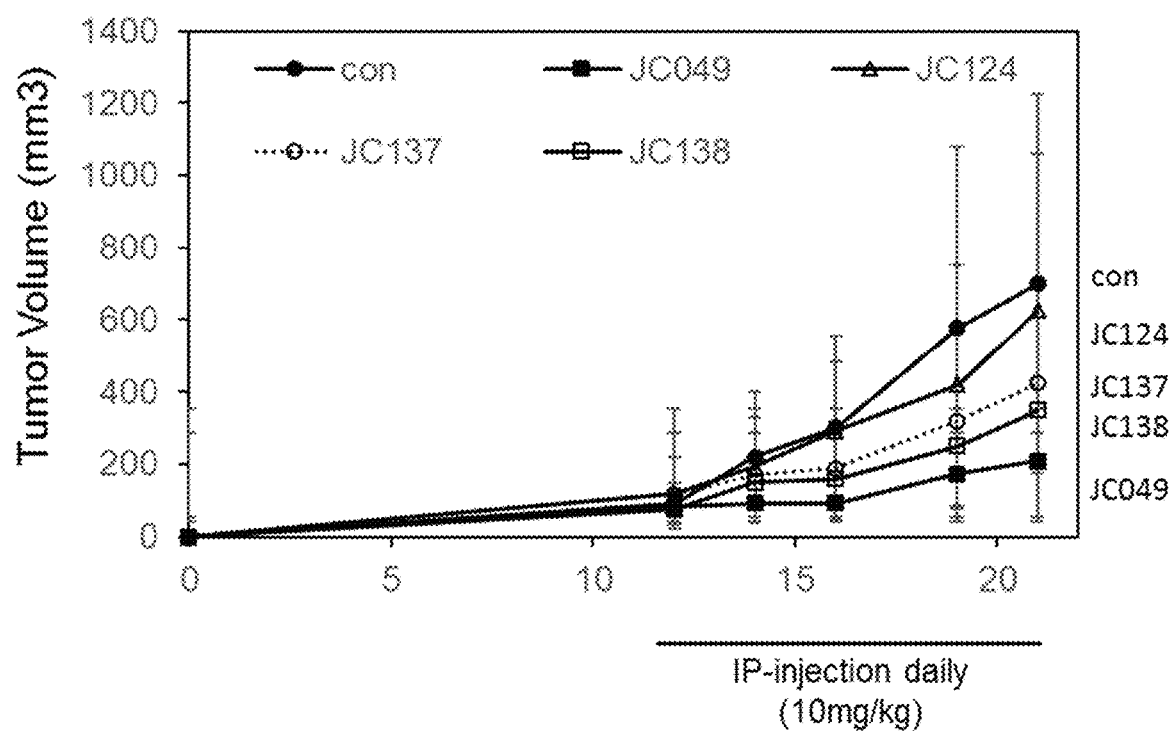
FIG. 16C. depicts JC Wnt inhibitors suppress CRC cells growth in vivo. The growth of SW480 tumor xenografts are inhibited by JC inhibitors as indicated. Animals were treated with 10 mg/kg of the indicated drug on day 12 to 22. JC049 and JC138 significantly reduced tumor volumes.
Figure 16D:
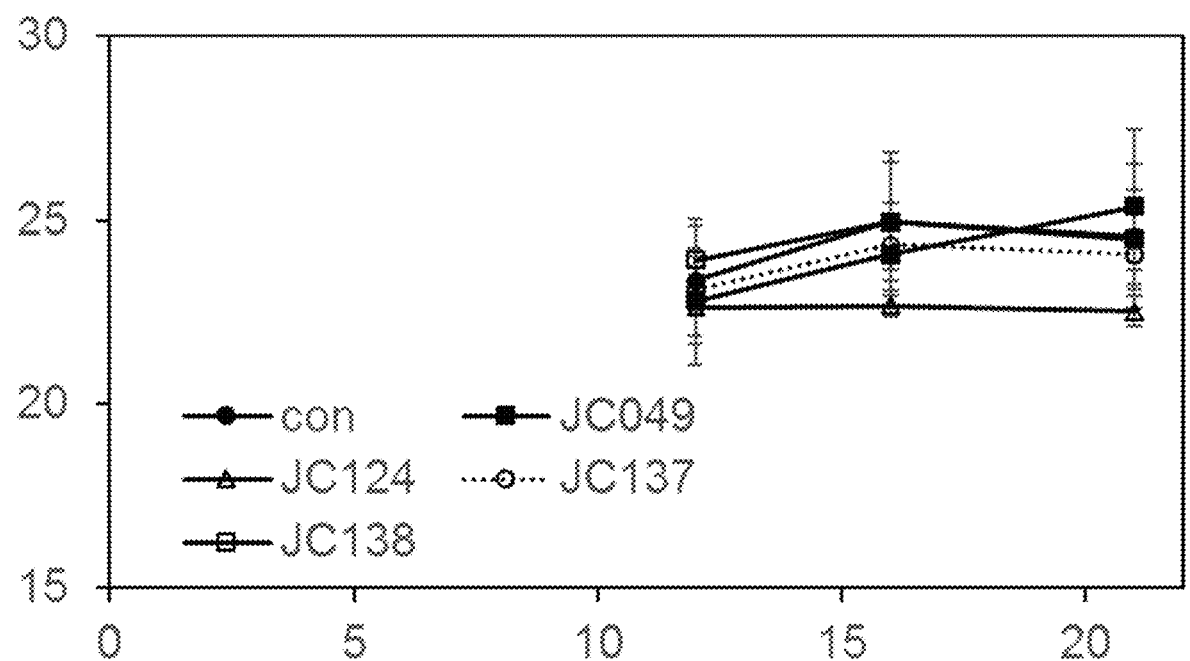
FIG. 16D. depicts that treatment with JC Wnt inhibitors has no effect on nude mice body weight.

It was identified that compounds JC001, JC018, JC018, JC021, JC022, JC026, JC028, JC032, JC048, JC049, JC060, JC070, JC072, JC081, and JC094 significantly inhibited Wnt/D-catenin-mediated transcription (FIGS. 5A, B and 6A-C). JC001, JC026, JC049, JC060, JC070, JC081, JC082, JC094, JC098, and JC099. were chosen for mouse xenograft studies of human colon cancer (FIGS. 7A-D, 8A-C, and 9A-C). It was found that JC026, JC049, JC060, JC081, JC082, JC094, and JC099 significantly inhibited the tumor growth of which JC049 showed the strongest inhibition (FIG. 7A-C). JC070 also showed some inhibition, but did not reach significance probably due to small sample size. At the end of the experiments, the mice were sacrificed and tumor weights were measured, confirming that these compounds significantly inhibited tumor growth. Finally, it was found that these compounds did not affect mouse body weight (FIG. 7D).

General Protocol for Cell Culture and Lentiviral Infection 293T cells were maintained in DMEM medium containing 10% FBS and antibiotics (penicillin and streptomycin) at 37° C. in 5% CO$_2$. Cells were stably infected with lentiviruses expressing the TopFlash reporter (293T/Top cells). The β-catenin mutant (β-cat*, the constitutively active mutant) construct was prepared using the retroviral expression vector by standard PCR. For viral transduction, retrovirus was obtained by co-trasfection of pQCXIP-β-cat* with packaging plasmids into 293T cells following the manufacturer's instructions. 293T/Top stable cells were seeded in 10 cm dish and incubated overnight. The next day cells were treated with retroviral particles. After 12 hours, the medium was replaced with fresh medium. 2 days post virus infection, the cells were selected with puromycin for 5 days to generate the 293T/Top/β-cat* stable cell line.

General Protocol for TCF-Luciferase Activity Assay

293 T/Top/β-cat* cells were plated at 40%-50% confluences in 12-well plate for 8 hours and then treated with Wnt inhibitors overnight. The luciferase activity of total cell lysates was measured using Luciferase Assay System (Promega). The related TCF-luciferase activity was normalized against the protein concentration of each cell lysate sample.

Mouse Xenografts $5 \times 10^5$ of SW480 cells were injected subcutaneously into the flank area of 6-8-week-old nude mice. Tumor volume was measured by using an electronic caliper and calculated with the formula length×width$^2$×0.5, every 2 days. 12 days after inoculation, tumor bearing mice were administered Wnt inhibitors (dissolved in 10% DMSO+20% Cremophor EL+70% normal saline) via intraperitoneal injection for 5 days per week for 10 days at 10 mg/kg. Animal body weights were measured before drug treatments and at the end of the experiments. At the end of the experiments, animals were euthanized with carbon dioxide, followed by cervical dislocation. The tumors were dissected and weighed on the digital balance. We housed mice in pathogen-free facilities under 12-h light and 12-h dark cycle. The animal protocol and experimental procedures were approved by the Division of Laboratory Animal Medicine of UCLA and were in accordance with the US National Institute of Health guidelines.

General Protocol for Isolation of Cancer Stem Cells and Tumor-Sphere Formation Assays For the identification of ALDH$^+$HCT116 cancer stem cells, HCT116 cells were trypsinized to single cells and subsequently stained with anti-ALDEFLUOR kits (Stem Cell Technologies) following the manufacturer's guidelines to label the ALDH$^+$ populations.

To isolate ALDH-MDA-MB-231 breast cancer stem cells, MDA-MB-231 cells were trypsinized to single cells and subsequently stained with anti-ALDEFLUOR kits (Stem Cell Technologies) following the manufacturer's guidelines to label the ALDH$^+$ populations. ALDH$^+$ subpopulations were separated by a FACSVantage SE cell sorter (Beckton Dickson).

To isolate ALDH$^+$CD44$^{high}$SCC1 cancer stem cells, SCC1 cells were trypsinized to single cells and subsequently stained with anti-ALDEFLUOR kits and then incubated with anti-CD44-APC (BD PharMingen Cat #559942) for 30 min on ice. ALDH$^+$CD44$^{high}$SCC1 cells were sorted by a FACSVantage SE cell sorter.

To isolate CD13$^{high}$CD133$^{high}$Hep3B liver cancer stem cells, Hep3B cells were trypsinized to single cells and stained with anti-CD13-APC (Miltenyi Biotec, Cat #130-103-669) and anti-CD133-PE (Miltenyi Biotec, Cat #130-098-826) antibody for 30 min on ice. CD13$^{high}$CD133$^{high}$Hep3B cells were sorted by a FACSVantage SE cell sorter.

For the tumorsphere formation assay, the sorted single cells were plated on ultralow attachment six-well plates (Corning) at a density of 25,000 viable cells per well for cancer stem cells. Cells were grown in a serum-free mammary epithelial basal medium (MEBM; Lonza), supplemented with B27 (Invitrogen), 20 ng/ml EGF (R&D Systems), 10 ng/ml FGF (R&D Systems), 4 mg/ml Gentamycin (Invitrogen), 1 ng/ml Hydrocortisone (Sigma-Aldrich), 5 mg/ml Insulin, 100 nM of beta-mercaptoethanol (Sigma-Aldrich) and 250 nM of Wnt inhibitors as indicated. Tumorspheres were observed under the microscope 2 weeks later.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A compound having a structure represented by Formula Ib or a pharmaceutically acceptable salt thereof:

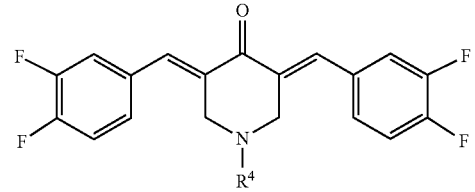

Formula Ib wherein

R$^4$ is substituted alkenyl, substituted acyl, substituted C(O)alkyl, substituted C(O)Oalkyl, substituted C(O)Oaryl, substituted C(O)Oheteroaryl, substituted C(O)N(R$^{5a}$R$^{5b}$), or substituted alkylsulfonyl, further wherein each substituted alkenyl, substituted acyl, substituted C(O)alkyl, substituted C(O)Oalkyl, substituted C(O)Oaryl, substituted C(O)Oheteroaryl, substituted C(O)N(R$^{5a}$R$^{5b}$), or substituted alkylsulfonyl is substituted with at least one basic nitrogen; and R$^{5a}$ and R$^{5b}$ are each independently hydrogen, alkyl, or aryl.

2. The compound of claim 1, wherein R$^4$ is substituted C(O)alkyl.

3. The compound of claim 1, wherein the basic nitrogen is NH$_2$.

4. The compound of claim 1, wherein the basic nitrogen is alkylamino.

5. The compound of claim 1, wherein the basic nitrogen is dialkylamino.

6. The compound of claim 1, wherein the basic nitrogen is methylamino, diethylamino, or di(methoxyethyl)amino.

7. The compound of claim 1, wherein the basic nitrogen is a basic nitrogen-containing heterocycle.

8. The compound of claim 1, wherein the basic nitrogen is azepanyl, pyrrolidinyl, piperidyl, morpholinyl, piperazinyl, piperidonyl, or thiomorpholinyl.
9. The compound of claim 1, wherein the basic nitrogen is pyrrolidine, N-methyl pyrrolidine, N-methylpiperazine, or 1-(4-fluorophenyl)piperazine.
10. A compound selected from:
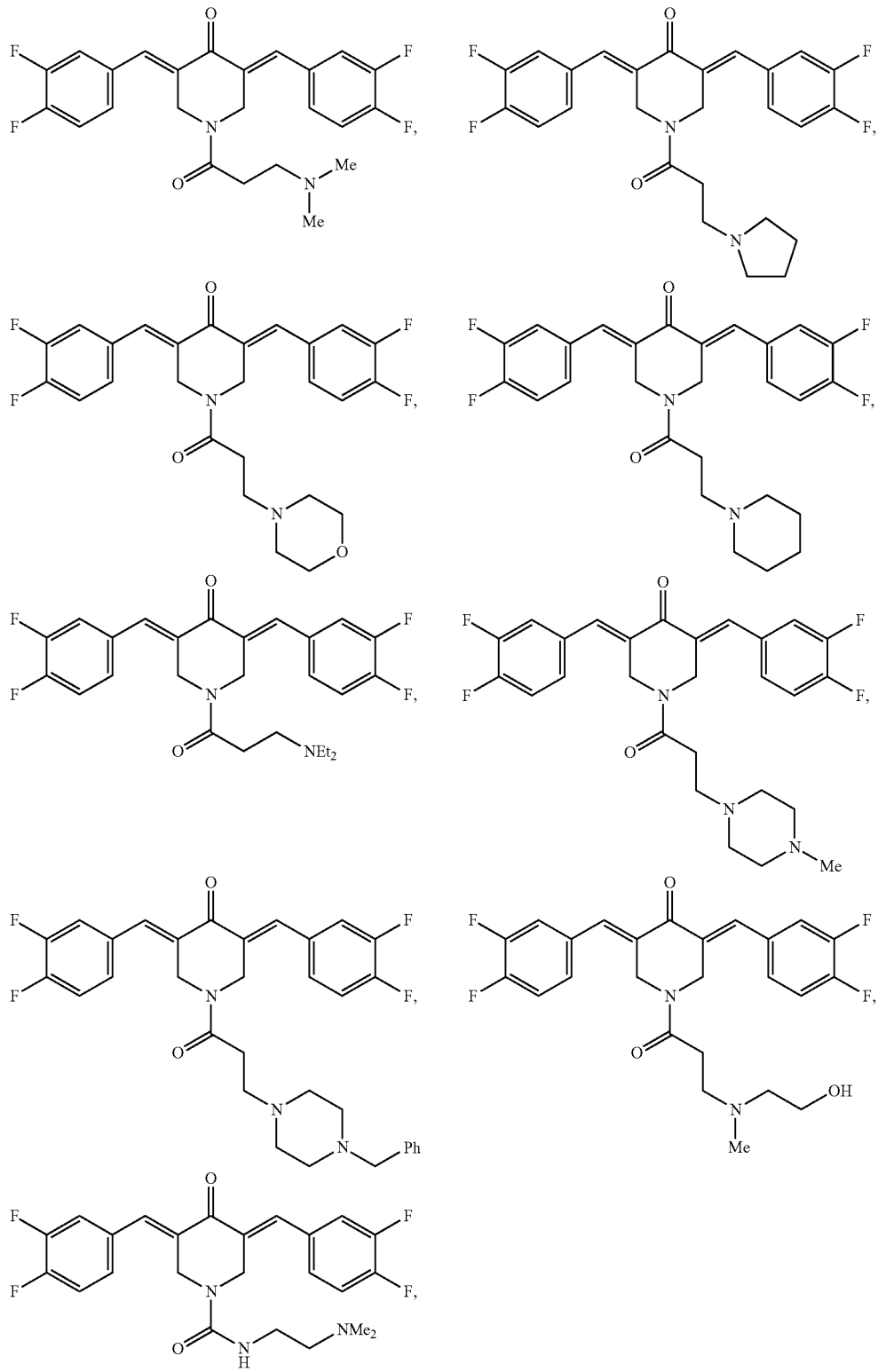

-continued
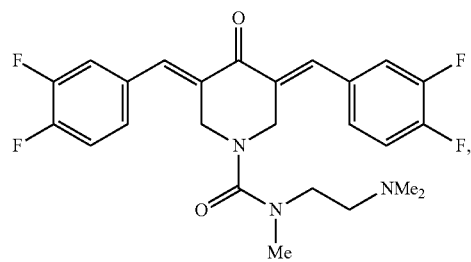
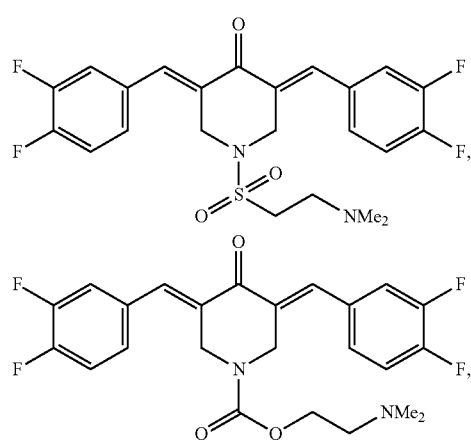
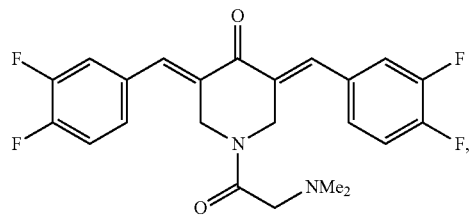
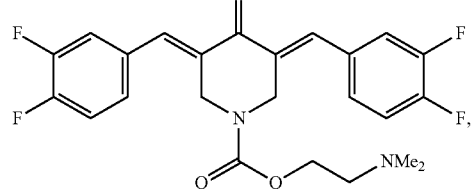
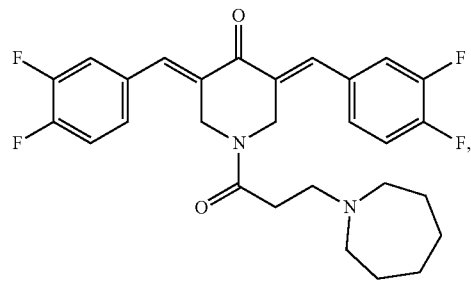
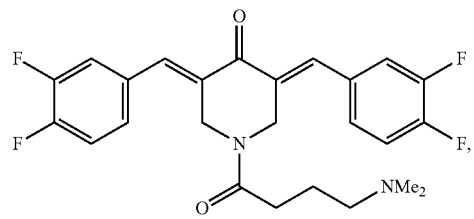
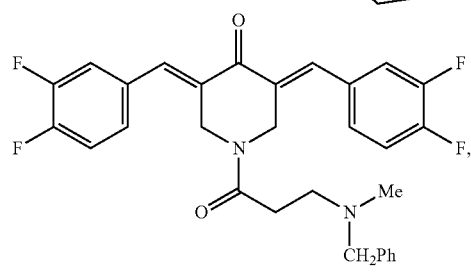
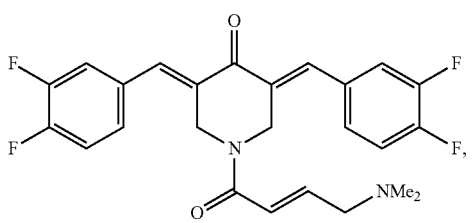
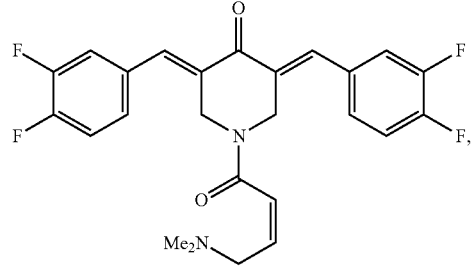

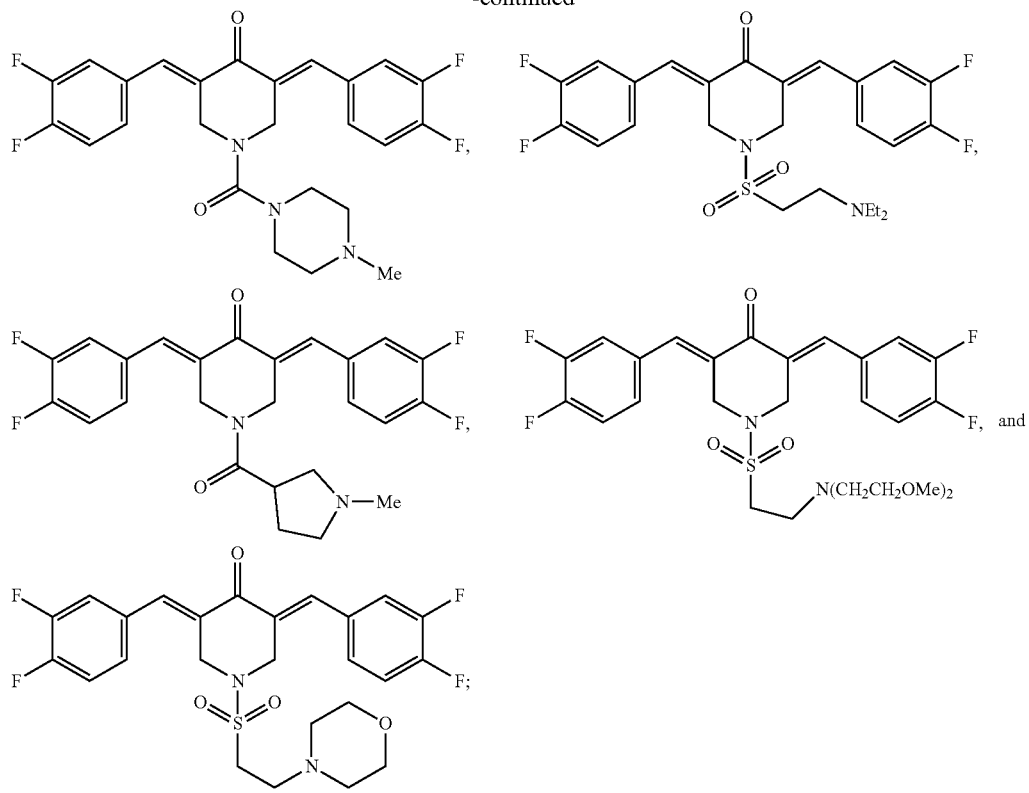

or a pharmaceutically acceptable salt thereof.

11. The compound of claim 1, wherein the compound is

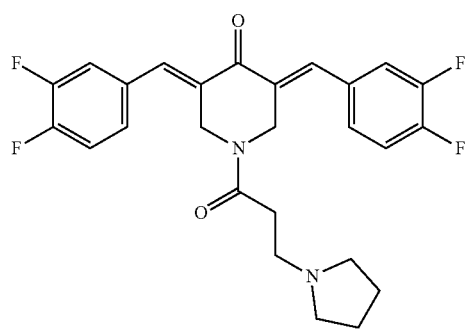 [SMILES: O=C1/C(=C/c2ccc(F)c(F)c2)CN(C(=O)CCN2CCCC2)C/C1=C\c1ccc(F)c(F)c1]

or a pharmaceutically acceptable salt thereof.

12. The compound of claim 1, wherein the compound is

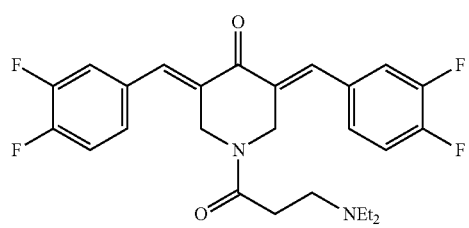

or a pharmaceutically acceptable salt thereof.

13. A pharmaceutical composition comprising the compound of claim 1 and a pharmaceutically acceptable excipient.

14. A method of inhibiting β-catenin, comprising administering to a subject in need thereof a compound of claim 1.

15. A method of treating cancer, comprising administering to a subject in need thereof a compound of claim 1, wherein the cancer is bladder cancer, bone cancer, brain cancer, breast cancer, cardiac cancer, cervical cancer, colon cancer, colorectal cancer, esophageal cancer, fibrosarcoma, gastric cancer, gastrointestinal cancer, head, spine and neck cancer, Kaposi's sarcoma, kidney cancer, leukemia, liver cancer, lymphoma, melanoma, multiple myeloma, pancreatic cancer, penile cancer, testicular germ cell cancer, thymoma and thymic carcinoma, lung cancer, ovarian cancer, and prostate cancer.

16. A method of treating cancer, comprising administering to a subject in need thereof the compound of claim 10, wherein the cancer is bladder cancer, bone cancer, brain cancer, breast cancer, cardiac cancer, cervical cancer, colon cancer, colorectal cancer, esophageal cancer, fibrosarcoma, gastric cancer, gastrointestinal cancer, head, spine and neck cancer, Kaposi's sarcoma, kidney cancer, leukemia, liver cancer, lymphoma, melanoma, multiple myeloma, pancreatic cancer, penile cancer, testicular germ cell cancer, thymoma and thymic carcinoma, lung cancer, ovarian cancer, and prostate cancer.

* * * * *